(12) United States Patent
Hahn et al.

(10) Patent No.: US 12,324,352 B1
(45) Date of Patent: Jun. 3, 2025

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Seung Hoon Hahn, Cheonan-si (KR); Junggeun Lee, Cheonan-si (KR); Ki Hwan Yoon, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/954,578

(22) Filed: Nov. 21, 2024

(30) Foreign Application Priority Data

Dec. 1, 2023 (KR) .......................... 10-2023-0172026
Dec. 1, 2023 (KR) .......................... 10-2023-0172303

(51) Int. Cl.
*H10K 85/60* (2023.01)
*C07D 405/10* (2006.01)
*H10K 50/12* (2023.01)

(52) U.S. Cl.
CPC ......... *H10K 85/654* (2023.02); *C07D 405/10* (2013.01); *H10K 85/615* (2023.02); *H10K 85/657* (2023.02); *H10K 85/6572* (2023.02); *H10K 85/6574* (2023.02); *H10K 85/6576* (2023.02); *H10K 50/12* (2023.02)

(58) Field of Classification Search
None
See application file for complete search history.

(56) References Cited

U.S. PATENT DOCUMENTS

2023/0172055 A1\* 6/2023 Park .................. C07D 491/048
257/40

FOREIGN PATENT DOCUMENTS

| KR | 10-2023-0078931 A | 6/2023 | |
|---|---|---|---|
| KR | 10-2023-0107479 A | 7/2023 | |
| WO | WO-2023132694 A1 \* | 7/2023 | ............. C09K 11/06 |

\* cited by examiner

*Primary Examiner* — Robert S Loewe
(74) *Attorney, Agent, or Firm* — Vorys, Sater, Seymour and Pease LLP; Mih Suhn Koh

(57) ABSTRACT

Provided are a compound of P-5 to P-100 that can improve the luminous efficiency, stability, and lifespan of the organic electronic element employing the compound, an organic electronic element using the same, and an electronic device thereof.

20 Claims, 6 Drawing Sheets

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting materials can be classified into high molecular type and low molecular type according to molecular weight, and can be classified into fluorescent materials derived from singlet excited state of electrons and phosphorescent materials derived from triplet excited state of electrons according to light emitting mechanism. Additionally, light emitting materials can be classified into blue, green, and red light emitting materials according to light emitting color, and yellow and orange light emitting materials required to realize better natural colors.

However, when only one substance is used as a light emitting material, the maximum light-emitting wavelength shifts to a longer wavelength due to molecular interactions, resulting in a decrease in color purity or a decrease in device efficiency due to light emitting attenuation effects. Therefore, a host/dopant system can be used as a light-emitting material to increase color purity and light-emitting efficiency through energy transfer. The principle is that when a small amount of a dopant having a smaller energy band gap than that of the host forming the emitting layer is mixed in the emitting layer, excitons generated in the emitting layer are transported to the dopant to emit light with high efficiency. Here, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are interrelated. As efficiency increases, the driving voltage decreases relatively. As the driving voltage decreases, the crystallization of organic substances due to Joule heating generated during operation decreases, which results in a tendency for the lifespan to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, it is necessary to delay the penetration and diffusion of metal oxide from the anode electrode (ITO), which is one of the causes of shortened lifespan of organic electronic elements, into the organic layer, and to have stable characteristics against Joule heating generated when the element is operated. Additionally, since OLED devices are mainly formed by a deposition method, it is necessary to develop materials that can withstand the deposition process for a long time, that is, materials with strong heat resistance.

That is, in order to fully exhibit the excellent characteristics of an organic electronic element, it should be preceded that the material constituting the organic material layer in the element, such as a hole injection material, a hole transport material, a light emitting material, an electron transport material, an electron injection material, etc., is supported by a stable and efficient material. But the development of stable and efficient organic material layer materials for organic electronic elements has not yet been sufficiently accomplished. Therefore, the development of new materials is continuously required, and in particular, the development of a host material for the emitting layer is urgently needed.

DETAILED DESCRIPTION OF THE INVENTION

Summary

In order to solve the problems of the above-mentioned background technology, the present invention has discovered a compound with a novel structure, and also discovered that when the compound is applied to an organic electronic element, the luminous efficiency, stability, and lifespan of the element can be greatly improved.

Accordingly, the purpose of the present invention is to provide a novel compound, an organic electronic element using the same, and an electronic device thereof.

Technical Solution

The present invention provides a composition for an organic electronic element comprising a mixture of a compound represented by Formula 1 and a compound represented by Formula 5.

Formula 1

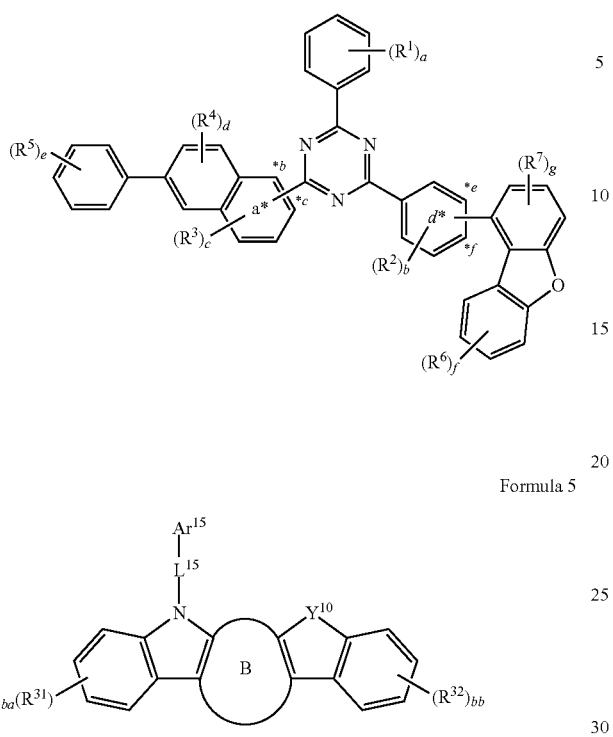

Formula 5

In addition, in another aspect, the present invention provides an organic electronic element comprising the composition for the organic electronic element or the compound represented by Formula 1, and an electronic device thereof.

Effects of the Invention

By using the compound according to the present invention, high luminous efficiency, low driving voltage and high heat resistance of the element can be achieved, and color purity and lifespan of the element can be greatly improved.

Figure 1:
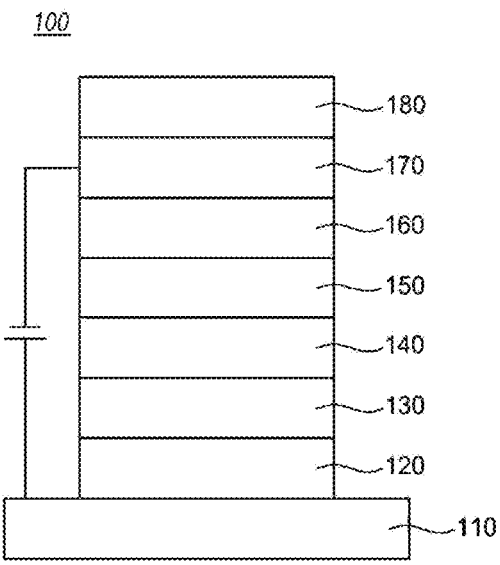
FIG. 1 to FIG. 3 are exemplary views of an organic electroluminescent device according to the present invention.

DESCRIPTION OF THE NUMERALS IN THE DRAWINGS 100, 200, 300: organic electronic element 110: the first electrode
120: hole injection layer 130: hole transport layer
140: emitting layer 150: electron transport layer
160: electron injection layer 170: second electrode
180: light efficiency enhancing Layer 210: buffer layer
220: emitting auxiliary layer 320: first hole injection layer
330: first hole transport layer 340: first emitting layer
350: first electron transport layer 360: first charge generation layer
361: second charge generation layer 420: second hole injection layer
430: second hole transport layer 440: second emitting layer
450: second electron transport layer CGL: charge generation layer
ST1: first stack ST2: second stack

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and includes an aromatic ring formed by the participation of adjacent substituents in a bond or reaction. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of ring-forming carbon. For example, "heterocyclic group" includes compound below.

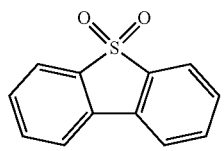 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

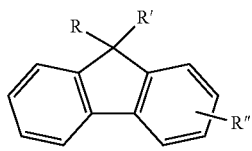

The term "spiro compound", as used herein, has a 'spiro union', and a spiro union means a connection in which 2 rings share only one atom. Wherein, atoms shared in the 2 rings are called 'spiro atoms', and these compounds are called 'monospiro-', 'di-spiro-' and 'tri-spiro-', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include one or more heteroatoms, but are not limited thereto.

Unless otherwise stated, the term "substituted or unsubstituted", as used herein, means that substitution is substituted by at least one substituent selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiophen group, a $C_6$-$C_{20}$ arylthiophen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited thereto.

Unless otherwise expressly stated, the Formula used in the present invention, as used herein, is applied in the same manner as the substituent definition according to the definition of the exponent of the following Formula.

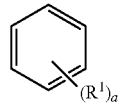

wherein, when a is an integer of 0, the substituent $R^1$ is absent, when a is an integer of 1, the sole substituent $R^1$ is linked to any one of the carbon constituting the benzene ring, when a is an integer of 2 or 3, each substituent $R^1$s may be the same and different, when a is an integer of 4 to 6, and is linked to the benzene ring in a similar manner, whereas the indication of hydrogen bound to the carbon forming the benzene ring is omitted.

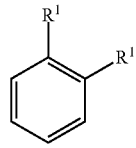

(a = 2)

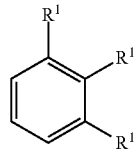

(a = 3)

As used herein, the term "composition" is intended to be interpreted broadly, comprising compounds as well as solutions, dispersions, liquids and solid mixtures (mixture, admixture). The composition of the present invention may comprise the compound of the present invention alone, or the compounds are comprised in a combination of 2 or more different types, or the compounds may be comprised in combinations of 2 or more types with other compounds. In other words, the composition may comprise a compound corresponding to Formula 1 alone, a mixture of 2 or more compounds of Formula 1, or a mixture of a compound of Formula 1 and a compound not corresponding to the present invention. Wherein, the compound not corresponding to the present invention may be a single compound, and may be 2 or more types of compounds. Here, when the compound is comprised in a combination of 2 or more types of other compounds, the other compounds may be already known compounds of each organic material layer, or may be compounds to be developed in the future. Wherein, the compound contained in the organic material layer may consist of only the same type of compound, but may also be a mixture of 2 or more types of different compounds represented by Formula 1.

Hereinafter, a compound according to an aspect of the present invention, a composition and an organic electronic element comprising the same will be described.

The present invention provides a composition for an organic electronic element comprising a mixture of a compound represented by Formula 1 and a compound represented by Formula 5.

Formula 1

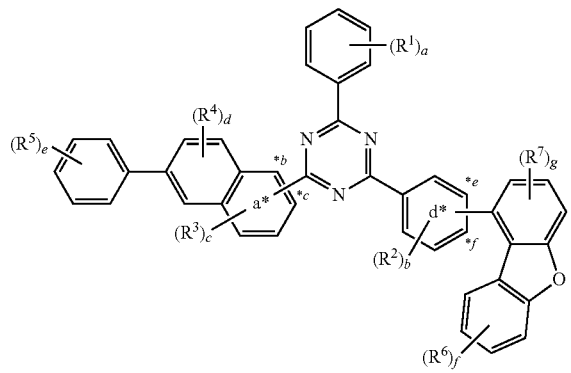

Formula 5

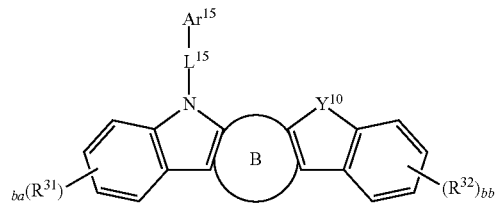

Wherein:
$R^1$, $R^2$, $R^3$, $R^4$, $R^5$, $R^6$ and $R^7$ are the same or different from each other and are each independently a hydrogen; or deuterium;
*a is bonded to either *b or *c,
*d is bonded to either *e or *f,
a and e are independently an integer of 0 to 5, b and f are independently an integer of 0 to 4, c, d and g are independently an integer of 0 to 3,
$L^{15}$ is each independently selected from the group consisting of a single bond; a $C_6$-$C_{60}$ arylene group; fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;
Wherein in case $L^{15}$ is an arylene group, it may be preferably a $C_6$-$C_{30}$ arylene group, more preferably a $C_6$-$C_{25}$ arylene group, for example, phenylene, biphenylene, naphthylene, terphenylene, anthracenylene, etc.

Wherein in case $L^{15}$ is a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc.

Wherein in case $L^{15}$ is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, $Ar^{15}$ is each independently selected from the group consisting of an $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a fused ring group of a $C_3$-$C_{60}$ aliphatic ring and a $C_6$-$C_{60}$ aromatic ring; and -L'-N(R')(R");

Wherein in case $Ar^{15}$ is an aryl group, it may be preferably a $C_6$-$C_{30}$ aryl group, more preferably a $C_6$-$C_{25}$ aryl group, for example, it may be phenyl, biphenyl, terphenyl, naphthalene, phenanthrene, triphenylene, etc, Wherein in case $Ar^{15}$ is a heterocyclic group, it may be preferably a $C_2$-$C_{30}$ heterocyclic group, more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc.

Wherein in case $Ar^{15}$ is an aliphatic ring group, preferably a $C_3$-$C_{30}$ aliphatic ring group, more preferably a $C_3$-$C_{24}$ aliphatic ring group.

Wherein in case $Ar^{15}$ is a fused ring group, preferably a fused ring group of an $C_3$-$C_{30}$ aliphatic ring and an $C_6$-$C_{60}$ aromatic ring, more preferably a fused ring group of an $C_3$-$C_{24}$ aliphatic ring and an $C_6$-$C_{24}$ aromatic ring.

Wherein L' is selected from the group consisting of a single bond; a $C_6$-$C_{60}$ arylene group; fluorenylene group; a $C_2$-$C_{60}$ heterocyclic group including at least one heteroatom of O, N, S, Si or P; and a $C_3$-$C_{60}$ aliphatic ring;

Wherein in case L' is an arylene group, it may be preferably a $C_6$-$C_{30}$ arylene group, more preferably a $C_6$-$C_{25}$ arylene group, for example, phenylene, biphenylene, naphthylene, terphenylene, anthracenylene, etc.

Wherein in case L' is a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, benzocarbazole, naphthobenzofuran, naphthobenzothiophene, etc.

Wherein in case L' is an aliphatic ring group, preferably a $C_3$-$C_{30}$ aliphatic ring group, more preferably a $C_3$-$C_{24}$ aliphatic ring group.

Wherein R' and R" are each independently selected from the group consisting of an $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a fused ring group of a $C_3$-$C_{60}$ aliphatic ring and a $C_6$-$C_{60}$ aromatic ring;

Wherein in case R' and R" are an aryl group, it may be preferably a $C_6$-$C_{30}$ aryl group, more preferably a $C_6$-$C_{25}$ aryl group, for example, it may be phenyl, biphenyl, terphenyl, naphthalene, phenanthrene, triphenylene, etc, Wherein in case R' and R" are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc.

Wherein in case R' and R" are an aliphatic ring group, preferably a $C_3$-$C_{30}$ aliphatic ring group, more preferably a $C_3$-$C_{24}$ aliphatic ring group.

Wherein in case R' and R" are a fused ring group, preferably a fused ring group of an $C_3$-$C_{30}$ aliphatic ring and an $C_6$-$C_{60}$ aromatic ring, more preferably a fused ring group of an $C_3$-$C_{24}$ aliphatic ring and an $C_6$-$C_{24}$ aromatic ring.

$Y^{10}$ is O, S, $CR^{51}R^{52}$ or $NR^{53}$,

Ring B is $C_6$-$C_{20}$ aryl group, $R^{31}$ and $R^{32}$ are each the same or different, and each independently selected from the group consisting of a hydrogen; deuterium; halogen; cyano group; nitro group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxy group; and a $C_6$-$C_{60}$ aryloxy group; or an adjacent plurality of $R^{31}$ or plurality of $R^{32}$ may be bonded to each other to form a ring, $R^{51}$, $R^{52}$ and $R^{53}$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxy group; and a $C_6$-$C_{60}$ aryloxy group; alternatively, $R^{51}$ and $R^{52}$ can be bonded to each other to form a spiro ring, Wherein in case $R^{31}$, $R^{32}$, $R^{51}$, $R^{52}$ and $R^{53}$ are an aryl group, preferably an $C_6$-$C_{60}$ aryl group, more preferably an $C_6$-$C_{25}$ aryl group, such as phenyl, biphenyl, terphenyl, naphthalene, phenanthrene, etc.

Wherein in case $R^{31}$, $R^{32}$, $R^{51}$, $R^{52}$ and $R^{53}$ are a heterocyclic group, it may be preferably a $C_2$-$C_{30}$ heterocyclic group, and more preferably a $C_2$-$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc., Wherein in case $R^{31}$, $R^{32}$, $R^{51}$, $R^{52}$ and $R^{53}$ are a fused ring group, preferably a fused ring group of an $C_3$-$C_{30}$ aliphatic ring and an $C_6$-$C_{60}$ aromatic ring, more preferably a fused ring group of an $C_3$-$C_{24}$ aliphatic ring and an $C_6$-$C_{24}$ aromatic ring.

Wherein in case $R^{31}$, $R^{32}$, $R^{51}$, $R^{52}$ and $R^{53}$ are an alkyl group, it may be preferably a $C_1$-$C_{30}$ alkyl group, and more preferably a $C_1$-$C_{24}$ alkyl group.

Wherein in case $R^{31}$, $R^{32}$, $R^{51}$, $R^{52}$ and $R^{53}$ are alkoxyl groups, they may be preferably $C_1$-$C_{24}$ alkoxyl groups.

Wherein in case $R^{31}$, $R^{32}$, $R^{51}$, $R^{52}$ and $R^{53}$ are an aryloxy group, it may be preferably an $C_6$-$C_{24}$ aryloxy group.

ba and bb are each independently an integer of 0 to 4, wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; a $C_3$-$C_{20}$ cycloalkyl group; a $C_7$-$C_{20}$ arylalkyl group; a $C_8$-$C_{20}$ arylalkenyl group; and -L'-N(R')(R"); also the hydrogen of these substituents may be further substituted with one or more deuterium, and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Preferably, the composition for an organic electronic element may be used as a host for an emitting layer.

Also, Formula 1 comprises a compound selected from any one of Formulas 1-1 to 1-4.

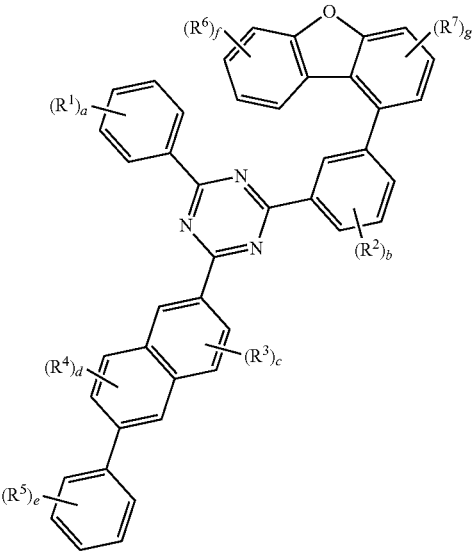

Formula 1-1

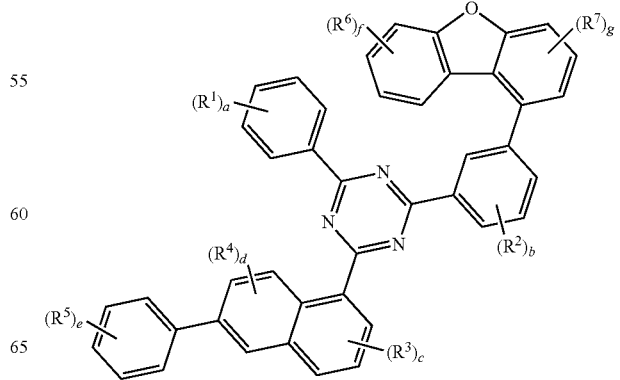

Formula 1-2

Formula 1-3
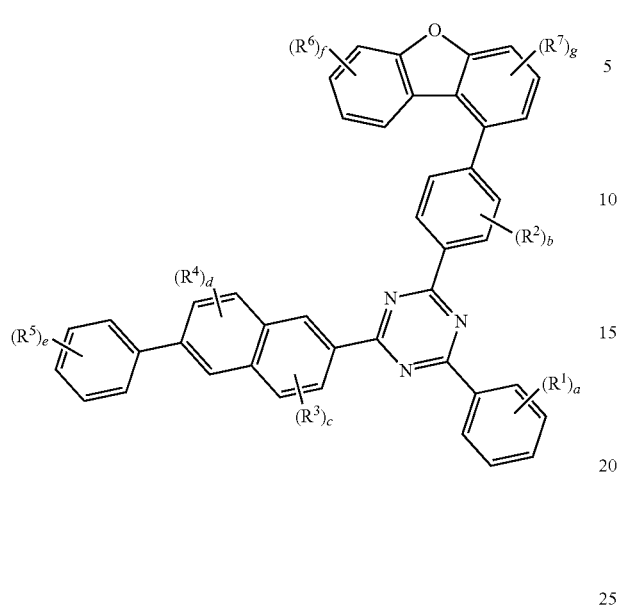
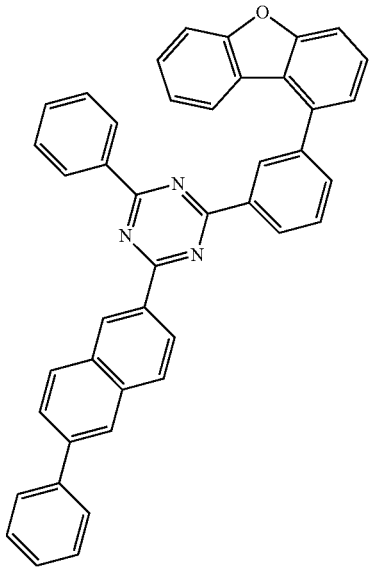
P-1
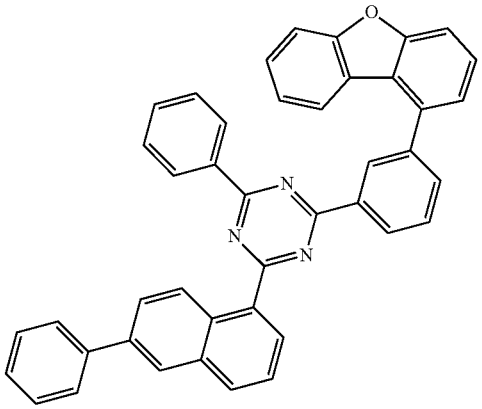
P-2
Formula 1-4
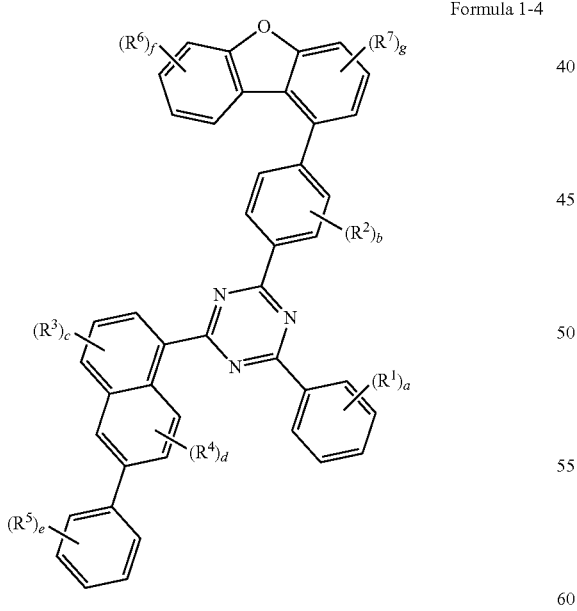
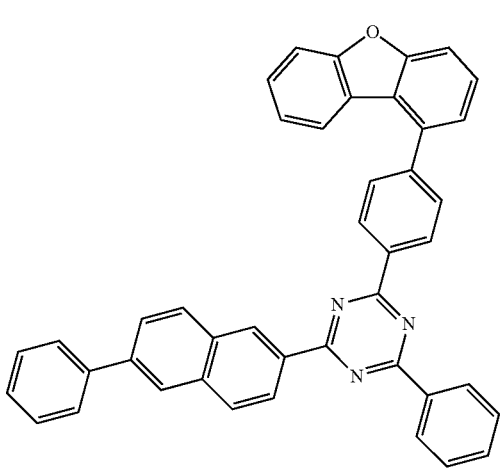
P-3
Wherein, $R^1$, $R^2$, $R^3$, $R^4$, $R^5$, $R^6$, $R^7$, a, b, c, d, e, f and g are the same as defined in Formula 1.
Specifically, the compound represented by Formula 1 may be any one of the following compounds P-1 to P-100, but is not limited thereto.

P-4
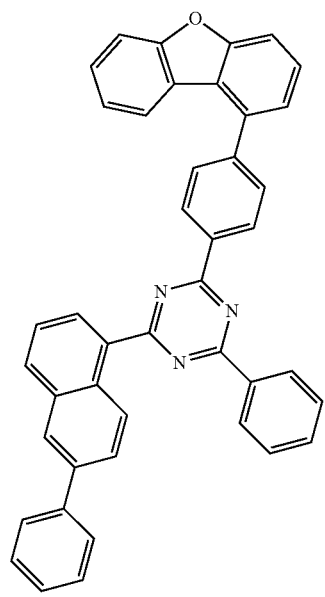
P-6
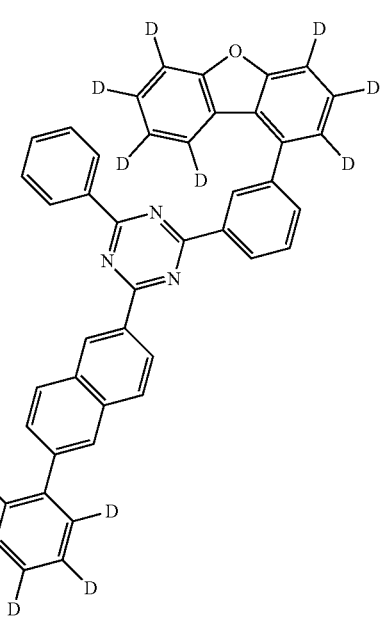
P-5
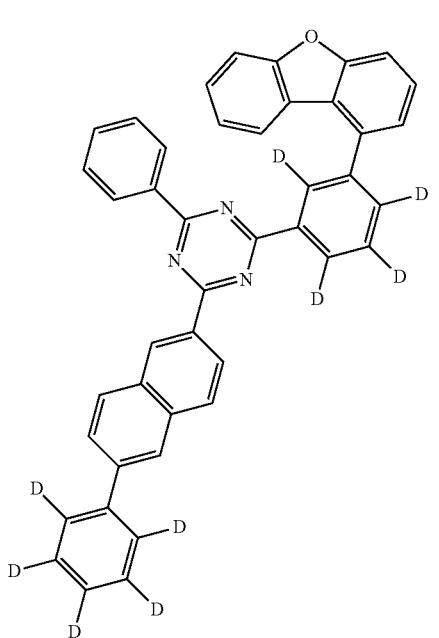
P-7

P-8
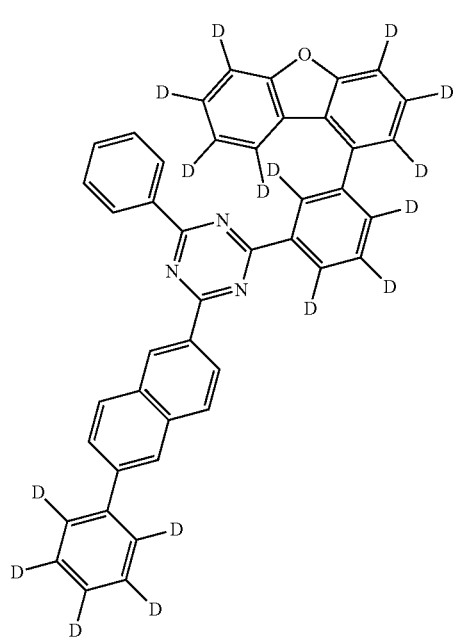
P-10
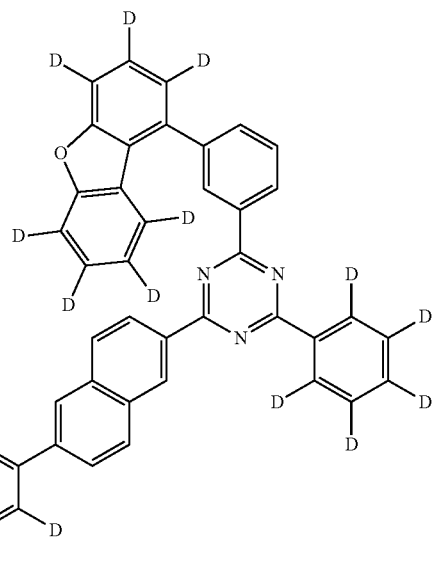
P-9
P-11

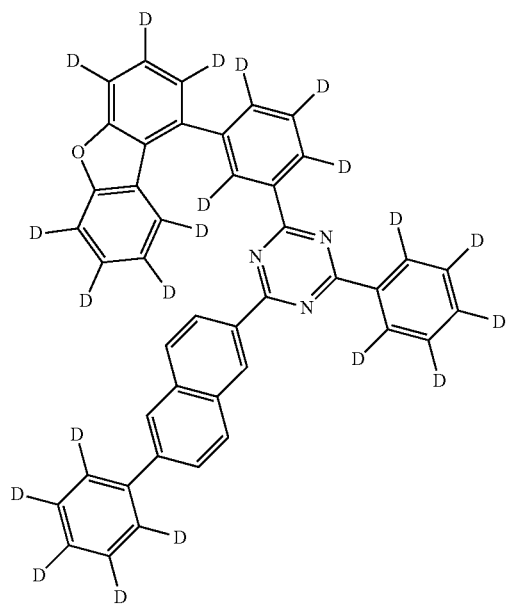
P-12
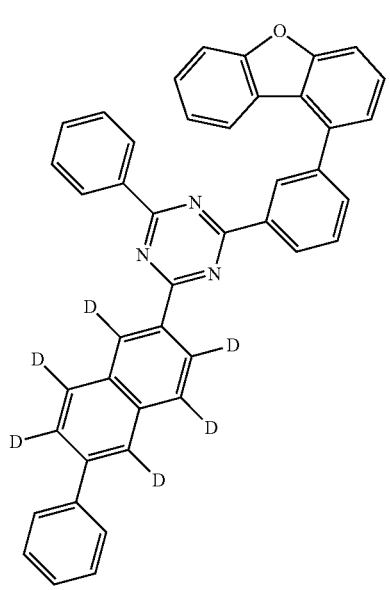
P-13
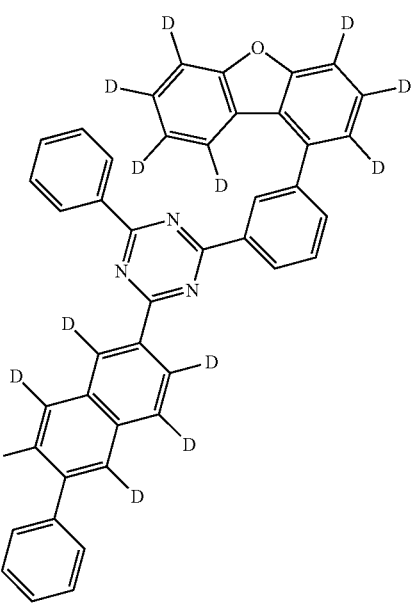
P-14
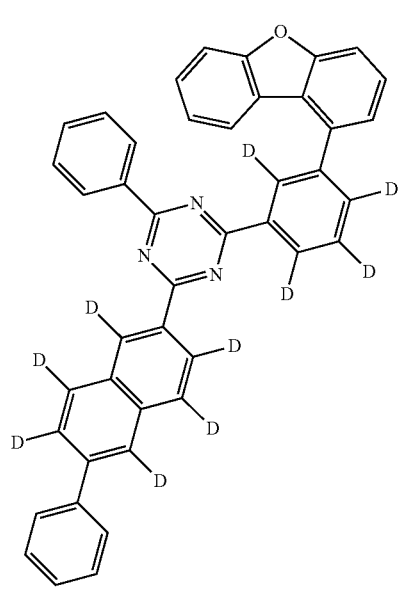
P-15

P-16
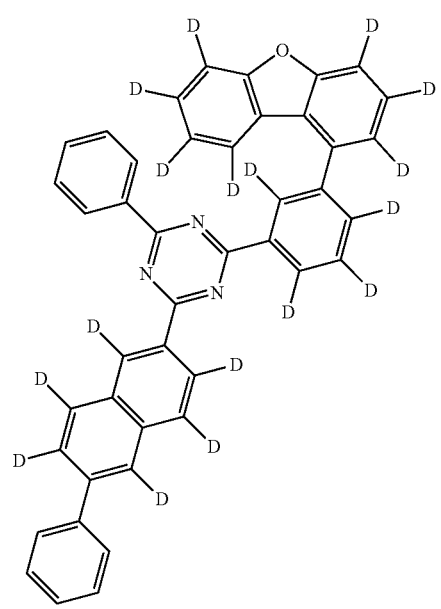
P-17
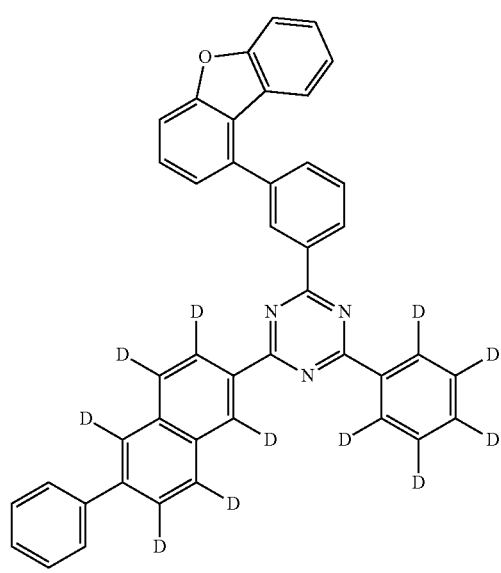
P-18
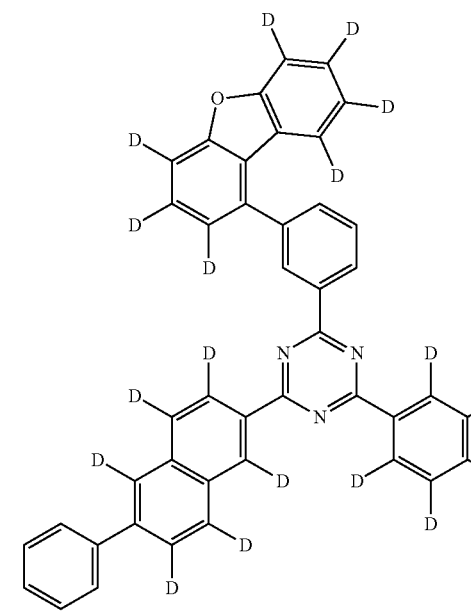
P-19
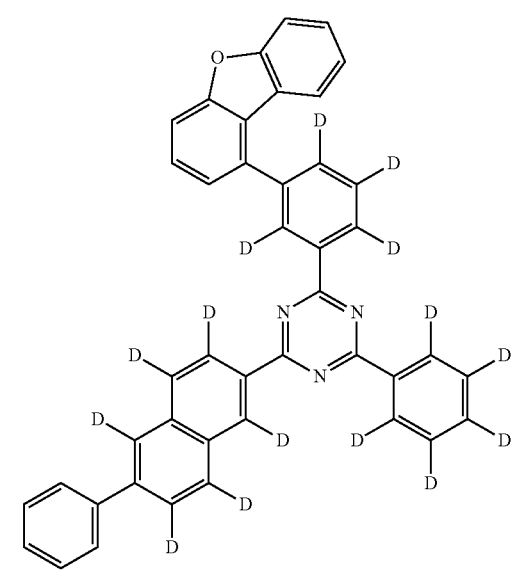

P-20
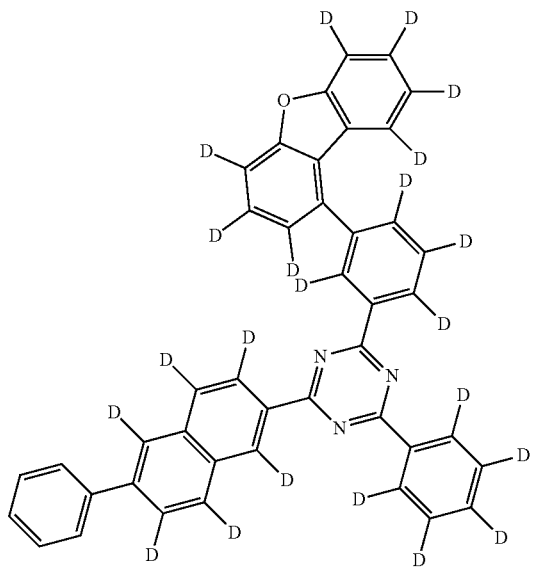
P-22
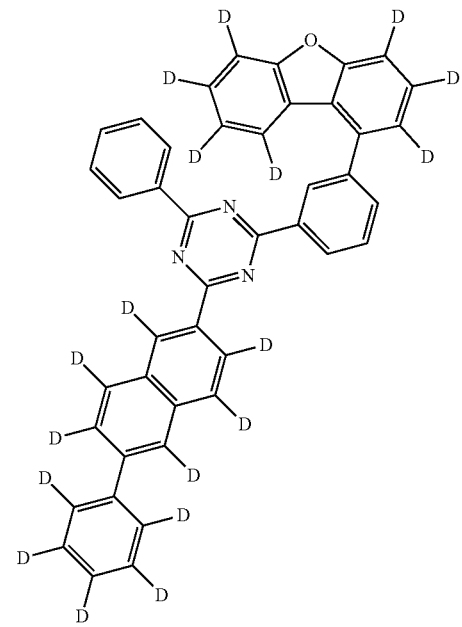
P-21
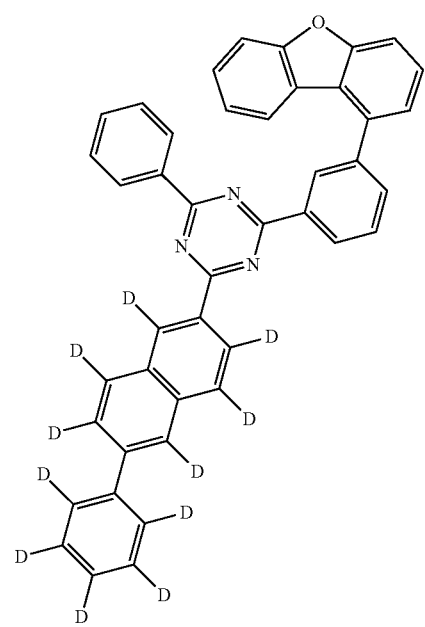
P-23
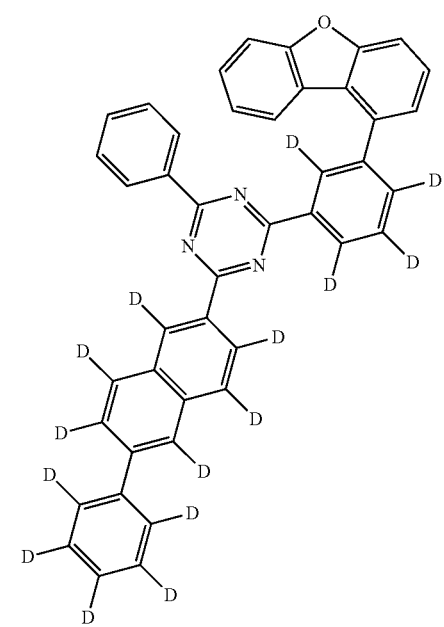

P-24
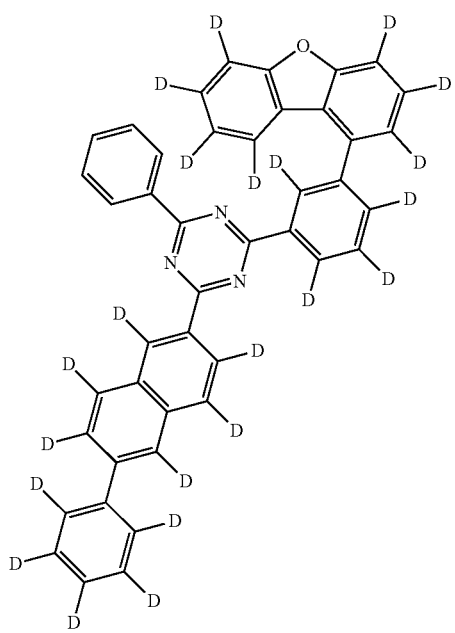
P-25
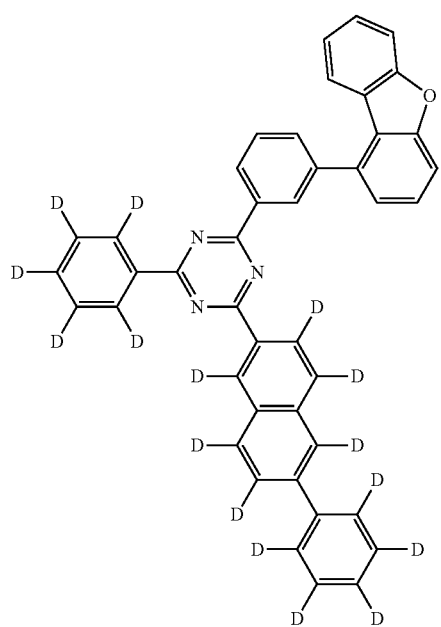
P-26
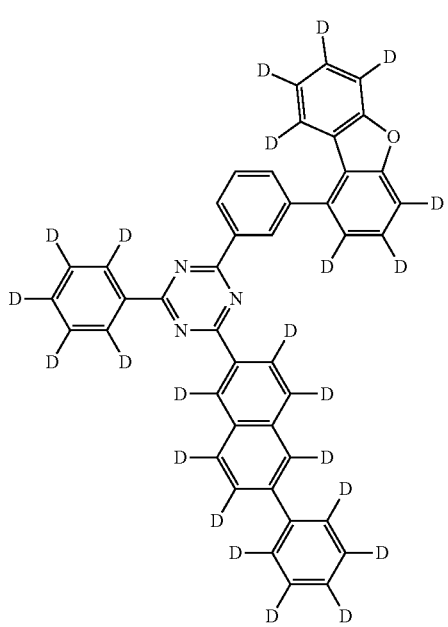
P-27
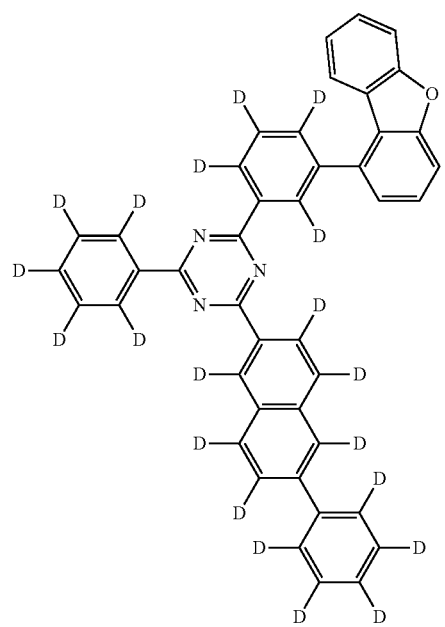

P-28
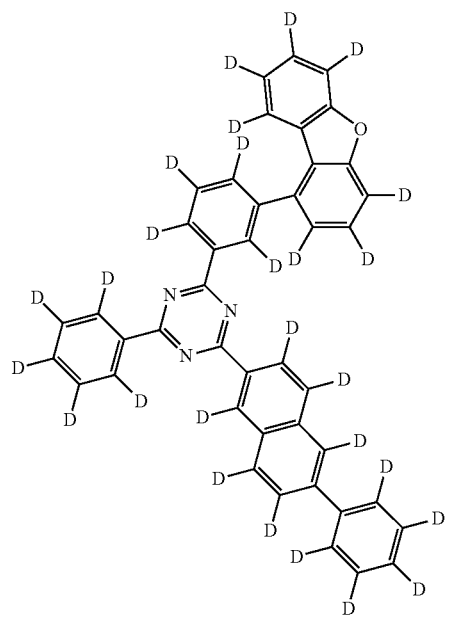
P-29
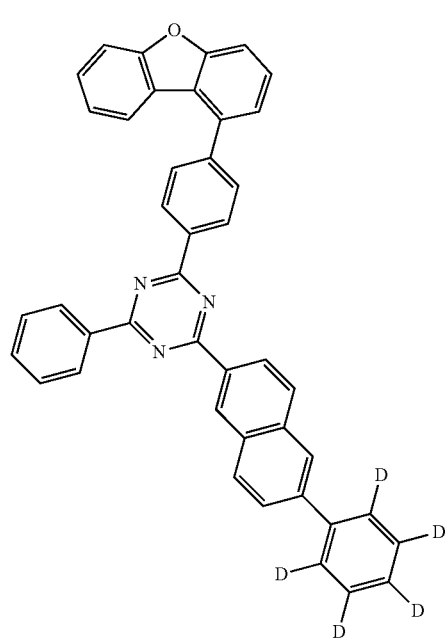
P-30
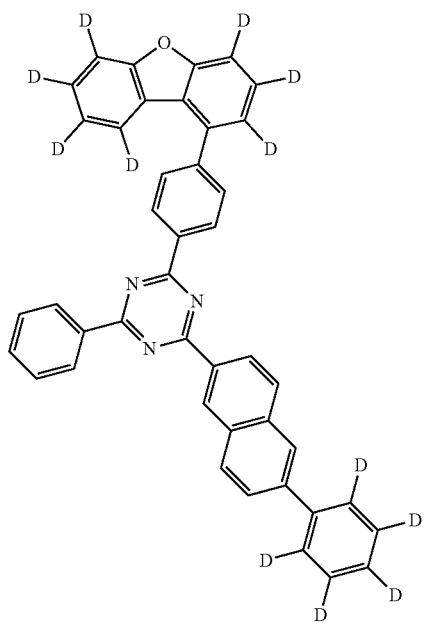
P-31
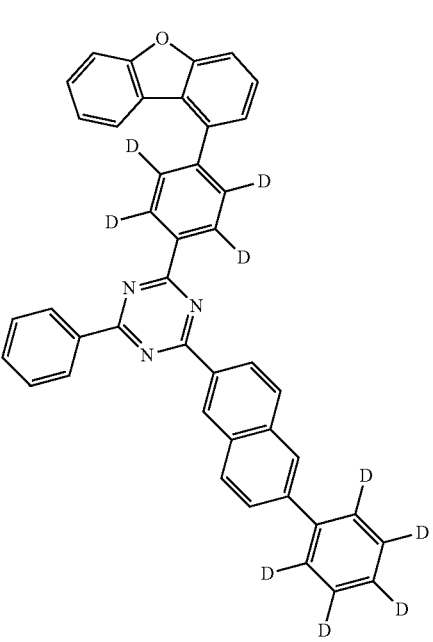

P-32
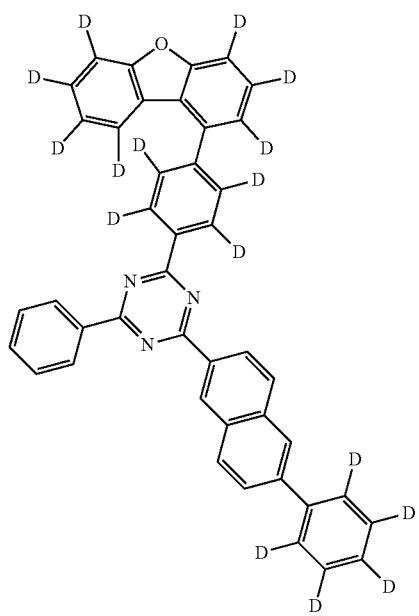
P-33
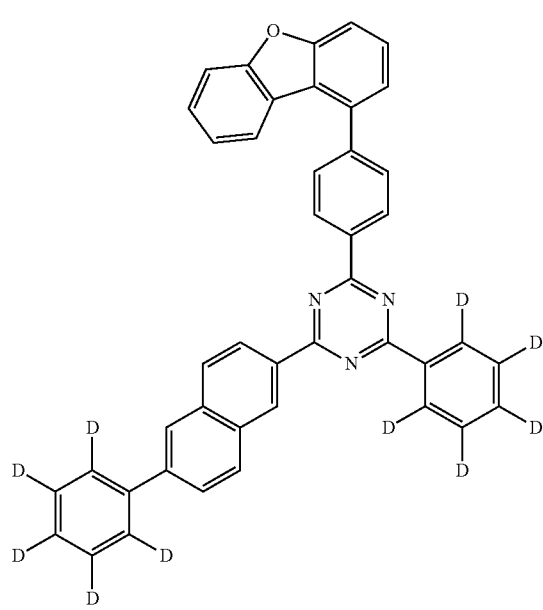
P-34
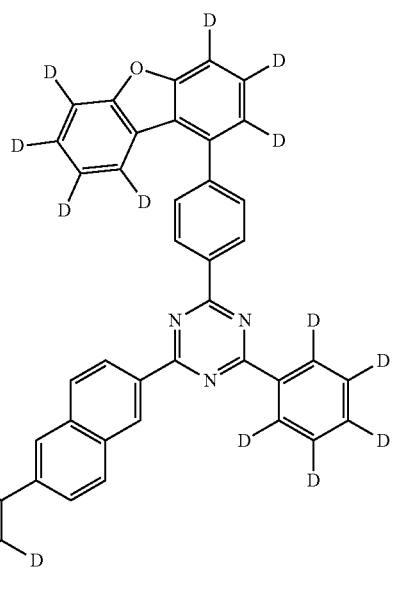
P-35
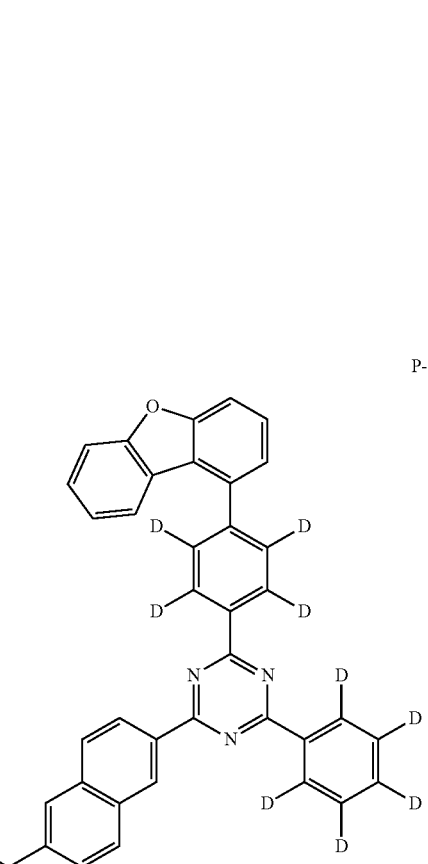

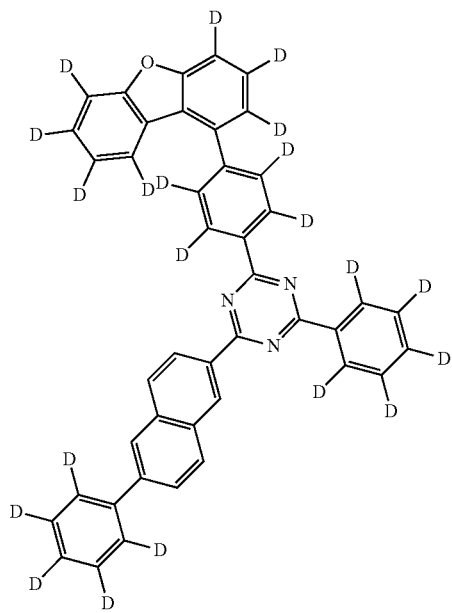
P-36
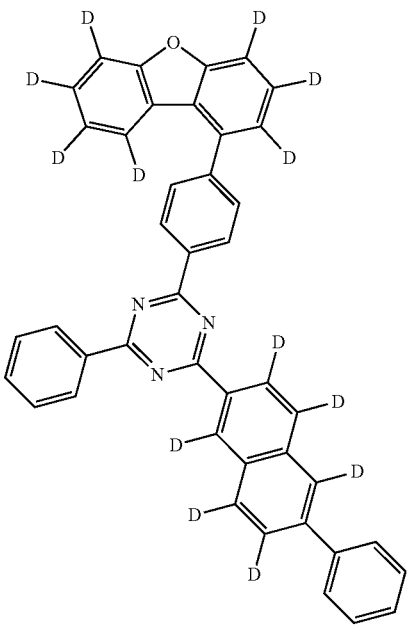
P-38
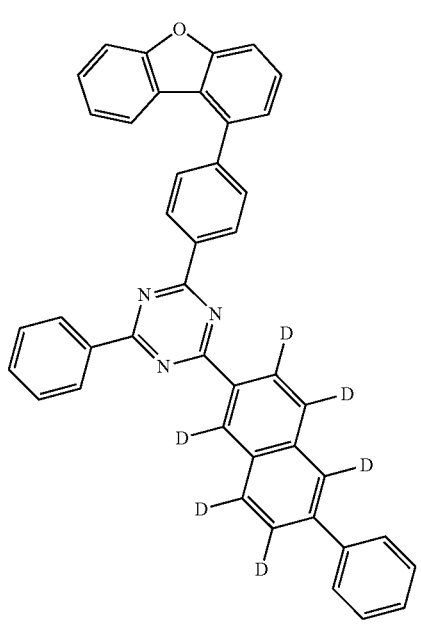
P-37
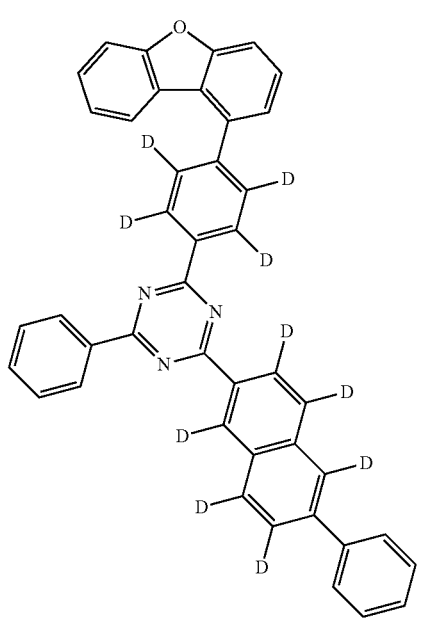
P-39

-continued
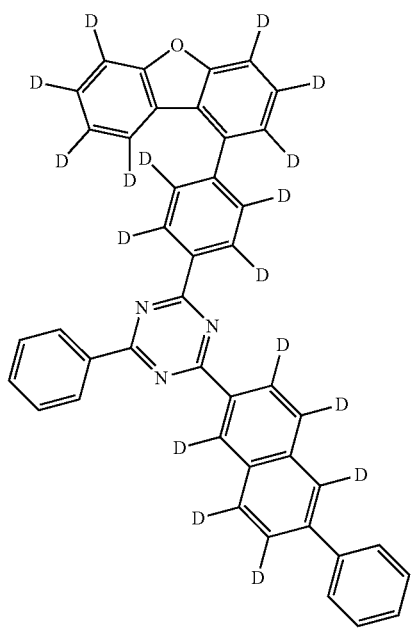
P-40
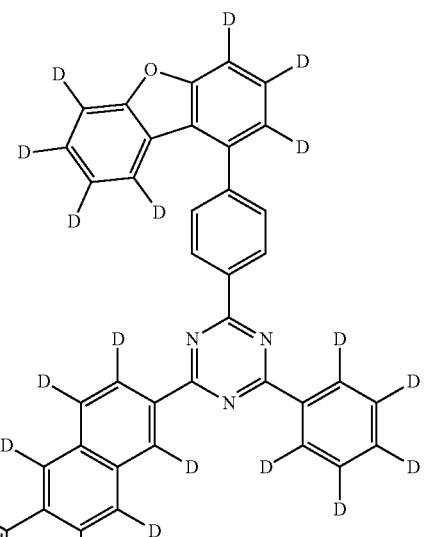
P-42
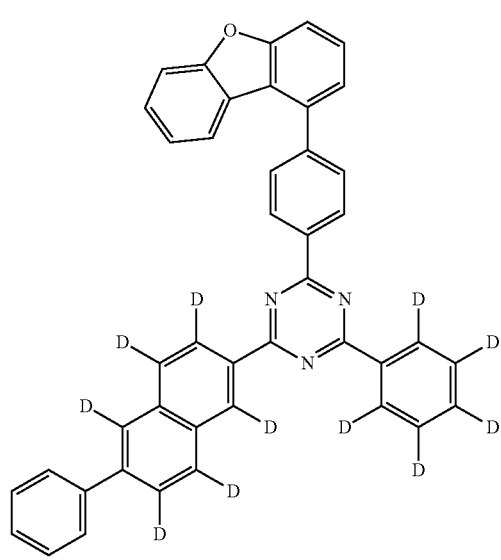
P-41
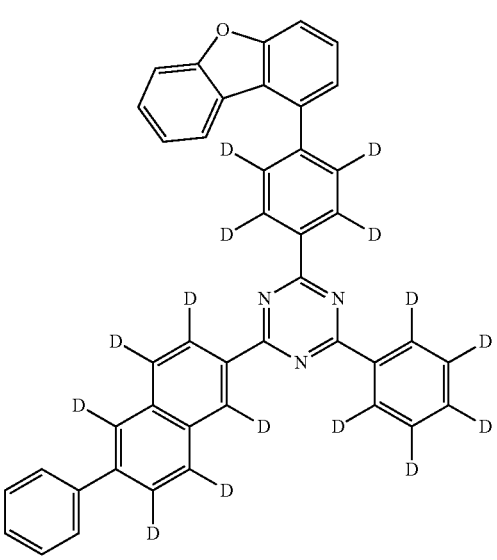
P-43

P-44
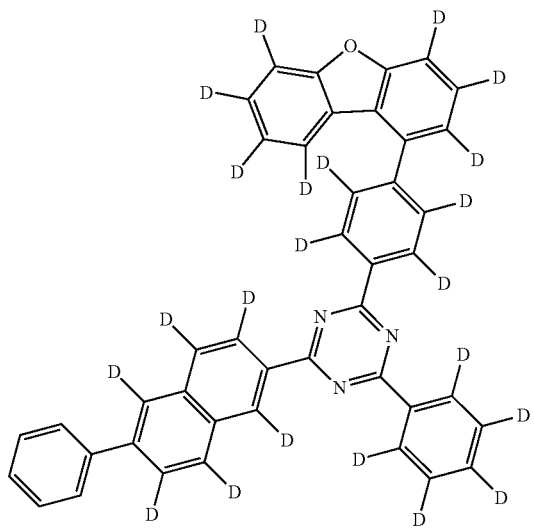
P-45
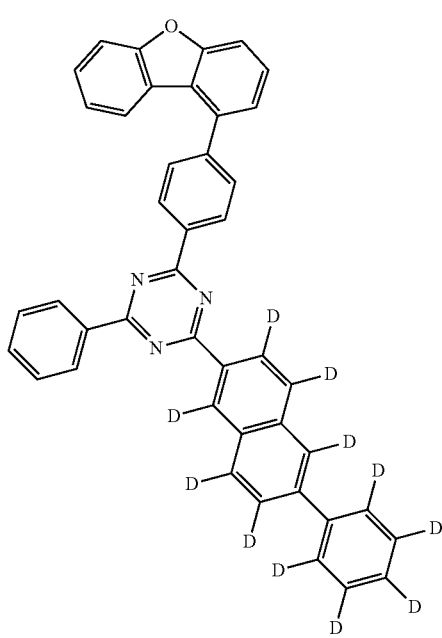
P-46
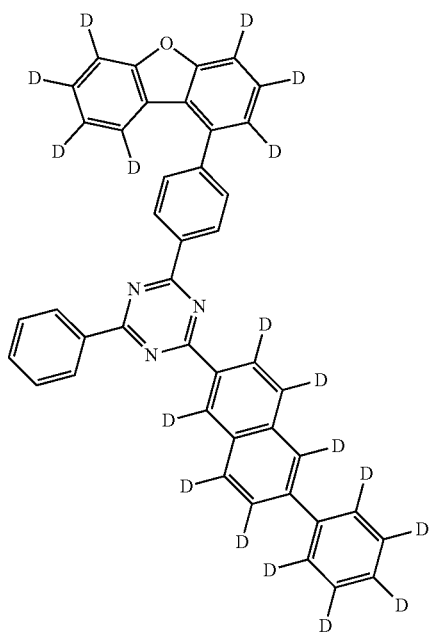
P-47
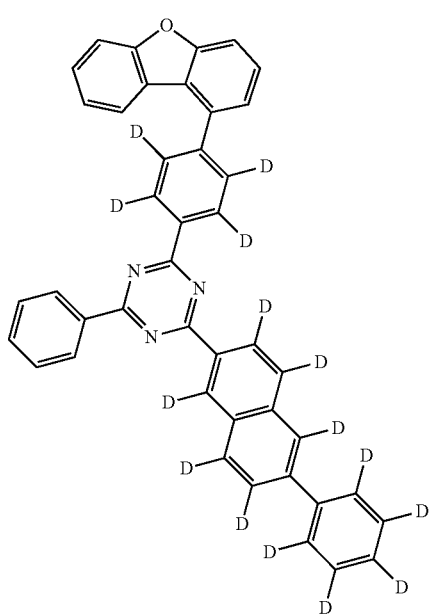

P-48
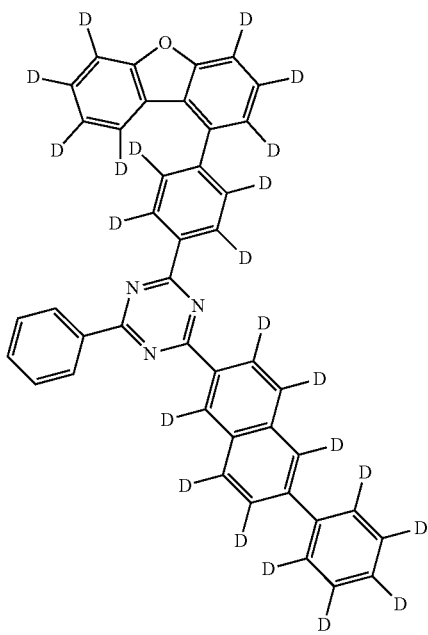
P-49
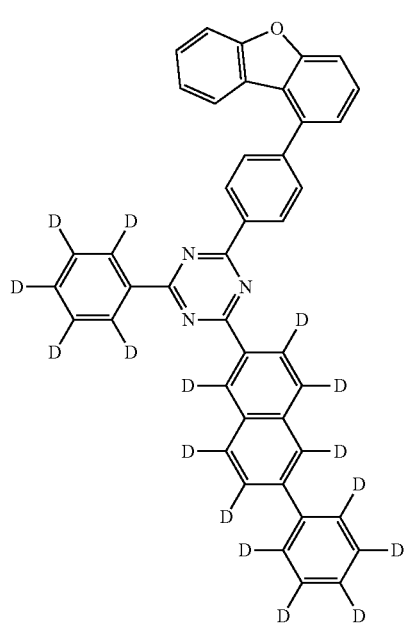
P-50
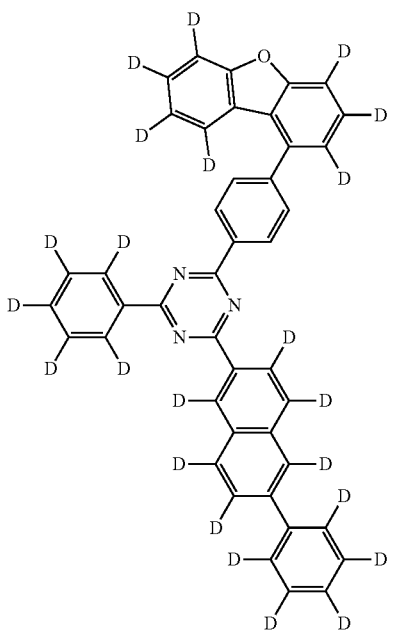
P-51
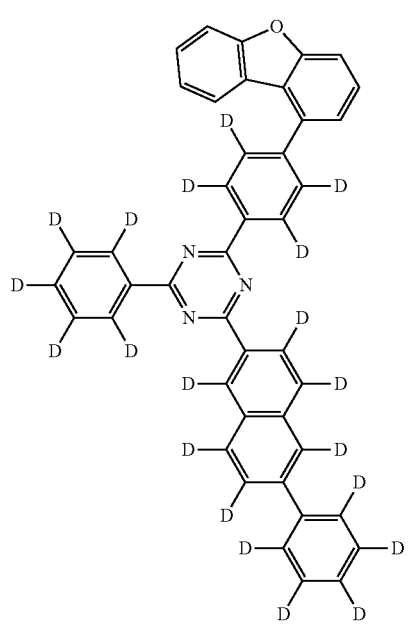

P-52
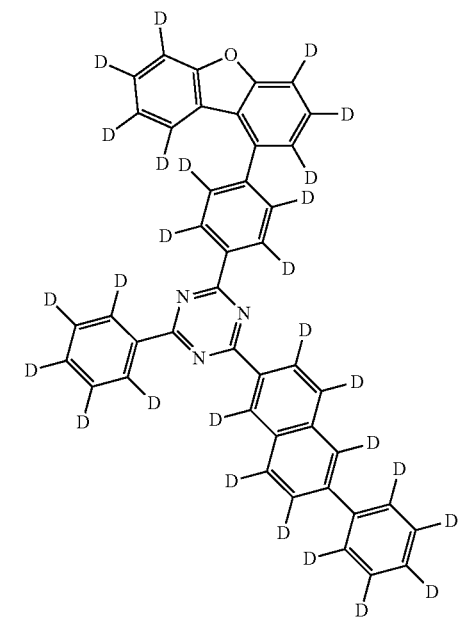
P-53
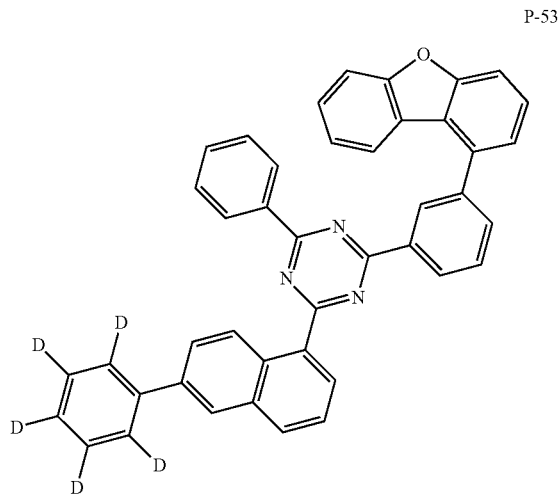
P-54
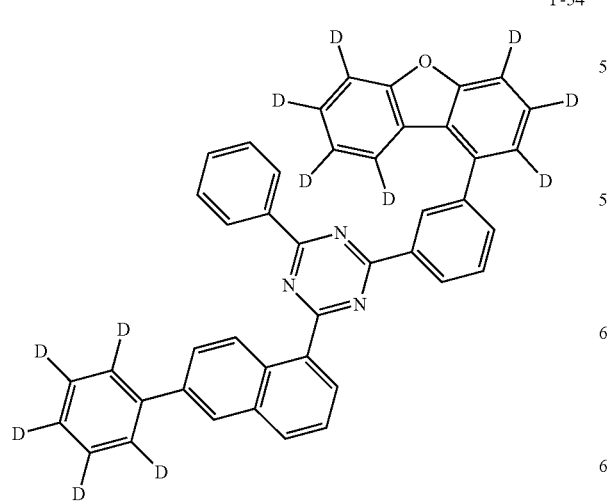
P-55
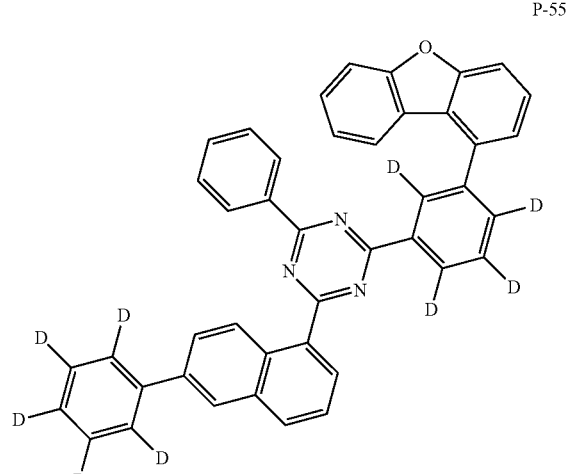
P-56
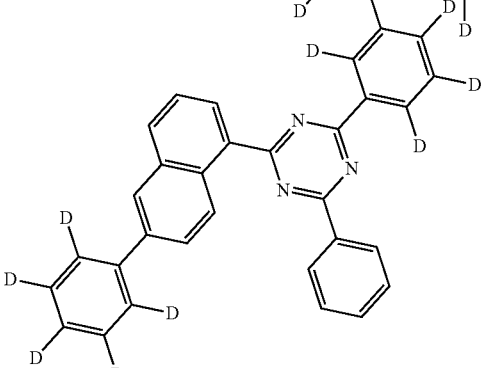
P-57
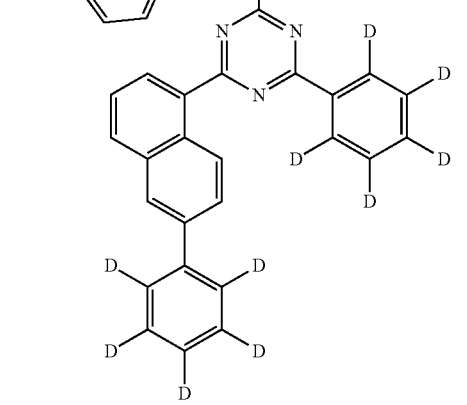

P-58
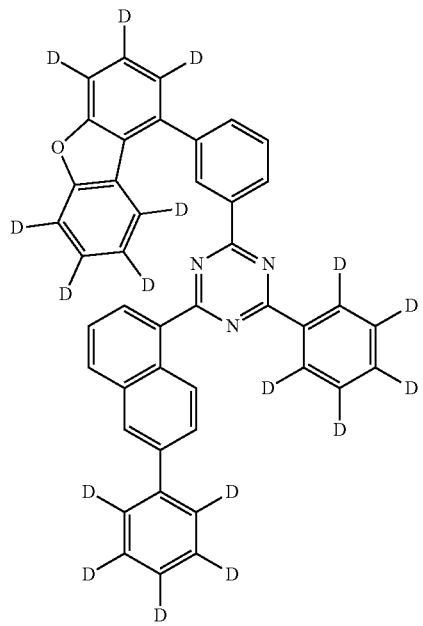
P-59
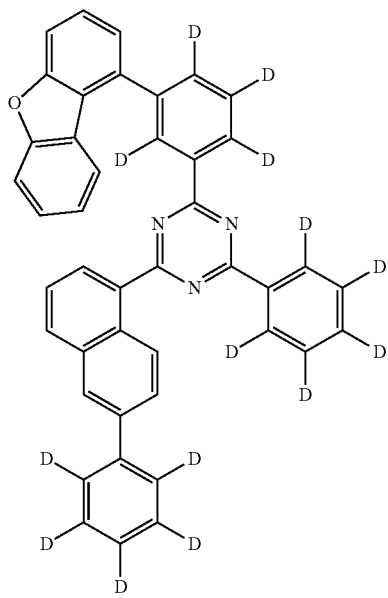
P-60
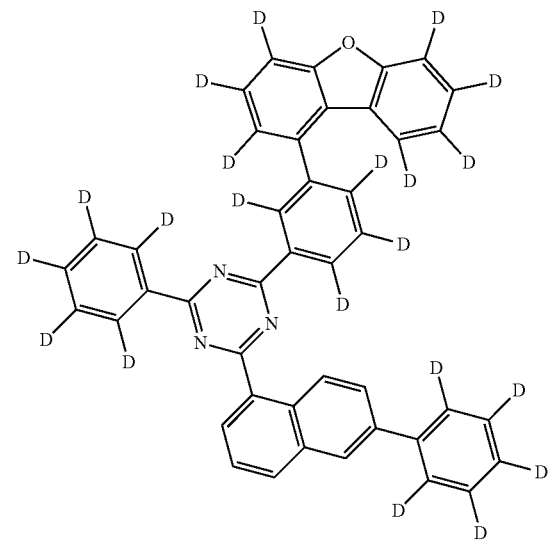
P-61
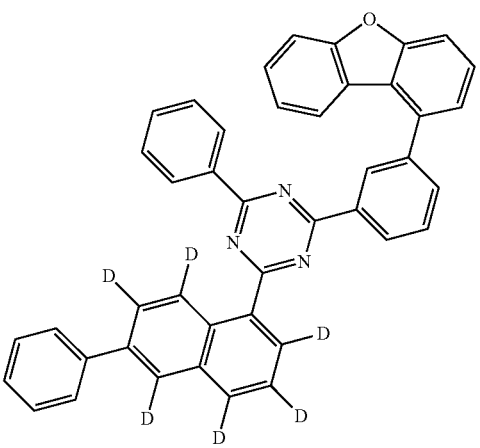
P-62
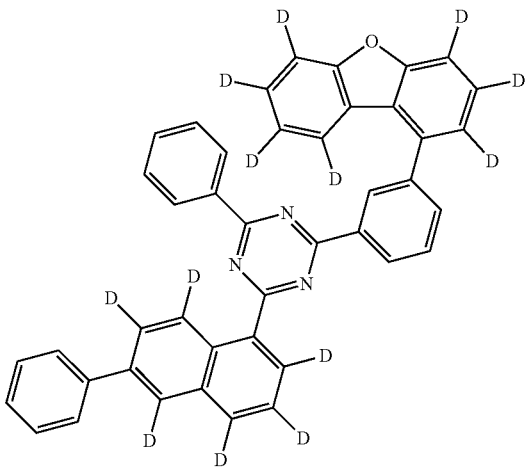

P-63
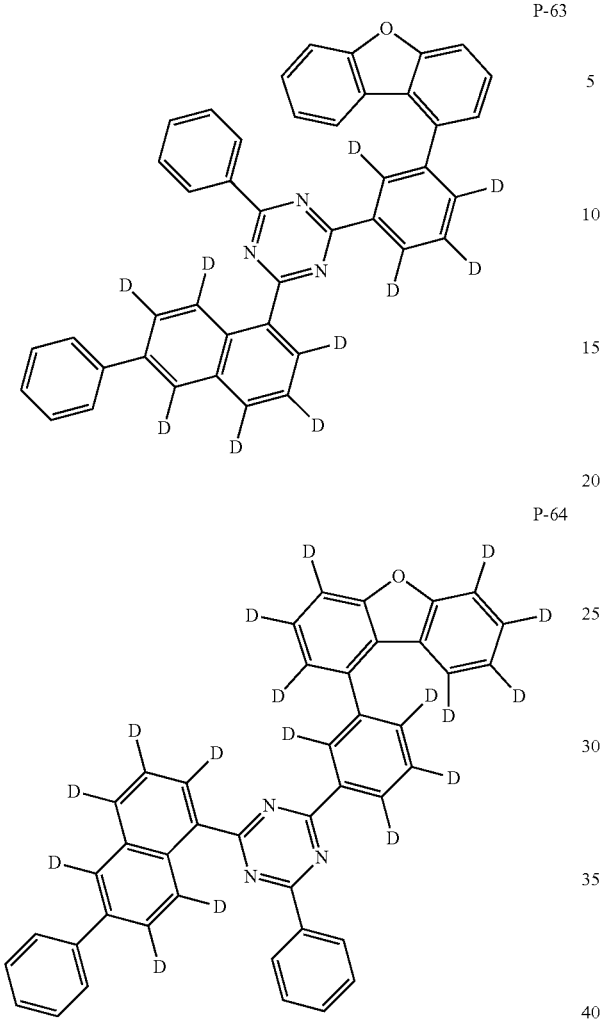
P-64
P-66
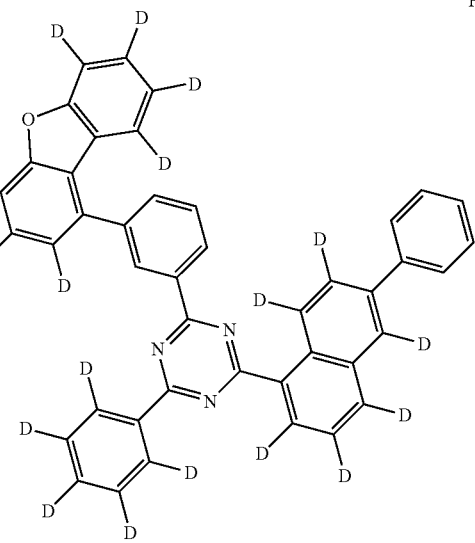
P-65
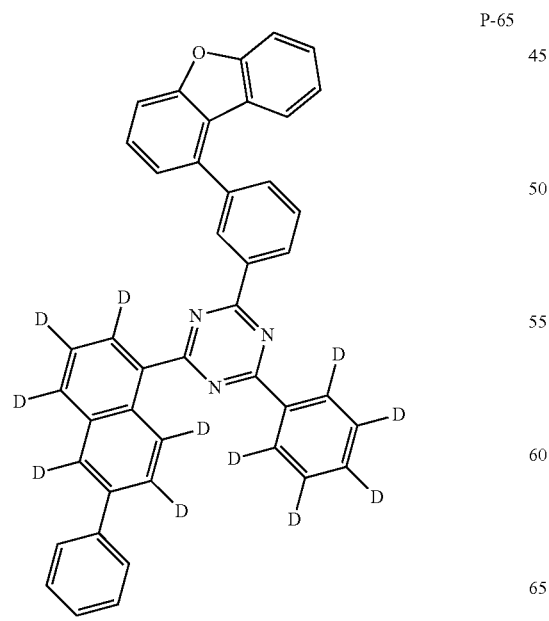
P-67
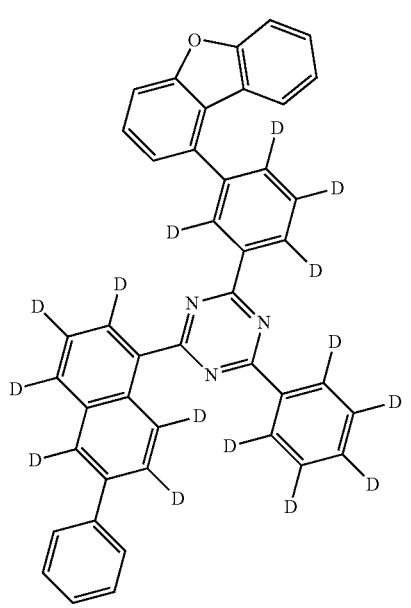

P-68
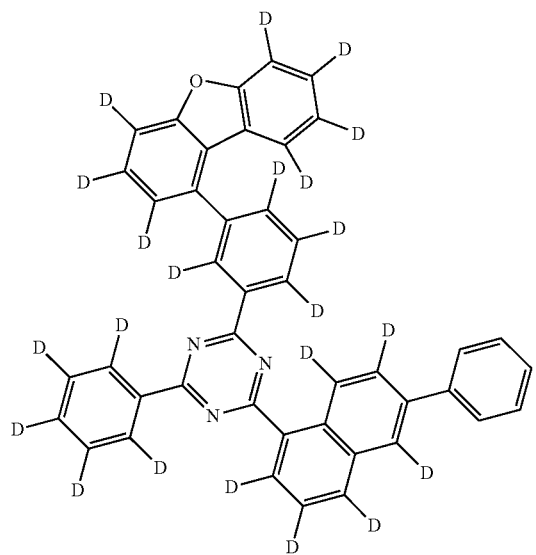
P-69
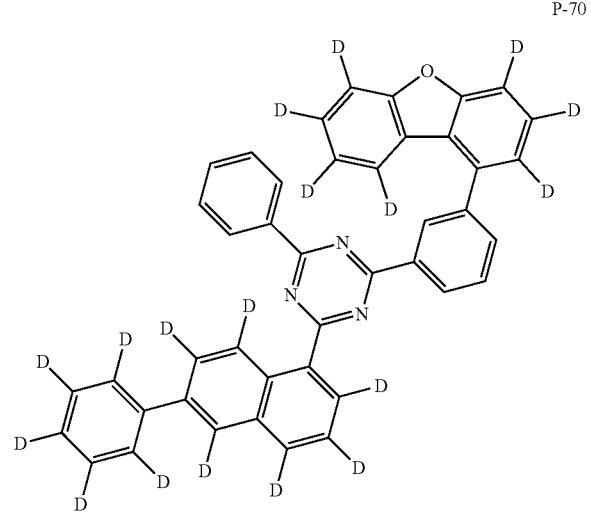
P-70
P-71
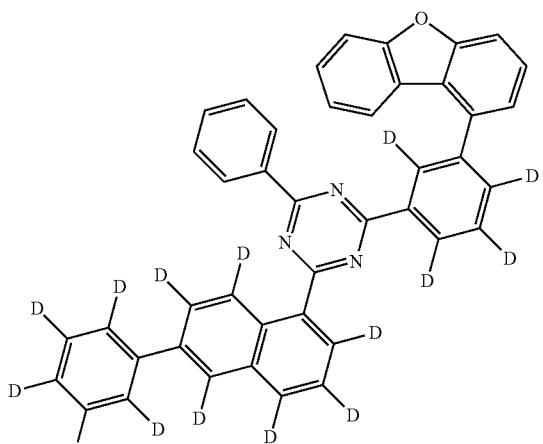
P-72
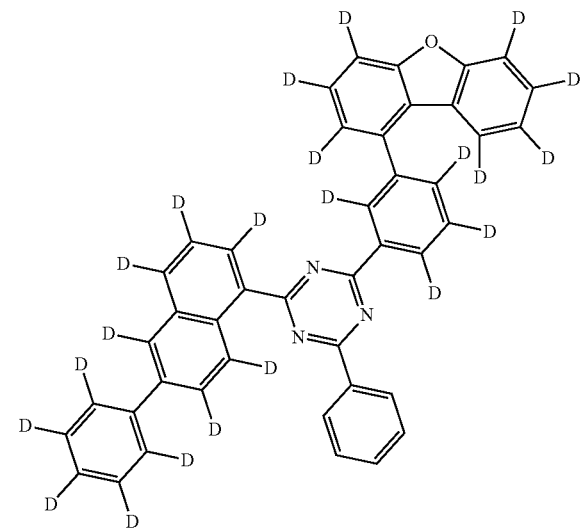
P-73
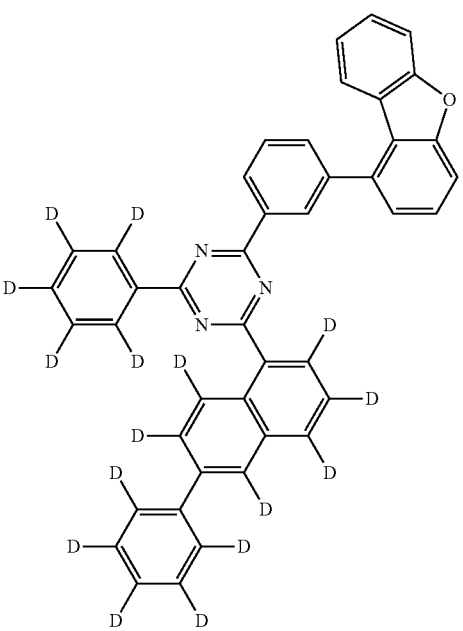

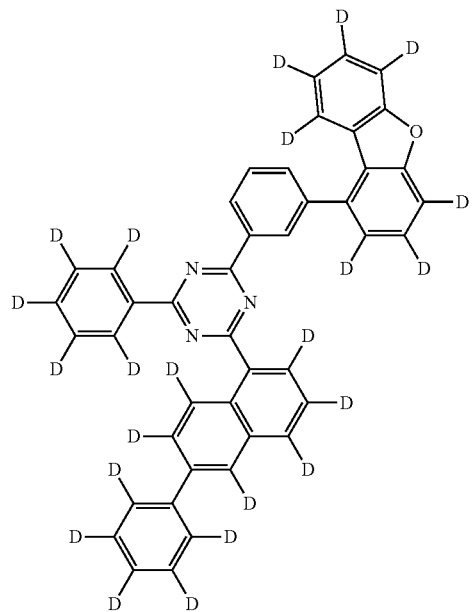
P-74
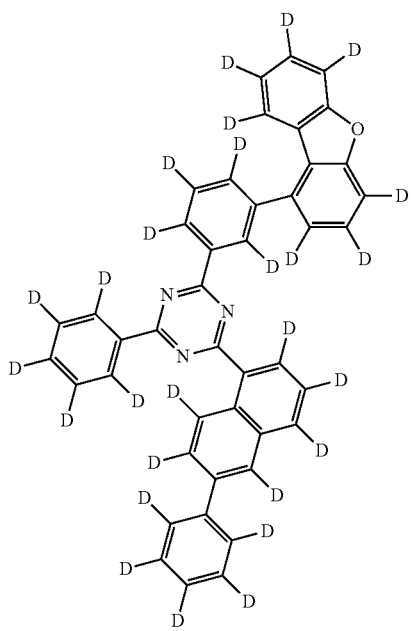
P-76
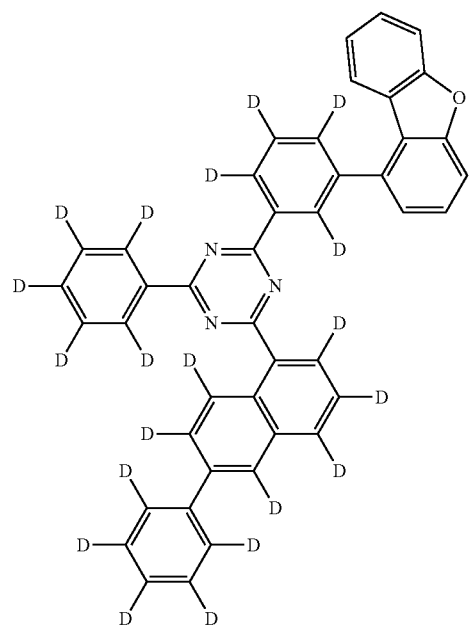
P-75
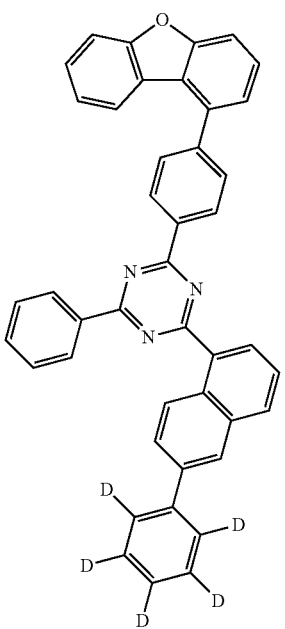
P-77

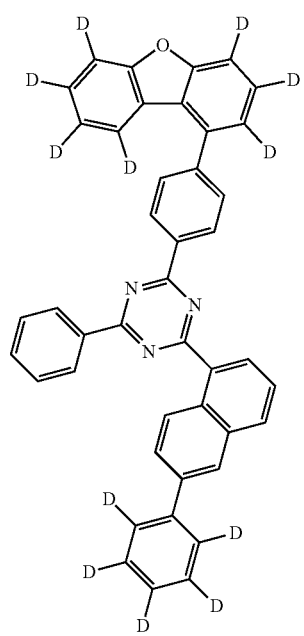
P-78
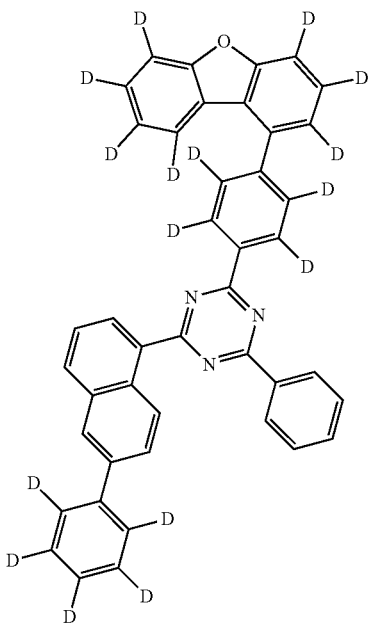
P-80
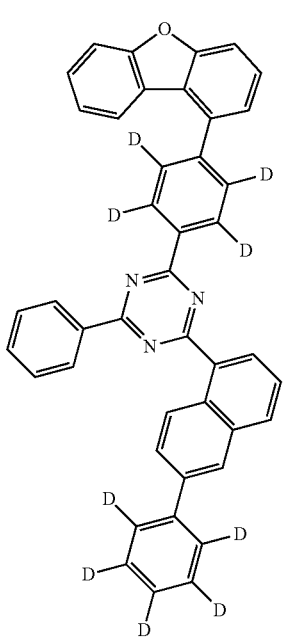
P-79
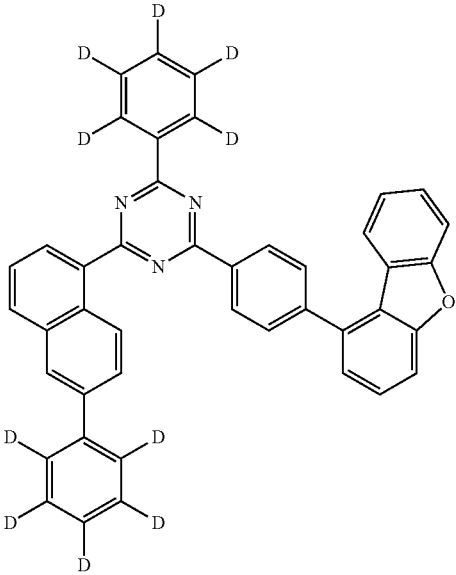
P-81

P-82
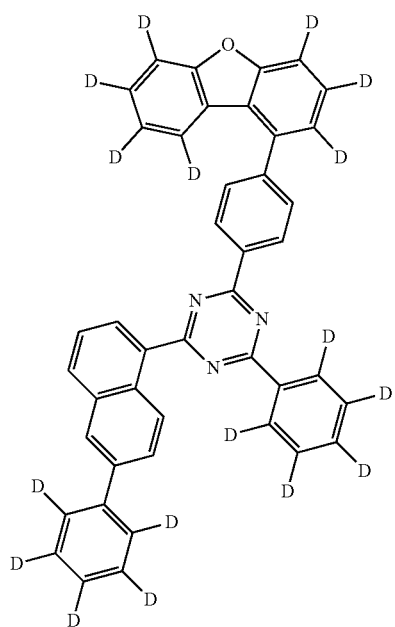
P-84
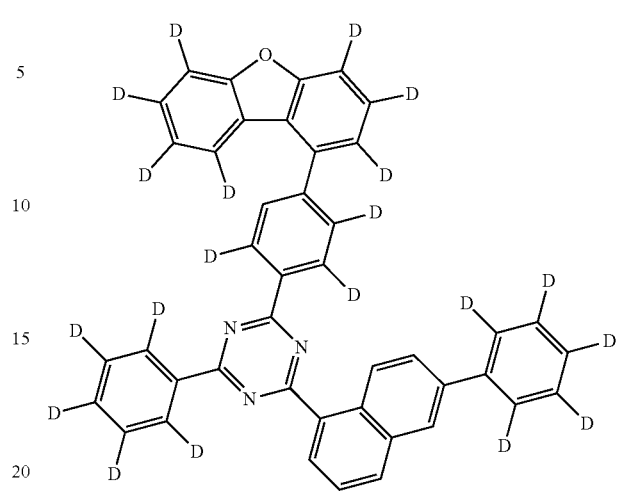
P-83
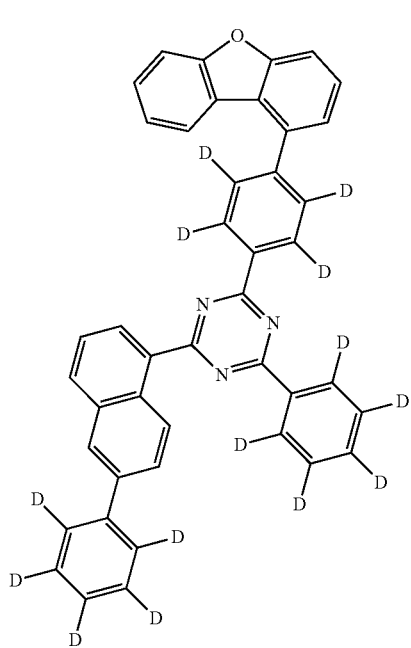
P-85
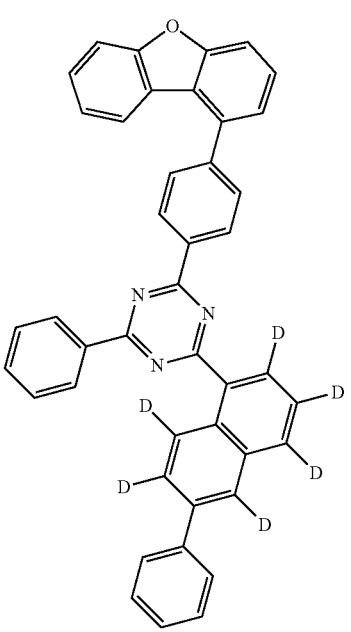

P-86
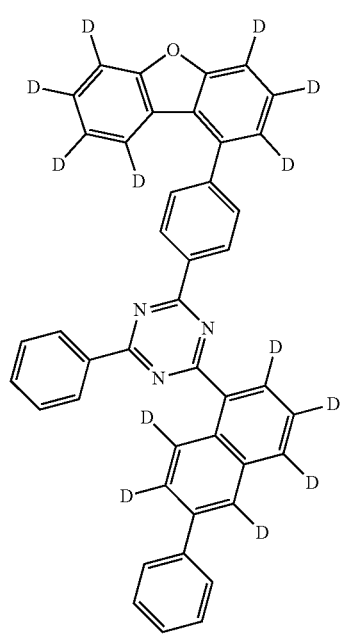
P-87
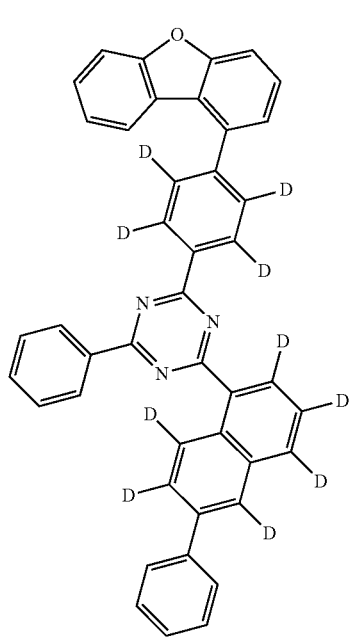
P-88
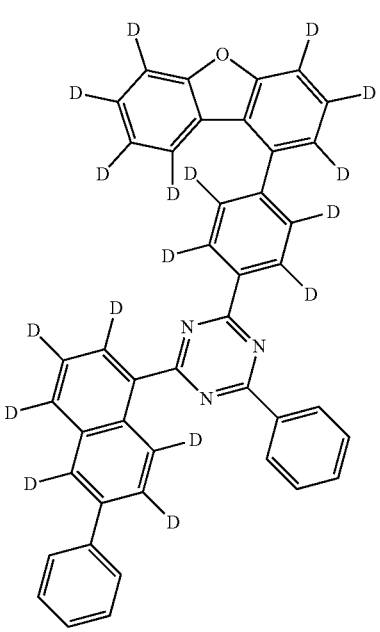
P-89
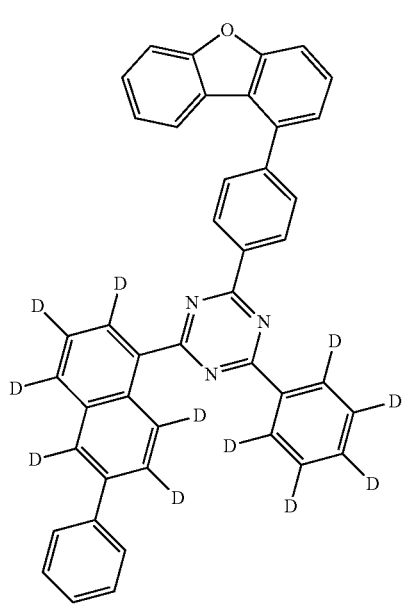

P-90
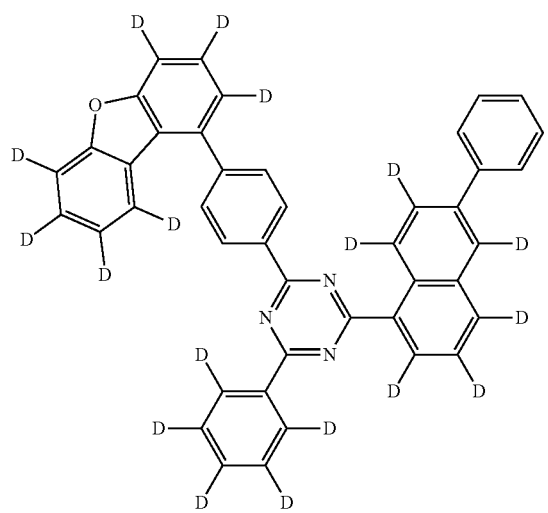
P-91
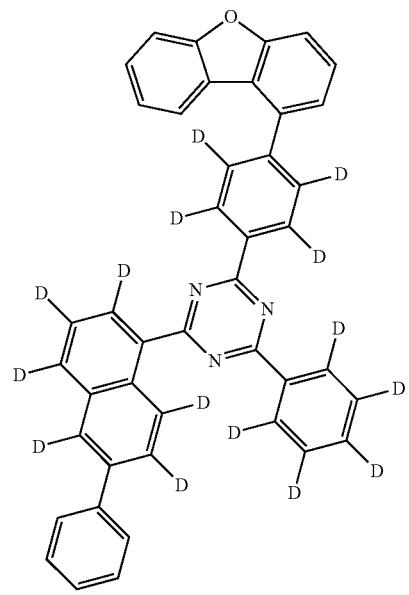
P-92
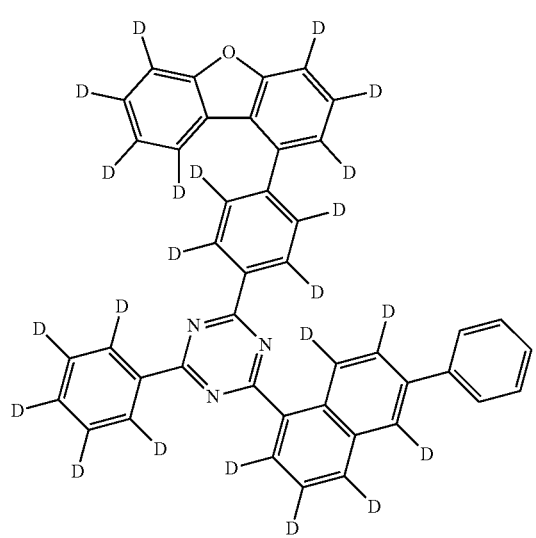
P-93
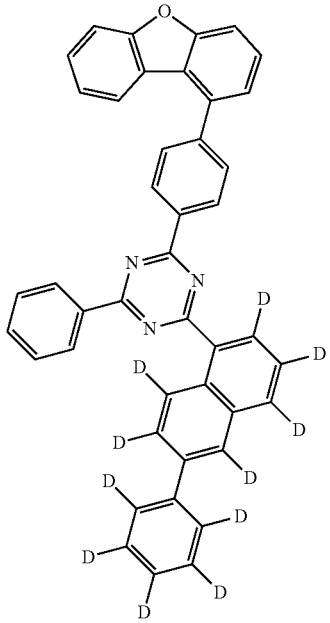
P-94
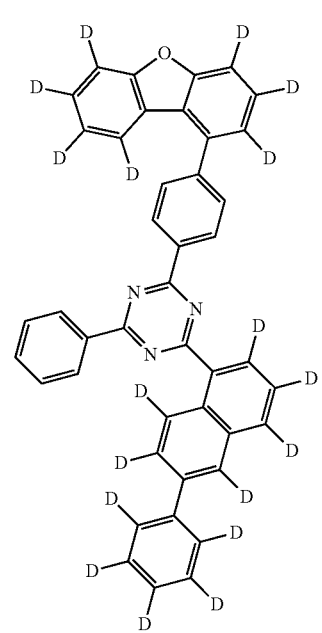

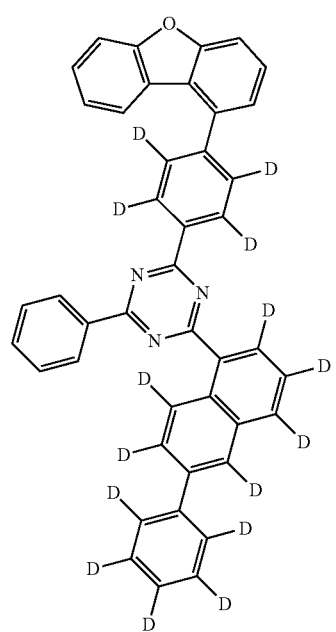
P-95
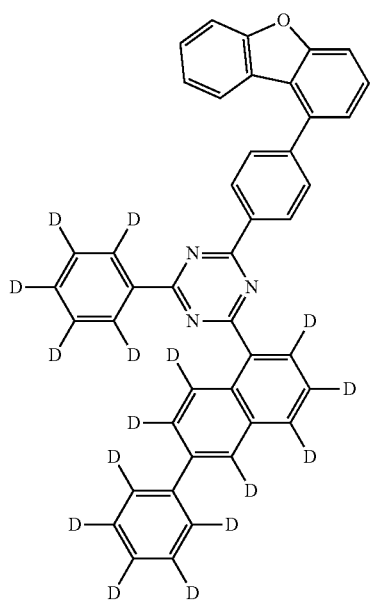
P-97
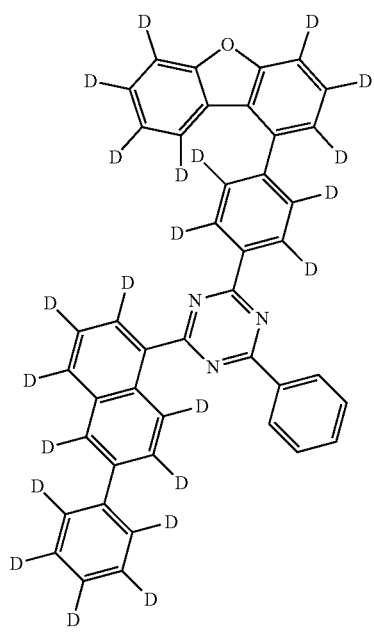
P-96
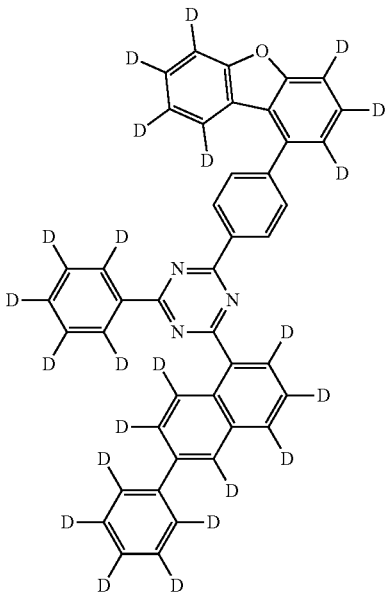
P-98

P-99
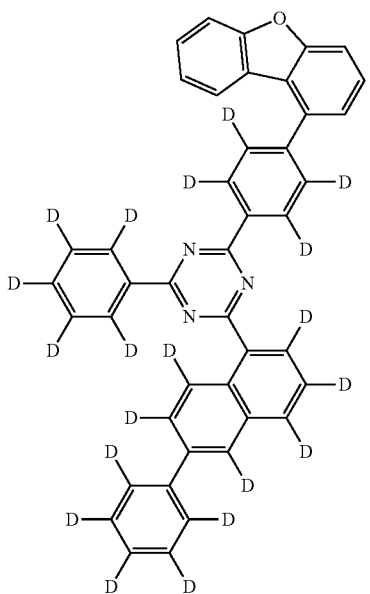
P-100
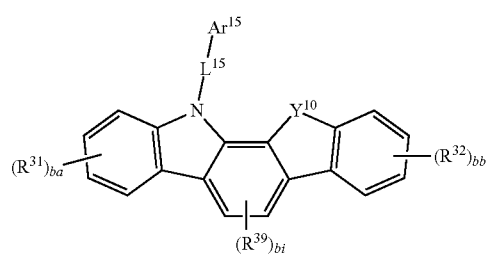
Preferably, Formula 1 may be a compound represented by any one of the compounds P-5 to P-100.
Formula 5 can be represented by any one of Formulas 5-1 to 5-6.
<Formula 5-1>
<Formula 5-2>
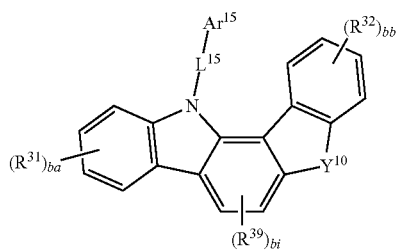
<Formula 5-3>
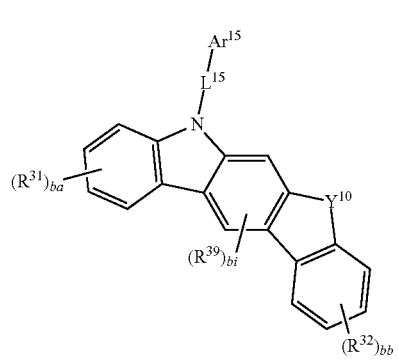
<Formula 5-4>
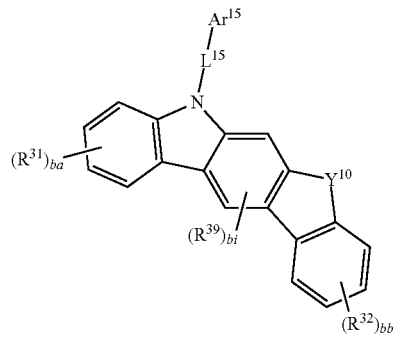
<Formula 5-5>
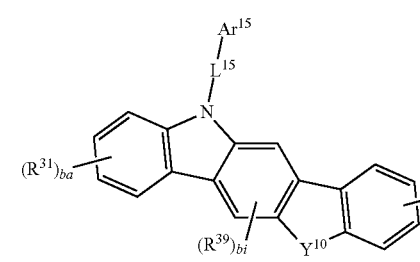
<Formula 5-6>
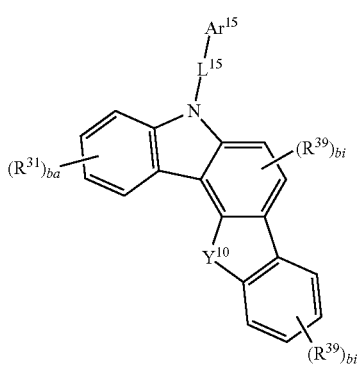

Wherein:
Y$^{10}$, L$^{15}$, Ar$^{15}$, R$^{31}$, R$^{32}$, ba and bb are the same as defined in Formula 5, R$^{39}$ is the same as the definition of R$^{31}$, or an adjacent plurality of R$^{39}$ may be bonded to each other to form a ring, bi is an integer of 0 to 2.

Formula 5 can be represented by any one of Formulas 5-7 to 5-9.

<Formula 5-7>

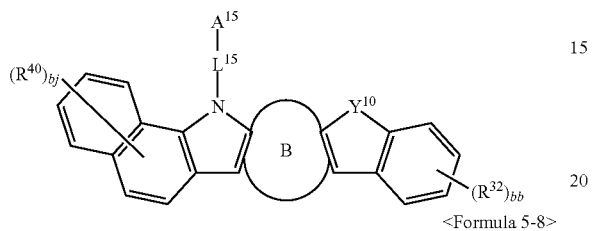

<Formula 5-8>

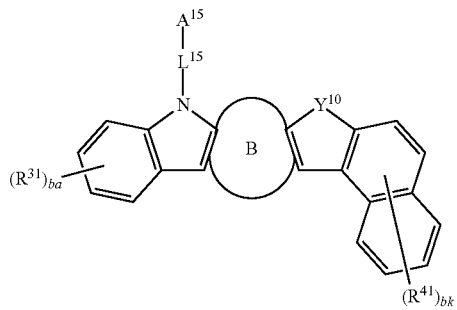

<Formula 5-9>

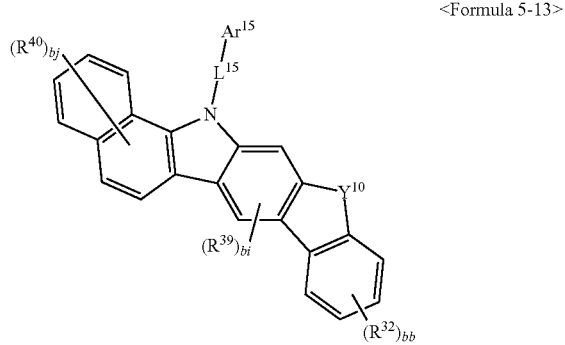

Wherein:
Y$^{10}$, L$^{15}$, Ar$^{15}$, Ring B, R$^{32}$ and bb are the same as defined in Formula 5, R$^{40}$ is the same as the definition of R$^{31}$, or an adjacent plurality of R$^{40}$ may be bonded to each other to form a ring, bj is an integer of 0 to 6.

Formula 5 can be represented by any one of Formulas 5-10 to 5-12.

<Formula 5-10>

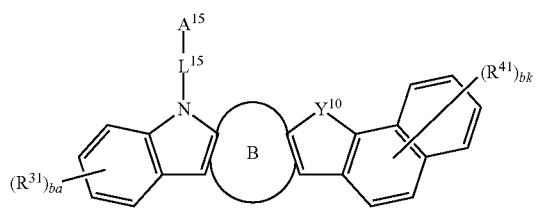

<Formula 5-11>

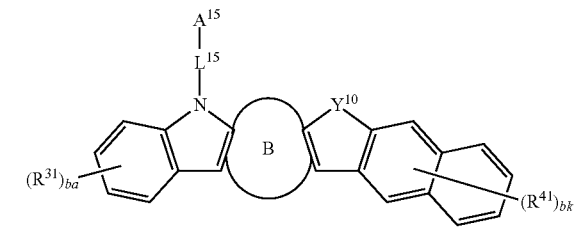

<Formula 5-12>

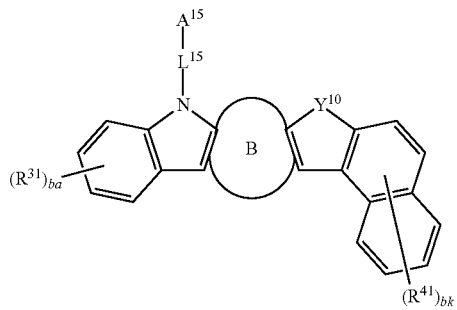

Wherein:
Y$^{10}$, L$^{15}$, Ar$^{15}$, Ring B, R$^{31}$ and ba are the same as defined in Formula 5, R$^{41}$ is the same as the definition of R$^{31}$, or an adjacent plurality of R$^{41}$ may be bonded to each other to form a ring, bk is an integer of 0 to 6.

Formula 5 can be represented by any one of Formulas 5-13 to 5-18.

<Formula 5-13>

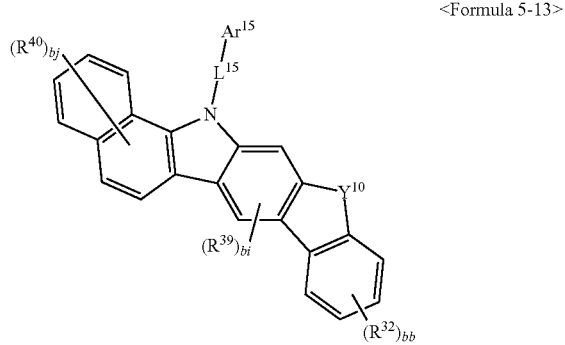

<Formula 5-14>

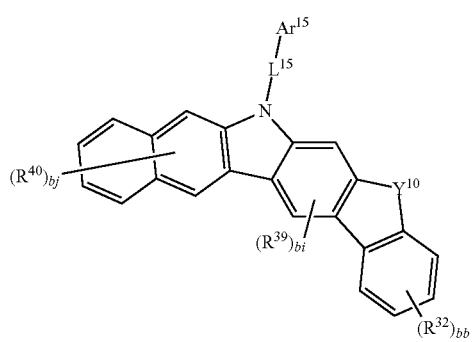

-continued

<Formula 5-15>

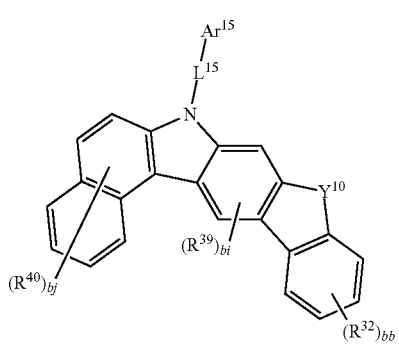

<Formula 5-16>

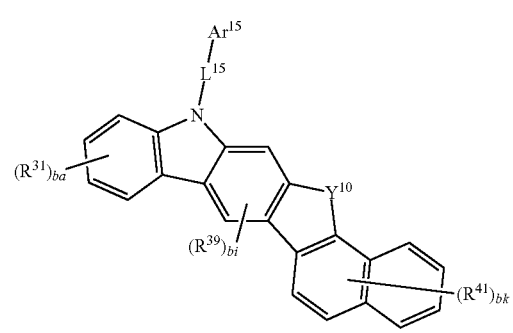

<Formula 5-17>

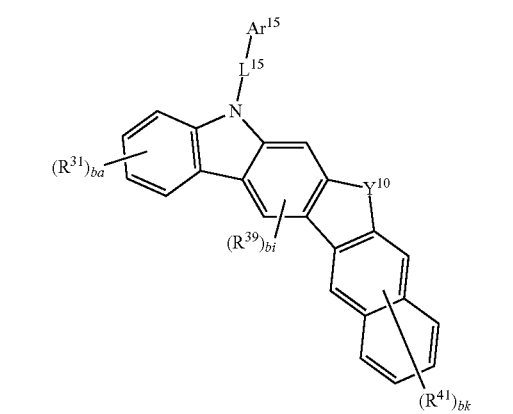

<Formula 5-18>

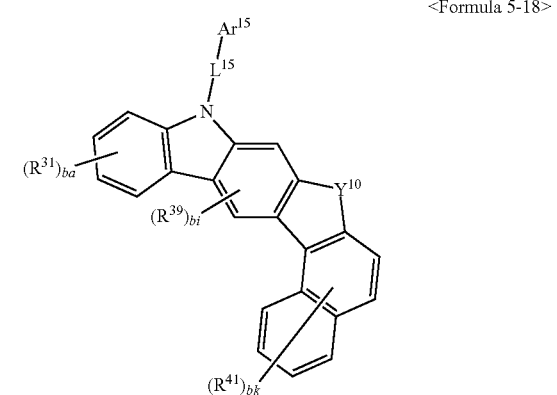

Wherein:
$Y^{10}$, $L^{15}$, $Ar^{15}$, $R^{31}$, $R^{32}$, ba and bb are the same as defined in Formula 5, $R^{39}$, $R^{40}$ and $R^{41}$ are the same as the definition of $R^{31}$, or an adjacent plurality of $R^{39}$ or plurality of $R^{40}$ or plurality of $R^{41}$ may be bonded to each other to form a ring, bi is an integer of 0 to 2, bj and bk are an integer of 0 to 6, independently of each other.

Formula 5 can be represented by Formula 5-19.

<Formula 5-19>

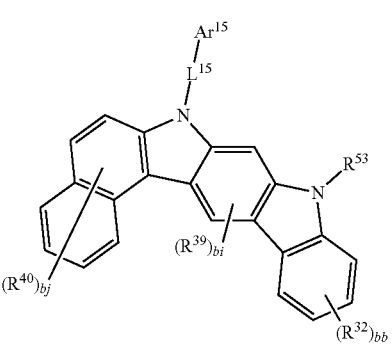

Wherein:

$L^{15}$, $Ar^{15}$, $R^{53}$, $R^{32}$ and bb are the same as defined in Formula 5, $R^{39}$ and $R^{40}$ are the same as the definition of $R^{31}$, or an adjacent plurality of $R^{39}$ or plurality of $R^{40}$ may be bonded to each other to form a ring, bi is an integer of 0 to 2, bj is an integer from 0 to 6.

Specifically, the compound represented by Formula 5 may be any one of the following compounds S-1 to S-116, but is not limited thereto.

S-1

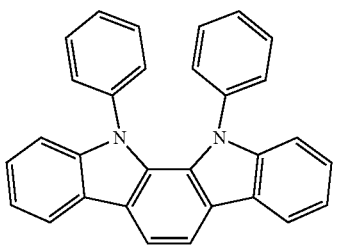

S-2

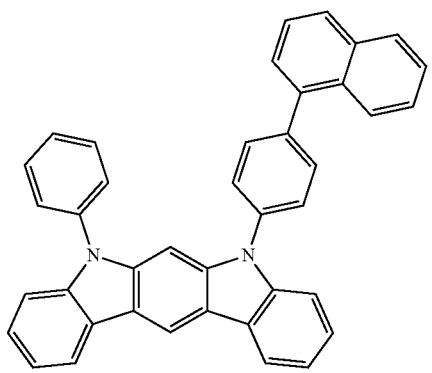

-continued
S-3
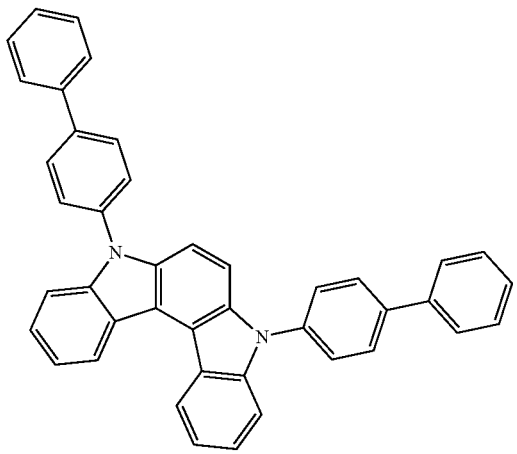
S-4
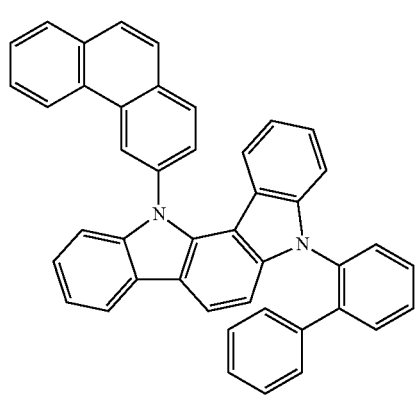
S-5
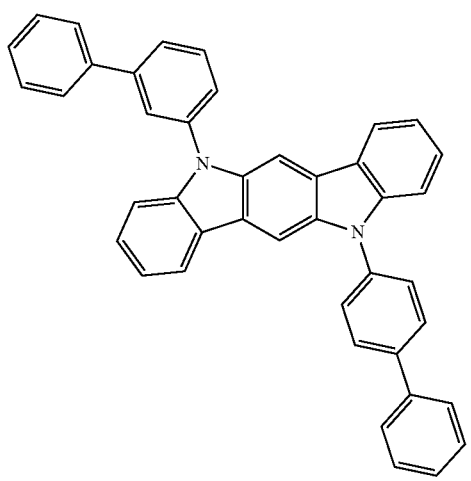
S-6
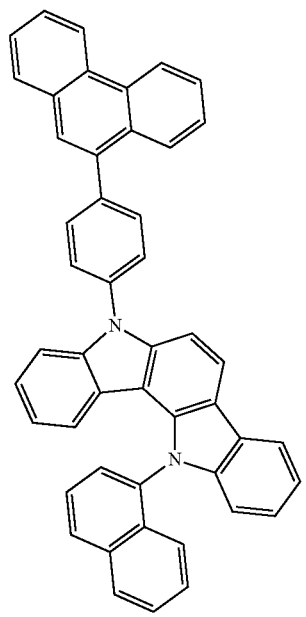
S-7
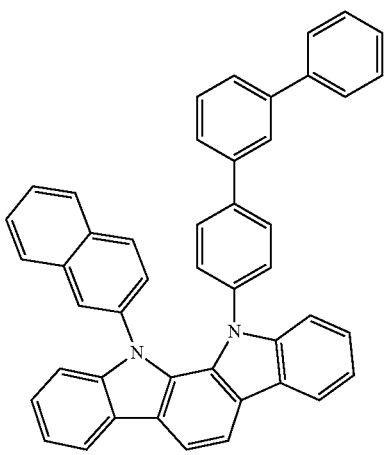
S-8
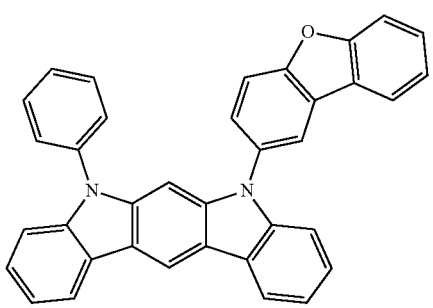

S-9
S-11
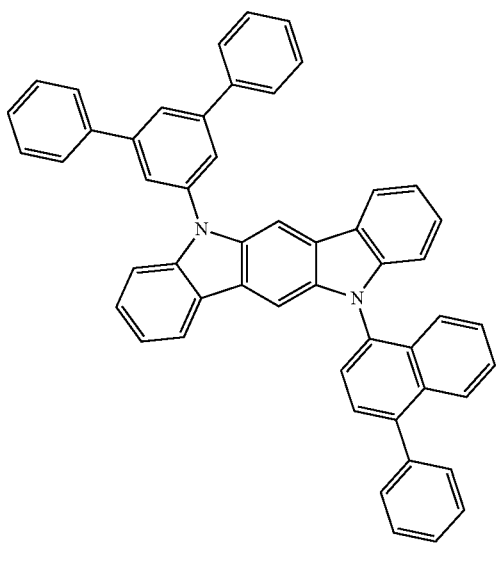
S-12
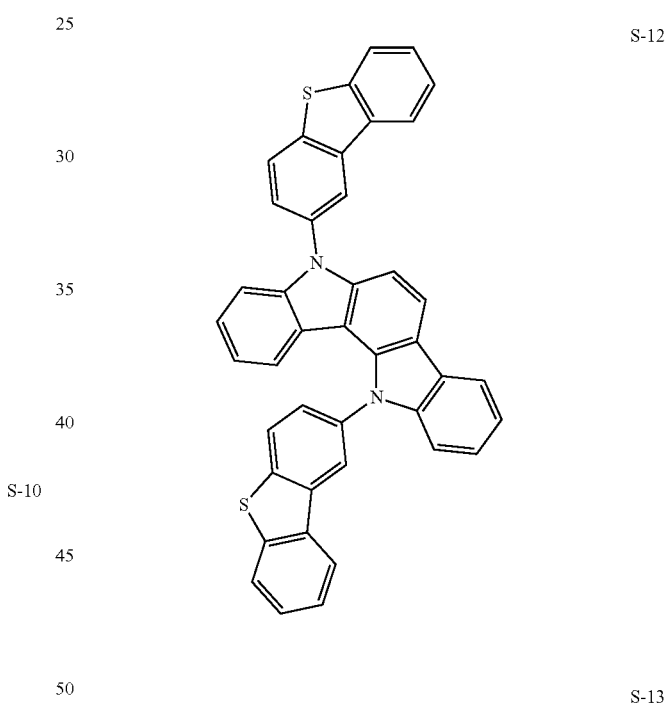
S-10
S-13
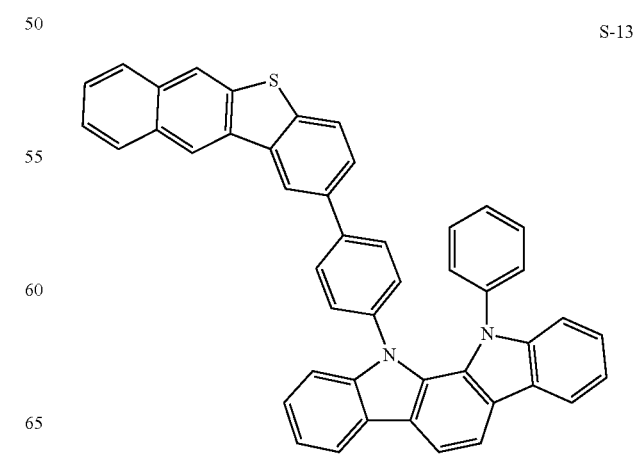

S-14
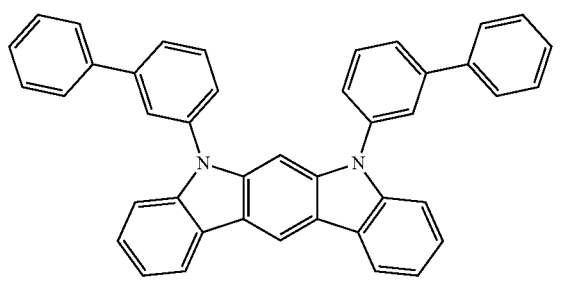
S-15
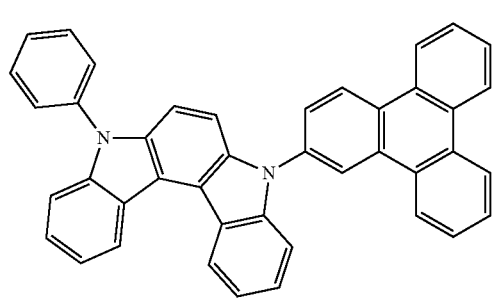
S-16
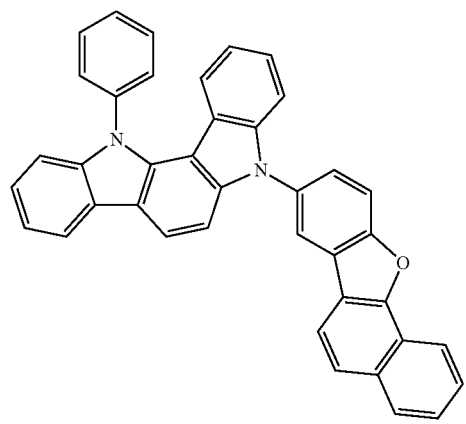
S-17
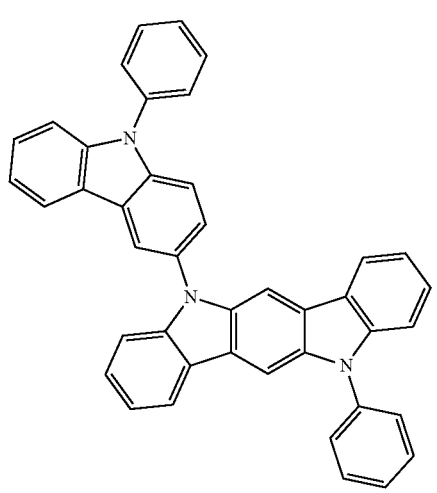
S-18
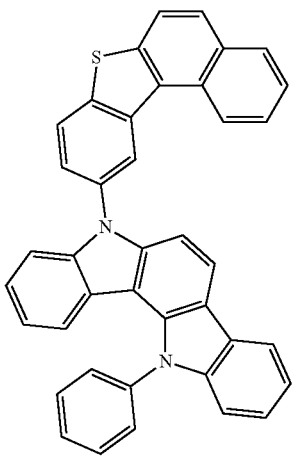
S-19
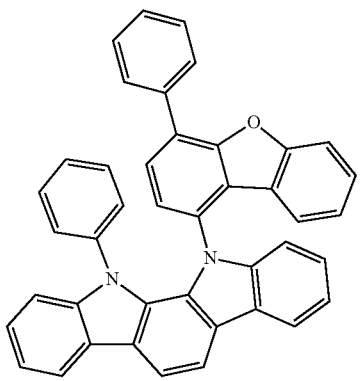
S-20
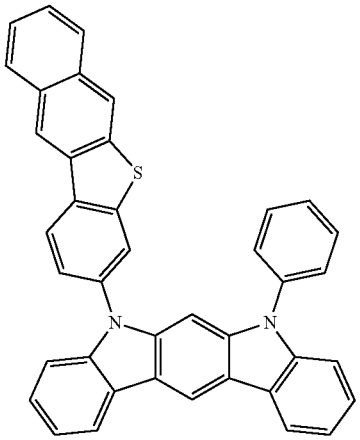

-continued
S-21
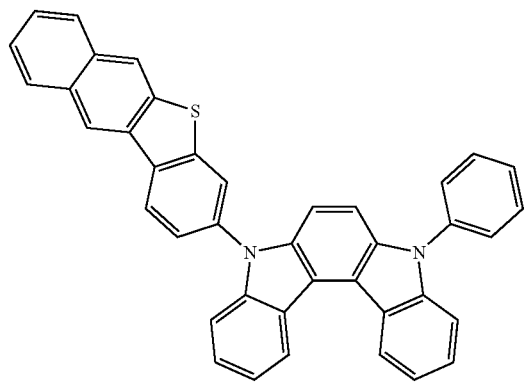
S-22
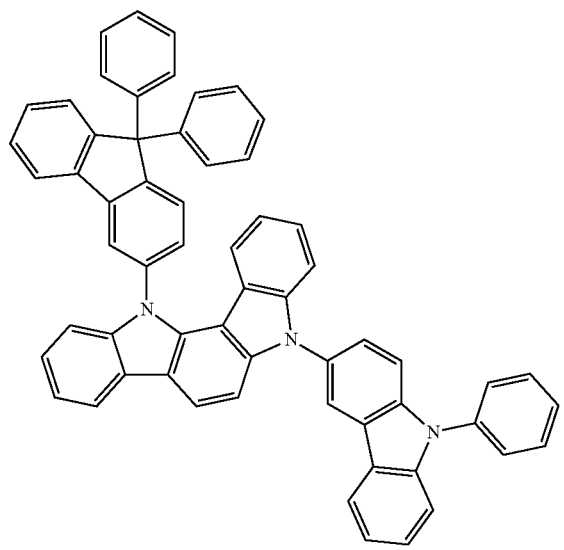
S-23
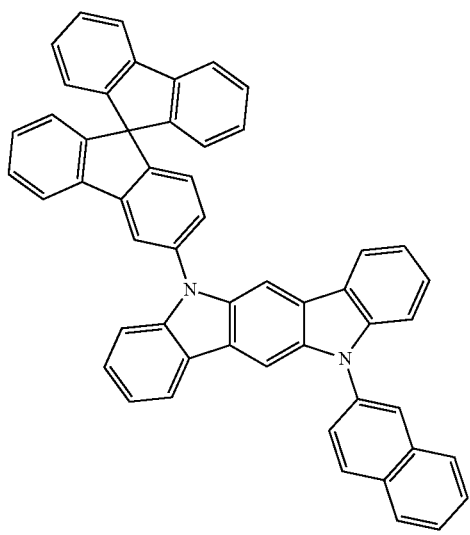
S-24
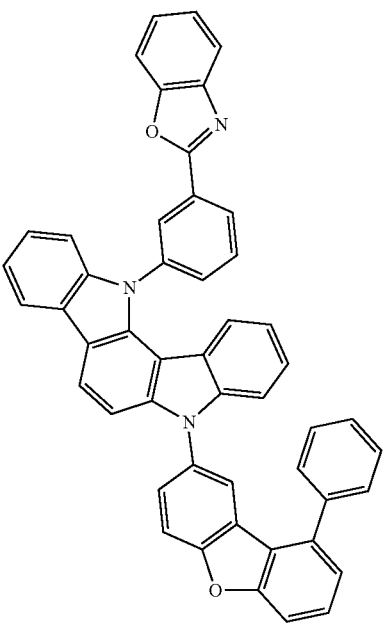
S-25
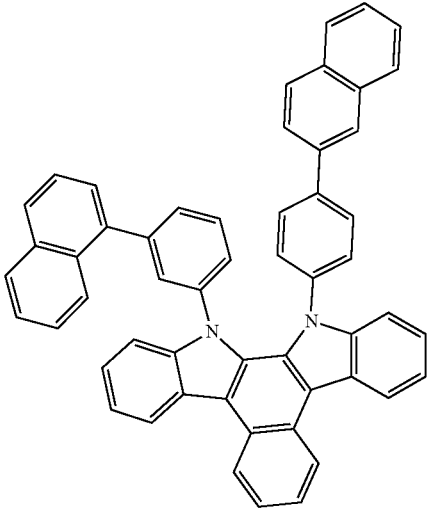
S-26
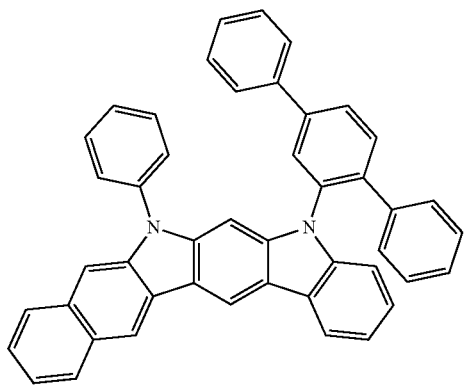

-continued
S-27
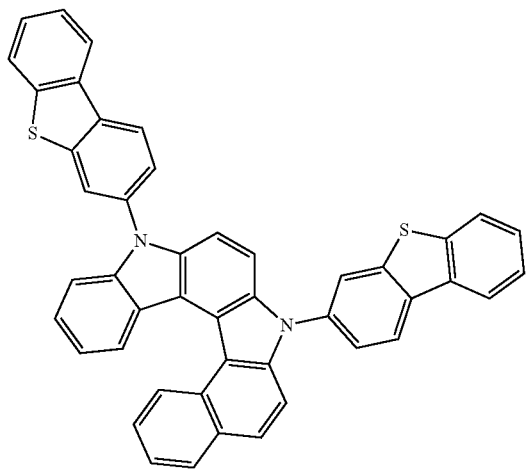
S-28
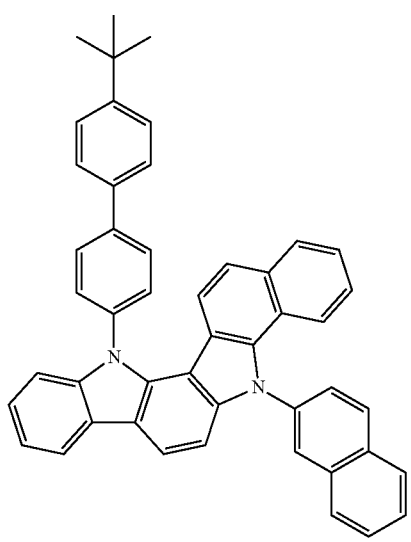
S-29
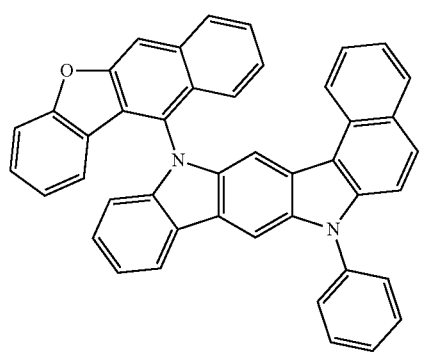
-continued
S-30
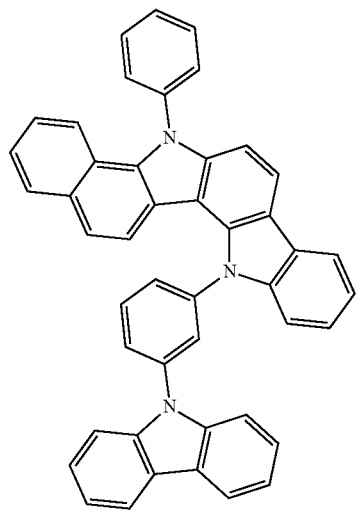
S-31
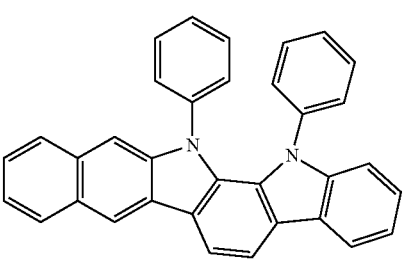
S-32
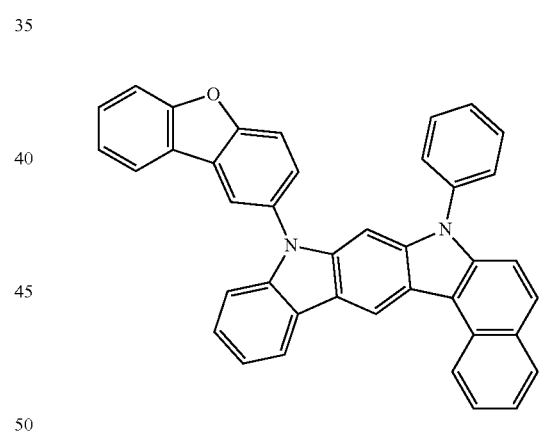
S-33
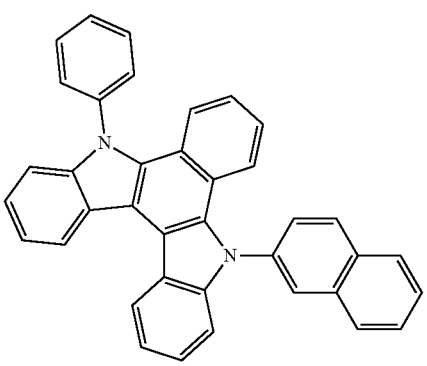

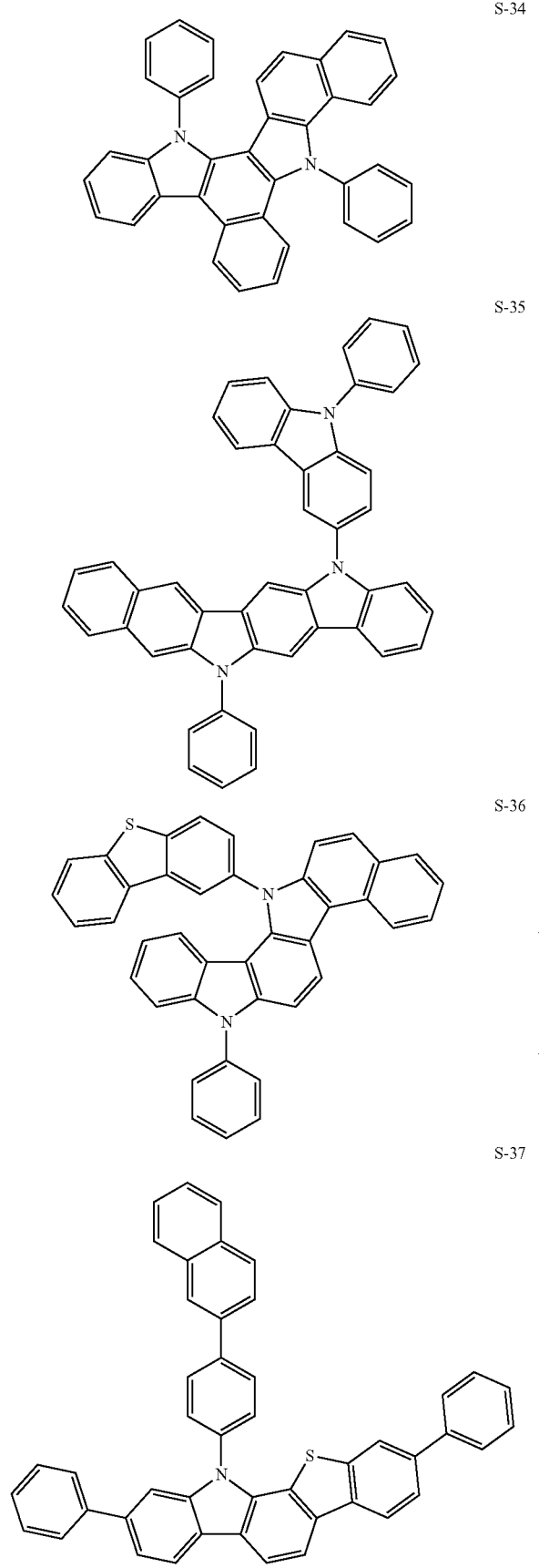

-continued
S-41
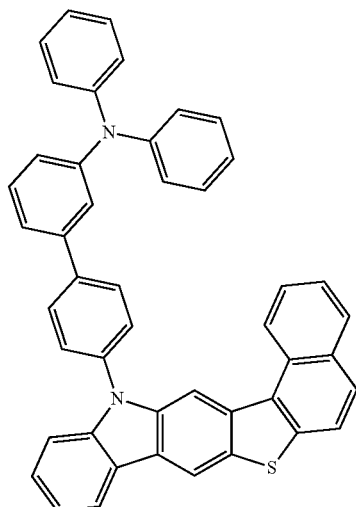
S-42
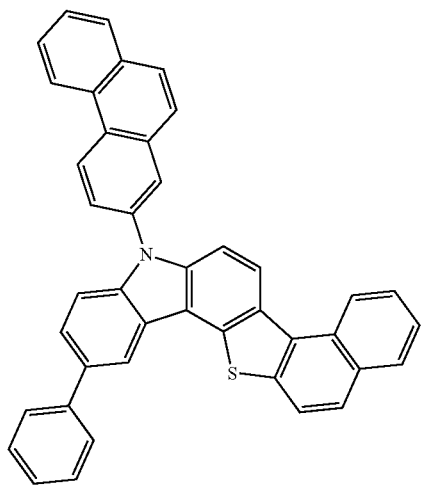
S-43
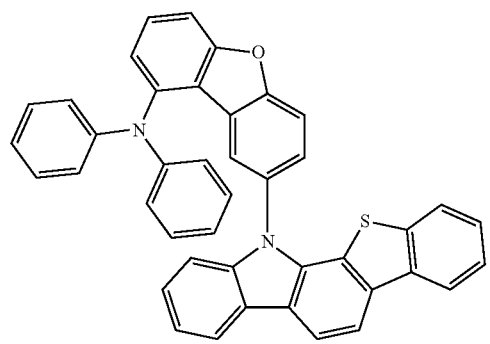
-continued
S-44
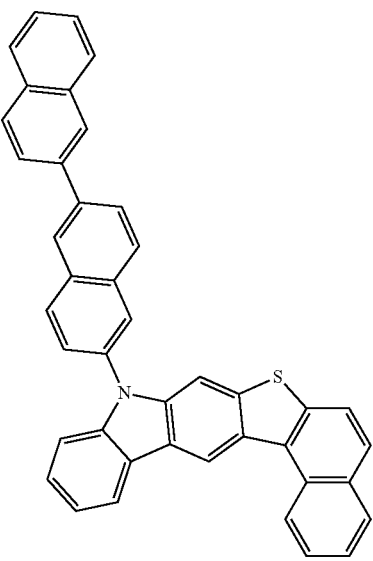
S-45
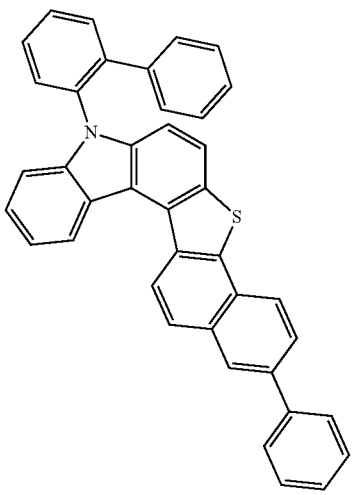
S-46
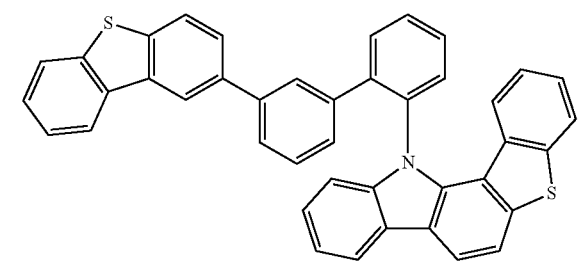

-continued
S-47
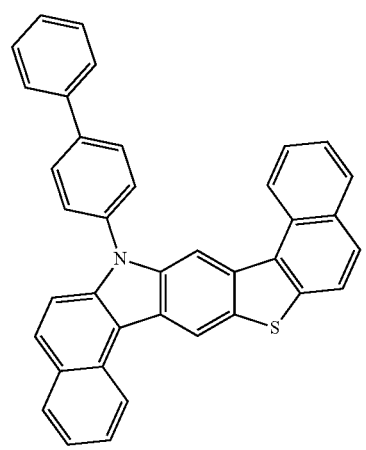
S-48
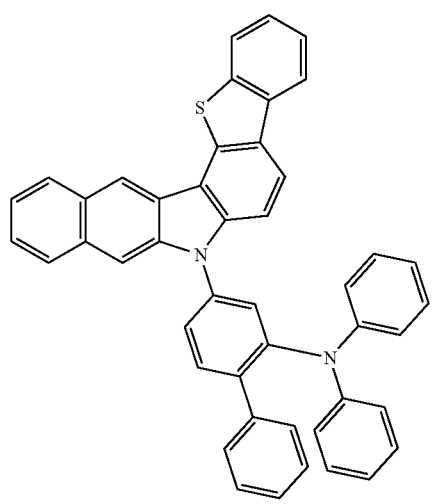
S-49
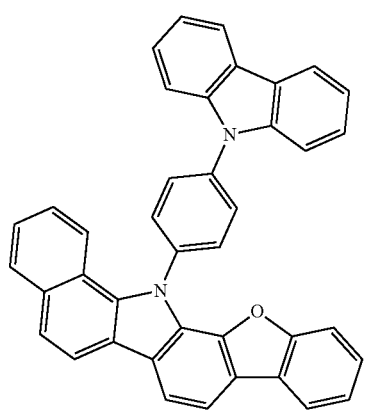
-continued
S-50
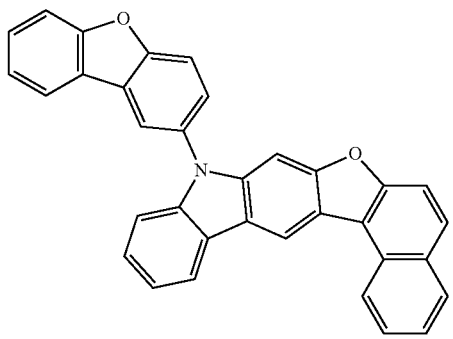
S-51
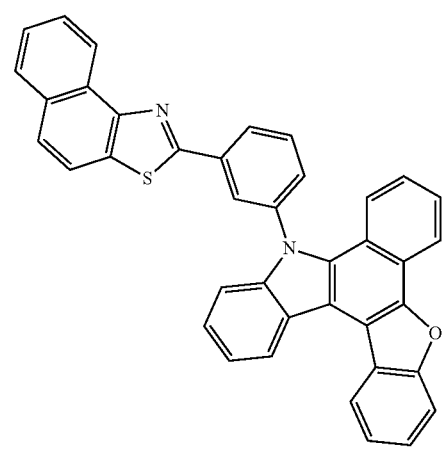
S-52
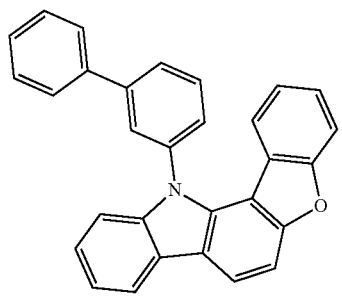
S-53
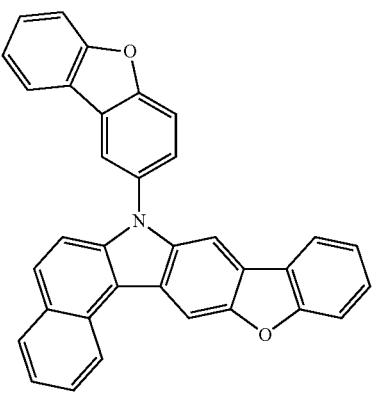

-continued
S-54
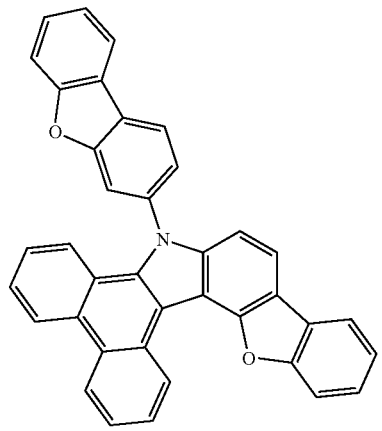
S-55
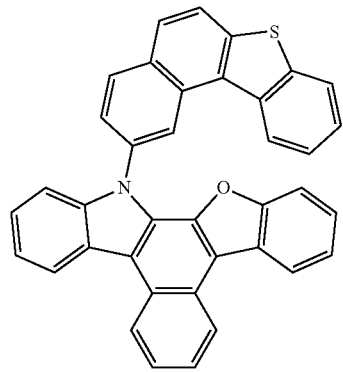
S-56
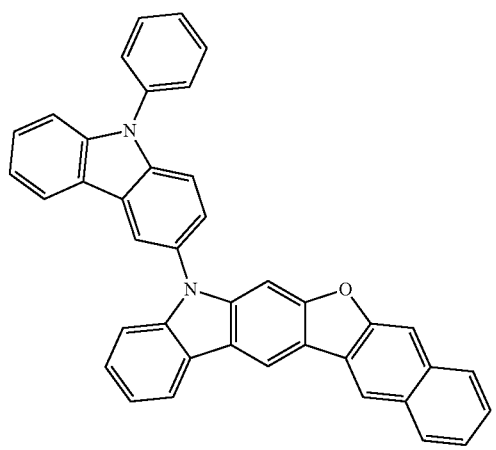
S-57
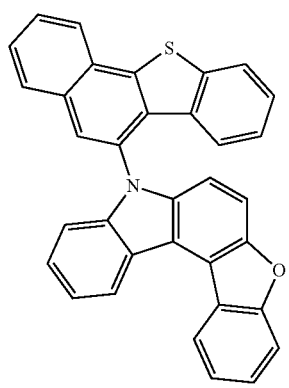
-continued
S-58
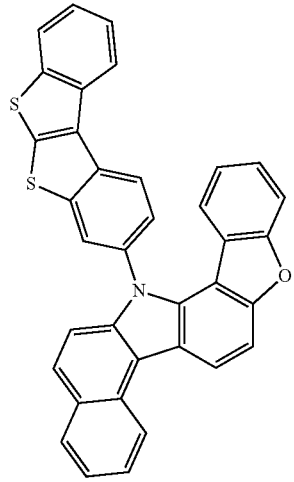
S-59
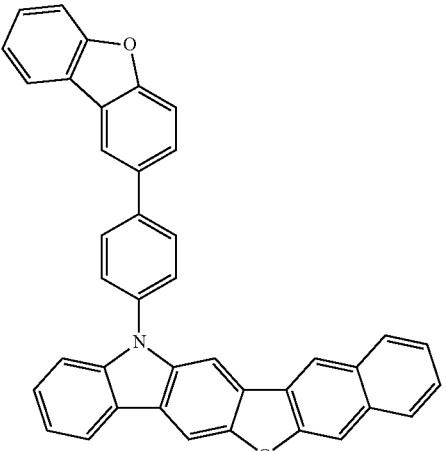
S-60
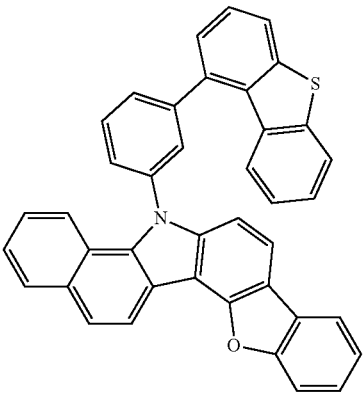

S-61
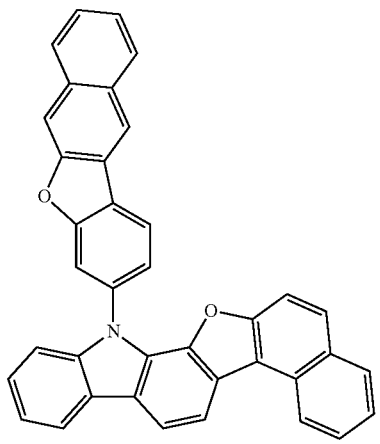
S-62
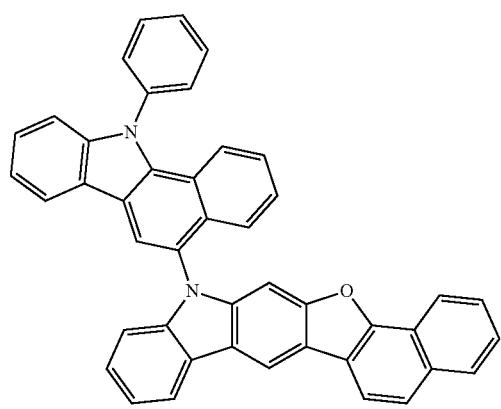
S-63
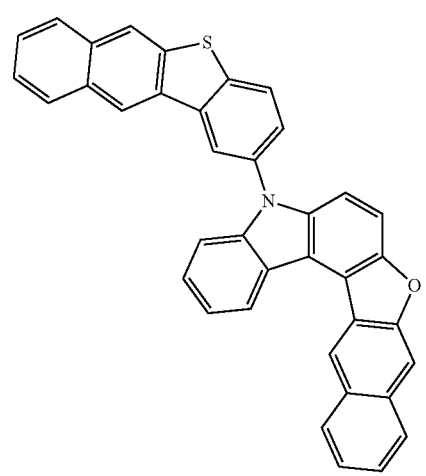
S-64
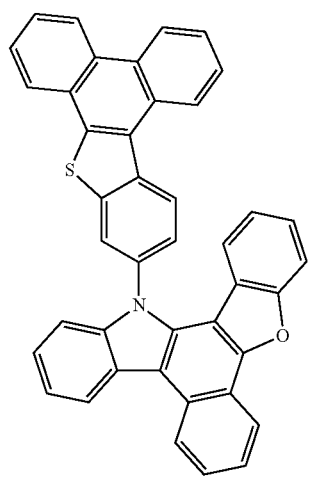
S-65
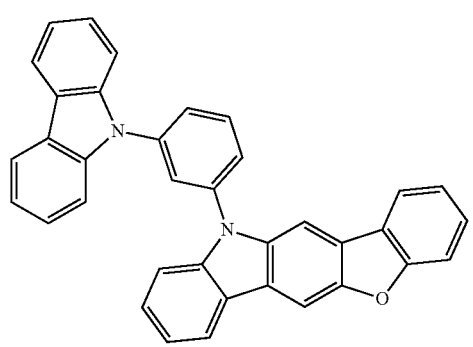
S-66
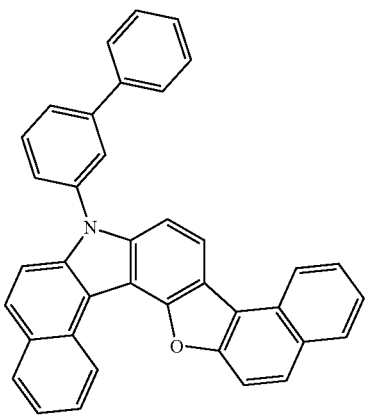
S-67
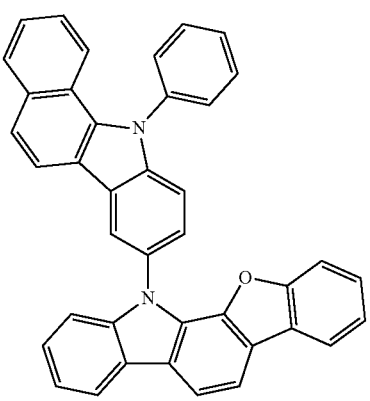

-continued
S-68
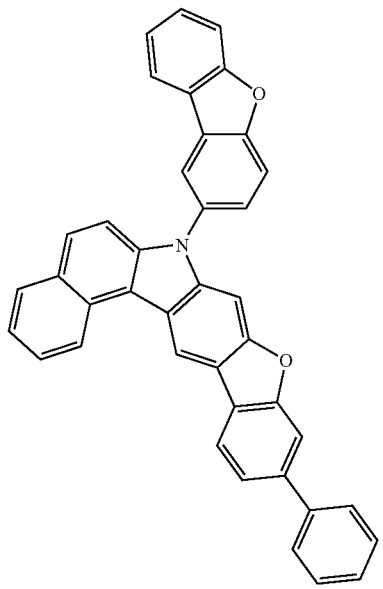
S-69
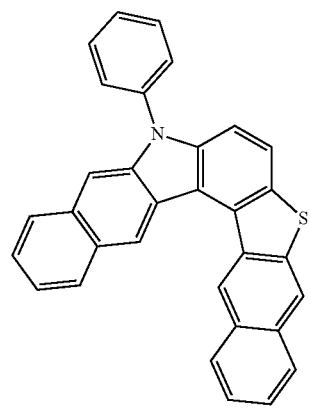
S-70
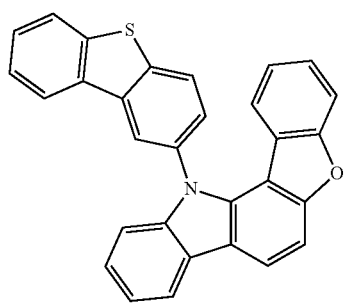
-continued
S-71
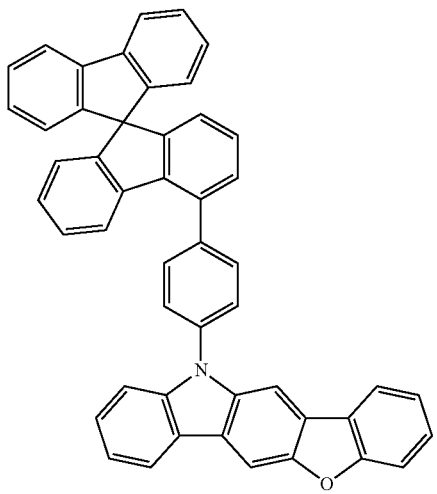
S-72
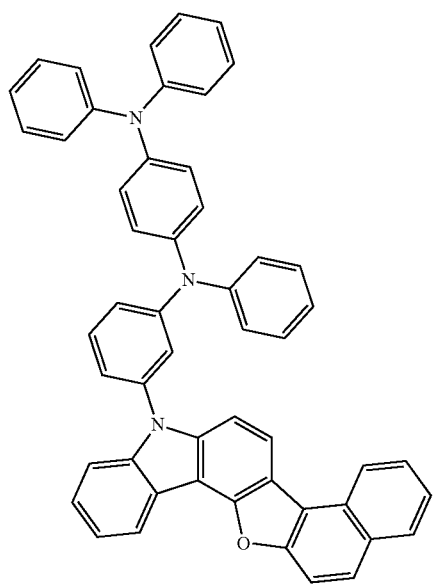
S-73
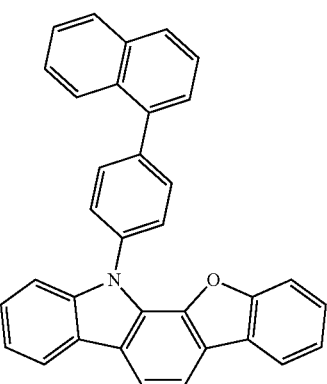

S-74
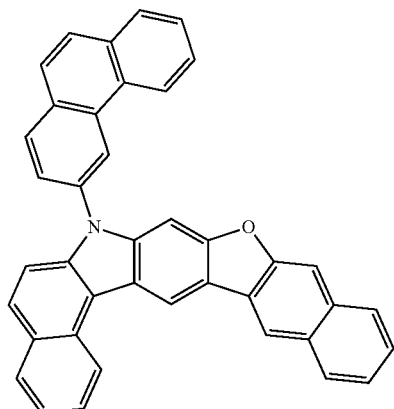
S-75
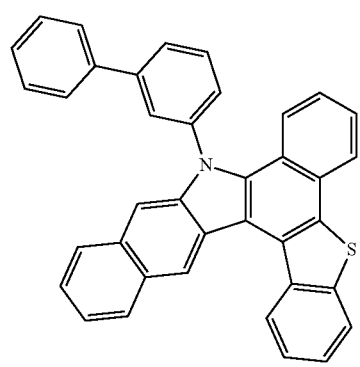
S-76
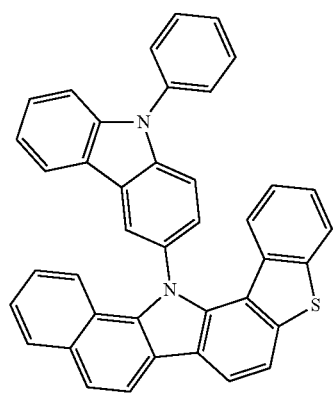
S-77
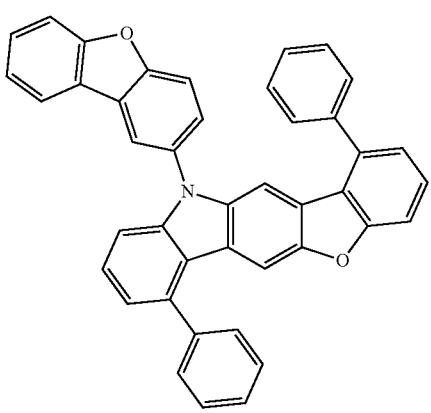
S-78
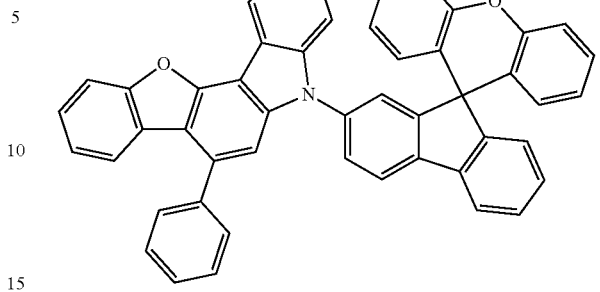
S-79
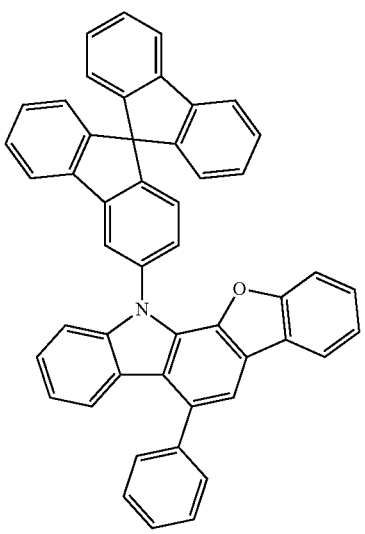
S-80
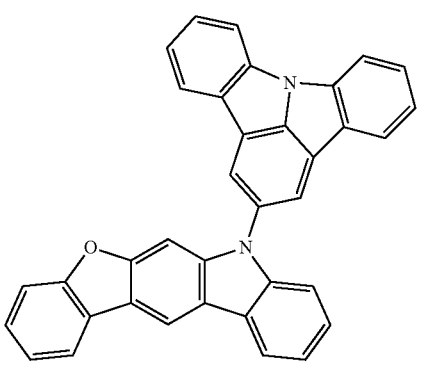
S-81
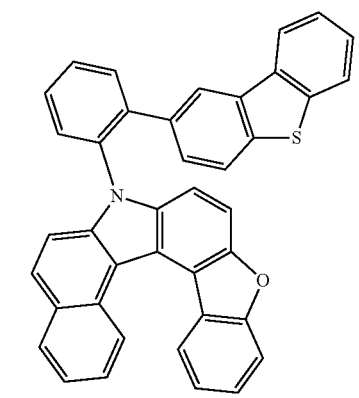

S-82
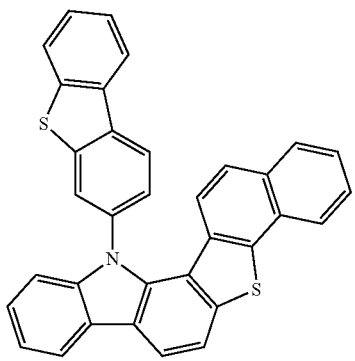
S-85
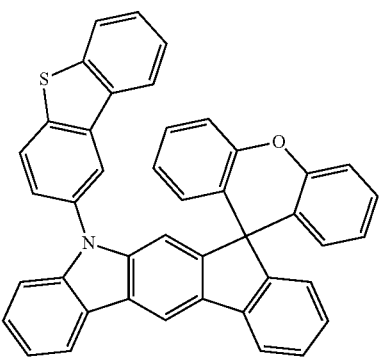
S-83
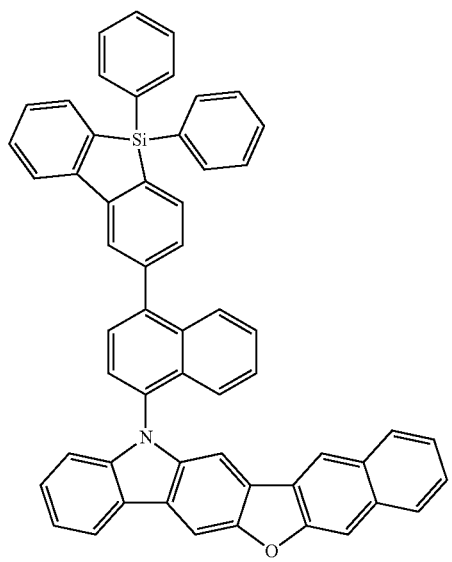
S-86
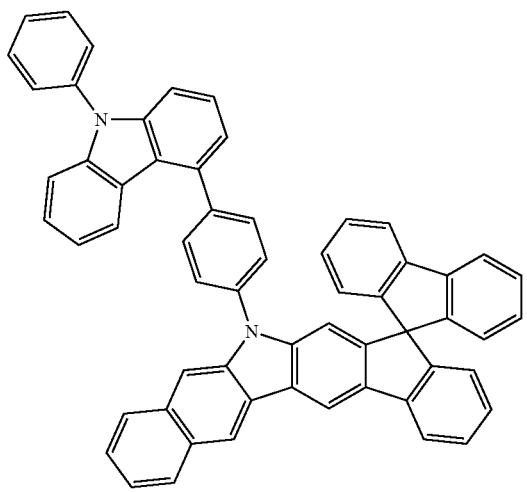
S-84
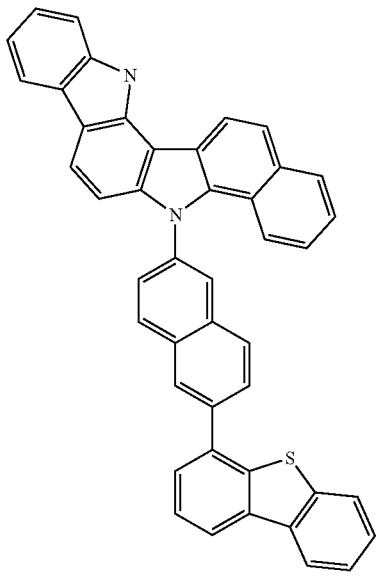
S-87
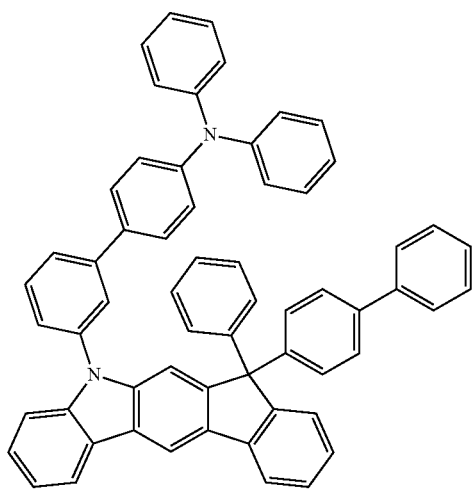

-continued
S-88
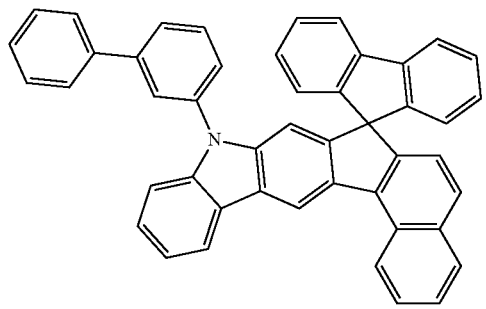
S-89
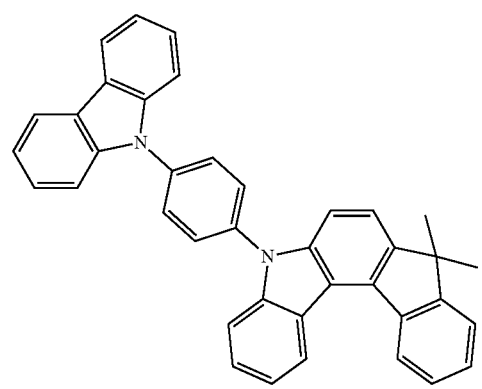
S-90
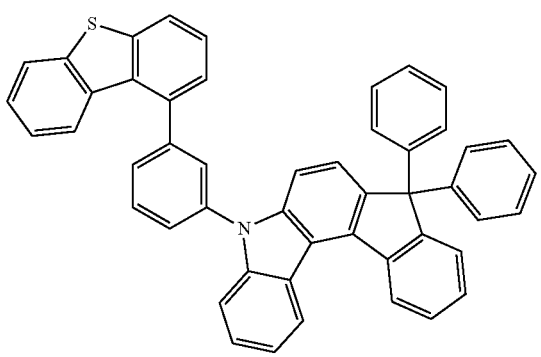
S-91
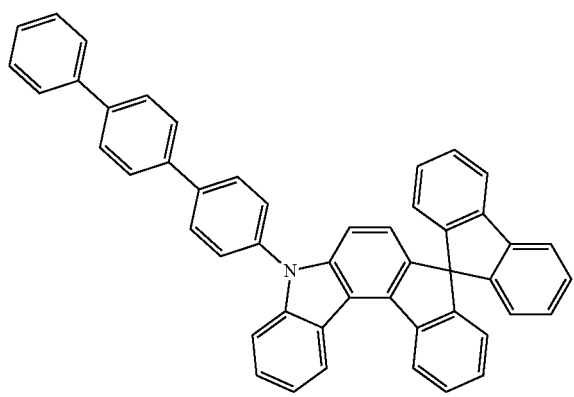
-continued
S-92
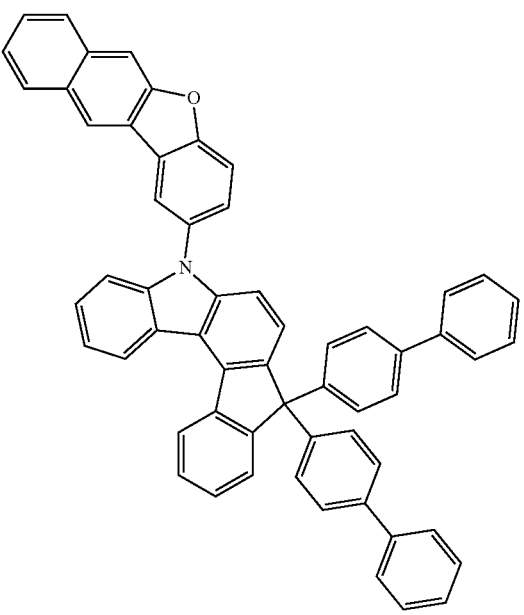
S-93
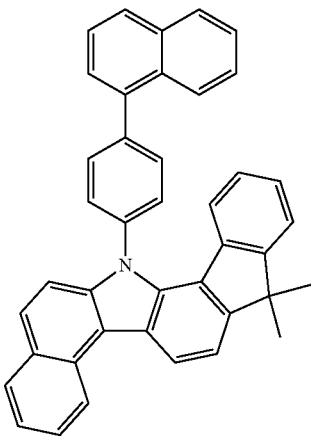
S-94
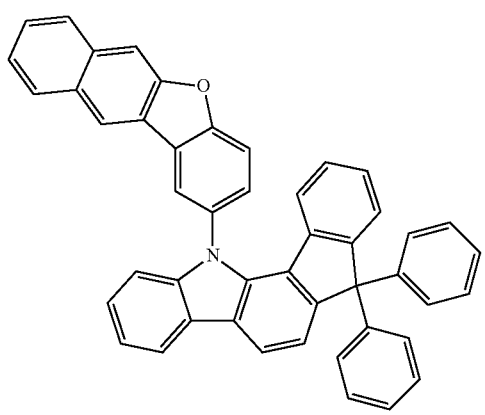

S-95
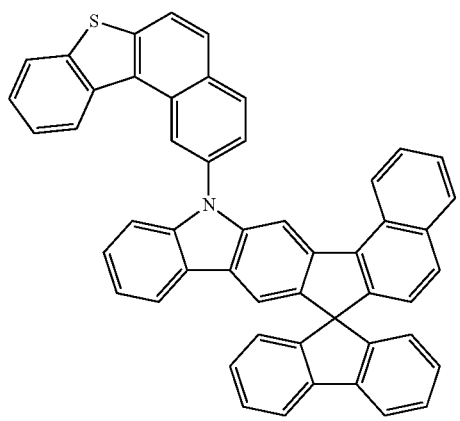
S-96
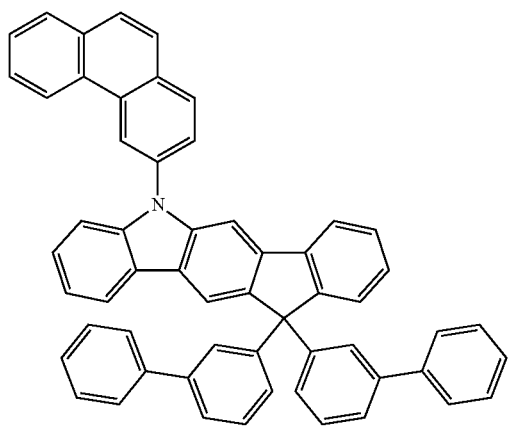
S-97
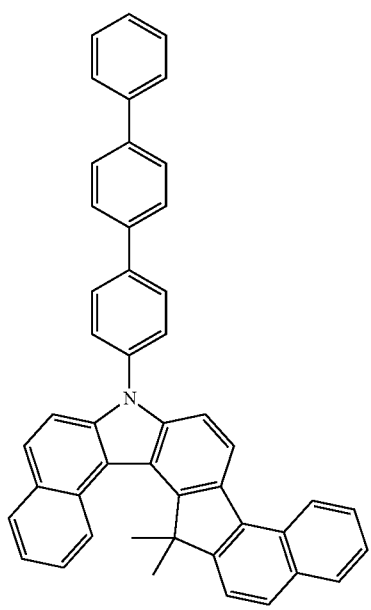
S-98
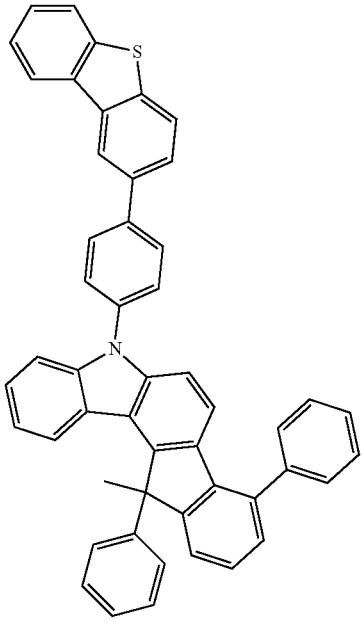
S-99
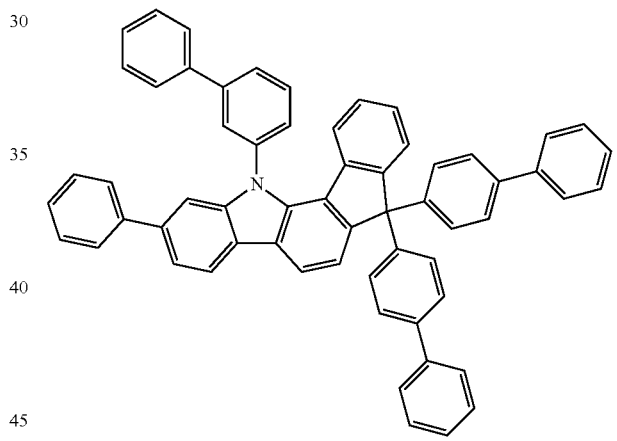
S-100
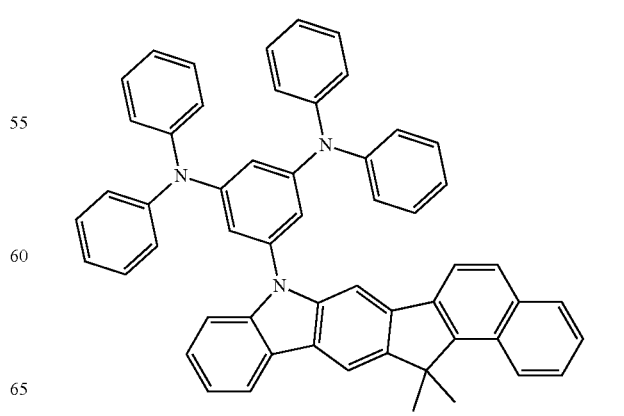

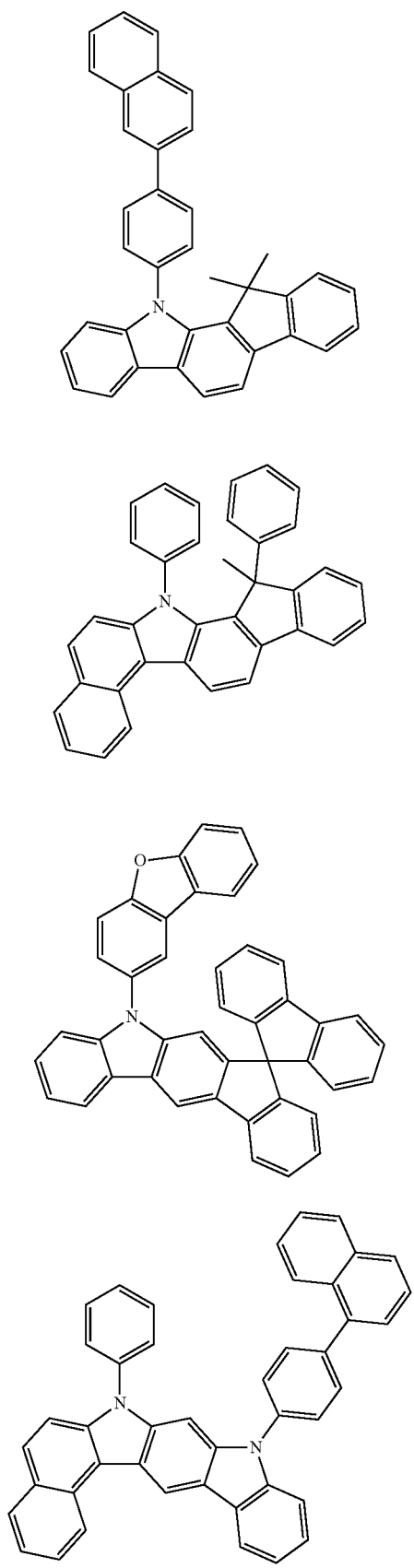
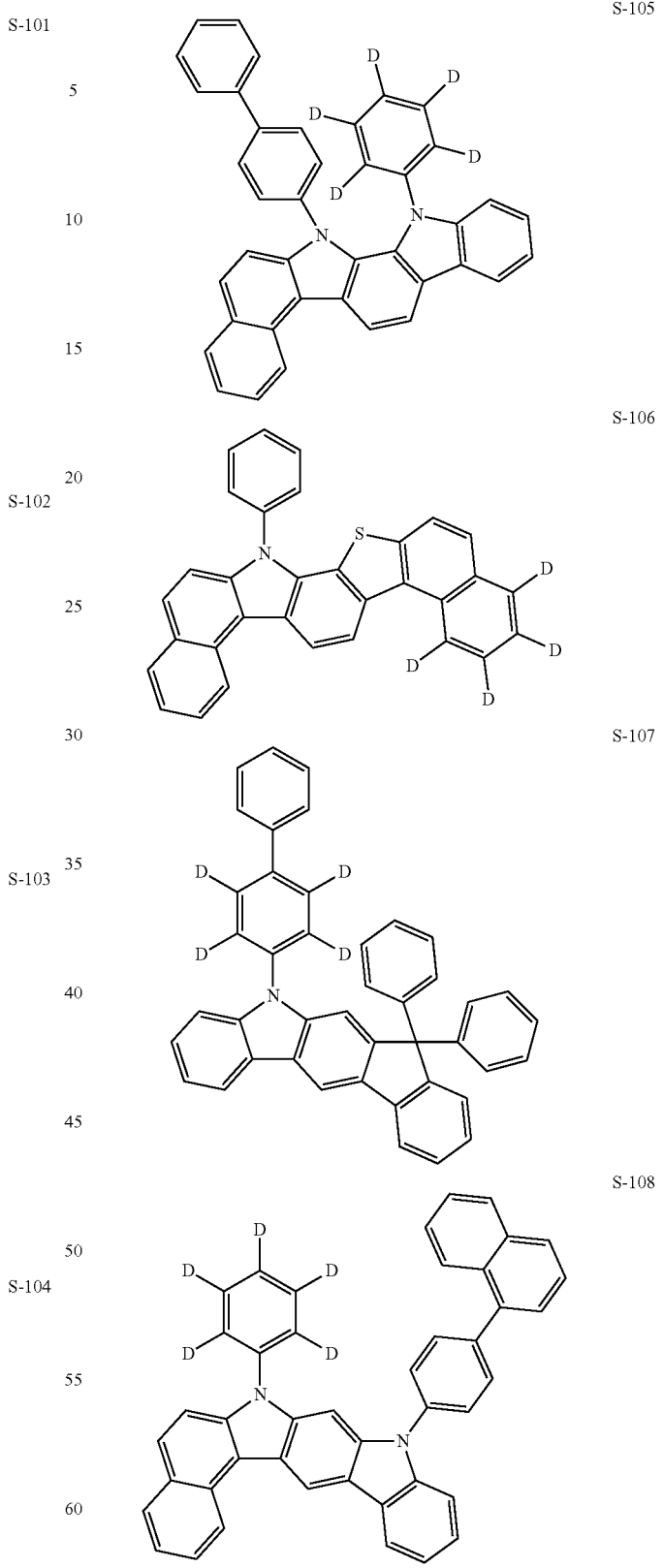
Also, in another aspect, the present invention provides an organic electronic element comprising a first electrode; a second electrode; and an organic material layer formed between the first electrode and the second electrode; wherein the organic material layer comprises the composition for the organic electronic element or a compound represented by Formula 1.

In another aspect, the present invention provides a method for reusing a compound of Formula 1 comprising:

recovering a crude organic light emitting material comprising the compound of Formula 1 from a deposition apparatus used in the process for depositing the organic emitting material to prepare an organic light emitting device;

removing impurities from the crude organic light emitting material;

recovering the organic light emitting material after the impurities are removed; and purifying the recovered organic light emitting material to have a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent is preferably a single solvent of N-Methylpyrrolidone (NMP); or a polar solvent mixed any one selected from the group consisting of 1,3-Dimethyl-2-imidazolidinone, 2-pyrrolidone, N,N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a mixture of a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention comprises a first electrode (110), a second electrode (170), an organic material layer comprising single compound or 2 or more compounds represented by Formula 1 between the first electrode (110) and the second electrode (170). Wherein, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
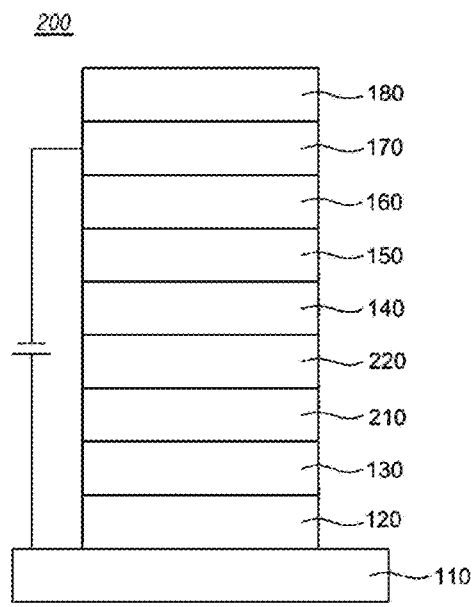

The organic material layer may sequentially comprise a hole injection layer (120), a hole transport layer (130), an emitting layer (140), an electron transport layer (150), and an electron injection layer (160) on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150), etc. may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound or materials for organic electronic element according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, the composition for an organic electronic element of the present invention or the compound represented by Formula 1 can be used as a host material of an emitting layer.

Figure 3:
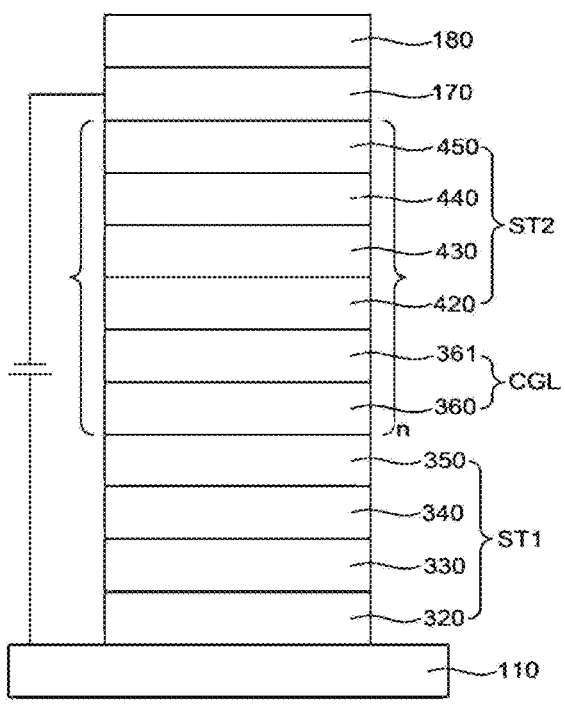
Figure 4:
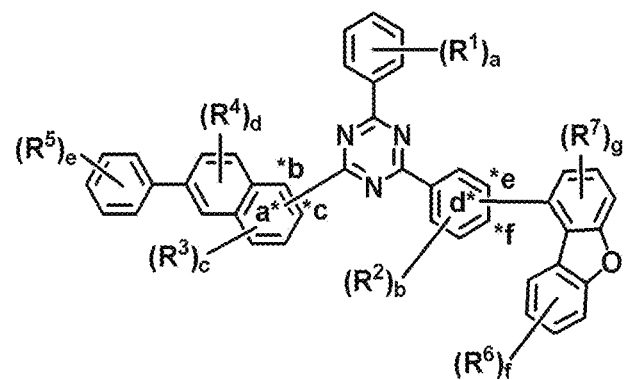
FIG. 4 shows a Formula according to one aspect of the present invention.

The organic material layer may comprise 2 or more stacks comprising a hole transport layer, an emitting layer and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, etc. may vary depending on which substituent is bonded at which position, therefore the choice of core and the combination of sub-substituents associated therewith is also very important, and in particular, when the optimal combination of energy levels and T1 values, and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound or a composition for an organic electronic element as an electron transport material.

As another specific example, the present invention provides an organic electronic element used by mixing the same or different compounds of the compound represented by Formula 1 to the organic material layer. Preferably, the organic material layer comprises an emitting layer, wherein the emitting layer comprises a composition for an organic electronic element or a compound represented by Formula 1

Also, the present invention provides a composition for an organic electronic element or a compound represented by Formula 1, and provides an organic electronic element comprising the composition for an organic electronic element or the compound represented by Formula 1

Also, the present invention also provides an electronic device comprising a display device comprising the organic electronic element; and a control unit for driving the display device.

According to another aspect, the present invention provides a display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis examples of the compound represented by Formula 1 and Formula 5 according to the present invention and preparation examples of the organic electronic element will be described in detail by way of example, but are not limited to the following examples.

[Synthesis Example 1] Compound Represented by Formula 1

The compound (Final Product) represented by Formula 1 according to the present invention is synthesized as in Reaction Scheme 1, but is not limited thereto.

<Reaction Scheme 1>

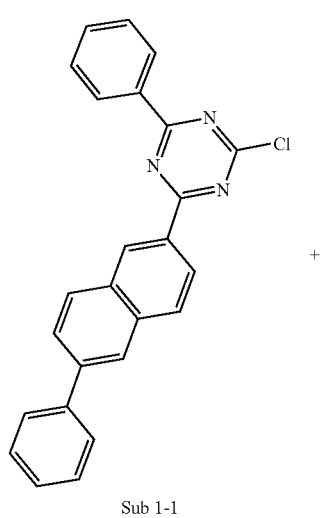

Sub 2

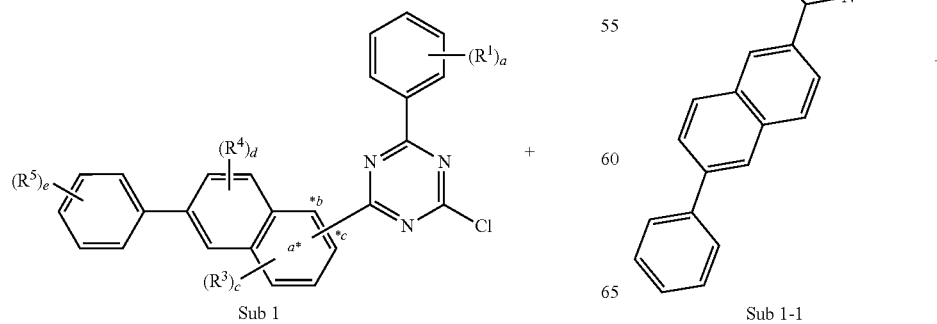

Final Products

Wherein, $R^1$, $R^2$, $R^3$, $R^4$, $R^5$, $R^6$, $R^7$, a, b, c, d, e, f, g, *a, *b, *c, *d, *e and *f are the same as defined in Formula 1.

I. Synthesis of Final Product

1. Synthesis Example of P-1

Sub 1

Sub 1-1

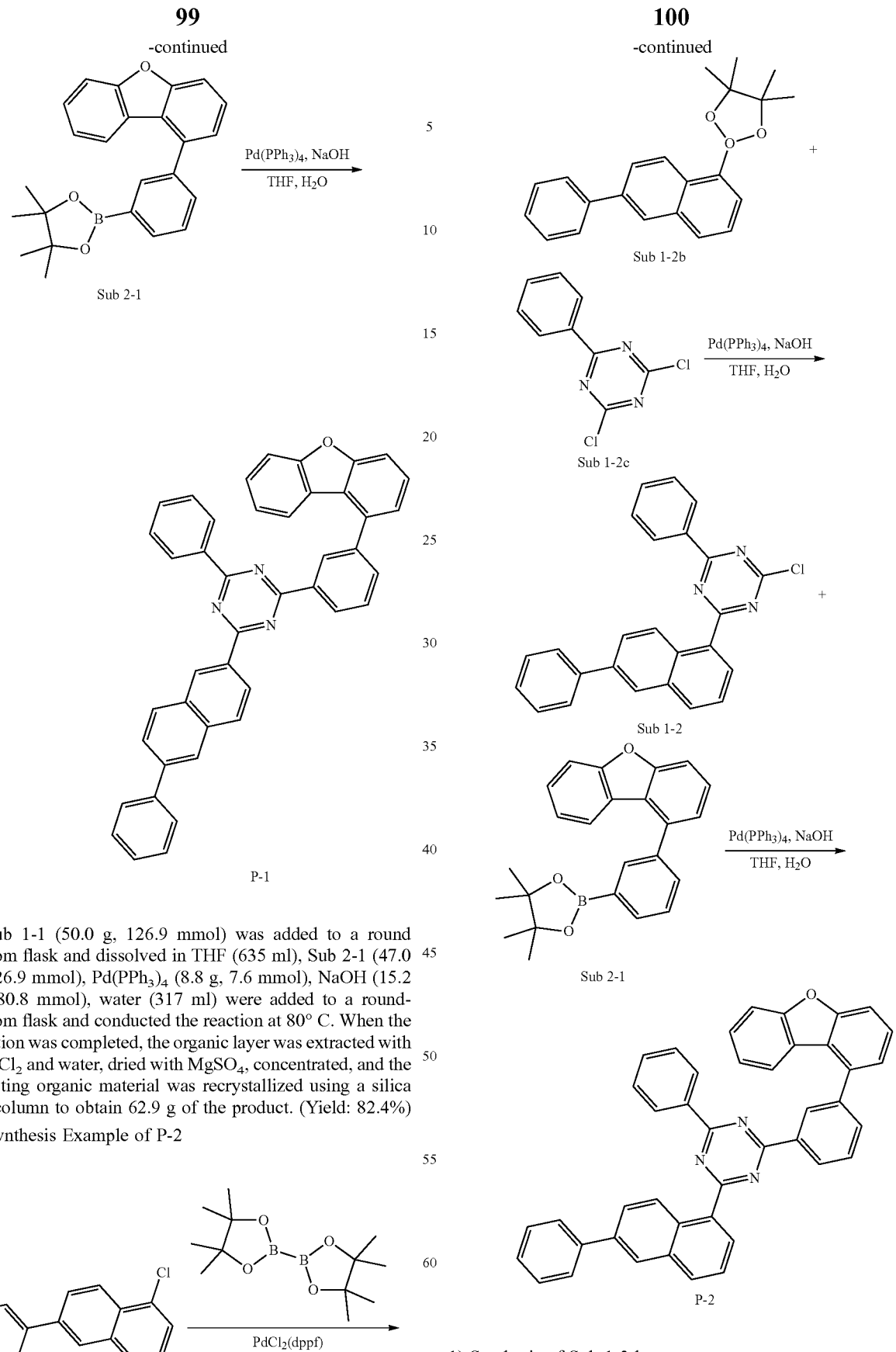

Sub 1-1 (50.0 g, 126.9 mmol) was added to a round bottom flask and dissolved in THF (635 ml), Sub 2-1 (47.0 g, 126.9 mmol), Pd(PPh₃)₄ (8.8 g, 7.6 mmol), NaOH (15.2 g, 380.8 mmol), water (317 ml) were added to a round-bottom flask and conducted the reaction at 80° C. When the reaction was completed, the organic layer was extracted with CH₂Cl₂ and water, dried with MgSO₄, concentrated, and the resulting organic material was recrystallized using a silica gel column to obtain 62.9 g of the product. (Yield: 82.4%)

2. Synthesis Example of P-2

1) Synthesis of Sub 1-2-b

Sub 1-2-a (100.0 g, 418.9 mmol) was added in a round bottom flask, and dissolved in DMF (2094 ml), and 4,4,4', 4',5,5,5',5'-octamethyl-2,2'-bi(1,3,2-dioxaborolane) (138.3 g, 544.59 mmol), Pd(dppf)Cl$_2$ (15.33 g, 21.0 mmol), KOAc (123.4 g, 1256.8 mmol) were added and stirred at 150° C. for 2 hours. When the reaction was completed, the organic layer was extracted with CH$_2$Cl$_2$ and water, dried with MgSO$_4$, concentrated, and the resulting organic material was recrystallized using a silica gel column to obtain 112.88 g of the product. (Yield: 81.6%)

2) Synthesis of Sub 1-2

Sub 1-2-b (70.0 g, 212.0 mmol) was added in a round bottom flask, and dissolved in THF (1060 ml), and Sub 1-2-c (47.9 g, 212.0 mmol), Pd(PPh$_3$)$_4$ (14.7 g, 12.7 mmol), NaOH (25.4 g, 635.9 mmol), Water (530 ml) were added and the experiment was conducted in the same manner as P-1 to obtain 69.4 g of the product. (Yield: 83.1%)

3) Synthesis of P-2

Sub 1-2 (60.0 g, 152.3 mmol) was added in a round bottom flask, and dissolved in THF (762 ml), and Sub 2-1 (56.4 g, 152.3 mmol), Pd(PPh$_3$)$_4$ (9.1 g, 10.6 mmol), NaOH (18.3 g, 457.0 mmol), Water (381 ml) were added and the experiment was conducted in the same manner as P-1 to obtain 74.7 g of the product. (Yield: 81.5%)

3. Synthesis Example of P-3

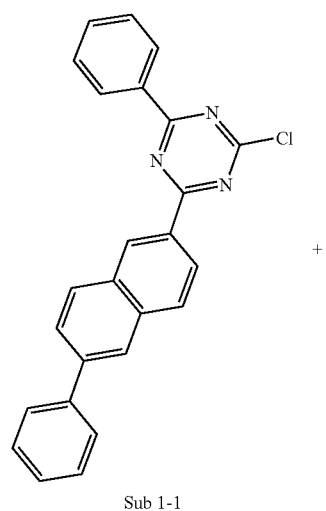

Sub 1-1

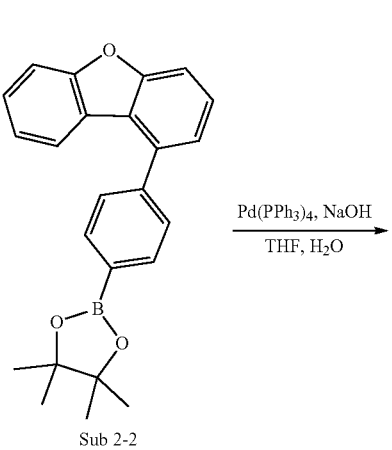

Sub 2-2

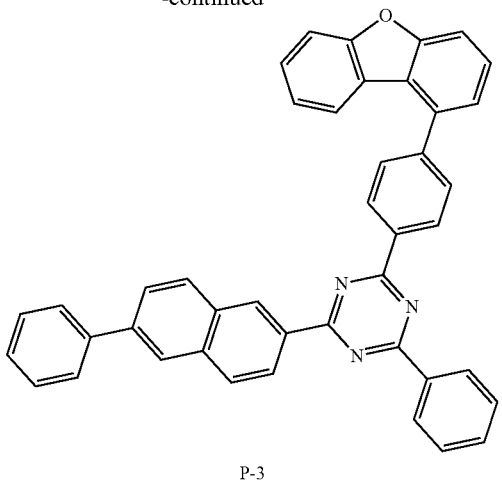

P-3

Sub 1-1 (50.0 g, 126.9 mmol) was added in a round bottom flask, and dissolved in THF (635 ml), and Sub 2-2 (47.0 g, 126.9 mmol), Pd(PPh$_3$)$_4$ (8.8 g, 7.6 mmol), NaOH (15.2 g, 380.8 mmol), Water (317 ml) were added and the experiment was conducted in the same manner as P-1 to obtain 62.6 g of the product. (Yield: 82.0%)

4. Synthesis Example of P-4

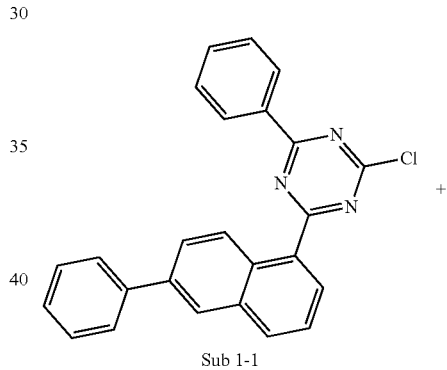

Sub 1-1

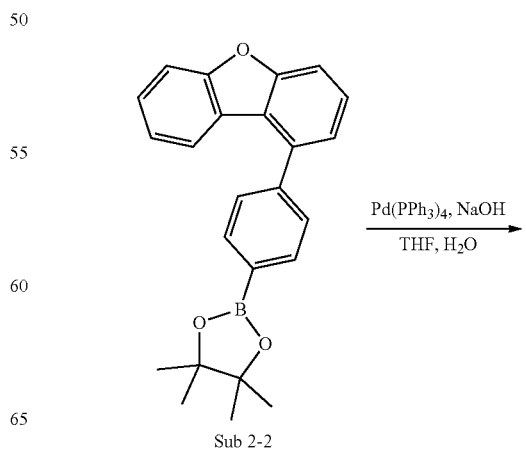

Sub 2-2

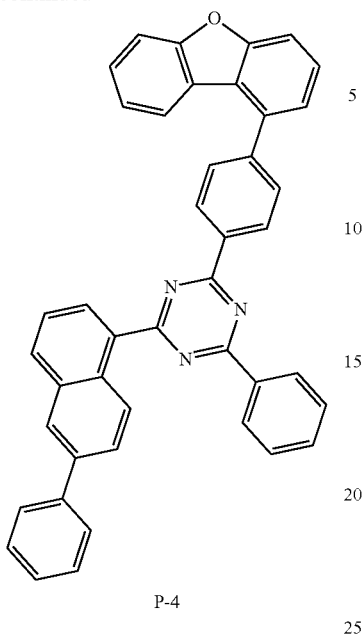
P-4
Sub 1-2 (50.0 g, 126.9 mmol) was added in a round bottom flask, and dissolved in THF (635 ml), and Sub 2-2 (47.0 g, 126.9 mmol), Pd(PPh₃)₄ (8.8 g, 7.6 mmol), NaOH (15.2 g, 380.8 mmol), Water (317 ml) were added and the experiment was conducted in the same manner as P-1 to obtain 62.4 g of the product. (Yield: 81.7%)
5. Synthesis Example of P-5
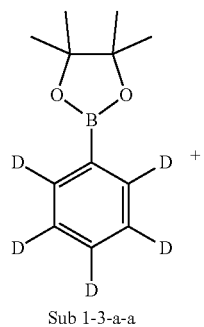
Sub 1-3-a-a
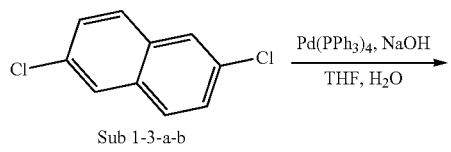
Sub 1-3-a-b
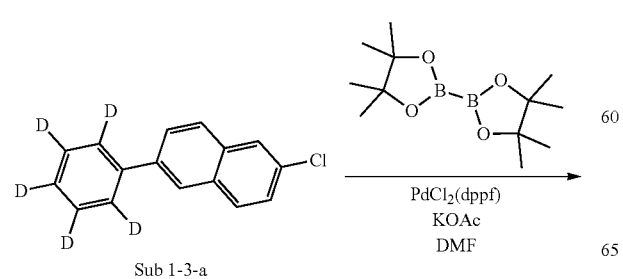
Sub 1-3-a
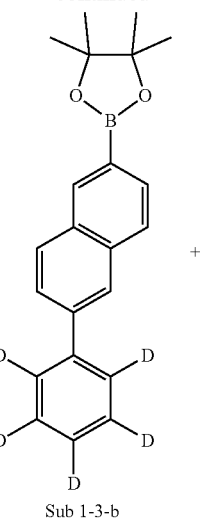
Sub 1-3-b
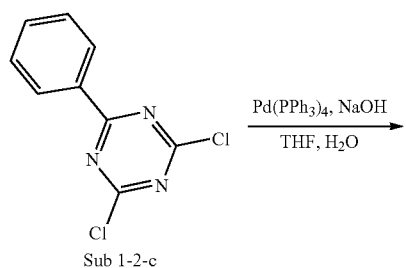
Sub 1-2-c
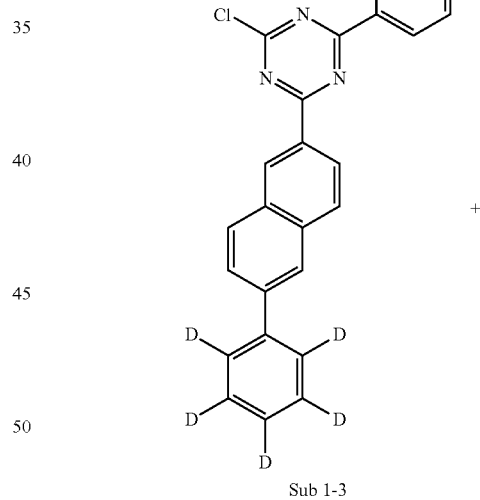
Sub 1-3
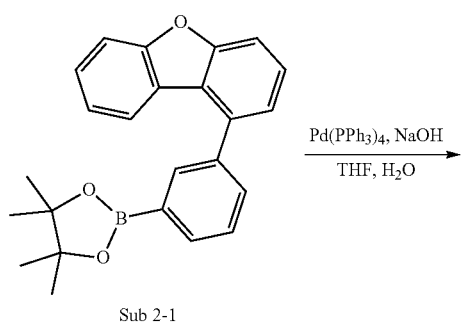
Sub 2-1

105
-continued

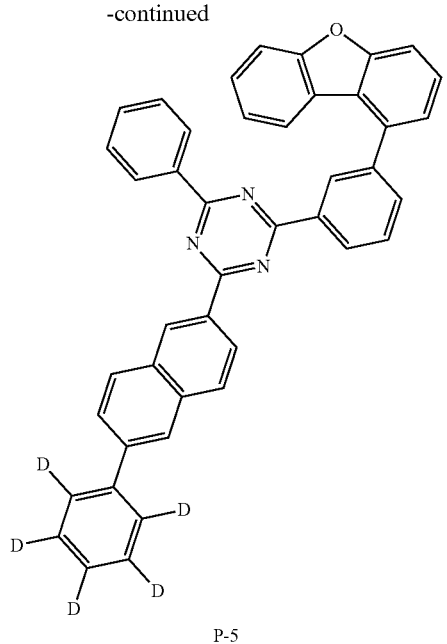

P-5

1) Synthesis of Sub 1-3-a

Sub 1-3-a-a (100.0 g, 478.2 mmol) was added in a round bottom flask, and dissolved in THF (2391 ml), and Sub 1-3-a-b (94.2 g, 478.2 mmol), Pd(PPh$_3$)$_4$ (33.2 g, 28.7 mmol), NaOH (57.4 g, 1434.7 mmol), Water (1196 ml) were added and the experiment was conducted in the same manner as P-1 to obtain 90.1 g of the product. (Yield: 77.3%)

2) Synthesis of Sub 1-3-b

Sub 1-3-a (70.0 g, 287.2 mmol) was added in a round bottom flask, and dissolved in DMF (1436 ml), and 4,4,4',4',5,5,5',5'-octamethyl-2,2'-bi(1,3,2-dioxaborolane) (94.8 g, 373.35 mmol), Pd(dppf)Cl$_2$ (10.5 g, 14.4 mmol), KOAc (84.6 g, 861.6 mmol) were added and the experiment was conducted in the same manner as Sub 1-2b to obtain 77.6 g of the product. (Yield: 80.6%)

3) Synthesis of Sub 1-3

Sub 1-3-b (70.0 g, 208.8 mmol) was added in a round bottom flask, and dissolved in THF (1044 ml), Sub 1-2-c (47.2 g, 208.8 mmol), Pd(PPh$_3$)$_4$ (14.5 g, 12.5 mmol), NaOH (25.1 g, 626.4 mmol), water (522 ml) were added and the experiment was conducted in the same manner as P-1 to obtain 67.6 g of the product. (Yield: 81.2%)

4) Synthesis of P-5

Sub 1-3 (60.0 g, 150.4 mmol) was added in a round bottom flask, and dissolved in THF (752 ml), Sub 2-1 (55.7 g, 150.4 mmol), Pd(PPh$_3$)$_4$ (10.4 g, 9.0 mmol), NaOH (18.0 g, 451.2 mmol), water (376 ml) were added and the experiment was conducted in the same manner as P-1 to obtain 73.7 g of the product. (Yield: 80.8%)

106

6. Synthesis Example of P-13

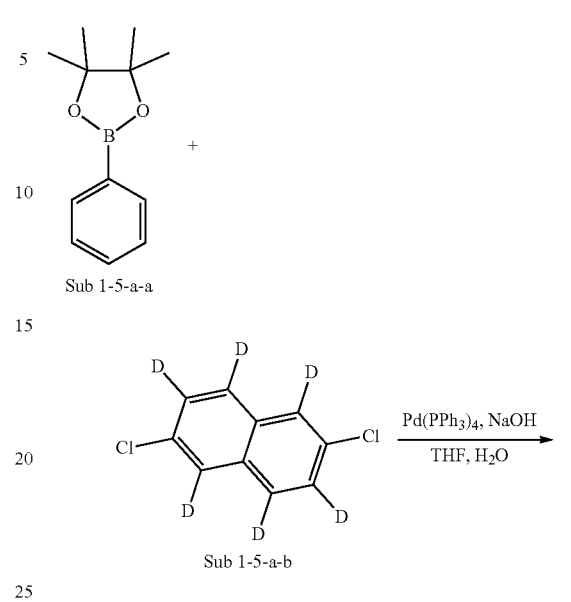

Sub 1-5-a-a

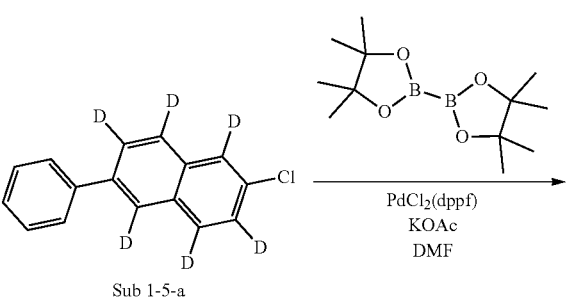

Sub 1-5-a-b

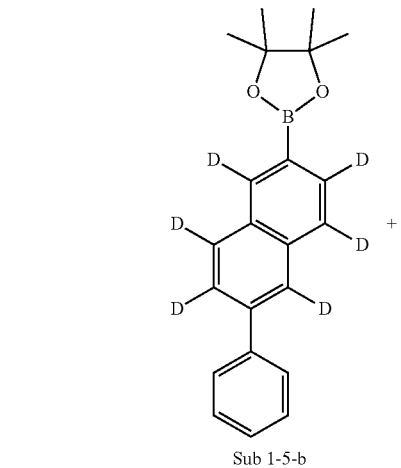

Sub 1-5-a

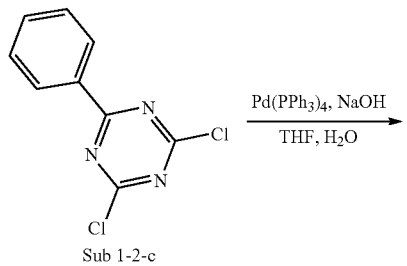

Sub 1-5-b

Sub 1-2-c

-continued

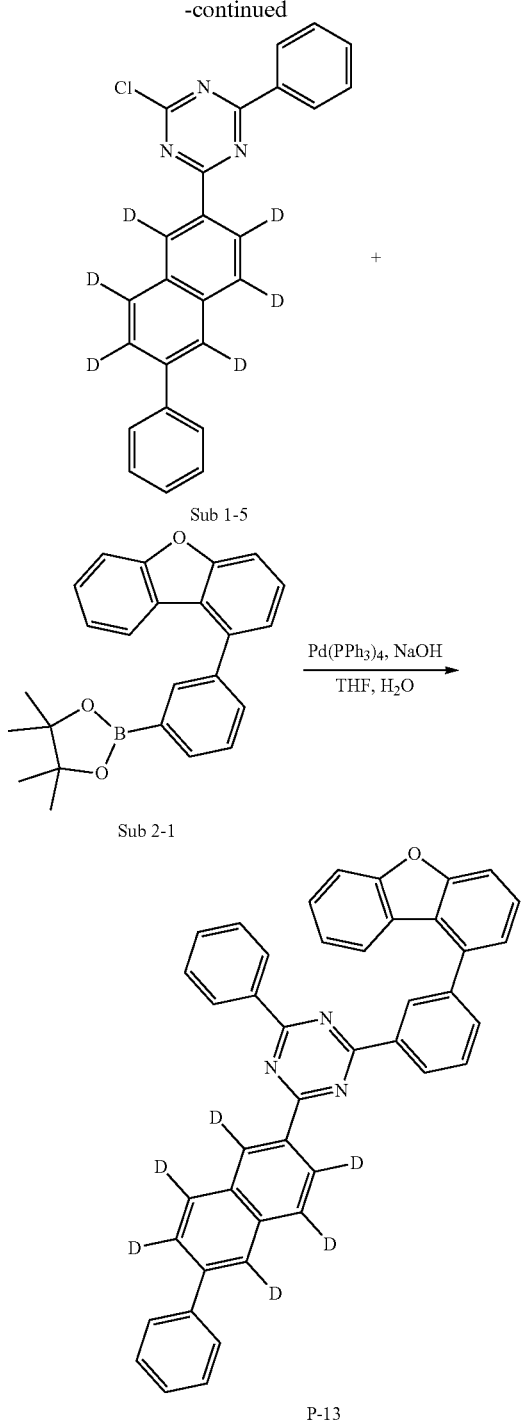

1) Synthesis of Sub 1-5-a

Sub 1-5-a-a (100.0 g, 490.0 mmol) was added in a round bottom flask, and dissolved in THF (2450 ml), and Sub 1-5-a-b (99.5 g, 490.0 mmol), Pd(PPh$_3$)$_4$ (34.0 g, 28.7 mmol), NaOH (58.8 g, 1470.0 mmol), Water (1225 ml) were added and the experiment was conducted in the same manner as P-1 to obtain 92.2 g of the product. (Yield: 76.9%)

2) Synthesis of Sub 1-5-b

Sub 1-5-a (70.0 g, 286.0 mmol) was added in a round bottom flask, and dissolved in DMF (1430 ml), and 4,4,4',4',5,5,5',5'-octamethyl-2,2'-bi(1,3,2-dioxaborolane) (94.4 g, 371.8 mmol), Pd(dppf)Cl$_2$ (10.5 g, 14.3 mmol), KOAc (84.2 g, 858.0 mmol) were added and the experiment was conducted in the same manner as Sub 1-2b to obtain 77.6 g of the product. (Yield: 80.7%)

3) Synthesis of Sub 1-5

Sub 1-5-b (70.0 g, 208.2 mmol) was added in a round bottom flask, and dissolved in THF (1041 ml), Sub 1-2-c (47.1 g, 208.2 mmol), Pd(PPh$_3$)$_4$ (14.4 g, 12.5 mmol), NaOH (25.0 g, 624.5 mmol), water (520 ml) were added and the experiment was conducted in the same manner as P-1 to obtain 66.9 g of the product. (Yield: 80.4%)

4) Synthesis of P-13

Sub 1-5 (60.0 g, 150.0 mmol) was added in a round bottom flask, and dissolved in THF (750 ml), Sub 2-1 (55.6 g, 150.0 mmol), Pd(PPh$_3$)$_4$ (10.4 g, 9.0 mmol), NaOH (18.0 g, 450.1 mmol), water (375 ml) were added and the experiment was conducted in the same manner as P-1 to obtain 73.9 g of the product. (Yield: 81.1%)

7. Synthesis Example of P-21

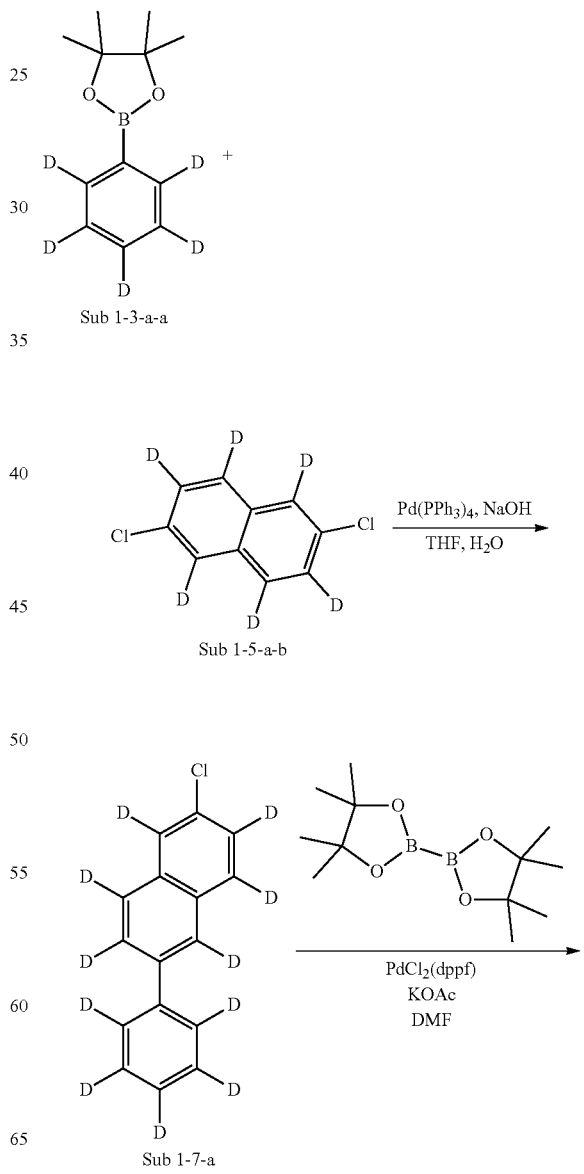

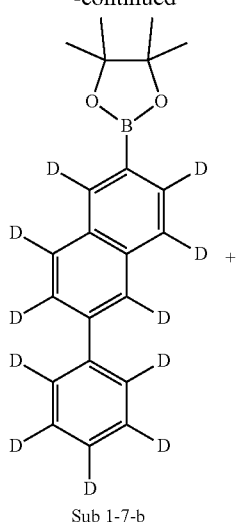

Sub 1-7-b

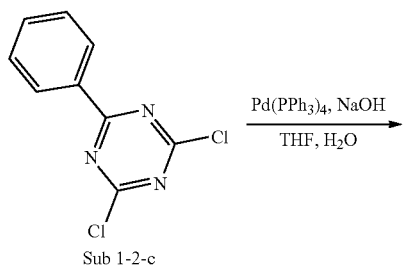

Sub 1-2-c

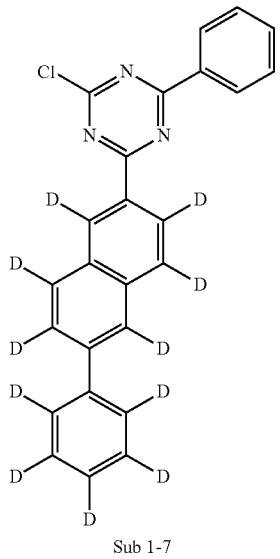

Sub 1-7

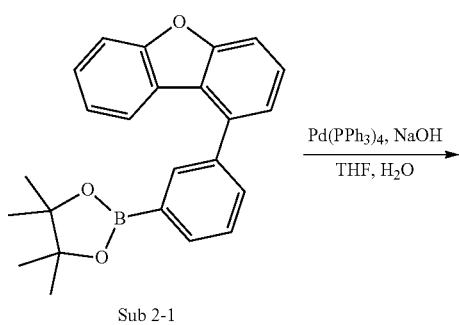

Sub 2-1

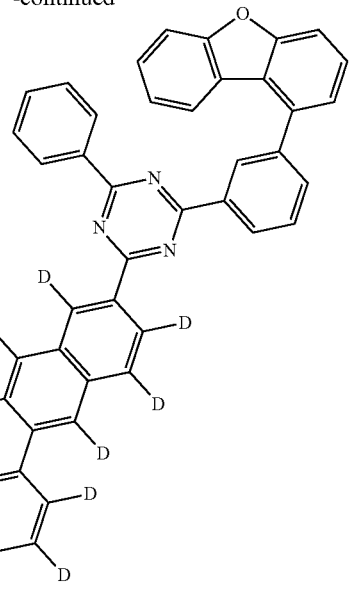

P-21

1) Synthesis of Sub 1-7-a

Sub 1-3-a-a (100.0 g, 478.2 mmol) was added in a round bottom flask, and dissolved in THF (2391 ml), and Sub 1-5-a-b (97.1 g, 478.2 mmol), Pd(PPh$_3$)$_4$ (33.2 g, 28.7 mmol), NaOH (57.4 g, 1434.7 mmol), Water (1196 ml) were added and the experiment was conducted in the same manner as P-1 to obtain 91.9 g of the product. (Yield: 76.9%)

2) Synthesis of Sub 1-7-b

Sub 1-7-a (70.0 g, 280.2 mmol) was added in a round bottom flask, and dissolved in DMF (1401 ml), and 4,4,4',4',5,5,5',5'-octamethyl-2,2'-bi(1,3,2-dioxaborolane) (92.5 g, 364.3 mmol), Pd(dppf)Cl$_2$ (10.2 g, 14.0 mmol), KOAc (82.5 g, 840.7 mmol) were added and the experiment was conducted in the same manner as Sub 1-2b to obtain 77.8 g of the product. (Yield: 81.3%)

3) Synthesis of Sub 1-7

Sub 1-7-b (70.0 g, 205.1 mmol) was added in a round bottom flask, and dissolved in THF (1025 ml), Sub 1-2-c (46.4 g, 205.1 mmol), Pd(PPh$_3$)$_4$ (14.2 g, 12.3 mmol), NaOH (24.6 g, 615.3 mmol), water (513 ml) were added and the experiment was conducted in the same manner as P-1 to obtain 67.3 g of the product. (Yield: 81.0%)

4) Synthesis of P-21

Sub 1-7 (60.0 g, 148.2 mmol) was added in a round bottom flask, and dissolved in THF (741 ml), Sub 2-1 (54.9 g, 148.2 mmol), Pd(PPh$_3$)$_4$ (10.3 g, 8.9 mmol), NaOH (17.8 g, 444.5 mmol), water (370 ml) were added and the experiment was conducted in the same manner as P-1 to obtain 73.7 g of the product. (Yield: 81.2%)

8. Synthesis Example of P-30

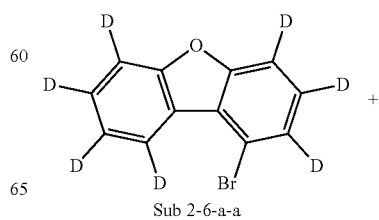

Sub 2-6-a-a

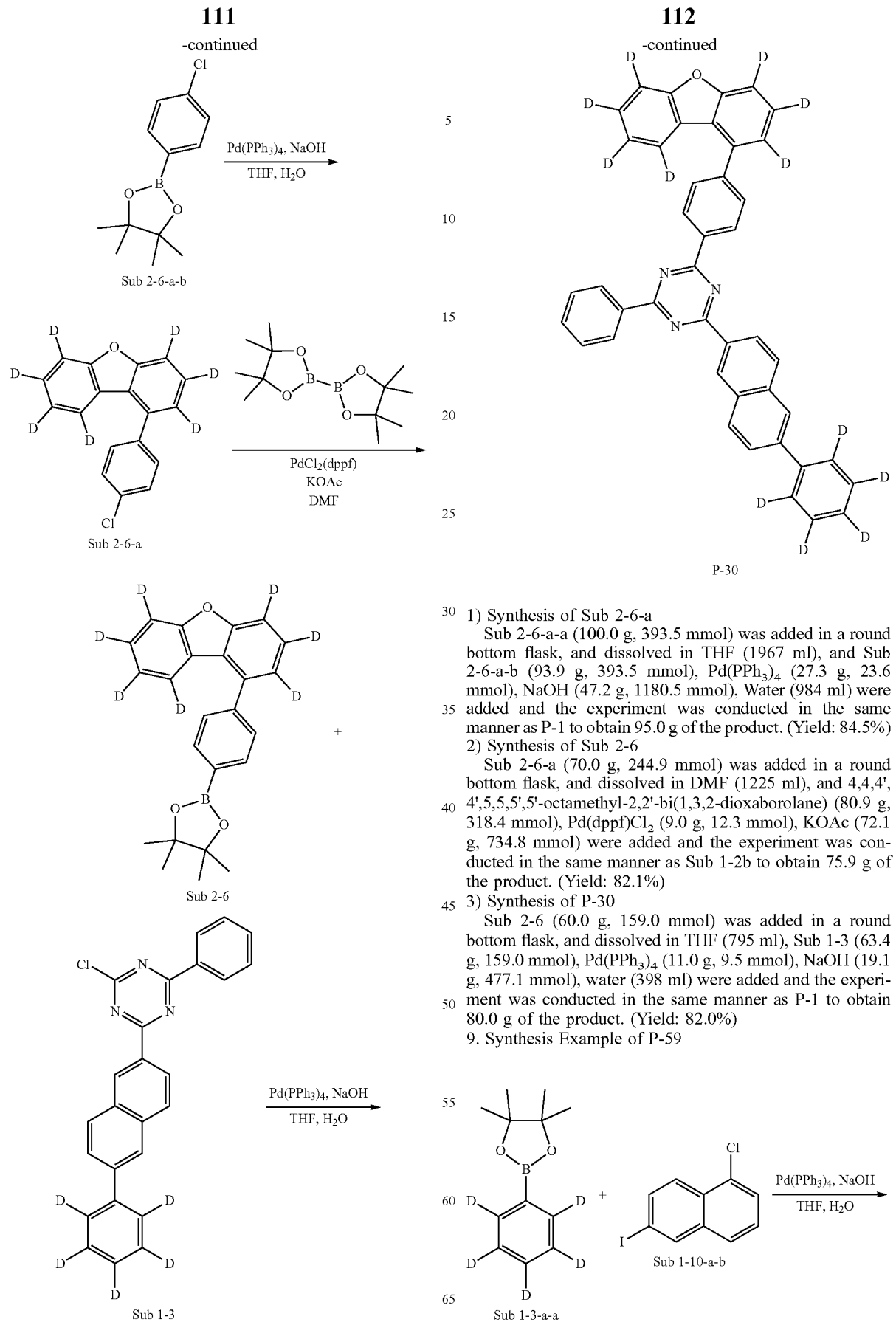

1) Synthesis of Sub 2-6-a
   Sub 2-6-a-a (100.0 g, 393.5 mmol) was added in a round bottom flask, and dissolved in THF (1967 ml), and Sub 2-6-a-b (93.9 g, 393.5 mmol), Pd(PPh$_3$)$_4$ (27.3 g, 23.6 mmol), NaOH (47.2 g, 1180.5 mmol), Water (984 ml) were added and the experiment was conducted in the same manner as P-1 to obtain 95.0 g of the product. (Yield: 84.5%)

2) Synthesis of Sub 2-6
   Sub 2-6-a (70.0 g, 244.9 mmol) was added in a round bottom flask, and dissolved in DMF (1225 ml), and 4,4,4',4',5,5,5',5'-octamethyl-2,2'-bi(1,3,2-dioxaborolane) (80.9 g, 318.4 mmol), Pd(dppf)Cl$_2$ (9.0 g, 12.3 mmol), KOAc (72.1 g, 734.8 mmol) were added and the experiment was conducted in the same manner as Sub 1-2b to obtain 75.9 g of the product. (Yield: 82.1%)

3) Synthesis of P-30
   Sub 2-6 (60.0 g, 159.0 mmol) was added in a round bottom flask, and dissolved in THF (795 ml), Sub 1-3 (63.4 g, 159.0 mmol), Pd(PPh$_3$)$_4$ (11.0 g, 9.5 mmol), NaOH (19.1 g, 477.1 mmol), water (398 ml) were added and the experiment was conducted in the same manner as P-1 to obtain 80.0 g of the product. (Yield: 82.0%)

9. Synthesis Example of P-59

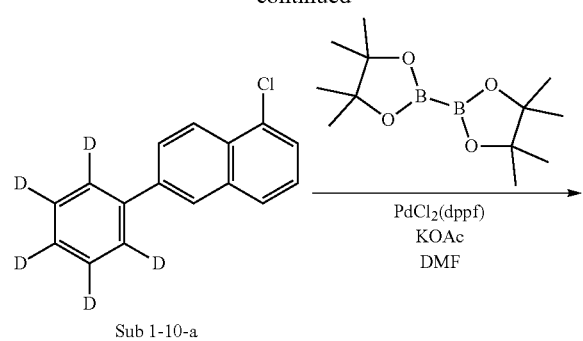
Sub 1-10-a
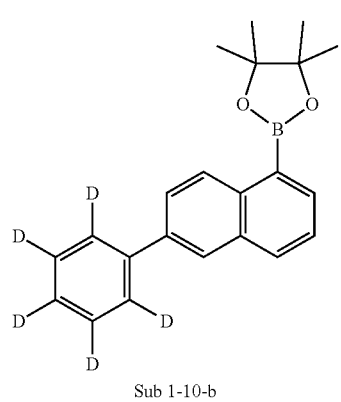
Sub 1-10-b
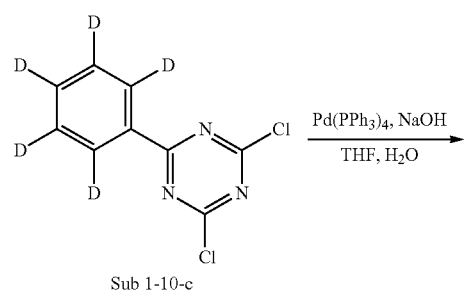
Sub 1-10-c
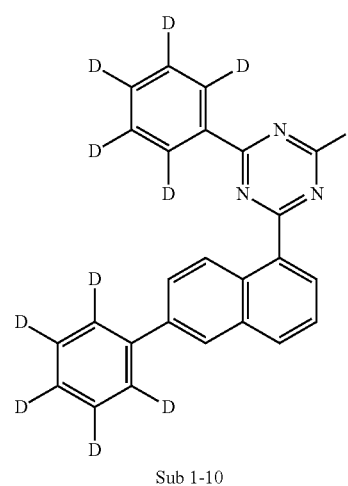
Sub 1-10
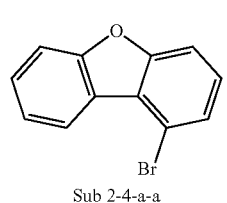
Sub 2-4-a-a
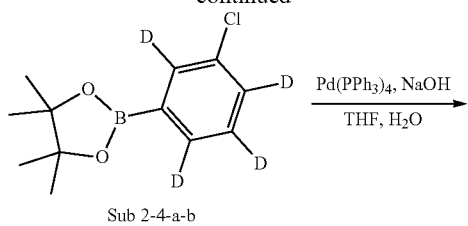
Sub 2-4-a-b
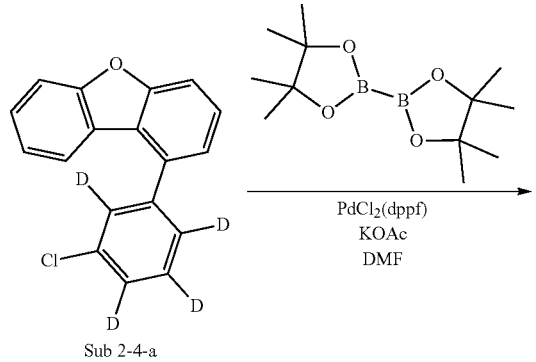
Sub 2-4-a
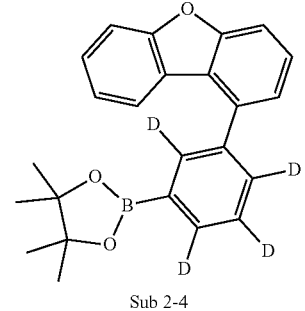
Sub 2-4
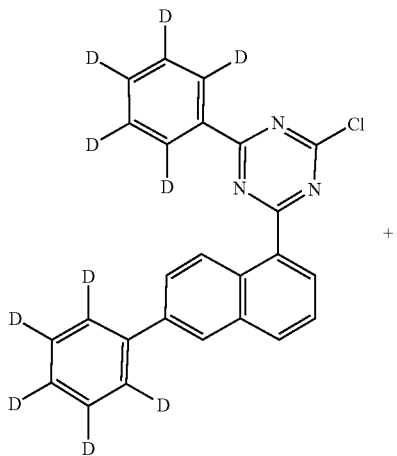
Sub 1-10
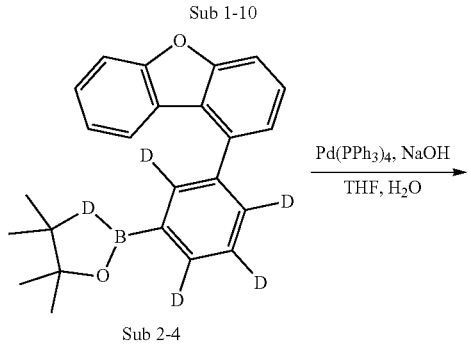
Sub 2-4

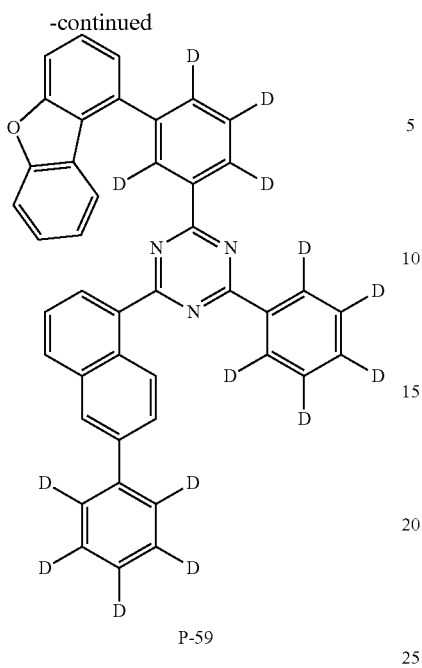

P-59

1) Synthesis of Sub 1-10-a

Sub 1-3-a-a (100.0 g, 478.2 mmol) was added in a round bottom flask, and dissolved in THF (2391 ml), and Sub 1-10-a-b (138.0 g, 478.2 mmol), Pd(PPh₃)₄ (33.2 g, 28.7 mmol), NaOH (57.4 g, 1434.7 mmol), Water (1196 ml) were added and the experiment was conducted in the same manner as P-1 to obtain 94.2 g of the product. (Yield: 80.8%)

2) Synthesis of Sub 1-10-b

Sub 1-10-a (70.0 g, 287.2 mmol) was added in a round bottom flask, and dissolved in DMF (1436 ml), and 4,4,4', 4',5,5,5',5'-octamethyl-2,2'-bi(1,3,2-dioxaborolane) (94.8 g, 373.35 mmol), Pd(dppf)Cl₂ (10.5 g, 14.4 mmol), KOAc (84.6 g, 861.6 mmol) were added and the experiment was conducted in the same manner as Sub 1-2b to obtain 78.9 g of the product. (Yield: 81.9%)

3) Synthesis of Sub 1-10

Sub 1-10-b (70.0 g, 208.8 mmol) was added in a round bottom flask, and dissolved in THE (1044 ml), Sub 1-10-c (48.3 g, 208.8 mmol), Pd(PPh₃)₄ (14.5 g, 12.5 mmol), NaOH (25.1 g, 626.4 mmol), water (522 ml) were added and the experiment was conducted in the same manner as P-1 to obtain 64.4 g of the product. (Yield: 82.4%)

4) Synthesis of Sub 2-4-a

Sub 2-4-a-a (100.0 g, 404.7 mmol) was added in a round bottom flask, and dissolved in THE (2024 ml), Sub 2-4-a-b (98.2 g, 404.7 mmol), Pd(PPh₃)₄ (28.1 g, 24.3 mmol), NaOH (48.6 g, 1214.1 mmol), water (1012 ml) were added and the experiment was conducted in the same manner as P-1 to obtain 91.3 g of the product. (Yield: 79.8%)

5) Synthesis of Sub 2-4

Sub 2-4-a (70.0 g, 247.6 mmol) was added in a round bottom flask, and dissolved in DMF (1238 ml), and 4,4,4', 4',5,5,5',5'-octamethyl-2,2'-bi(1,3,2-dioxaborolane) (81.7 g, 321.8 mmol), Pd(dppf)Cl₂ (9.1 g, 12.4 mmol), KOAc (72.9 g, 742.7 mmol) were added and the experiment was conducted in the same manner as Sub 1-2b to obtain 74.4 g of the product. (Yield: 80.3%)

6) Synthesis of P-59

Sub 1-10 (60.0 g, 148.5 mmol) was added in a round bottom flask, and dissolved in THE (743 ml), Sub 2-4 (55.6 g, 148.5 mmol), Pd(PPh₃)₄ (10.3 g, 8.9 mmol), NaOH (17.8 g, 445.6 mmol), water (371 ml) were added and the experiment was conducted in the same manner as P-1 to obtain 74.6 g of the product. (Yield: 81.6%)

Sub 1 of Reaction scheme 1 may be, but is not limited to, the compounds below, and the FD-MS (Field Desorption-Mass Spectrometry) values of compounds belonging to Sub 1 are as shown in Table 1.

Sub 1-1

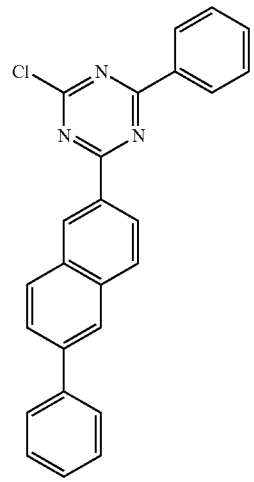

Sub 1-2

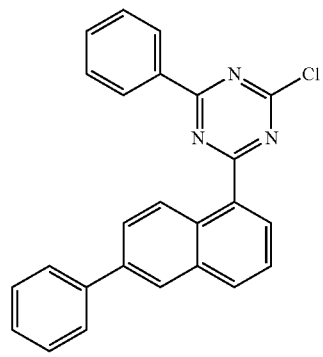

Sub 1-3

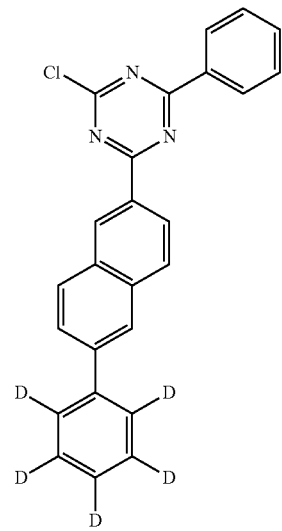

Sub 1-4
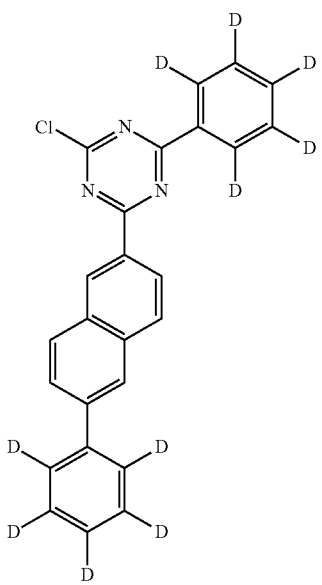
Sub 1-5
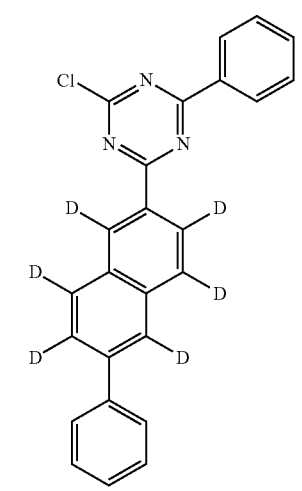
Sub 1-6
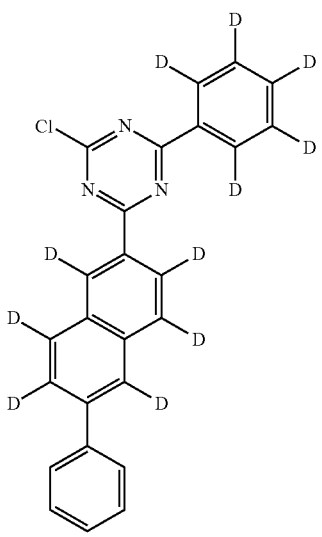
Sub 1-7
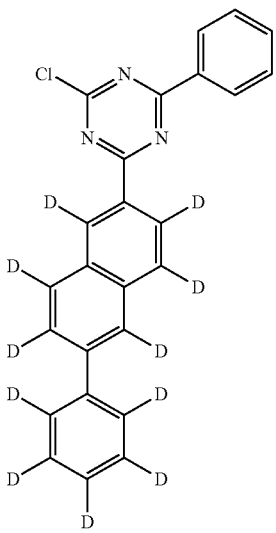
Sub 1-8
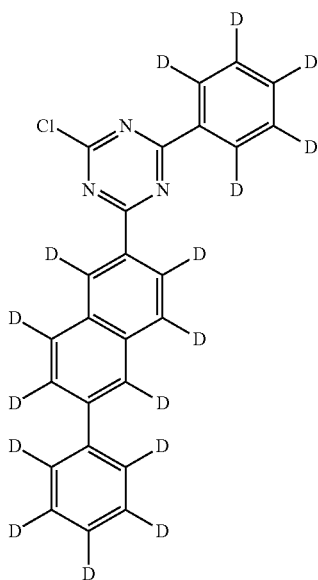
Sub 1-9
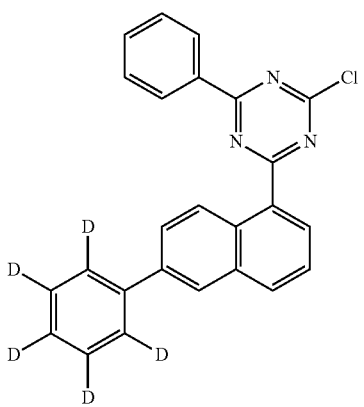

Sub 1-10
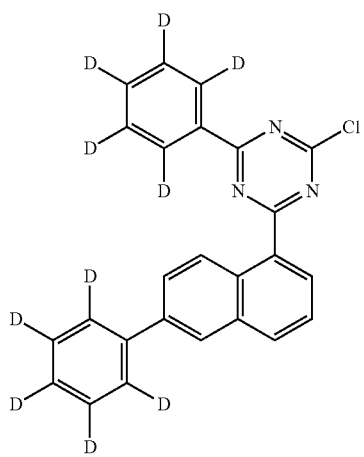
Sub 1-11
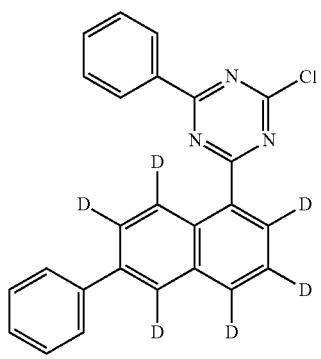
Sub 1-12
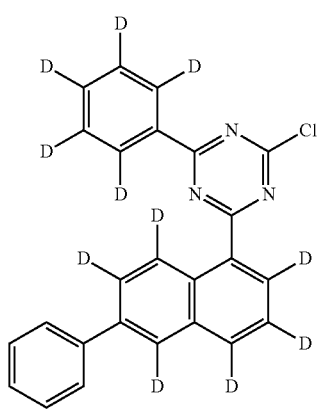
Sub 1-13
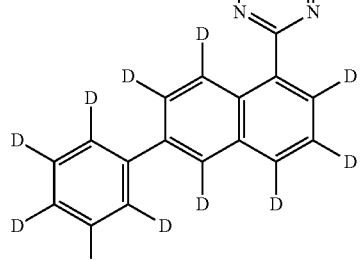
Sub 1-14
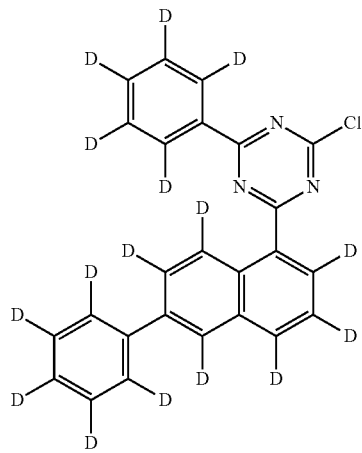
TABLE 1
| compound | FD-MS | compound | FD-MS |
| --- | --- | --- | --- |
| Sub 1-1 | m/z = 393.10($C_{25}H_{16}ClN_3$ = 393.87) | Sub 1-2 | m/z = 393.10($C_{25}H_{16}ClN_3$ = 393.87) |
| Sub 1-3 | m/z = 398.13($C_{25}H_{11}D_5ClN_3$ = 398.90) | Sub 1-4 | m/z = 403.17($C_{25}H_6D_{10}ClN_3$ = 403.94) |
| Sub 1-5 | m/z = 399.14($C_{25}H_{10}D_6ClN_3$ = 399.91) | Sub 1-6 | m/z = 404.17($C_{25}H_5D_{11}ClN_3$ = 404.94) |
| Sub 1-7 | m/z = 404.17($C_{25}H_5D_{11}ClN_3$ = 404.94) | Sub 1-8 | m/z = 409.20($C_{25}D_{16}ClN_3$ = 409.97) |
| Sub 1-9 | m/z = 398.13($C_{25}H_{11}D_5ClN_3$ = 398.90) | Sub 1-10 | m/z = 403.17($C_{25}H_6D_{10}ClN_3$ = 403.94) |
| Sub 1-11 | m/z = 399.14($C_{25}H_{10}D_6ClN_3$ = 399.91) | Sub 1-12 | m/z = 404.17($C_{25}H_5D_{11}ClN_3$ = 404.94) |
| Sub 1-13 | m/z = 404.17($C_{25}H_5D_{11}ClN_3$ = 404.94) | Sub 1-14 | m/z = 409.20($C_{25}D_{16}ClN_3$ = 409.97) |

Sub 2 of Reaction scheme 1 may be, but is not limited to, the compounds below, and the FD-MS (Field Desorption-Mass Spectrometry) values of the compounds belonging to Sub 2 are as shown in Table 2.
Sub 2-1
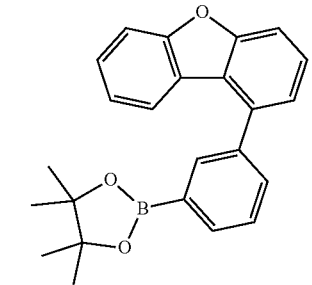
Sub 2-2
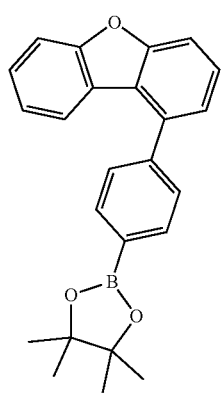
Sub 2-3
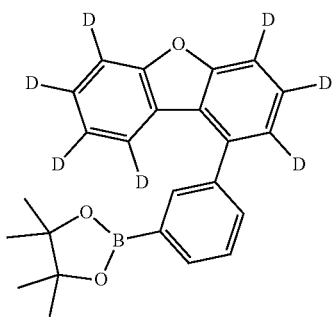
Sub 2-4
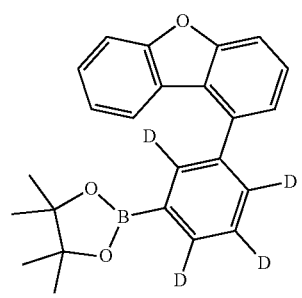
-continued
Sub 2-5
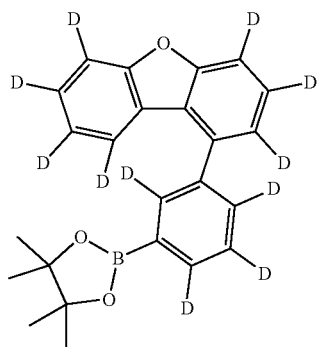
Sub 2-6
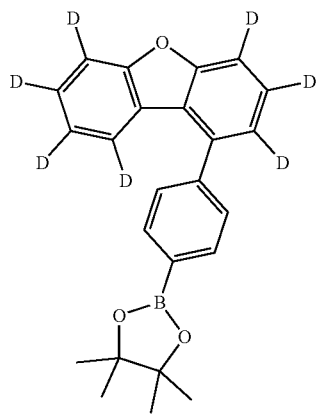
Sub 2-7
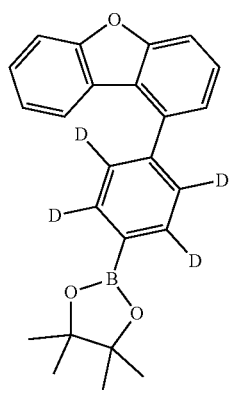
Sub 2-8
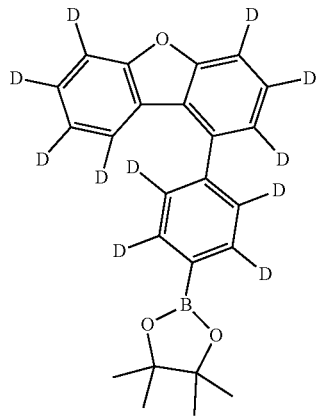

TABLE 2

| compound | FD-MS | compound | FD-MS |
|---|---|---|---|
| Sub 2-1 | m/z = 370.17($C_{24}H_{23}BO_3$ = 370.26) | Sub 2-2 | m/z = 370.17($C_{24}H_{23}BO_3$ = 370.26) |
| Sub 2-3 | m/z = 377.22($C_{24}H_{16}D_7BO_3$ = 377.30) | Sub 2-4 | m/z = 374.20($C_{24}H_{19}D_4BO_3$ = 374.28) |
| Sub 2-5 | m/z = 381.24($C_{24}H_{12}D_{11}BO_3$ = 381.32) | Sub 2-6 | m/z = 377.22($C_{24}H_{16}DBO_3$ = 377.30) |
| Sub 2-7 | m/z = 374.2($C_{24}H_{19}D_4BO_3$ = 374.28) | Sub 2-8 | m/z = 381.24($C_{24}H_{12}D_{11}BO_3$ = 381.32) |

The FD-MS (Field Desorption-Mass Spectrometry) values of compounds P-1 to P-100 of the present invention manufactured according to the above synthetic examples are as shown in Table 3.

TABLE 3

| compound | FD-MS | compound | FD-MS |
|---|---|---|---|
| P-1 | m/z = 601.22($C_{43}H_{27}N_3O$ = 601.71) | P-2 | m/z = 601.22($C_{43}H_{27}N_3O$ = 601.71) |
| P-3 | m/z = 601.22($C_{43}H_{27}N_3O$ = 601.71) | P-4 | m/z = 601.22($C_{43}H_{27}N_3O$ = 601.71) |
| P-5 | m/z = 606.25($C_{43}H_{22}D_5N_3O$ = 606.74) | P-6 | m/z = 613.29($C_{43}H_{15}D_{12}N_3O$ = 613.78) |
| P-7 | m/z = 610.27($C_{43}H_{18}D_9N_3O$ = 610.76) | P-8 | m/z = 617.32($C_{43}H_{11}D_{16}N_3O$ = 617.81) |
| P-9 | m/z = 611.28($C_{43}H_{17}D_{10}N_3O$ = 611.77) | P-10 | m/z = 618.32($C_{43}H_{10}D_{17}N_3O$ = 618.81) |
| P-11 | m/z = 615.30($C_{43}H_{13}D_{14}N_3O$ = 615.79) | P-12 | m/z = 622.35($C_{43}H_6D_{21}N_3O$ = 622.84) |
| P-13 | m/z = 607.25($C_{43}H_{21}D_6N_3O$ = 607.75) | P-14 | m/z = 614.30($C_{43}H_{14}D_{13}N_3O$ = 614.79) |
| P-15 | m/z = 611.28($C_{43}H_{17}D_{10}N_3O$ = 611.77) | P-16 | m/z = 618.32($C_{43}H_{10}D_{17}N_3O$ = 618.81) |
| P-17 | m/z = 612.28($C_{43}H_{16}D_{11}N_3O$ = 612.78) | P-18 | m/z = 619.33($C_{43}H_9D_{18}N_3O$ = 619.82) |
| P-19 | m/z = 616.31($C_{43}H_{12}D_{15}N_3O$ = 616.80) | P-20 | m/z = 623.35($C_{43}H_5D_{22}N_3O$ = 623.84) |
| P-21 | m/z = 612.28($C_{43}H_{16}D_{11}N_3O$ = 612.78) | P-22 | m/z = 619.33($C_{43}H_9D_{18}N_3O$ = 619.82) |
| P-23 | m/z = 616.31($C_{43}H_{12}D_{15}N_3O$ = 616.80) | P-24 | m/z = 623.35($C_{43}H_5D_{22}N_3O$ = 623.84) |
| P-25 | m/z = 617.32($C_{43}H_{11}D_{16}N_3O$ = 617.81) | P-26 | m/z = 624.36($C_{43}H_4D_{23}N_3O$ = 624.85) |
| P-27 | m/z = 621.34($C_{43}H_7D_{20}N_3O$ = 621.83) | P-28 | m/z = 628.38($C_{43}D_{27}N_3O$ = 628.87) |
| P-29 | m/z = 606.25($C_{43}H_{22}D_5N_3O$ = 606.74) | P-30 | m/z = 613.29($C_{43}H_{15}D_{12}N_3O$ = 613.78) |
| P-31 | m/z = 610.27($C_{43}H_{18}D_9N_3O$ = 610.76) | P-32 | m/z = 617.32($C_{43}H_{11}D_{16}N_3O$ = 617.81) |
| P-33 | m/z = 611.28($C_{43}H_{17}D_{10}N_3O$ = 611.77) | P-34 | m/z = 618.32($C_{43}H_{10}D_{17}N_3O$ = 618.81) |
| P-35 | m/z = 615.30($C_{43}H_{13}D_{14}N_3O$ = 615.79) | P-36 | m/z = 622.35($C_{43}H_6D_{21}N_3O$ = 622.84) |
| P-37 | m/z = 607.25($C_{43}H_{21}D_6N_3O$ = 607.75) | P-38 | m/z = 614.30($C_{43}H_{14}D_{13}N_3O$ = 614.79) |
| P-39 | m/z = 611.28($C_{43}H_{17}D_{10}N_3O$ = 611.77) | P-40 | m/z = 618.32($C_{43}H_{10}D_{17}N_3O$ = 618.81) |
| P-41 | m/z = 612.28($C_{43}H_{16}D_{11}N_3O$ = 612.78) | P-42 | m/z = 619.33($C_{43}H_9D_{18}N_3O$ = 619.82) |
| P-43 | m/z = 616.31($C_{43}H_{12}D_{15}N_3O$ = 616.80) | P-44 | m/z = 623.35($C_{43}H_5D_{22}N_3O$ = 623.84) |
| P-45 | m/z = 612.28($C_{43}H_{16}D_{11}N_3O$ = 612.78) | P-46 | m/z = 619.33($C_{43}H_9D_{18}N_3O$ = 619.82) |
| P-47 | m/z = 616.31($C_{43}H_{12}D_{15}N_3O$ = 616.80) | P-48 | m/z = 623.35($C_{43}H_5D_{22}N_3O$ = 623.84) |
| P-49 | m/z = 617.32($C_{43}H_{11}D_{16}N_3O$ = 617.81) | P-50 | m/z = 624.36($C_{43}H_4D_{23}N_3O$ = 624.85) |
| P-51 | m/z = 621.34($C_{43}H_7D_{20}N_3O$ = 621.83) | P-52 | m/z = 628.38($C_{43}D_{27}N_3O$ = 628.87) |
| P-53 | m/z = 606.25($C_{43}H_{22}D_5N_3O$ = 606.74) | P-54 | m/z = 613.29($C_{43}H_{15}D_{12}N_3O$ = 613.78) |
| P-55 | m/z = 610.27($C_{43}H_{18}D_9N_3O$ = 610.76) | P-56 | m/z = 617.32($C_{43}H_{11}D_{16}N_3O$ = 617.81) |
| P-57 | m/z = 611.28($C_{43}H_{17}D_{10}N_3O$ = 611.77) | P-58 | m/z = 618.32($C_{43}H_{10}D_{17}N_3O$ = 618.81) |
| P-59 | m/z = 615.30($C_{43}H_{13}D_{14}N_3O$ = 615.79) | P-60 | m/z = 622.35($C_{43}H_6D_{21}N_3O$ = 622.84) |
| P-61 | m/z = 607.25($C_{43}H_{21}D_6N_3O$ = 607.75) | P-62 | m/z = 614.30($C_{43}H_{14}D_{13}N_3O$ = 614.79) |
| P-63 | m/z = 611.28($C_{43}H_{17}D_{10}N_3O$ = 611.77) | P-64 | m/z = 618.32($C_{43}H_{10}D_{17}N_3O$ = 618.81) |
| P-65 | m/z = 612.28($C_{43}H_{16}D_{11}N_3O$ = 612.78) | P-66 | m/z = 619.33($C_{43}H_9D_{18}N_3O$ = 619.82) |
| P-67 | m/z = 616.31($C_{43}H_{12}D_{15}N_3O$ = 616.80) | P-68 | m/z = 623.35($C_{43}H_5D_{22}N_3O$ = 623.84) |
| P-69 | m/z = 612.28($C_{43}H_{16}D_{11}N_3O$ = 612.78) | P-70 | m/z = 619.33($C_{43}H_9D_{18}N_3O$ = 619.82) |
| P-71 | m/z = 616.31($C_{43}H_{12}D_{15}N_3O$ = 616.80) | P-72 | m/z = 623.35($C_{43}H_5D_{22}N_3O$ = 623.84) |
| P-73 | m/z = 617.32($C_{43}H_{11}D_{16}N_3O$ = 617.81) | P-74 | m/z = 624.36($C_{43}H_4D_{23}N_3O$ = 624.85) |
| P-75 | m/z = 621.34($C_{43}H_7D_{20}N_3O$ = 621.83) | P-76 | m/z = 628.38($C_{43}D_{27}N_3O$ = 628.87) |
| P-77 | m/z = 606.25($C_{43}H_{22}D_5N_3O$ = 606.74) | P-78 | m/z = 613.29($C_{43}H_{15}D_{12}N_3O$ = 613.78) |
| P-79 | m/z = 610.27($C_{43}H_{18}D_9N_3O$ = 610.76) | P-80 | m/z = 617.32($C_{43}H_{11}D_{16}N_3O$ = 617.81) |
| P-81 | m/z = 611.28($C_{43}H_{17}D_{10}N_3O$ = 611.77) | P-82 | m/z = 618.32($C_{43}H_{10}D_{17}N_3O$ = 618.81) |
| P-83 | m/z = 615.30($C_{43}H_{13}D_{14}N_3O$ = 615.79) | P-84 | m/z = 622.35($C_{43}H_6D_{21}N_3O$ = 622.84) |
| P-85 | m/z = 607.25($C_{43}H_{21}D_6N_3O$ = 607.75) | P-86 | m/z = 614.30($C_{43}H_{14}D_{13}N_3O$ = 614.79) |
| P-87 | m/z = 611.28($C_{43}H_{17}D_{10}N_3O$ = 611.77) | P-88 | m/z = 618.32($C_{43}H_{10}D_{17}N_3O$ = 618.81) |
| P-89 | m/z = 612.28($C_{43}H_{16}D_{11}N_3O$ = 612.78) | P-90 | m/z = 619.33($C_{43}H_9D_{18}N_3O$ = 619.82) |
| P-91 | m/z = 616.31($C_{43}H_{12}D_{15}N_3O$ = 616.80) | P-92 | m/z = 623.35($C_{43}H_5D_{22}N_3O$ = 623.84) |
| P-93 | m/z = 612.28($C_{43}H_{16}D_{11}N_3O$ = 612.78) | P-94 | m/z = 619.33($C_{43}H_9D_{18}N_3O$ = 619.82) |
| P-95 | m/z = 616.31($C_{43}H_{12}D_{15}N_3O$ = 616.80) | P-96 | m/z = 623.35($C_{43}H_5D_{22}N_3O$ = 623.84) |
| P-97 | m/z = 617.32($C_{43}H_{11}D_{16}N_3O$ = 617.81) | P-98 | m/z = 624.36($C_{43}H_4D_{23}N_3O$ = 624.85) |
| P-99 | m/z = 621.34($C_{43}H_7D_{20}N_3O$ = 621.83) | P-100 | m/z = 628.38($C_{43}D_{27}N_3O$ = 628.87) |

The compound represented by Formula 5 can be prepared by a known synthetic method (named reaction) or by referring to published patent publications, such as Korean Patent Registration No. 10-2395819 and U.S. Patent Publication No. 2023-0129535, but is not limited thereto.

Meanwhile, the FD-MS (Field Desorption-Mass Spectrometry) values of compounds S-1 to S-108 of the present invention are as shown in Table 4.

TABLE 4

| compound | FD-MS | compound | FD-MS |
| --- | --- | --- | --- |
| S-1 | m/z = 408.16($C_{30}H_{20}N_2$ = 408.50) | S-2 | m/z = 534.21($C_{40}H_{26}N_2$ = 534.66) |
| S-3 | m/z = 560.23($C_{42}H_{28}N_2$ = 560.70) | S-4 | m/z = 584.23($C_{44}H_{28}N_2$ = 584.72) |
| S-5 | m/z = 560.23($C_{42}H_{28}N_2$ = 560.70) | S-6 | m/z = 634.24($C_{48}H_{30}N_2$ = 634.78) |
| S-7 | m/z = 610.24($C_{46}H_{30}N_2$ = 610.76) | S-8 | m/z = 498.17($C_{36}H_{22}N_2O$ = 498.59) |
| S-9 | m/z = 574.20($C_{42}H_{26}N_2O$ = 574.68) | S-10 | m/z = 660.26($C_{50}H_{32}N_2$ = 660.82) |
| S-11 | m/z = 686.27($C_{52}H_{34}N_2$ = 686.86) | S-12 | m/z = 620.14($C_{42}H_{24}N_2S_2$ = 620.79) |
| S-13 | m/z = 640.20($C_{46}H_{28}N_2S$ = 640.80) | S-14 | m/z = 560.23($C_{42}H_{28}N_2$ = 560.70) |
| S-15 | m/z = 558.21($C_{42}H_{26}N_2$ = 558.68) | S-16 | m/z = 548.19($C_{40}H_{24}N_2O$ = 548.65) |
| S-17 | m/z = 573.22($C_{42}H_{27}N_3$ = 573.70) | S-18 | m/z = 564.17($C_{40}H_{24}N_2S$ = 564.71) |
| S-19 | m/z = 574.20($C_{42}H_{26}N_2O$ = 574.68) | S-20 | m/z = 564.17($C_{40}H_{24}N_2S$ = 564.71) |
| S-21 | m/z = 564.17($C_{40}H_{24}N_2S$ = 564.71) | S-22 | m/z = 813.31($C_{61}H_{39}N_3$ = 814.00) |
| S-23 | m/z = 696.26($C_{53}H_{32}N_2$ = 696.85) | S-24 | m/z = 691.23($C_{49}H_{29}N_3O_2$ = 691.79) |
| S-25 | m/z = 710.27($C_{54}H_{34}N_2$ = 710.88) | S-26 | m/z = 610.24($C_{46}H_{30}N_2$ = 610.76) |
| S-27 | m/z = 670.15($C_{46}H_{26}N_2S_2$ = 670.85) | S-28 | m/z = 640.29($C_{48}H_{36}N_2$ = 640.83) |
| S-29 | m/z = 598.20($C_{44}H_{26}N_2O$ = 598.71) | S-30 | m/z = 623.24($C_{46}H_{29}N_3$ = 623.76) |
| S-31 | m/z = 458.18($C_{34}H_{22}N_2$ = 458.56) | S-32 | m/z = 548.19($C_{40}H_{24}N_2O$ = 548.65) |
| S-33 | m/z = 508.19($C_{38}H_{24}N_2$ = 508.62) | S-34 | m/z = 508.19($C_{38}H_{24}N_2$ = 508.62) |
| S-35 | m/z = 623.24($C_{46}H_{29}N_3$ = 623.76) | S-36 | m/z = 564.17($C_{40}H_{24}N_2S$ = 564.71) |
| S-37 | m/z = 627.20($C_{46}H_{29}NS$ = 627.81) | S-38 | m/z = 505.10($C_{34}H_{19}NS_2$ = 505.65) |
| S-39 | m/z = 514.15($C_{36}H_{22}N_2S$ = 514.65) | S-40 | m/z = 575.17($C_{42}H_{25}NS$ = 575.73) |
| S-41 | m/z = 642.21($C_{46}H_{30}N_2S$ = 642.82) | S-42 | m/z = 575.17($C_{42}H_{25}NS$ = 575.73) |
| S-43 | m/z = 606.18($C_{42}H_{26}N_2OS$ = 606.74) | S-44 | m/z = 575.17($C_{42}H_{25}NS$ = 575.73) |
| S-45 | m/z = 551.17($C_{40}H_{25}NS$ = 551.71) | S-46 | m/z = 607.14($C_{42}H_{25}NS_2$ = 607.79) |
| S-47 | m/z = 525.16($C_{38}H_{23}NS$ = 525.67) | S-48 | m/z = 642.21($C_{46}H_{30}N_2S$ = 642.82) |
| S-49 | m/z = 548.19($C_{40}H_{24}N_2O$ = 548.65) | S-50 | m/z = 473.14($C_{34}H_{19}NO_2$ = 473.53) |
| S-51 | m/z = 566.15($C_{39}H_{22}N_2OS$ = 566.68) | S-52 | m/z = 459.16($C_{34}H_{21}NO$ = 459.55) |
| S-53 | m/z = 473.14($C_{34}H_{19}NO2$ = 473.53) | S-54 | m/z = 523.16($C_{38}H_{21}NO_2$ = 523.59) |
| S-55 | m/z = 539.13($C_{38}H_{21}NOS$ = 539.65) | S-56 | m/z = 548.19($C_{40}H_{24}N_2O$ = 548.65) |
| S-57 | m/z = 489.12($C_{34}H_{19}NOS$ = 489.59) | S-58 | m/z = 545.09($C_{36}H_{19}NOS_2$ = 545.67) |
| S-59 | m/z = 549.17($C_{40}H_{23}NO_2$ = 549.63) | S-60 | m/z = 565.15($C_{40}H_{23}NOS$ = 565.69) |
| S-61 | m/z = 523.16($C_{38}H_{21}NO_2$ = 523.59) | S-62 | m/z = 598.2($C_{44}H_{26}N_2O$ = 598.71) |
| S-63 | m/z = 539.13($C_{38}H_{21}NOS$ = 539.65) | S-64 | m/z = 589.15($C_{42}H_{23}NOS$ = 589.71) |
| S-65 | m/z = 498.17($C_{36}H_{22}N_2O$ = 498.59) | S-66 | m/z = 509.18($C_{38}H_{23}NO$ = 509.61) |
| S-67 | m/z = 548.19($C_{40}H_{24}N_2O$ = 548.65) | S-68 | m/z = 549.17($C_{40}H_{23}NO_2$ = 549.63) |
| S-69 | m/z = 449.12($C_{32}H_{19}NS$ = 449.57) | S-70 | m/z = 439.1($C_{30}H_{17}NOS$ = 439.53) |
| S-71 | m/z = 647.22($C_{49}H_{29}NO$ = 647.78) | S-72 | m/z = 717.28($C_{52}H_{35}N_3O$ = 717.87) |
| S-73 | m/z = 459.16($C_{34}H_{21}NO$ = 459.55) | S-74 | m/z = 533.18($C_{40}H_{23}NO$ = 533.63) |
| S-75 | m/z = 525.16($C_{38}H_{23}NS$ = 525.67) | S-76 | m/z = 564.17($C_{40}H_{24}N_2S$ = 564.71) |
| S-77 | m/z = 575.19($C_{42}H_{25}NO_2$ = 575.67) | S-78 | m/z = 663.22($C_{49}H_{29}NO_2$ = 663.78) |
| S-79 | m/z = 647.22($C_{49}H_{29}NO$ = 647.78) | S-80 | m/z = 496.16($C_{36}H_{20}N_2O$ = 496.57) |
| S-81 | m/z = 565.15($C_{40}H_{23}NOS$ = 565.69) | S-82 | m/z = 505.1($C_{34}H_{19}NS2$ = 505.65) |
| S-83 | m/z = 765.25($C_{56}H_{35}NOSi$ = 765.99) | S-84 | m/z = 615.17($C_{44}H_{25}NOS$ = 615.75) |
| S-85 | m/z = 603.17($C_{43}H_{25}NOS$ = 603.74) | S-86 | m/z = 772.29($C_{59}H_{36}N_2$ = 772.95) |
| S-87 | m/z = 802.33($C_{61}H_{42}N_2$ = 803.02) | S-88 | m/z = 607.23($C_{47}H_{29}N$ = 607.76) |
| S-89 | m/z = 524.23($C_{39}H_{28}N_2$ = 524.67) | S-90 | m/z = 665.22($C_{49}H_{31}NS$ = 665.85) |
| S-91 | m/z = 633.25($C_{49}H_{31}N$ = 633.79) | S-92 | m/z = 775.29($C_{59}H_{37}NO$ = 775.95) |
| S-93 | m/z = 535.23($C_{41}H_{29}N$ = 535.69) | S-94 | m/z = 623.22($C_{47}H_{29}NO$ = 623.76) |
| S-95 | m/z = 687.20($C_{51}H_{29}NS$ = 687.86) | S-96 | m/z = 735.29($C_{57}H_{37}N$ = 735.93) |
| S-97 | m/z = 611.26($C_{47}H_{33}N$ = 611.79) | S-98 | m/z = 679.23($C_{50}H_{33}NS$ = 679.88) |
| S-99 | m/z = 787.32($C_{61}H_{41}N$ = 788.01) | S-100 | m/z = 743.33($C_{55}H_{41}N_3$ = 743.95) |
| S-101 | m/z = 485.21($C_{37}H_{27}N$ = 485.63) | S-102 | m/z = 471.20($C_{36}H_{25}N$ = 471.60) |
| S-103 | m/z = 571.19($C_{43}H_{25}NO$ = 571.68) | S-104 | m/z = 584.23($C_{44}H_{28}N_2$ = 584.72) |
| S-105 | m/z = 539.24($C_{40}H_{21}D_5N_2$ = 539.69) | S-106 | m/z = 453.15($C_{32}H_{15}NS$ = 471.6) |
| S-107 | m/z = 563.26($C_{43}H_{26}D_4NO$ = 563.74) | S-108 | m/z = 589.26($C_{44}H_{23}D_5N_2$ = 584.72) |
| S-109 | m/z = 589.26($C_{44}H_{23}D_5N_2$ = 589.75) | S-110 | m/z = 562.23($C_{42}H_{22}D_4N_2$ = 562.71) |
| S-111 | m/z = 660.26($C_{50}H_{32}N_2$ = 660.82) | S-112 | m/z = 553.22($C_{40}H_{19}D_5N_2O$ = 553.68) |
| S-113 | m/z = 634.24($C_{48}H_{30}N_2$ = 634.78) | S-114 | m/z = 589.26($C_{44}H_{23}D_5N_2$ = 589.75) |
| S-115 | m/z = 588.25($C_{44}H_{24}D_4N_2$ = 588.75) | S-116 | m/z = 513.23($C_{38}H_{19}D_5N_2$ = 513.65) |

In the above, exemplary synthesis examples of the present invention represented by Formula and Formula 5 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095), Pd(II)-catalyzed oxidative cyclization reaction (*Org. Lett.* 2011, 13, 5504), and PPh$_3$-mediated reductive cyclization reaction (*J. Org. Chem.* 2005, 70, 5014), and it will be easily understood by those skilled in the art that the reaction proceeds even when other substituents defined in Formula or Formula 5 are bonded in addition to the substituents specified in the specific synthesis examples.

Manufacturing and Evaluation of Organic Electronic Element

[Example 1] Red Organic Light Emitting Device (Phosphorescent Host)

Compound A and Compound B were used on an ITO layer (anode) formed on a glass substrate, and Compound B was doped at a weight ratio of 98:2 to form a hole injection layer with a thickness of 10 nm. Then, Compound A was vacuum-deposited on the hole injection layer with a thickness of 110 nm to form a hole transport layer.

Next, compound C-R was vacuum-deposited on the hole transport layer to a thickness of 10 nm to form an emitting auxiliary layer. Thereafter, the host material of the emitting layer uses compound P-1, a compound of the present invention, as the first host, and compound S-32, a compound of the present invention, as the second host, and uses a mixture in which the first host and the second host are mixed at a weight ratio of 5:5. Bis-(1-phenylisoquinolyl)iridium(III) acetylacetonate (hereinafter abbreviated as '(piq)2Ir(acac)') was used as a dopant material, and the dopant was doped so that the weight ratio of the host and dopant was 95:5 to form a emitting layer with a thickness of 30 nm.

Next, compound E was vacuum-deposited on the emitting layer to form a hole blocking layer with a thickness of 10 nm, and an electron transport layer with a thickness of 30 nm was formed on the hole blocking layer using a mixture of compounds F and G at a weight ratio of 5:5. Afterwards, compound G was deposited on the electron transport layer to form an electron injection layer with a thickness of 0.2 nm, and then Al was deposited to form a cathode with a thickness of 150 nm.

compound A N-([1,1'-biphenyl]-4-yl)-9,9-dimethyl-N-(4-(9-phenyl-9H-carbazol-3-yl)phenyl)-9H-fluoren-2-amine compound B:4,4',4"-((1E,1'E,1"E)-cyclopropane-1,2,3-triylidenetris(cyanomethaneylylidene))tris(2,3,5,6-tetrafluorobenzonitrile)

compound C-R: N-(dibenzo[b,d]thiophen-2-yl)-N$^2$,N$^2$,N$^7$-triphenyldibenzo[b,d]thiophene-2,7-diamine compound E: 2-(4'-(9,9-dimethyl-9H-fluoren-2-yl)-[1,1'-biphenyl]-3-yl)-4,6-diphenyl-1,3,5-triazine compound F: 2,7-bis(4-(4,6-diphenyl-1,3,5-triazin-2-yl)phenyl)naphthalene compound G: (8-quinolinolato)lithium

[Example 2] to [Example 55]

An organic electroluminescent device was manufactured in the same manner as Example 1, except that the compound of the present invention described in Table 5 was used as the host material of the emitting layer.

[Comparative Example 1] to [Comparative Example 9]

An organic electroluminescent device was manufactured in the same manner as Example 1, except that Comparative Compounds A to C were used as the first host, or Comparative Compound 1 or Comparative Compound 2 was used as the second host, as the host material of the emitting layer.

[Comparative Compound A][Comparative Compound B]

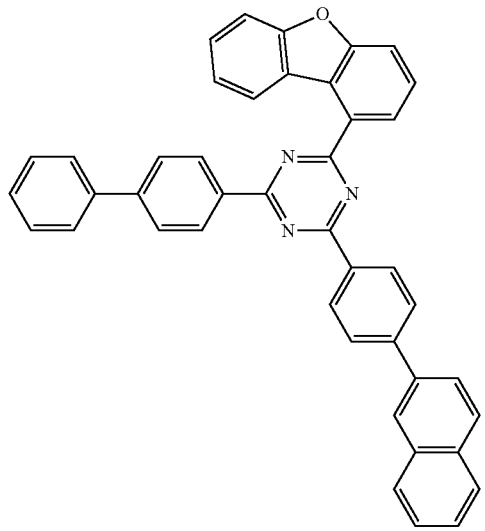

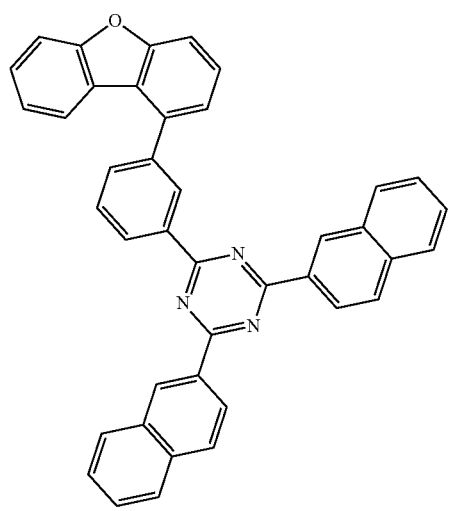

[Comparative Compound C]

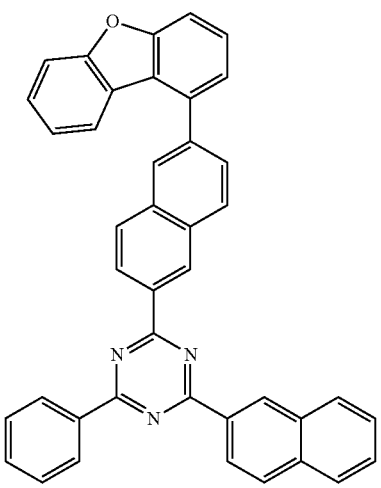 [SMILES: c1ccc(-c2nc(-c3ccc4ccccc4c3)nc(-c3ccc4cc(-c5cccc6oc7ccccc7c56)ccc4c3)n2)cc1]

[Comparative Compound 1][Comparative Compound 2]

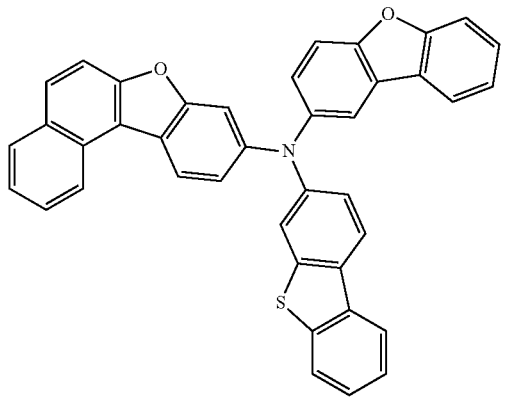

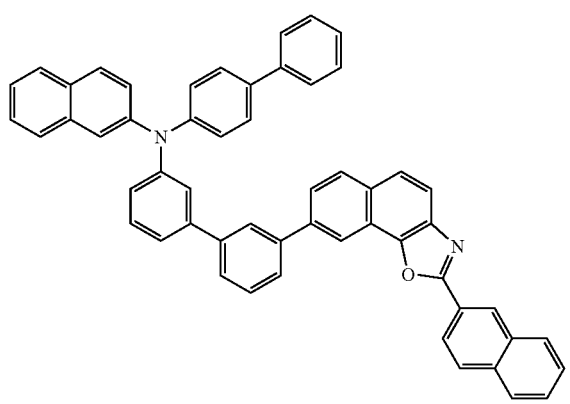

Example 56

An organic electroluminescent device was manufactured in the same manner as in Example 1, except that the compound P-1 of the present invention was used as a host material of the emitting layer without a second host.

[Example 57] to [Example 76]

An organic electroluminescent device was manufactured in the same manner as Example 56, except that the compound of the present invention described in Table 6 was used as the host material of the emitting layer.

[Comparative Example 10] to [Comparative Example 12]

An organic electroluminescent device was manufactured in the same manner as Example 56, except that one of the comparative compound A, comparative compound B, and comparative compound D was used as the host material of the emitting layer.

[Comparative Compound D]

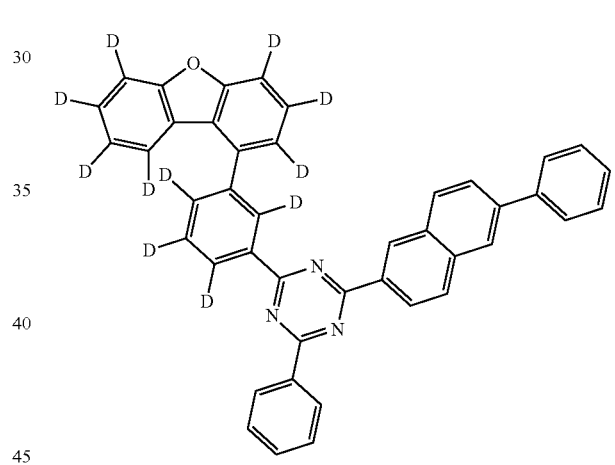

Electroluminescence (EL) characteristics were measured using PR-650 from Photoresearch by applying a forward bias DC voltage to the organic electroluminescence devices manufactured by Examples 1 to 76 of the present invention and Comparative Examples 1 to 12, and the T95 lifespan was measured using a lifespan measuring device manufactured by Maxscience at a reference luminance of 2,500 cd/in$^2$. Tables 5 and 6 show the results of fabrication and evaluation of components according to the examples.

This measuring device allows the performance of new materials to be evaluated against reference compounds under identical conditions, without being affected by possible daily variations in deposition rate, vacuum quality or other parameters.

Since, during the evaluation, one batch contains 4 identically prepared OLEDs including a comparison compound, and the performance of a total of 12 OLEDs is evaluated in 3 batches, the values of the experimental results obtained in this way exhibit statistical significance.

TABLE 5

| | First compound | Second compound | Driving voltage | Current Density (mA/cm²) | Brightness (cd/m²) | Efficiency (cd/A) | T(95) |
|---|---|---|---|---|---|---|---|
| comparative example 1 | comparative compound A | S-32 | 5.0 | 10.5 | 2500.0 | 23.7 | 96.8 |
| comparative example 2 | comparative compound B | S-32 | 5.3 | 10.8 | 2500.0 | 23.1 | 100.2 |
| comparative example 3 | comparative compound C | S-32 | 5.4 | 10.9 | 2500.0 | 22.9 | 99.5 |
| comparative example 4 | P-1 | comparative compound 1 | 4.9 | 8.7 | 2500.0 | 28.7 | 104.8 |
| comparative example 5 | P-25 | comparative compound 2 | 4.7 | 9.2 | 2500.0 | 27.3 | 108.7 |
| comparative example 6 | comparative compound A | comparative compound 1 | 5.3 | 11.7 | 2500.0 | 21.3 | 93.3 |
| comparative example 7 | comparative compound A | comparative compound 2 | 5.2 | 11.7 | 2500.0 | 21.4 | 92.9 |
| comparative example 8 | comparative compound B | comparative compound 1 | 5.4 | 11.4 | 2500.0 | 22.0 | 94.7 |
| comparative example 9 | comparative compound B | comparative compound 2 | 5.5 | 12.2 | 2500.0 | 20.5 | 93.0 |
| example1 | P-1 | S-32 | 4.3 | 5.7 | 2500.0 | 43.8 | 131.1 |
| example2 | P-2 | S-32 | 4.4 | 5.4 | 2500.0 | 46.5 | 130.1 |
| example3 | P-3 | S-32 | 4.4 | 5.6 | 2500.0 | 44.6 | 128.9 |
| example4 | P-4 | S-32 | 4.4 | 5.5 | 2500.0 | 45.4 | 129.4 |
| example5 | P-5 | S-32 | 4.3 | 5.6 | 2500.0 | 44.4 | 143.0 |
| example6 | P-10 | S-32 | 4.3 | 5.4 | 2500.0 | 46.2 | 143.4 |
| example7 | P-15 | S-32 | 4.4 | 5.7 | 2500.0 | 43.6 | 142.1 |
| example8 | P-20 | S-32 | 4.3 | 5.4 | 2500.0 | 46.4 | 141.4 |
| example9 | P-21 | S-32 | 4.5 | 5.5 | 2500.0 | 45.5 | 141.3 |
| example10 | P-26 | S-32 | 4.4 | 5.5 | 2500.0 | 45.7 | 141.4 |
| example11 | P-31 | S-32 | 4.5 | 5.4 | 2500.0 | 45.9 | 141.6 |
| example12 | P-36 | S-32 | 4.4 | 5.5 | 2500.0 | 45.2 | 141.3 |
| example13 | P-40 | S-32 | 4.3 | 5.6 | 2500.0 | 44.9 | 141.6 |
| example14 | P-43 | S-40 | 4.4 | 5.8 | 2500.0 | 42.9 | 138.9 |
| example15 | P-49 | S-40 | 4.4 | 5.8 | 2500.0 | 42.9 | 141.1 |
| example16 | P-54 | S-40 | 4.3 | 5.8 | 2500.0 | 43.4 | 141.1 |
| example17 | P-64 | S-40 | 4.3 | 5.8 | 2500.0 | 43.2 | 140.6 |
| example18 | P-67 | S-40 | 4.5 | 5.8 | 2500.0 | 43.1 | 139.4 |
| example19 | P-73 | S-40 | 4.3 | 5.8 | 2500.0 | 43.4 | 140.0 |
| example20 | P-78 | S-40 | 4.3 | 5.8 | 2500.0 | 42.8 | 140.9 |
| example21 | P-88 | S-40 | 4.5 | 5.8 | 2500.0 | 42.8 | 138.2 |
| example22 | P-91 | S-40 | 4.3 | 5.9 | 2500.0 | 42.5 | 138.3 |
| example23 | P-1 | S-55 | 4.3 | 6.1 | 2500.0 | 41.0 | 127.6 |
| example24 | P-2 | S-55 | 4.3 | 6.1 | 2500.0 | 41.1 | 126.2 |
| example25 | P-3 | S-55 | 4.4 | 6.1 | 2500.0 | 41.2 | 125.3 |
| example26 | P-4 | S-55 | 4.4 | 6.2 | 2500.0 | 40.6 | 124.9 |
| example27 | P-5 | S-55 | 4.2 | 6.0 | 2500.0 | 41.4 | 136.2 |
| example28 | P-15 | S-55 | 4.4 | 6.0 | 2500.0 | 42.0 | 137.1 |
| example29 | P-21 | S-60 | 4.3 | 6.4 | 2500.0 | 39.1 | 137.6 |
| example30 | P-40 | S-60 | 4.4 | 6.4 | 2500.0 | 39.2 | 137.1 |
| example31 | P-46 | S-60 | 4.4 | 6.4 | 2500.0 | 39.3 | 136.8 |
| example32 | P-64 | S-75 | 4.5 | 6.6 | 2500.0 | 38.0 | 135.5 |
| example33 | P-70 | S-75 | 4.4 | 6.9 | 2500.0 | 36.1 | 135.0 |
| example34 | P-78 | S-75 | 4.4 | 6.9 | 2500.0 | 36.0 | 135.8 |
| example35 | P-88 | S-75 | 4.4 | 7.0 | 2500.0 | 35.5 | 136.9 |
| example36 | P-1 | S-109 | 4.2 | 5.6 | 2500.0 | 44.8 | 134.9 |
| example37 | P-2 | S-109 | 4.3 | 5.6 | 2500.0 | 44.3 | 134.0 |
| example38 | P-3 | S-109 | 4.3 | 5.5 | 2500.0 | 45.5 | 132.1 |
| example39 | P-4 | S-109 | 4.4 | 5.6 | 2500.0 | 44.6 | 132.5 |
| example40 | P-5 | S-109 | 4.0 | 5.6 | 2500.0 | 44.8 | 146.1 |
| example41 | P-43 | S-109 | 4.2 | 5.7 | 2500.0 | 43.8 | 145.6 |
| example42 | P-49 | S-109 | 4.1 | 5.6 | 2500.0 | 44.3 | 145.5 |
| example43 | P-73 | S-109 | 4.2 | 5.7 | 2500.0 | 43.6 | 144.4 |
| example44 | P-91 | S-109 | 4.0 | 5.7 | 2500.0 | 44.0 | 145.2 |
| example45 | P-5 | S-112 | 4.3 | 5.6 | 2500.0 | 44.5 | 145.4 |
| example46 | P-13 | S-112 | 4.2 | 5.5 | 2500.0 | 45.8 | 146.3 |
| example47 | P-21 | S-112 | 4.0 | 5.6 | 2500.0 | 44.3 | 146.3 |
| example48 | P-25 | S-112 | 4.2 | 5.5 | 2500.0 | 45.7 | 145.0 |
| example49 | P-37 | S-112 | 4.1 | 5.6 | 2500.0 | 44.3 | 146.4 |
| example50 | P-49 | S-112 | 4.1 | 5.5 | 2500.0 | 45.3 | 144.3 |
| example51 | P-57 | S-112 | 4.2 | 5.5 | 2500.0 | 45.4 | 144.6 |
| example52 | P-69 | S-112 | 4.2 | 5.7 | 2500.0 | 44.2 | 146.1 |
| example53 | P-73 | S-112 | 4.1 | 5.5 | 2500.0 | 45.3 | 145.3 |
| example54 | P-85 | S-112 | 4.2 | 5.5 | 2500.0 | 45.6 | 145.5 |
| example55 | P-97 | S-112 | 4.2 | 5.7 | 2500.0 | 43.6 | 144.2 |

TABLE 6

| compound | | Driving voltage | Current density (mA/cm²) | Brightness (cd/m²) | Efficiency (cd/A) | T(95) |
|---|---|---|---|---|---|---|
| comparative example 10 | comparative compound A | 5.1 | 16.0 | 2500.0 | 15.6 | 88.9 |
| comparative example 11 | comparative compound B | 5.2 | 15.5 | 2500.0 | 16.1 | 90.2 |
| comparative example 12 | comparative compound D | 4.4 | 8.8 | 2500.0 | 28.4 | 104.7 |
| example56 | P-1 | 4.5 | 9.3 | 2500.0 | 26.8 | 100.3 |
| example57 | P-5 | 4.1 | 6.6 | 2500.0 | 38.1 | 125.2 |
| example58 | P-6 | 4.2 | 6.4 | 2500.0 | 39.1 | 127.4 |
| example59 | P-8 | 4.2 | 6.3 | 2500.0 | 39.4 | 127.0 |
| example60 | P-15 | 4.1 | 6.9 | 2500.0 | 36.2 | 121.3 |
| example61 | P-16 | 4.1 | 6.4 | 2500.0 | 38.9 | 121.9 |
| example62 | P-21 | 4.1 | 6.4 | 2500.0 | 39.1 | 121.7 |
| example63 | P-22 | 4.1 | 6.4 | 2500.0 | 39.0 | 126.9 |
| example64 | P-23 | 4.1 | 6.5 | 2500.0 | 38.2 | 123.1 |
| example65 | P-24 | 4.2 | 6.4 | 2500.0 | 39.3 | 122.3 |
| example66 | P-28 | 4.1 | 6.6 | 2500.0 | 37.7 | 129.6 |
| example67 | P-30 | 4.2 | 7.1 | 2500.0 | 35.0 | 112.6 |
| example68 | P-36 | 4.3 | 7.1 | 2500.0 | 35.3 | 119.9 |
| example69 | P-38 | 4.3 | 7.7 | 2500.0 | 32.4 | 117.0 |
| example70 | P-45 | 4.3 | 7.0 | 2500.0 | 35.6 | 114.2 |
| example71 | P-51 | 4.3 | 7.3 | 2500.0 | 34.2 | 117.9 |
| example72 | P-57 | 4.2 | 8.0 | 2500.0 | 31.2 | 111.8 |
| example73 | P-68 | 4.2 | 7.2 | 2500.0 | 34.9 | 118.4 |
| example74 | P-75 | 4.3 | 7.2 | 2500.0 | 34.8 | 119.8 |
| example75 | P-82 | 4.3 | 7.6 | 2500.0 | 33.0 | 111.6 |
| example76 | P-100 | 4.2 | 7.5 | 2500.0 | 33.3 | 113.4 |

Figure 5:
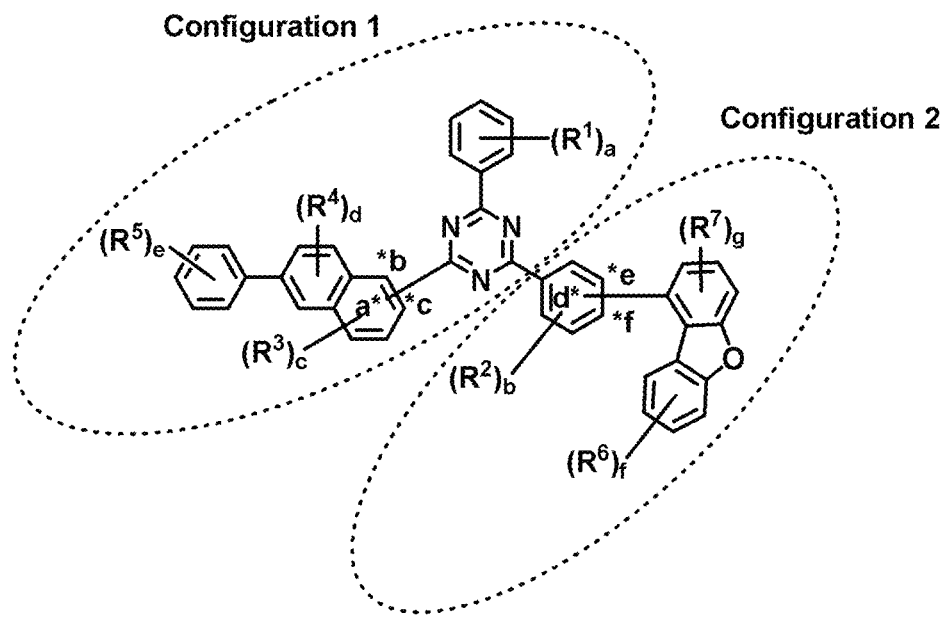
FIG. 5 shows the composition of a compound represented by Formula 1 of the present invention.

In order to interpret the results of Tables 5 and 6, the configuration of the compound represented by Formula 1 of the present invention will be explained as Configuration 1 and Configuration 2 of FIG. 5.

First, we explain the results in Table 5.

As can be seen from the results in Table 5, when a red organic electroluminescence device is manufactured using the material for an organic electroluminescence device of the present invention as a host material of a emitting layer, the driving voltage, luminescence efficiency, and lifespan of the organic electroluminescence device can be improved compared to the comparative examples in which comparative compounds A to C having a similar basic skeleton to the compound of the present invention are used as a first host, or comparative compound 1 or comparative compound 2 is used as a second host.

Comparative compounds A to C can be viewed as structural isomers having a similar molecular weight and skeleton to the compound represented by Formula 1 of the present invention, but do not have the same composition as Formula 1 of the present invention.

To confirm the energy level difference of the compound due to these differences, the data measured using the DFT method (B3LYP/6-31g(D)) of the Gaussian program are as shown in Table 7.

TABLE 7

| | comparative compound A | comparative compound B | comparative compound C | P-1 |
|---|---|---|---|---|
| LUMO(eV) | −1.9829 | −1.9973 | −2.0580 | −1.9693 |

As can be seen from the results in Table 7, it can be seen that the LUMO energy levels of the compound represented by Formula 1 of the present invention and the comparative compounds are formed differently.

To explain in more detail, the compound represented by Formula 1 of the present invention and comparative compounds A to C serve as electron transport hosts in the emitting layer, but in the case of comparative compounds A to C, the LUMO energy level is formed deeper than that of the compound represented by Formula 1 of the present invention, so that excessive electron injection into the emitting layer occurs, thereby breaking the charge balance of the element. On the contrary, the compound represented by Formula 1 of the present invention has a LUMO level that is an intermediate value between the electron transport region and the dopant of the emitting layer, so that electrons in the electron transport region can be prevented from being directly accumulated in the dopant of the emitting layer, and since the formation of an exciplex between the first host and the second host is facilitated, the charge balance is optimized, so it appears that this has an effect on the operation, efficiency, and lifespan of the element.

When Comparative Compound 1 and Comparative Compound 2 are used as a second host of the emitting layer, hole injection into the emitting layer occurs excessively quickly due to the characteristics of the amine group present in the molecule, thereby breaking the charge balance of the element. However, when the compound represented by Formula 5 of the present invention is applied as a second host, appropriate hole injection into the emitting layer is possible, and since the structural stability is increased compared to the amine structure, when used as a host for the emitting layer together with the compound represented by Formula 1 of the present invention as a first host, the charge balance is maximized, and it appears that the operation, efficiency, and lifespan of the device are increased.

Next, we explain the results in Table 6.

First, in the case of Comparative Examples 10 and 11, the energy level of the compound is formed differently from that of the compound of the present invention as a material different from the skeleton of the compound represented by Formula 1 of the present invention. Therefore, even when comparative compounds A and B are used as sole hosts of the emitting layer, the charge balance of the element is not correct compared to compounds having the skeleton of the compound of the present invention, as explained by the results in Table 7.

The compound of Comparative Example 12 differs from the compounds of Examples 56 to 76 in the presence or absence of deuterium substitution or the substitution position of deuterium.

Figure 6:
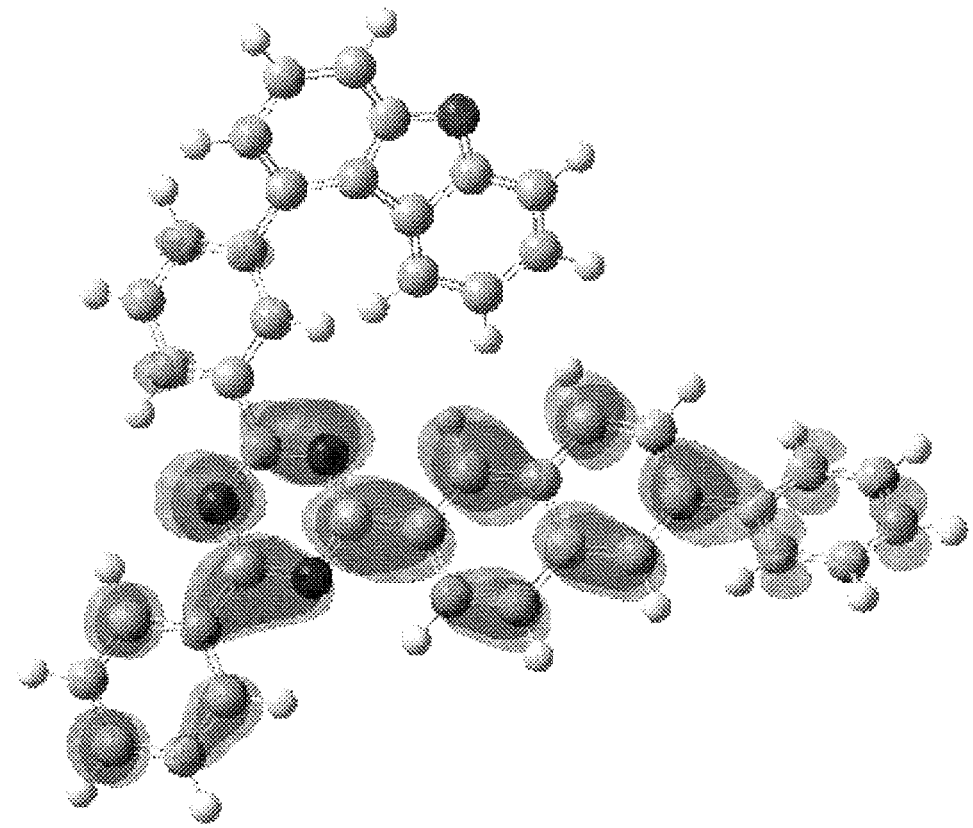
FIG. 6 is a LUMO electron cloud image of compound P-1 of the present invention.
Figure 7:
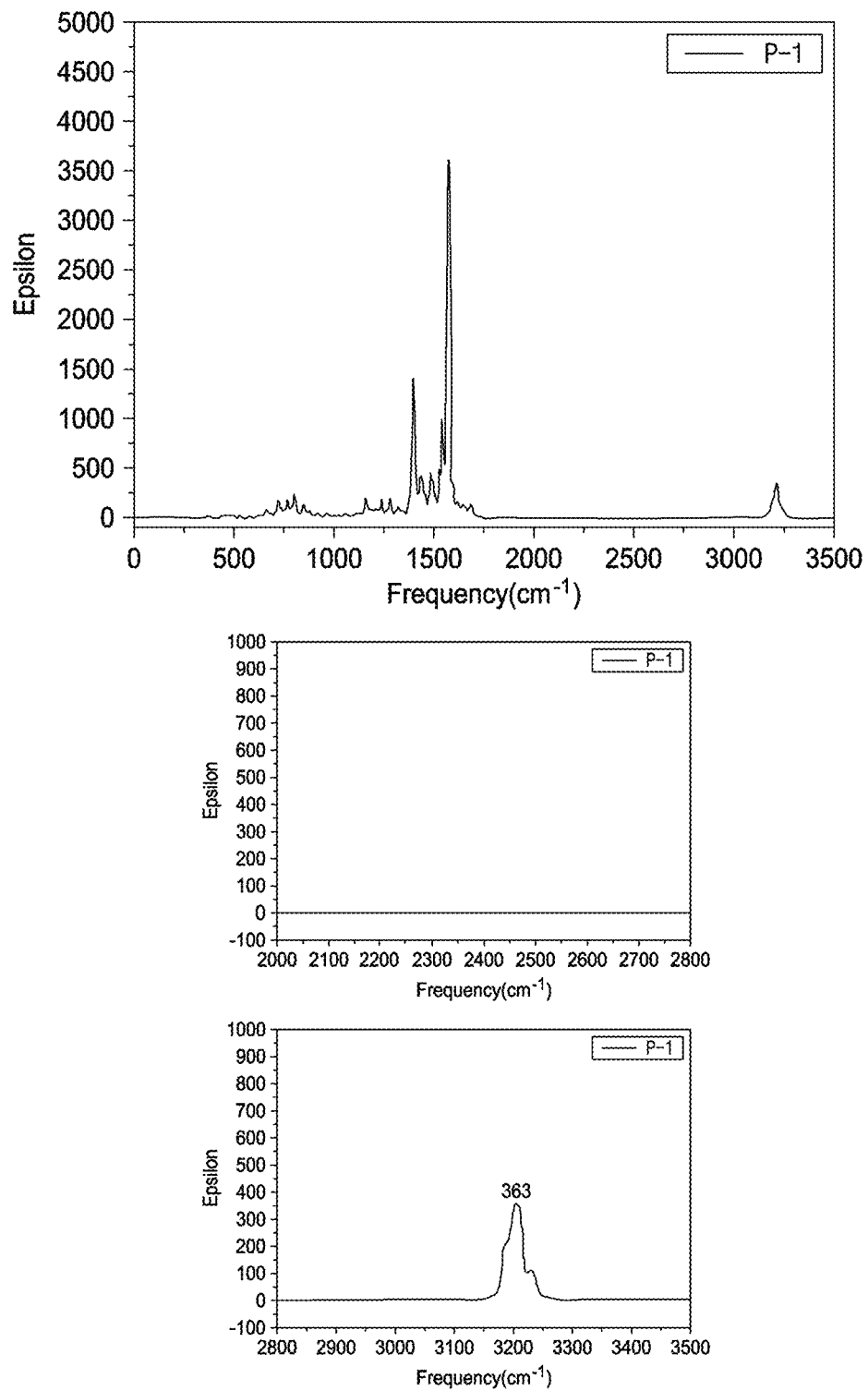
FIG. 7 is IR spectrum data of compound P-1 of the present invention.
Figure 8:
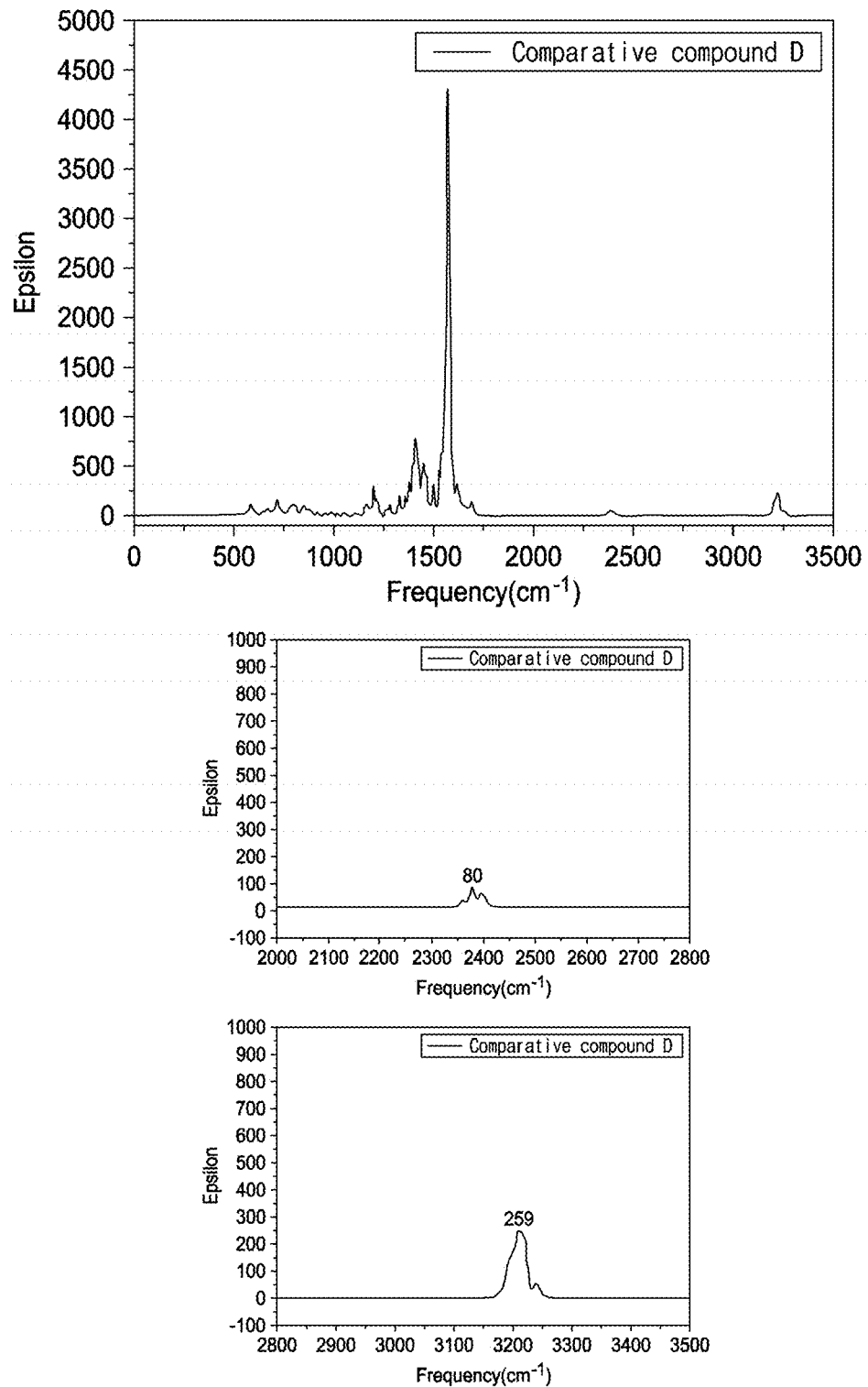
FIG. 8 shows IR spectrum data of comparative compound D.
Figure 9:
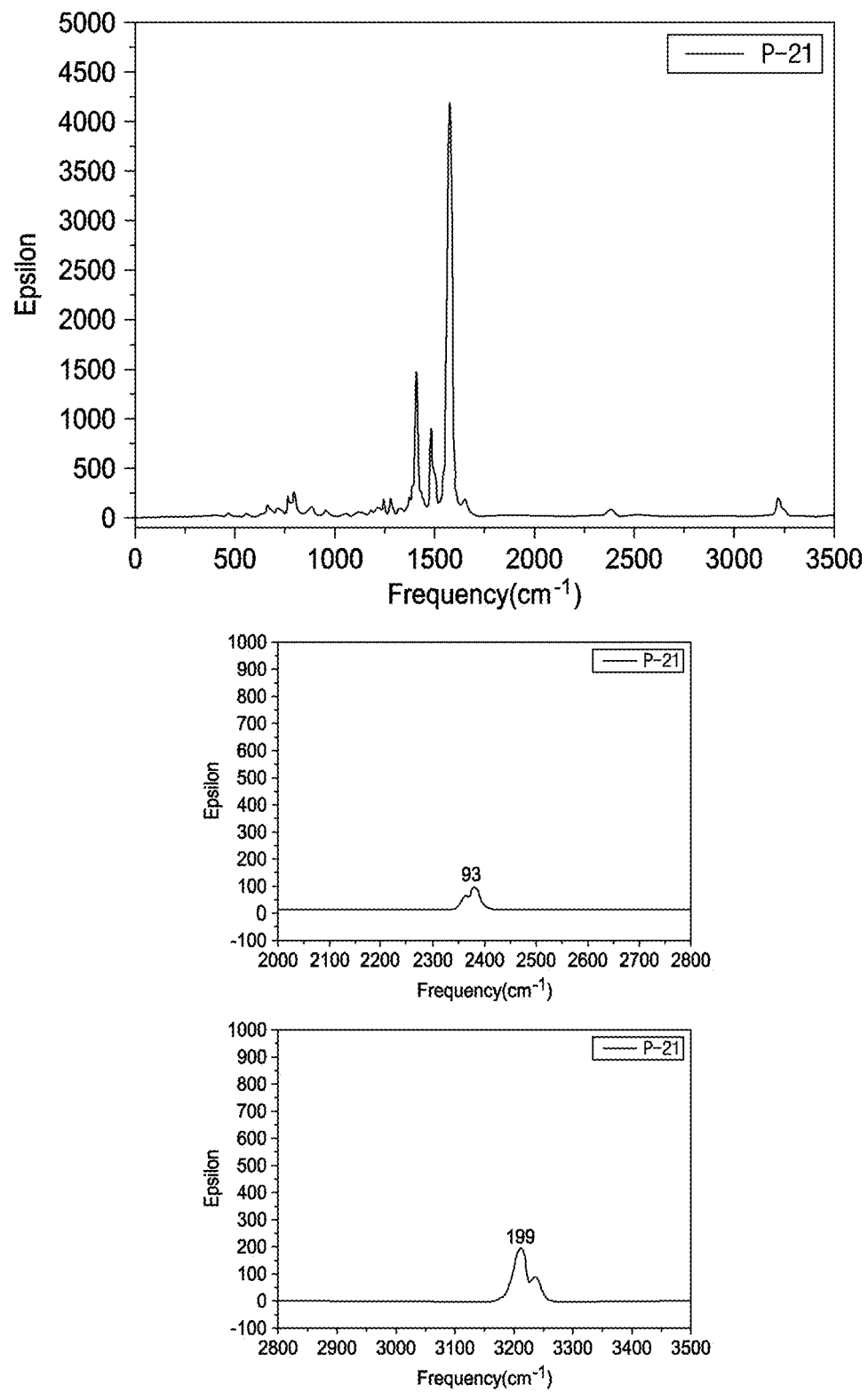
FIG. 9 is IR spectrum data of compound P-21 of the present invention.

In order to confirm the change in the properties of the compound according to the position where deuterium is substituted, the data for measuring the electron cloud of the compound using the DFT method (B3LYP/6-31g(D)) of the Gaussian program is shown in FIG. 6, and the data for measuring the IR spectrum are shown in FIGS. 7 to 9.

First, FIG. 6 is the LUMO electron cloud of the P-1 compound.

As can be seen from FIG. 6, it can be confirmed that the LUMO electron cloud is formed intensively in the Configuration 1 portion of Formula 1 of the present invention. That is, electrons coming from the electron transport region are transferred to the dopant through the Configuration 1 portion of Formula 1.

Since the deuterium-carbon bond length is generally shorter than the hydrogen-carbon bond length, molecules with deuterium-carbon bonds have a reduced molecular hardcore volume, which can reduce electronic polarizability.

This has the effect of lowering the crystallinity of the thin film, that is, creating an amorphous state, which ultimately improves electron mobility and significantly affects the lifespan of the element. It is judged that compounds P-5 to P-100, in which one or more deuterium atoms are substituted in the Configuration 1 portion, maximize efficiency and lifespan in the device due to the effects described above compared to compound P-1 or comparative compound D.

Next, FIGS. 7 to 9 are IR spectra of compound P-1, comparative compound D, and compound P-21.

As can be seen from FIGS. 7 to 9, there is a difference in the IR spectrum depending on the deuterium substitution position of the compound. In FIGS. 7 (Compound P-1) to 9 (Compound P-21), a peak exists around 3,200 cm$^{-1}$ due to the C-H Stretching mode, but the epsilon value around 3,200 cm$^{-1}$ of compound P-1 (FIG. 7) in which deuterium is not substituted is the largest. However, in the case of comparative compound D (FIG. 8) and compound P-21 of the present invention (FIG. 9) in which deuterium is substituted, the epsilon value around 3,200 cm$^{-1}$ decreases and a peak is generated by the C-D Stretching mode around 2,400 cm$^{-1}$.

That is, compared to the non-deuterium-substituted compound P-1, the deuterium-substituted comparative compound D and compound P-21 are structurally more stable because high frequency vibrations are suppressed, and the non-radiative decay is reduced, so the lifespan and efficiency of the element also appear to increase.

Comparative Compound D and Compound P-21 are the same in that they have 11 deuterium atoms in the molecule, but they differ in that in the case of Comparative Compound D, deuterium is substituted in the Configuration 2 portion, while in the case of Compound P-21, deuterium is substituted in the Configuration 1 portion. As can be confirmed in FIGS. 8 and 9, it can be confirmed that the high frequency vibration of Compound P-21 is suppressed to a greater extent than that of Comparative Compound D. That is, even if they are compounds with the same skeleton, the high frequency vibration suppression effect of compounds P-5 to P-100 in which deuterium is substituted in the Configuration 1 portion is greater, so the lifespan and efficiency improvement effect in the above-mentioned element is greater than that of the compound in which deuterium is substituted only in Configuration 2. This suggests that even for structural isomers with the same skeleton, the degree of change in the properties of the compound can vary depending on the position at which deuterium is substituted, and the device results accordingly can also vary significantly.

That is, as can be seen from the results in Tables 5 to 7 and FIGS. 6 to 9, even if the compounds have similar compositions, it can be confirmed that the compound of the present invention, which satisfies all complex factors such as the type of specific substituent and the substitution position of the substituent, exhibits a remarkable effect compared to other comparative compounds in organic electronic elements, and through this, it can be seen that the compound of the present invention exhibits a remarkable effect in an organic electronic element compared to simple structural isomers or compounds having a similar structure not described in this specification.

These results suggest that even for compounds with similar molecular components, the properties of the compound, such as hole characteristics, luminous efficiency characteristics, energy levels, hole injection and mobility characteristics, charge balance of holes and electrons, volume density, and intermolecular distance, can differ significantly to an extent that is difficult to predict depending on the type and position of the substituted substituent, and that the performance of an element may vary due to complex factors, rather than a single configuration affecting the outcome of the entire device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound selected from the group consisting of compounds P-5 to P-100:

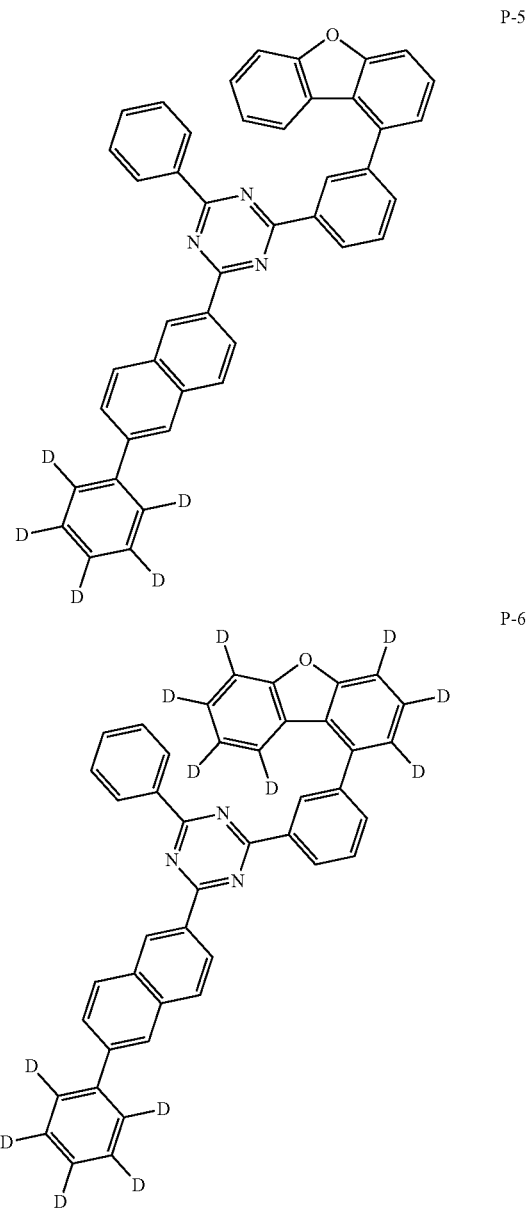

P-7
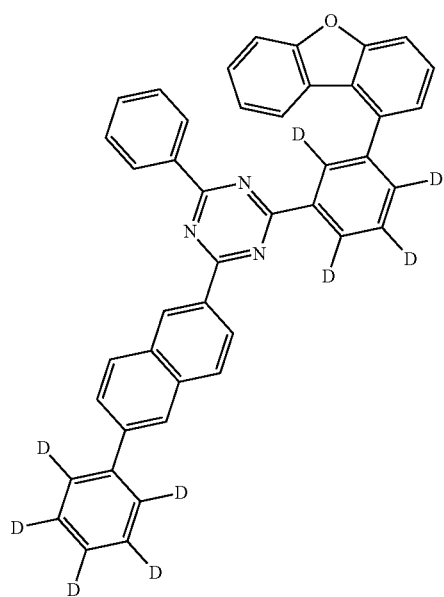
P-8
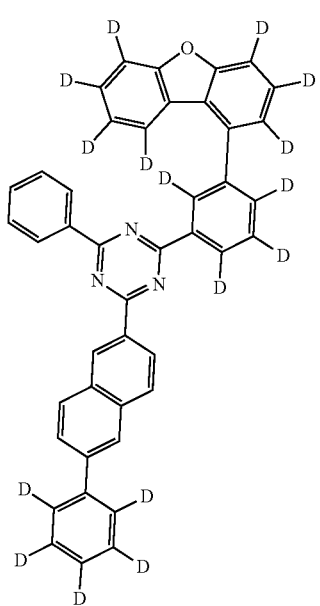
P-9
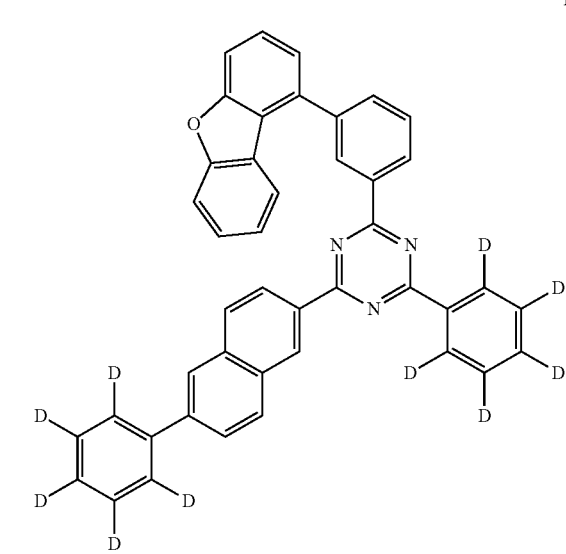
P-10
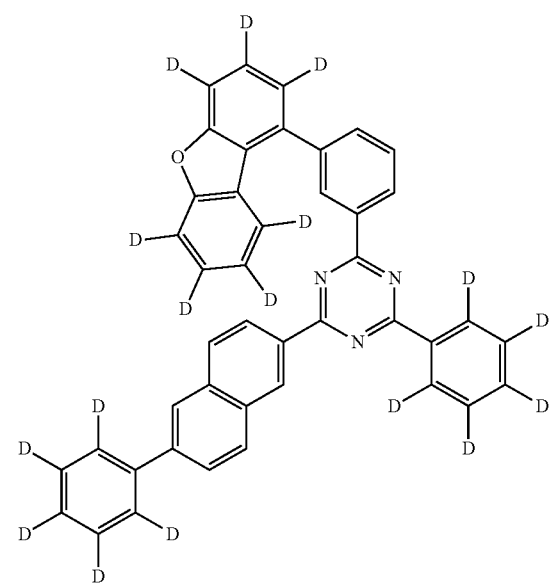

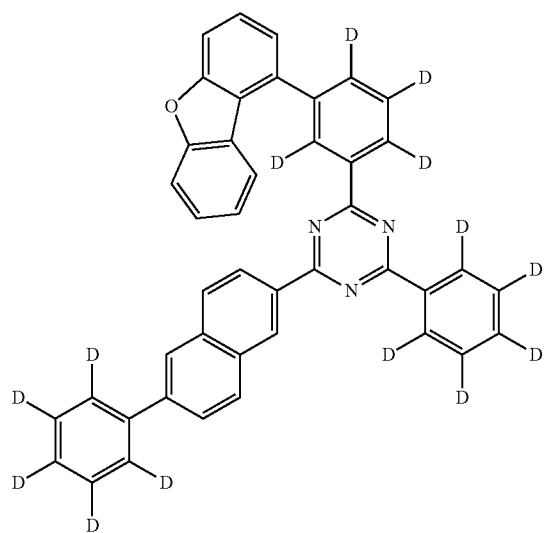
P-11
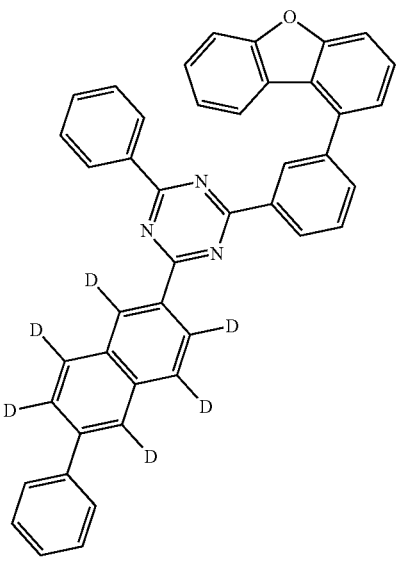
P-13
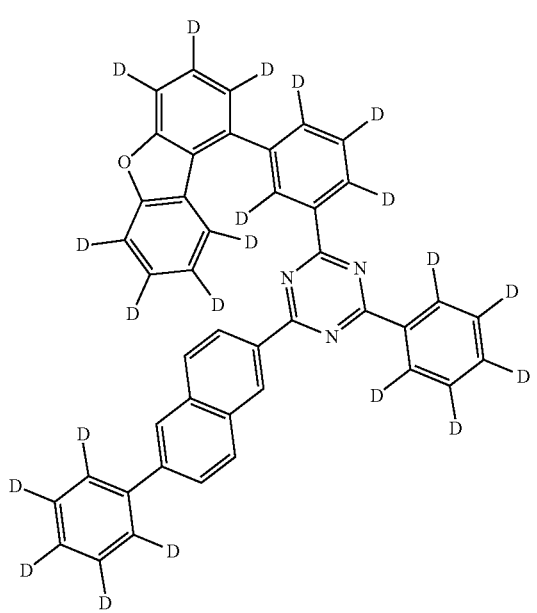
P-12
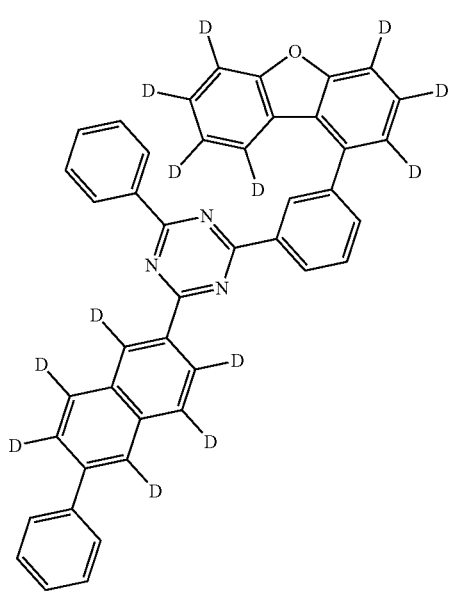
P-14

P-15
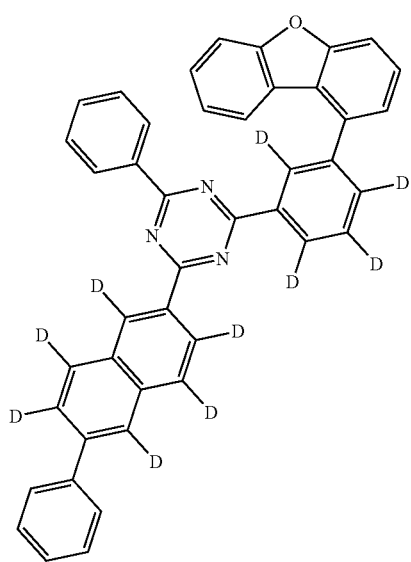
P-17
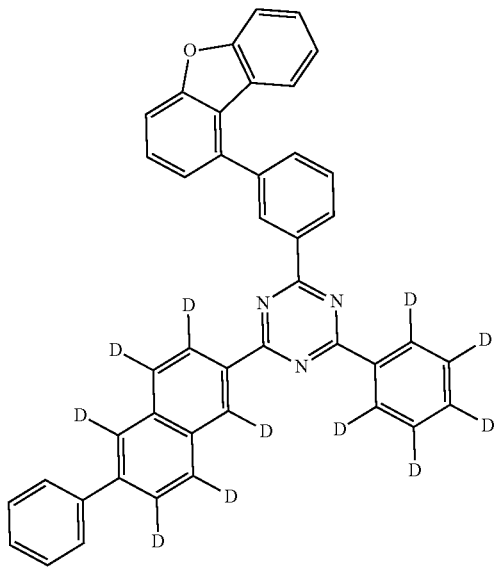
P-16
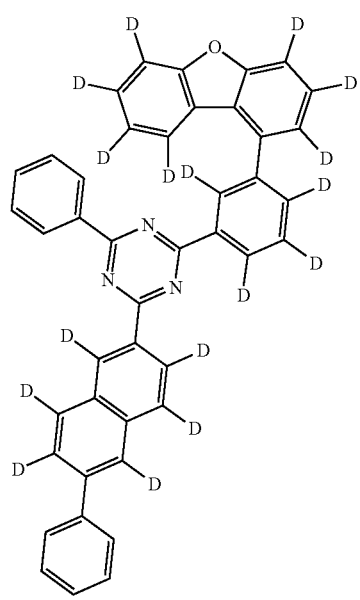
P-18
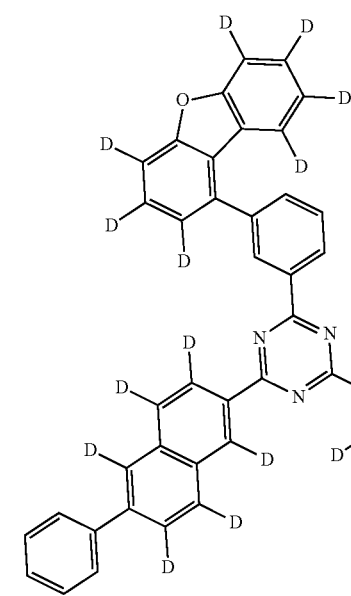

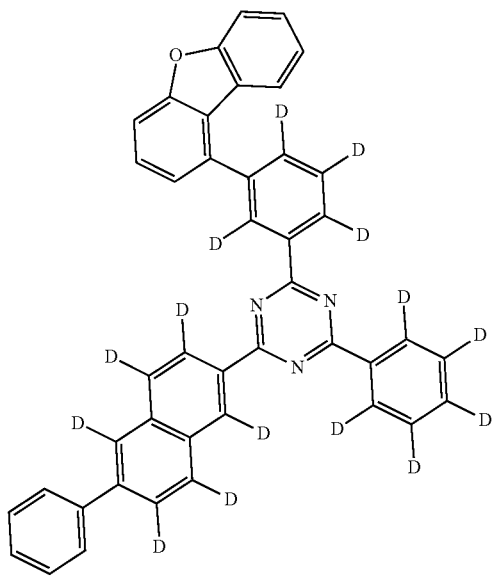
P-19
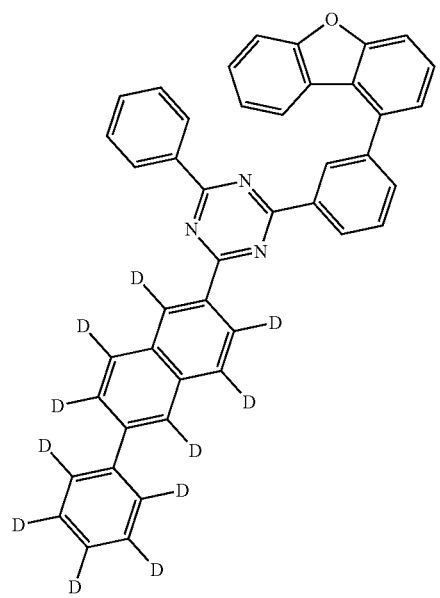
P-21
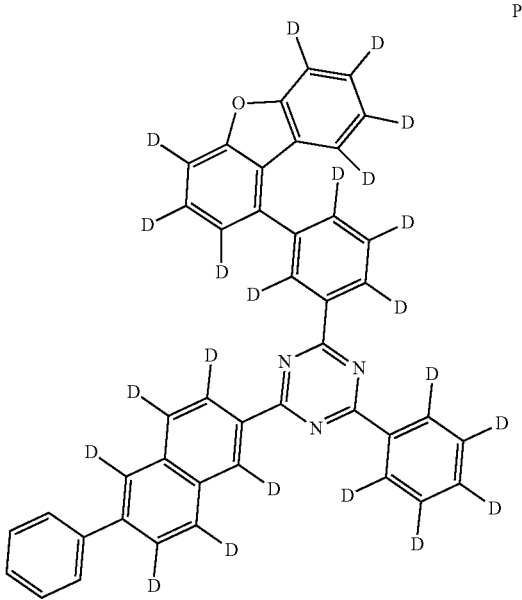
P-20
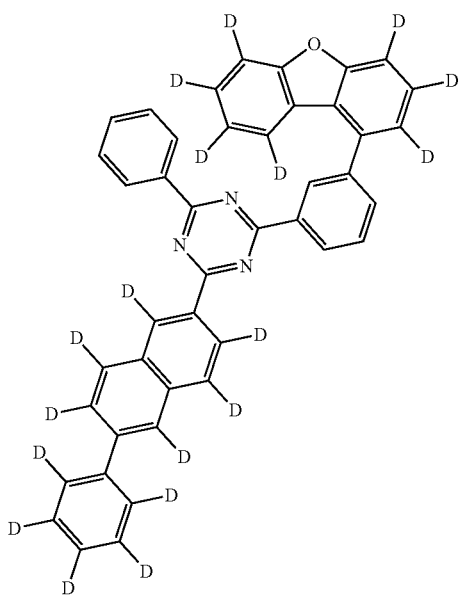
P-22

-continued
P-23
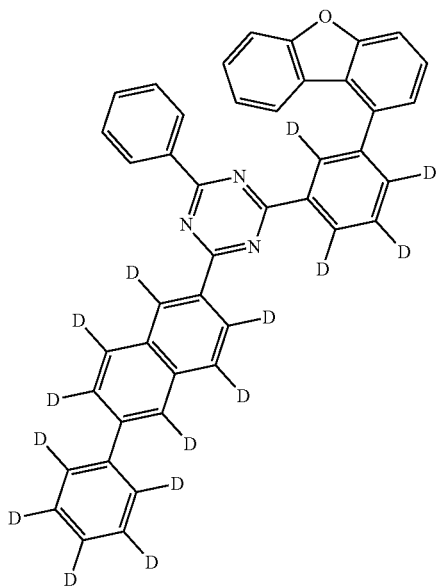
P-24
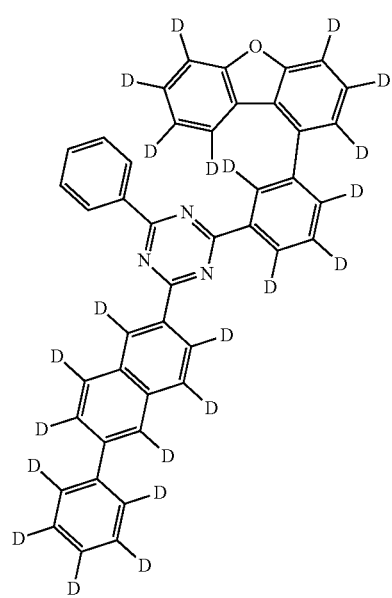
P-25
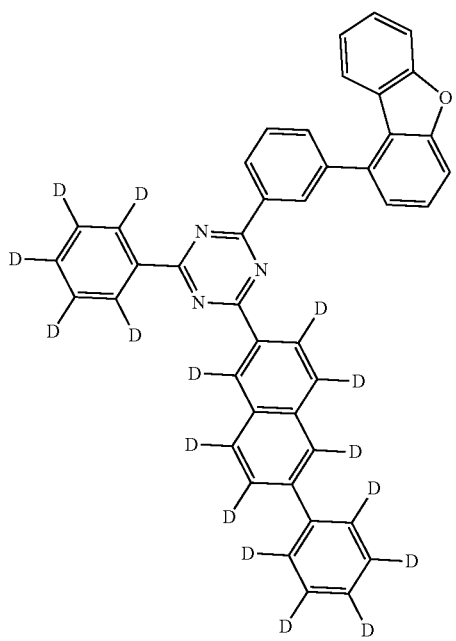
P-26
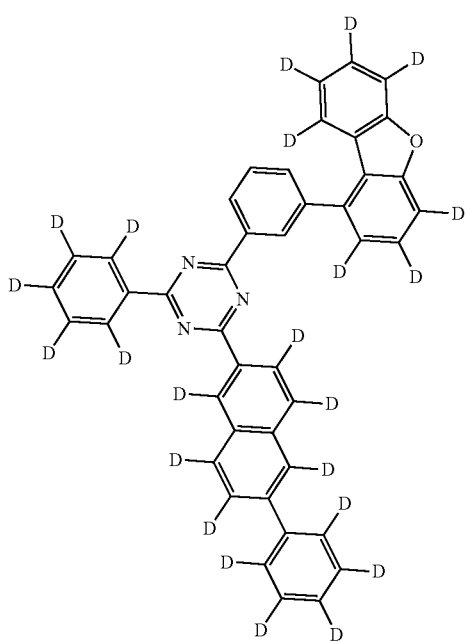

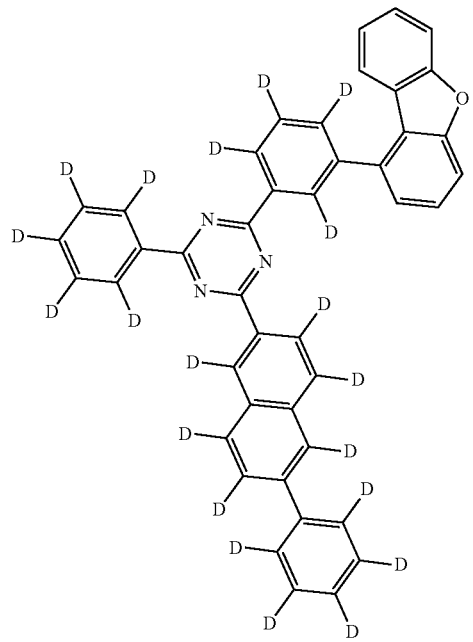
P-27
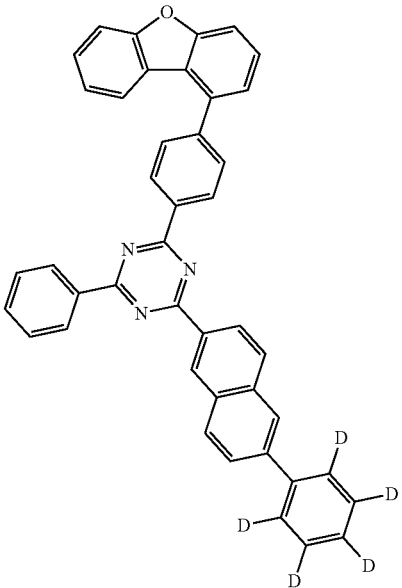
P-29
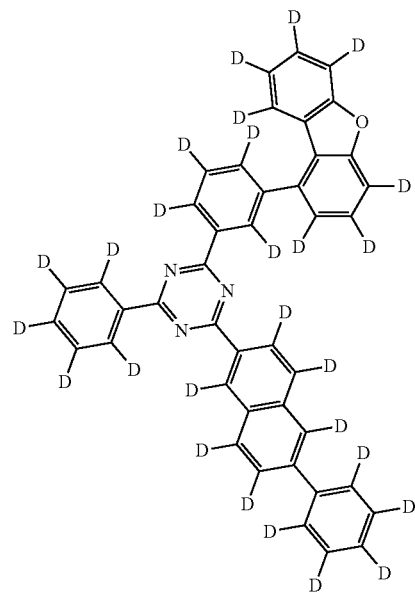
P-28
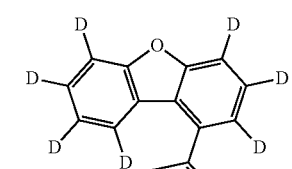
P-30

P-31
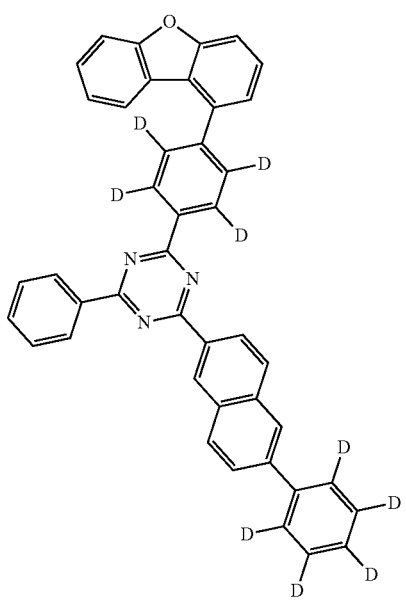
P-32
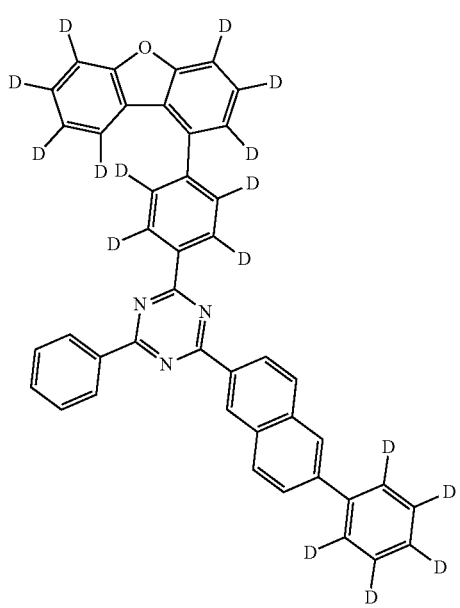
P-33
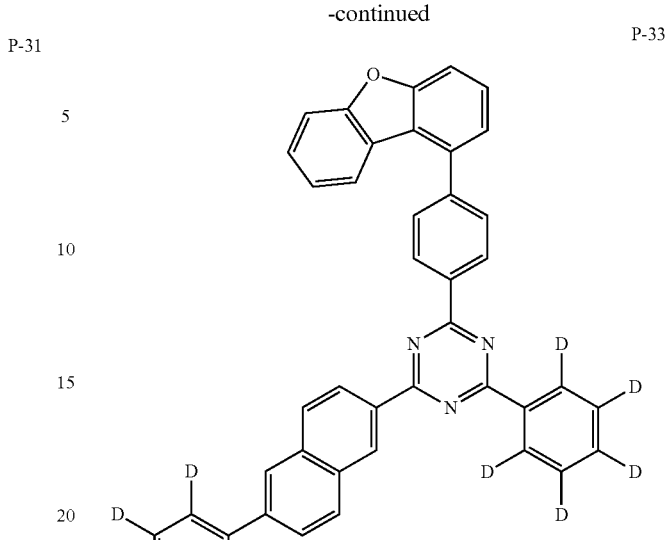
P-34
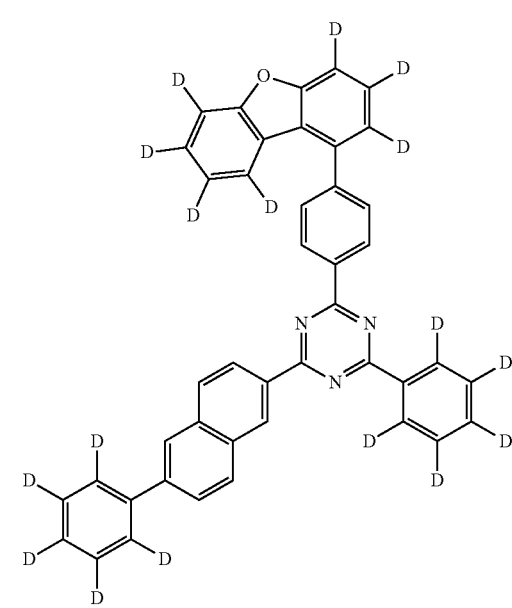

P-35
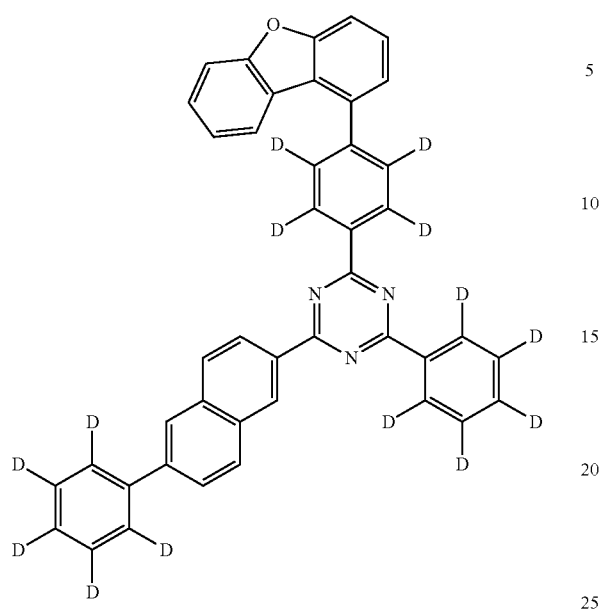
P-37
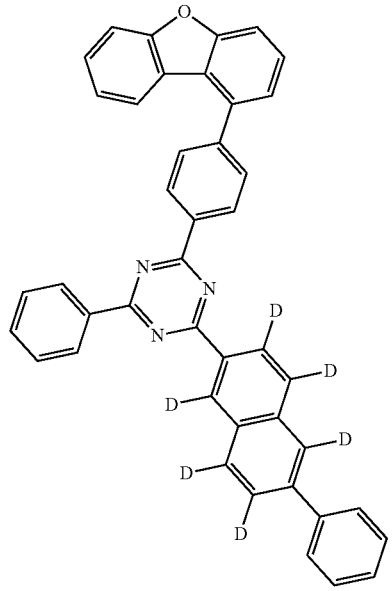
P-36
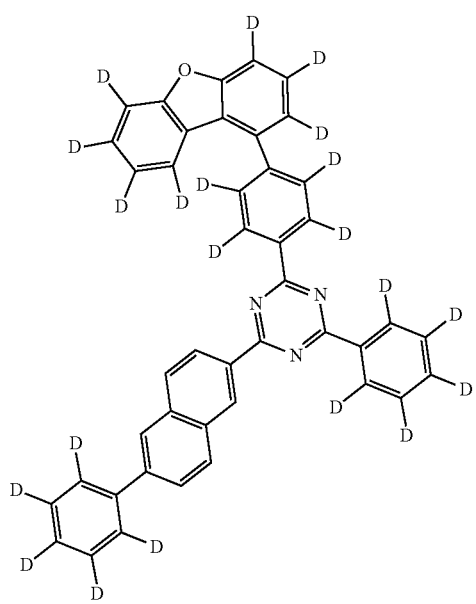
P-38
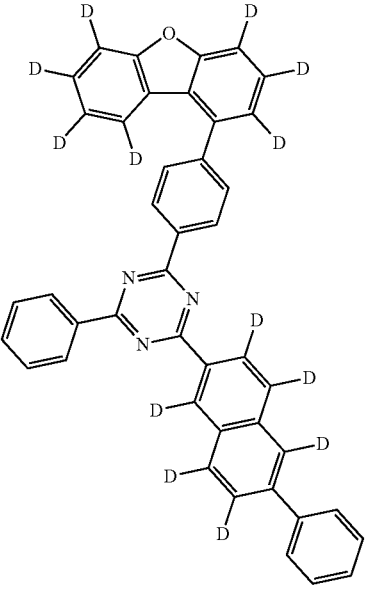

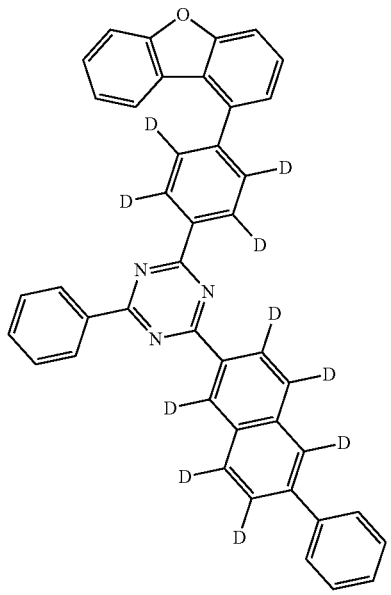
P-39
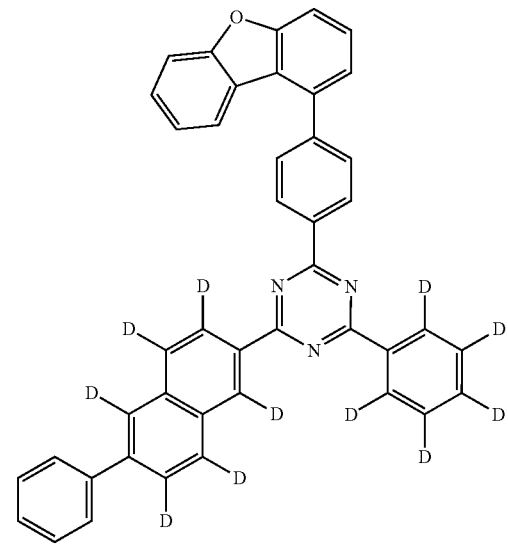
P-41
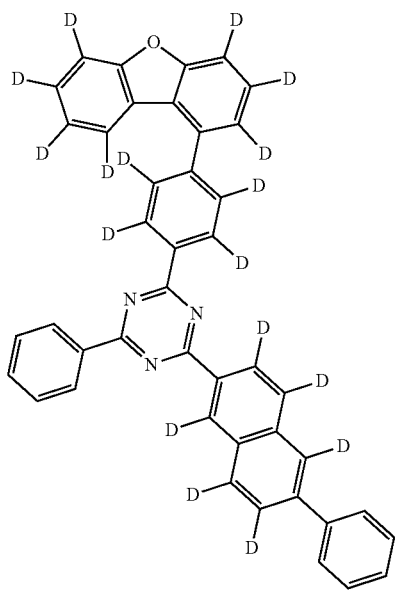
P-40
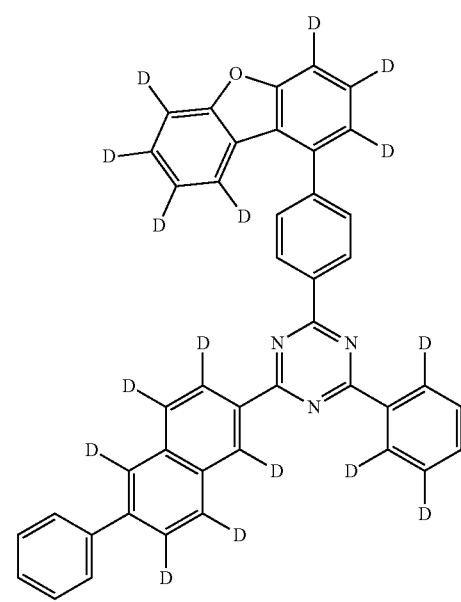
P-42

P-43
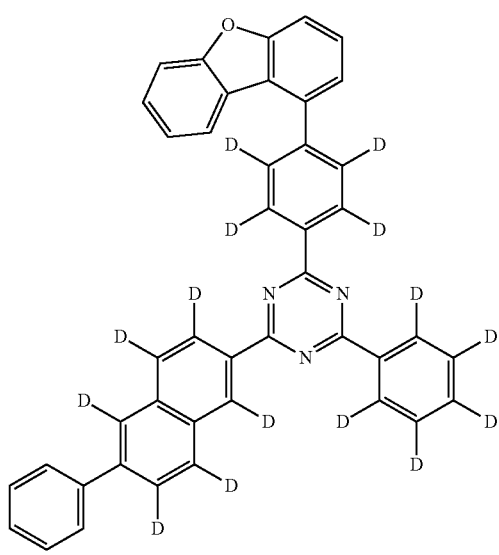
P-44
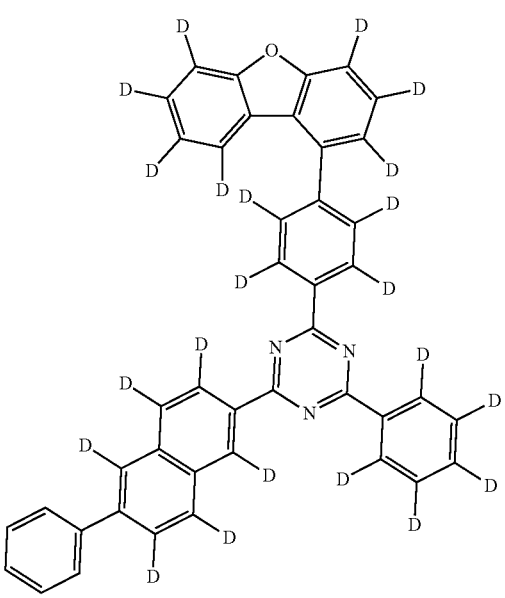
P-45
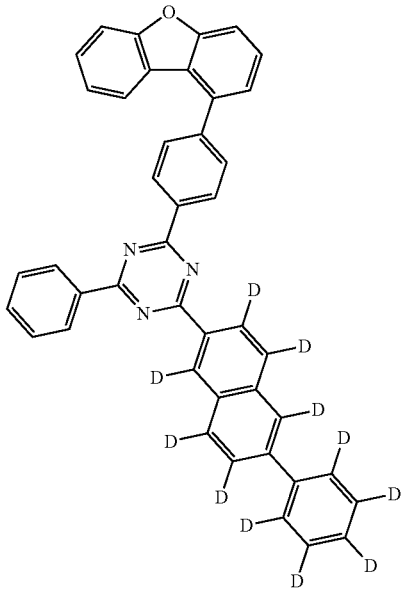
P-46
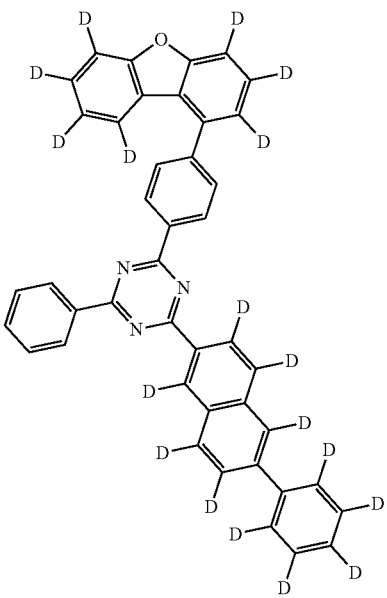

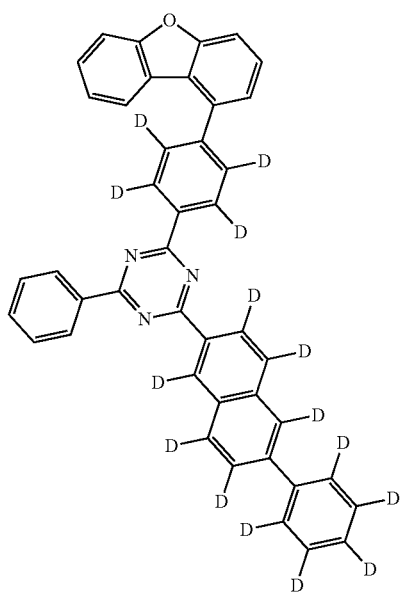
P-47
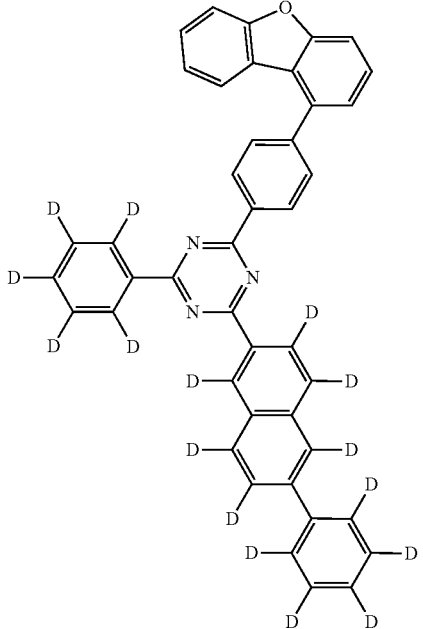
P-49
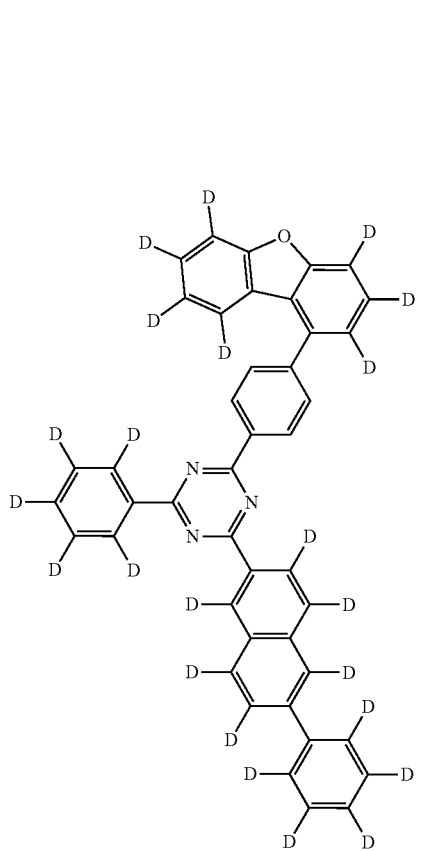
P-50
P-48

-continued
P-51
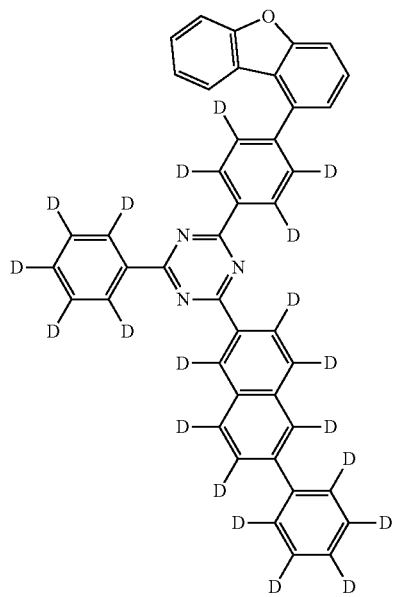
P-52
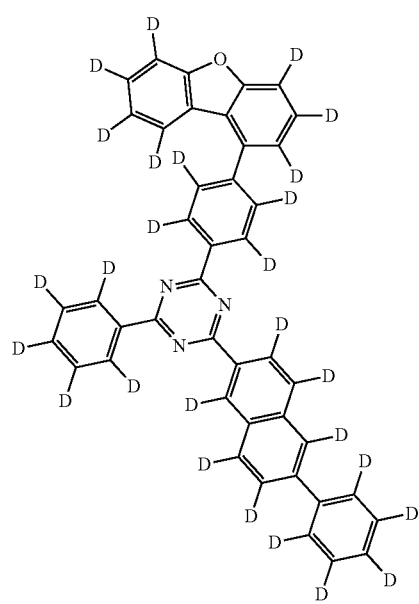
P-53
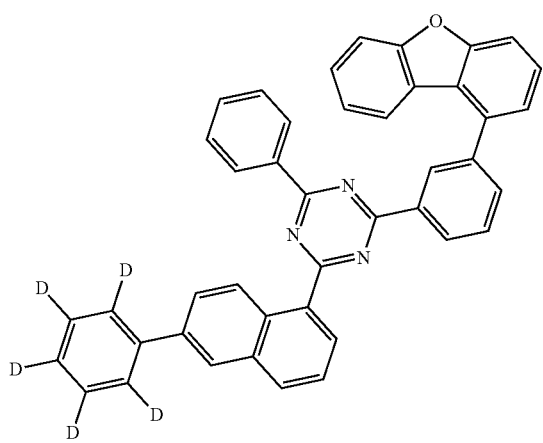
-continued
P-54
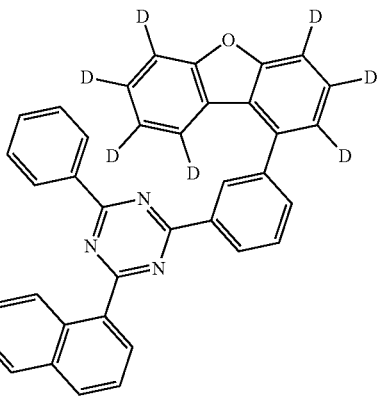
P-55
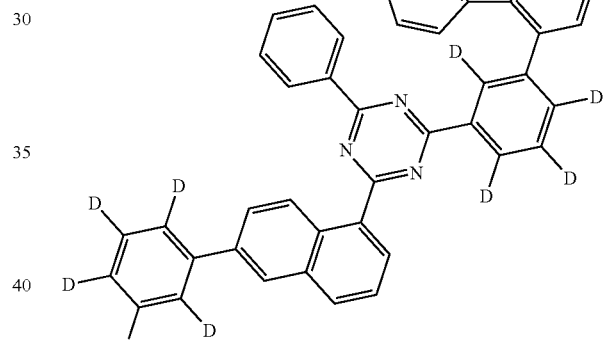
P-56
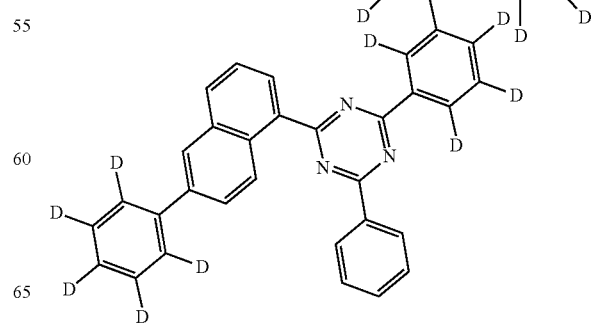

P-57
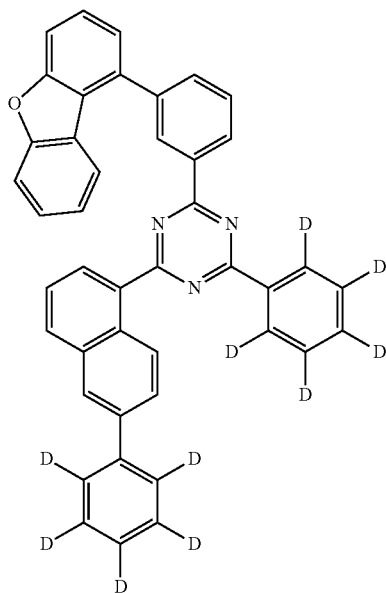
P-58
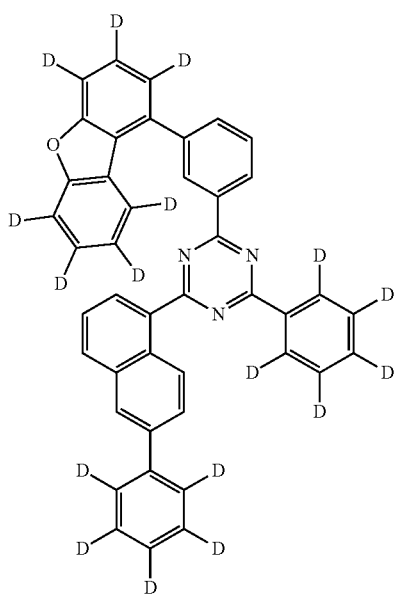
P-59
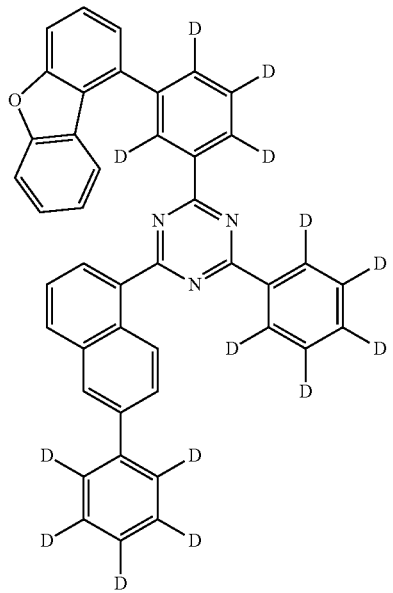
P-60
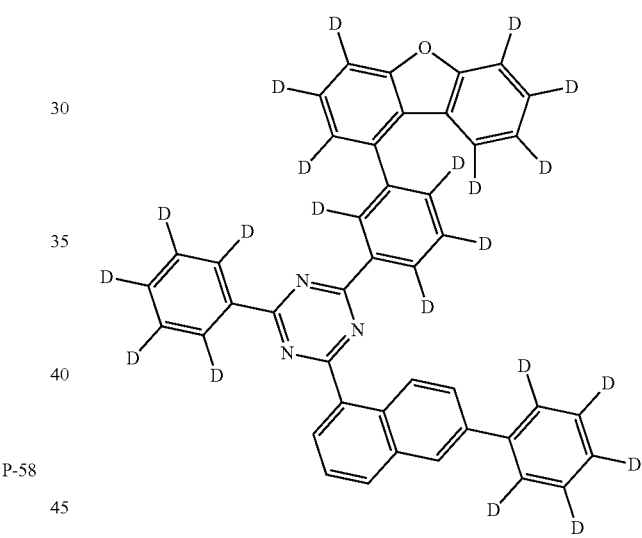
P-61
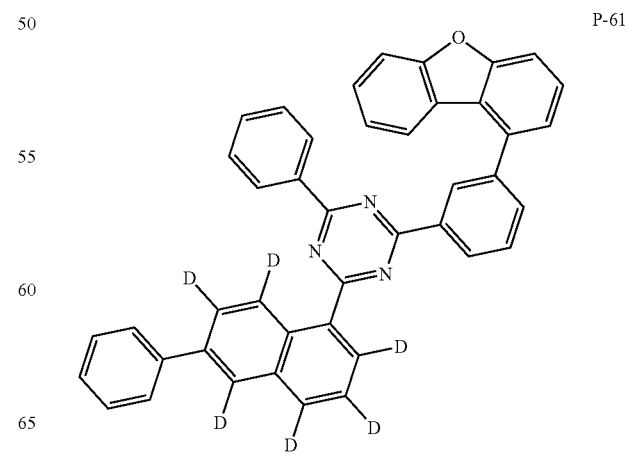

P-62
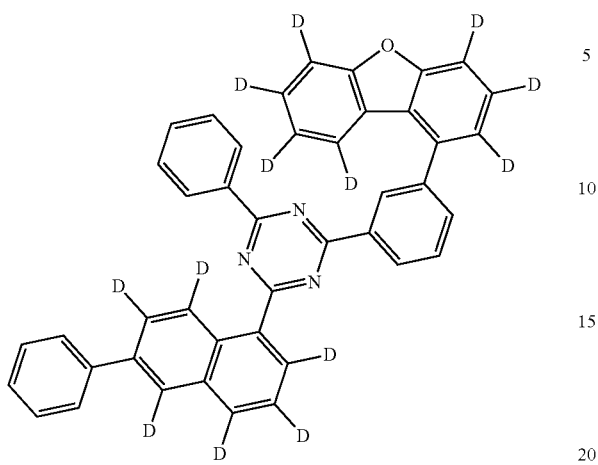
P-63
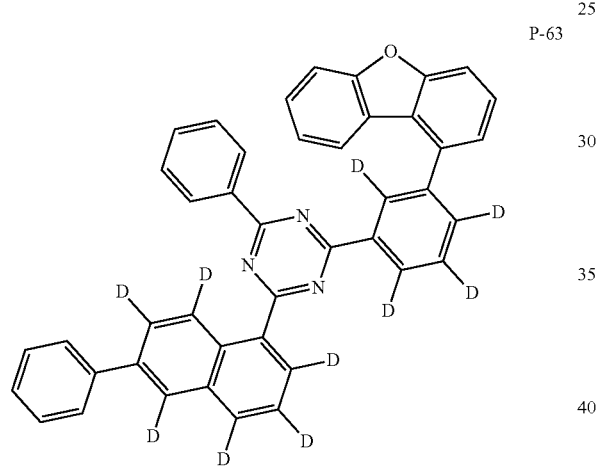
P-64
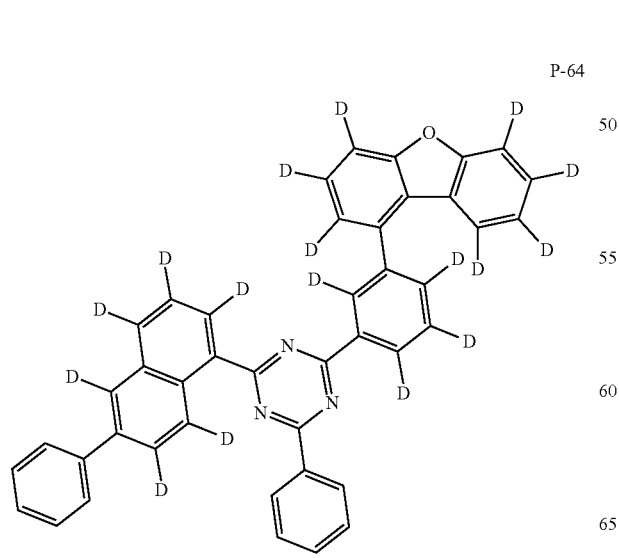
P-65
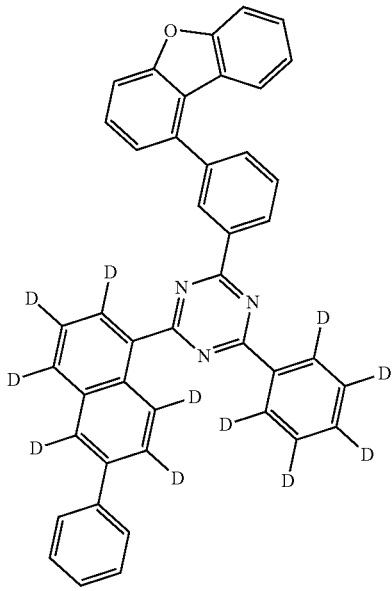
P-66
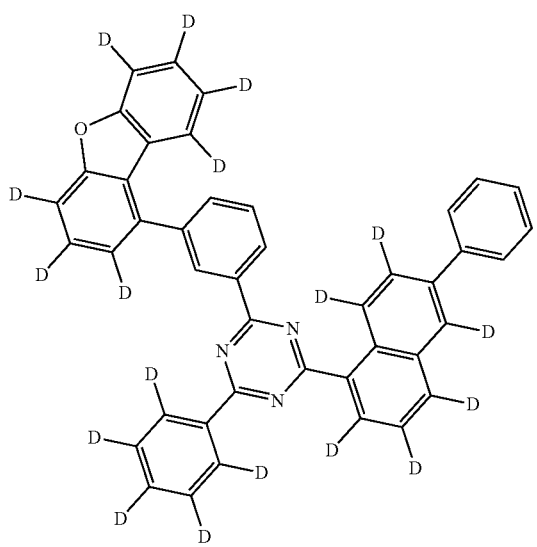

P-67
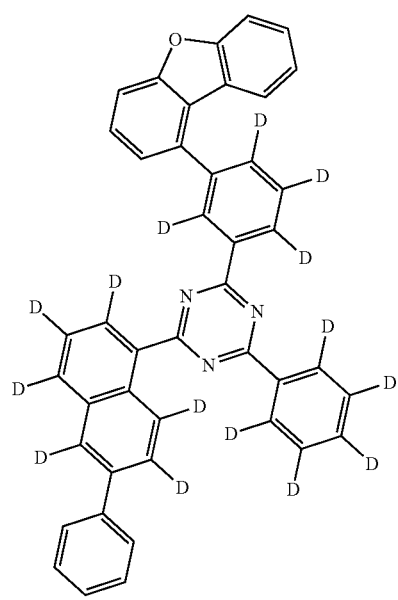
P-68
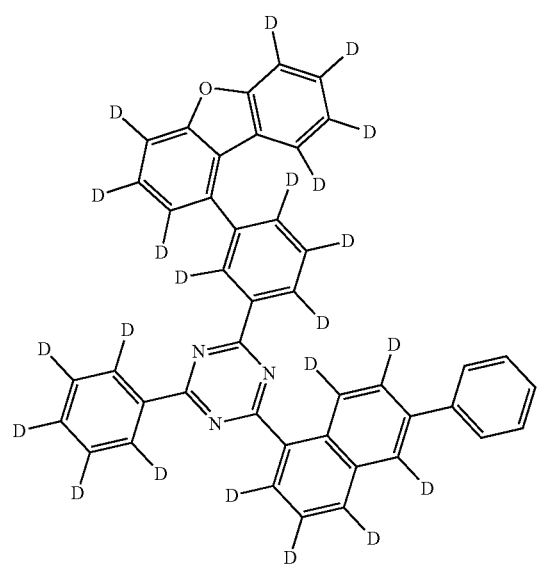
P-69
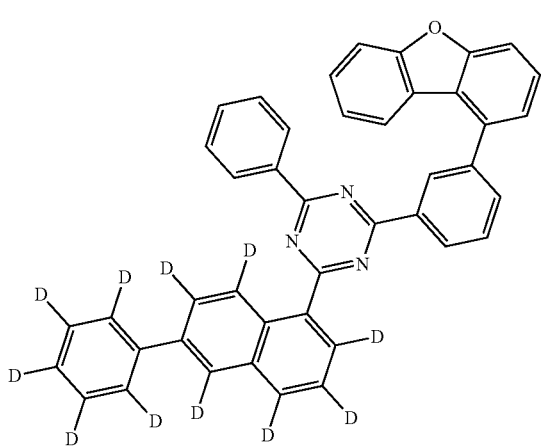
P-70
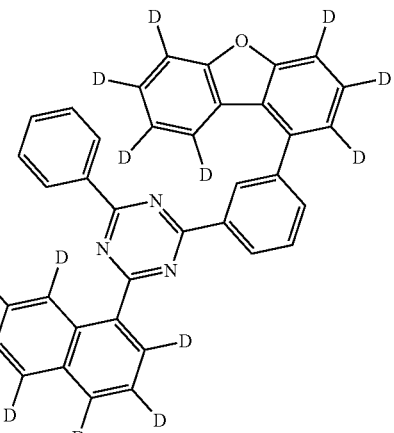
P-71
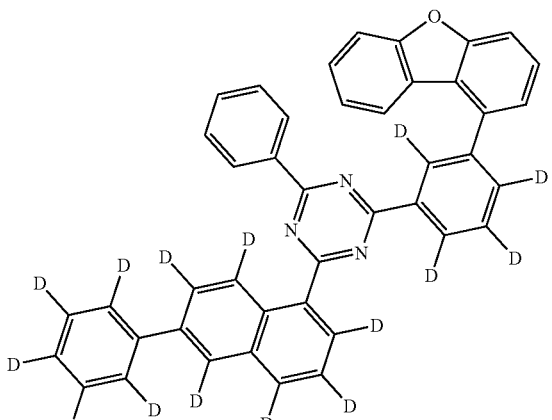
P-72
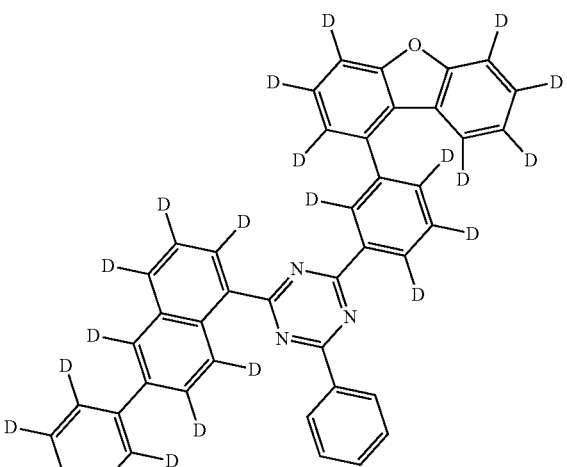

P-73
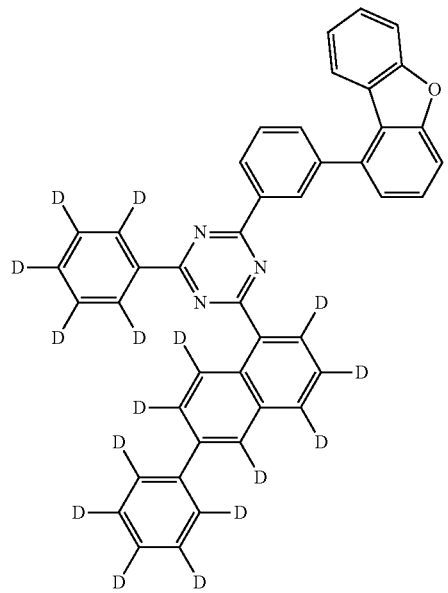
P-75
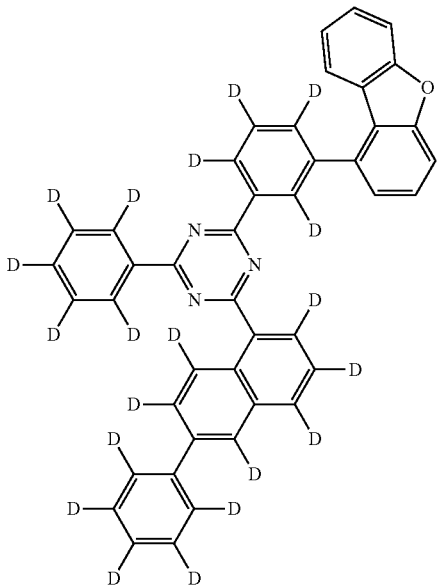
P-74
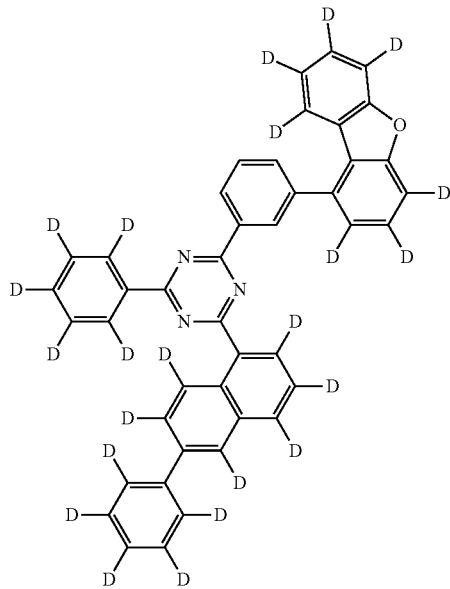
P-76
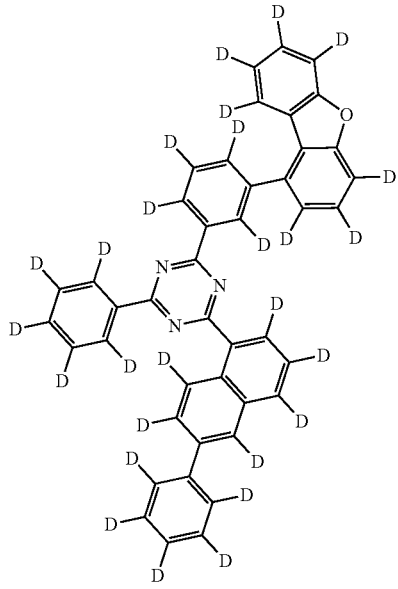

P-77
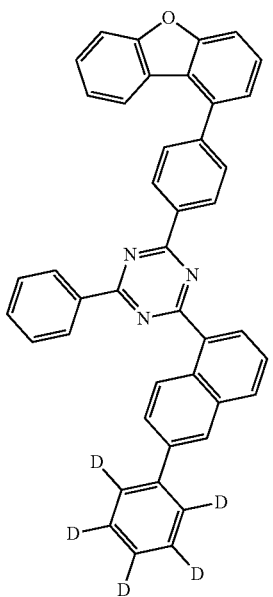
P-78
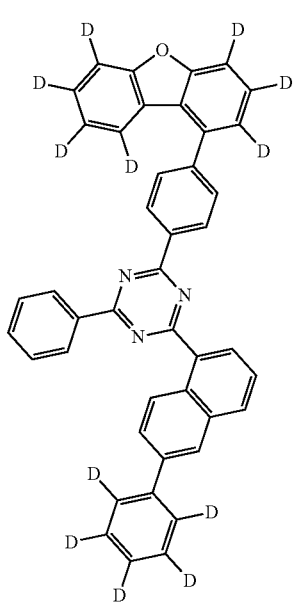
P-79
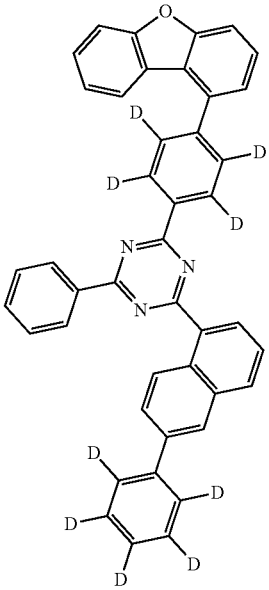
P-80
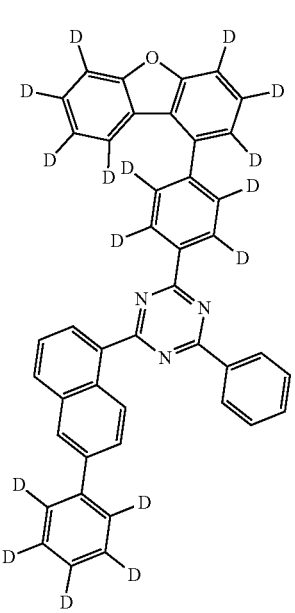

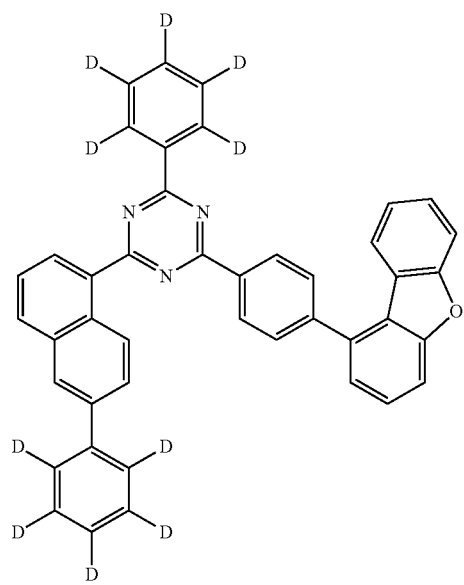
P-81
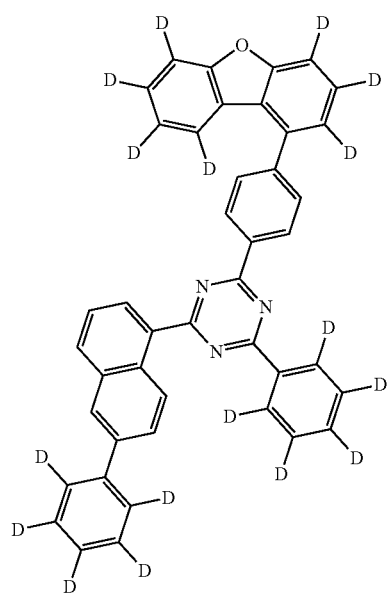
P-82
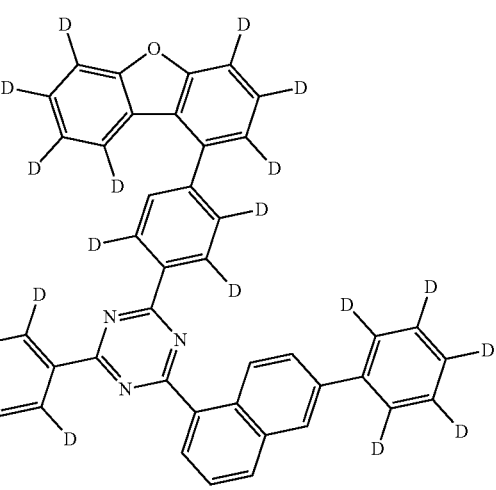
P-83
P-84

P-85
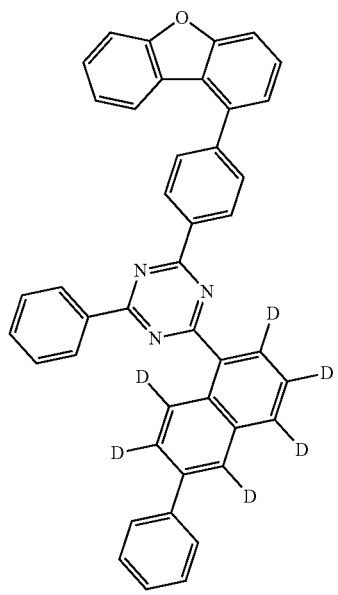
P-86
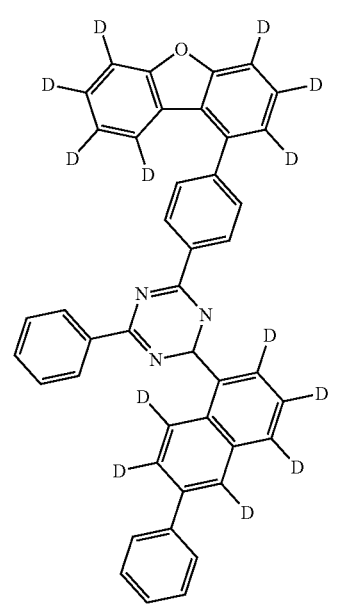
P-87
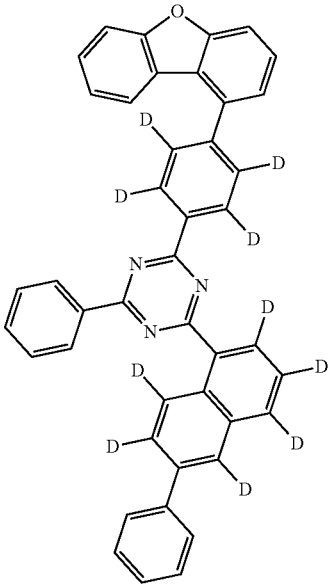
P-88
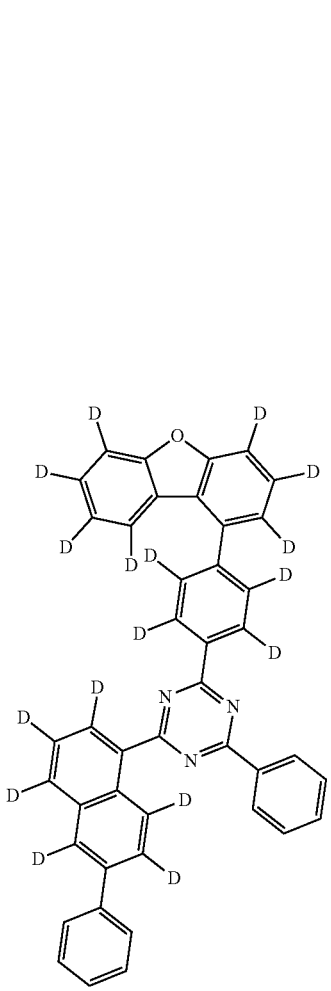

P-89
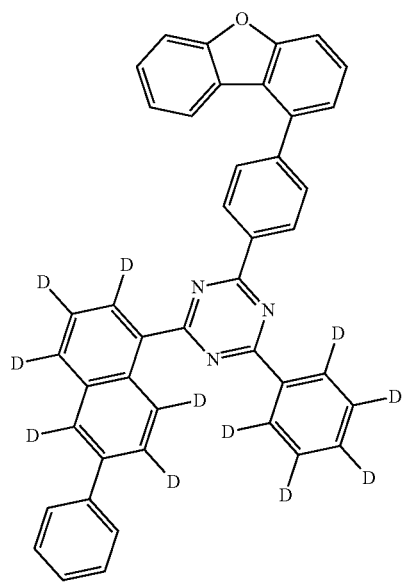
P-90
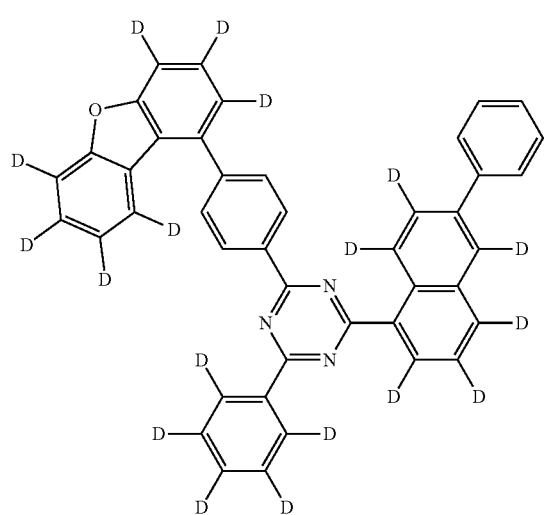
P-91
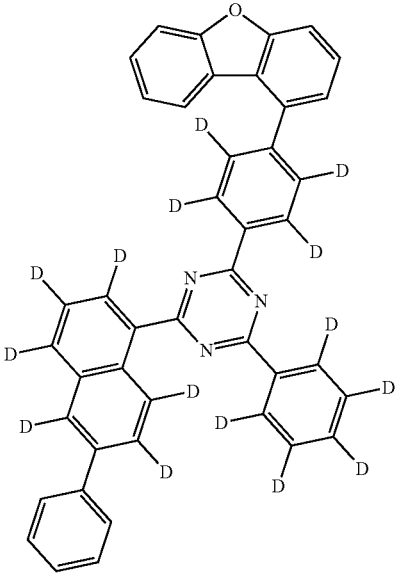
P-92
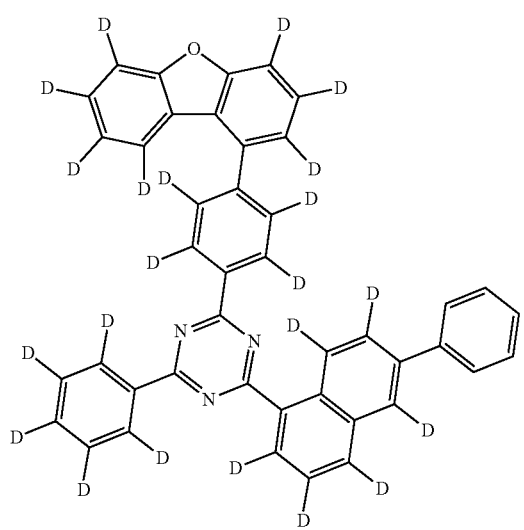

-continued
P-93
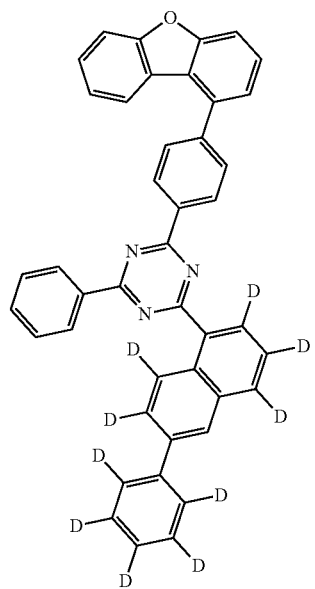
P-94
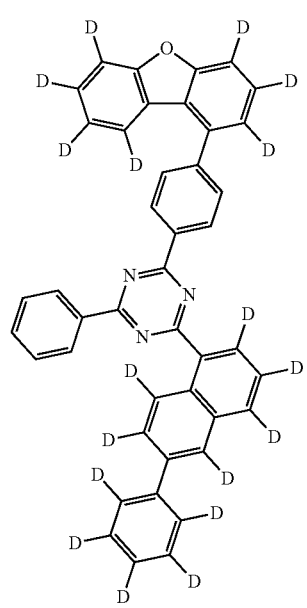
P-95
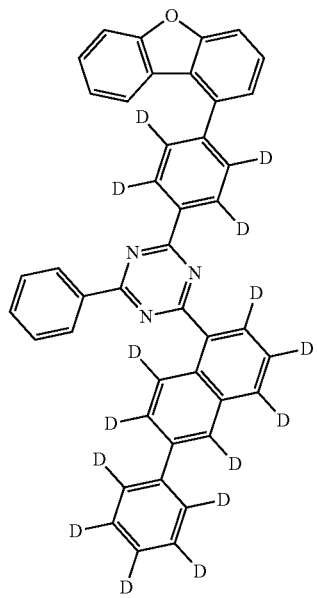
P-96
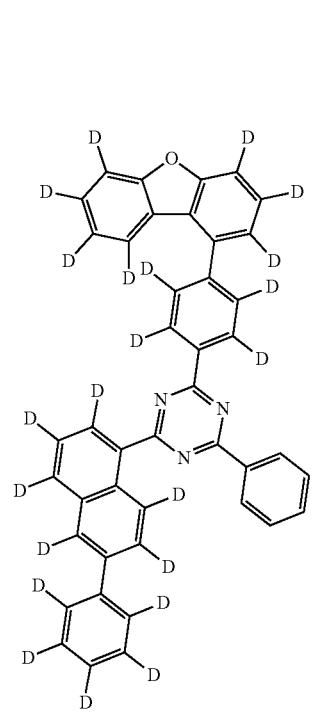

179
-continued

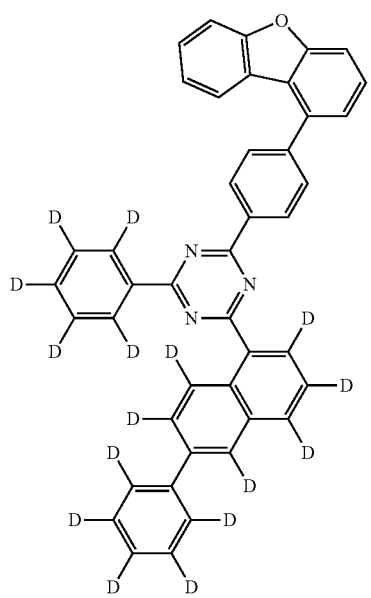

P-97

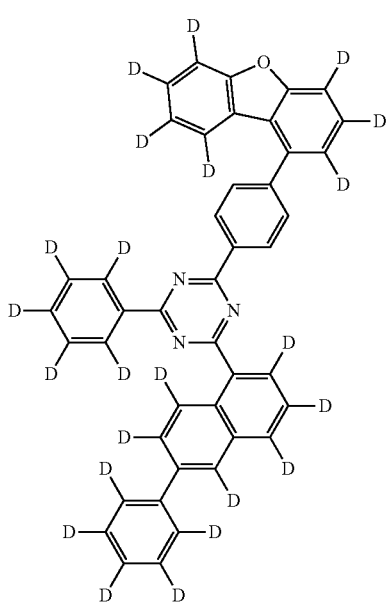

P-98

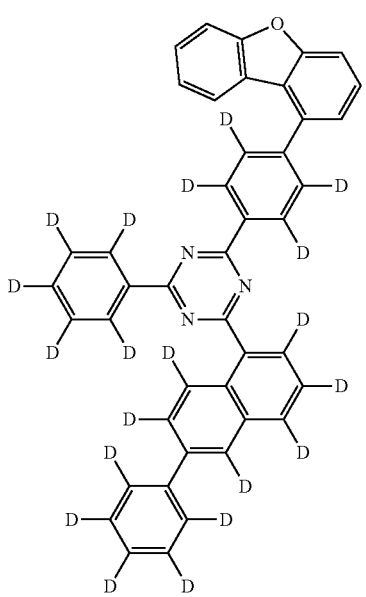

P-99

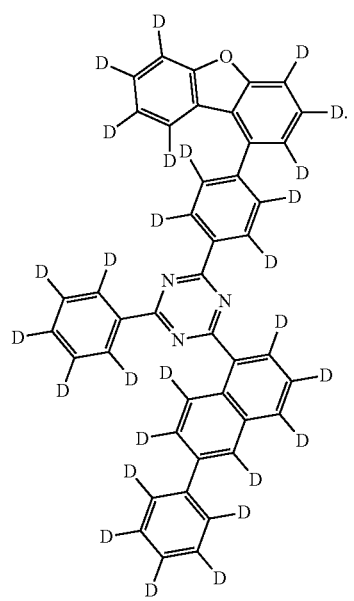

P-100

2. An organic electronic element comprising a first electrode; a second electrode; and an organic material layer formed between the first electrode and the second electrode, wherein the organic material layer comprises the compound of claim 1.

3. The organic electronic element according to claim 2, further comprising a light efficiency enhancing layer formed on at least one surface of the first electrode and the second electrode, the surface being opposite to the organic material layer.

4. The organic electronic element according to claim 2, wherein the organic material layer comprises 2 or more stacks comprising a hole transport layer, an emitting layer and an electron transport layer sequentially formed on the first electrode.

5. The organic electronic element according to claim 4, the organic material layer further comprises a charge generation layer formed between the 2 or more stacks.

6. The organic electronic element according to claim 2, wherein the organic material layer comprising the compound is an emitting layer.

7. An electronic device comprising a display device comprising the organic electronic element of claim 2; and a control unit for driving the display device.

8. The electronic device according to claim 7, wherein the organic electronic element is at least one of an OLED, an organic solar cell, an organic photo conductor (OPC), organic transistor (organic TFT) and an element for monochromic or white illumination.

9. A composition for an organic electronic element comprising a mixture of a compound represented by Formula 1 and a compound represented by Formula 5:

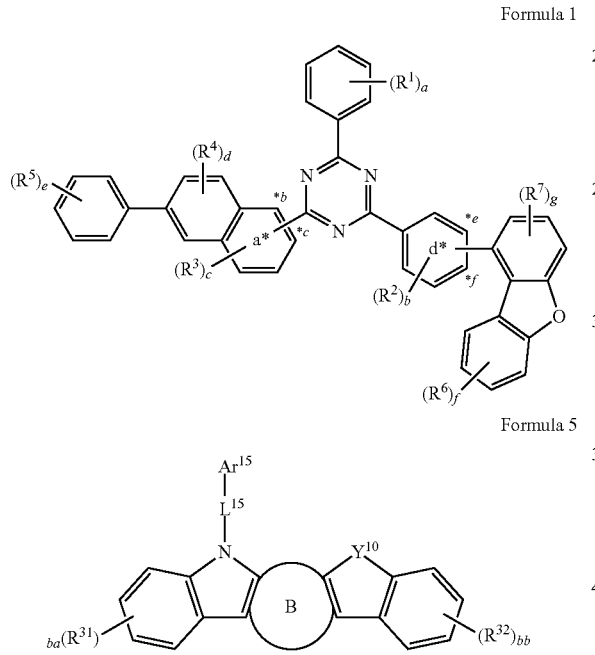

Formula 1

Formula 5 wherein:

$R^1$, $R^2$, $R^3$, $R^4$, $R^5$, $R^6$ and $R^7$ are the same or different from each other and are each independently hydrogen or deuterium,

*a is bonded to either *b or *c,

*d is bonded to either *e or *f, a and e are independently an integer of 0 to 5, b and f are independently an integer of 0 to 4, c, d and g are independently an integer of 0 to 3, $L^{15}$ is each independently selected from the group consisting of a single bond; a $C_6$-$C_{60}$ arylene group; a fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring, $Ar^{15}$ is selected from the group consisting of an $C_6$-$C_{60}$ aryl group; a fluorenyl group; a $C_2$-$C_{60}$ heterocyclic group including at least one heteroatom of O, N, S, Si or P; a $C_3$-$C_{60}$ aliphatic ring; a fused ring group of a $C_3$-$C_{60}$ aliphatic ring and a $C_6$-$C_{60}$ aromatic ring; and -L'-N(R')(R"), wherein L' is selected from the group consisting of a single bond; a $C_6$-$C_{60}$ arylene group; a fluorenylene group; a $C_2$-$C_{60}$ heterocyclic group including at least one heteroatom of O, N, S, Si or P; and a $C_3$-$C_{60}$ aliphatic ring, and wherein R' and R" are each independently selected from the group consisting of an $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a fused ring group of a $C_3$-$C_{60}$ aliphatic ring and a $C_6$-$C_{60}$ aromatic ring, $Y^{10}$ is O, S, $CR^{51}R^{52}$ or $NR^{53}$, Ring B is a $C_6$-$C_{20}$ aryl group, $R^{31}$ and $R^{32}$ are each the same or different, and each independently selected from the group consisting of hydrogen; deuterium; halogen; a cyano group; a nitro group; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxy group; and a $C_6$-$C_{60}$ aryloxy group; or an adjacent plurality of $R^{31}$ or plurality of $R^{32}$ may be bonded to each other to form a ring, $R^{51}$, $R^{52}$ and $R^{53}$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxy group; and a $C_6$-$C_{60}$ aryloxy group; alternatively, $R^{51}$ and $R^{52}$ can be bonded to each other to form a spiro ring, ba and bb are each independently an integer of 0 to 4, wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; a $C_3$-$C_{20}$ cycloalkyl group; a $C_7$-$C_{20}$ arylalkyl group; a $C_8$-$C_{20}$ arylalkenyl group; and -L'-N(R')(R"); also the hydrogen of these substituents may be further substituted with one or more deuterium, and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

10. The composition for an organic electronic element according to claim 9, wherein the composition is used as a host for an emitting layer.

11. The composition for an organic electronic element according to claim 9, wherein Formula 1 comprises a compound selected from the group consisting of Formulas 1-1 to 1-4:

Formula 1-1
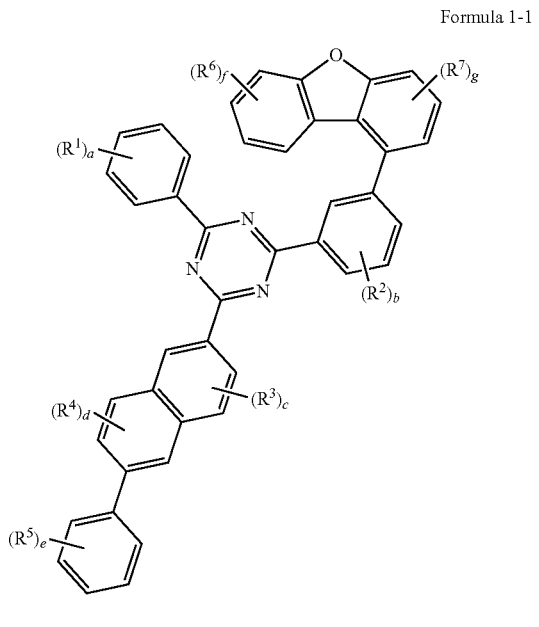
Formula 1-2
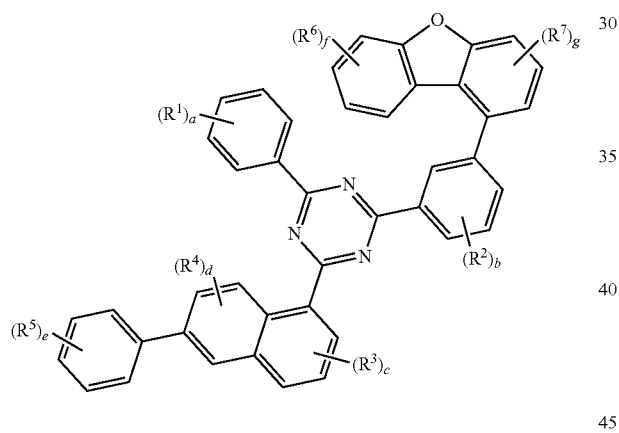
Formula 1-3
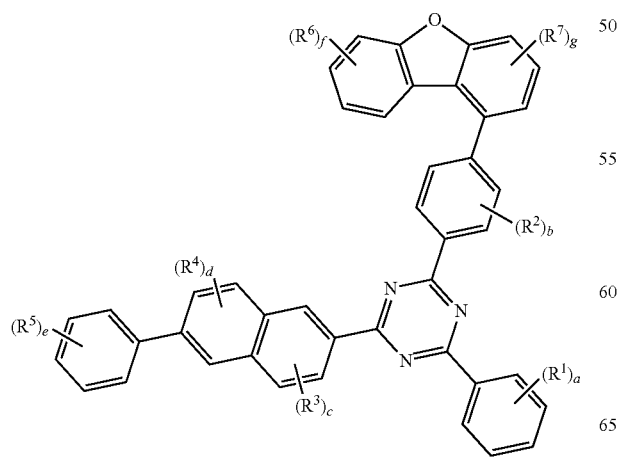
Formula 1-4
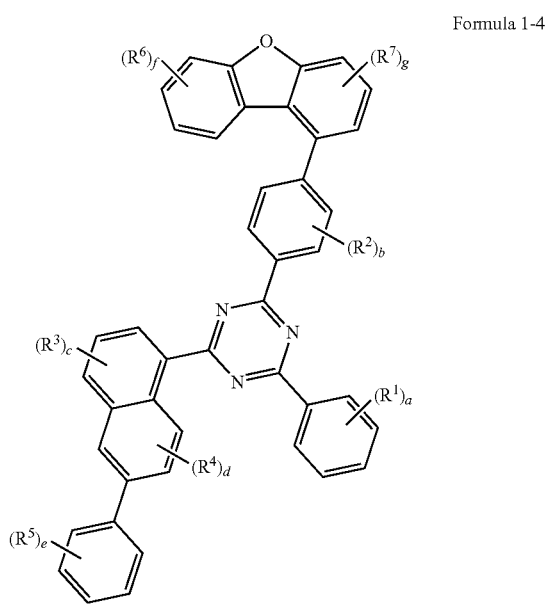
wherein, $R^1$, $R^2$, $R^3$, $R^4$, $R^5$, $R^6$, $R^7$, a, b, c, d, e, f and g are the same as defined in Formula 1.
12. The composition for an organic electronic element according to claim 9, wherein the compound represented by Formula 1 is any one of compounds P-1 to P-100:
P-1
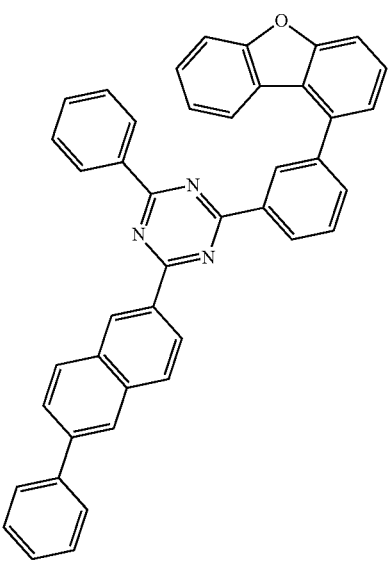

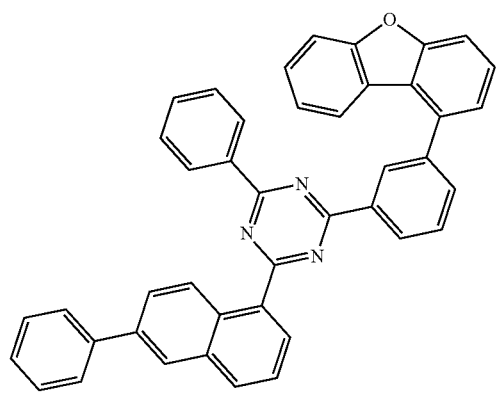
P-2
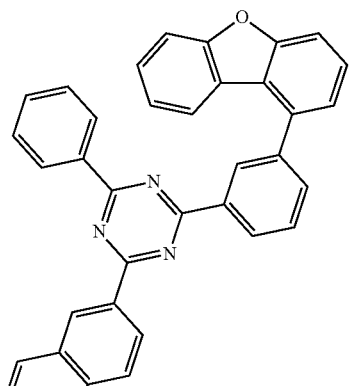
P-5
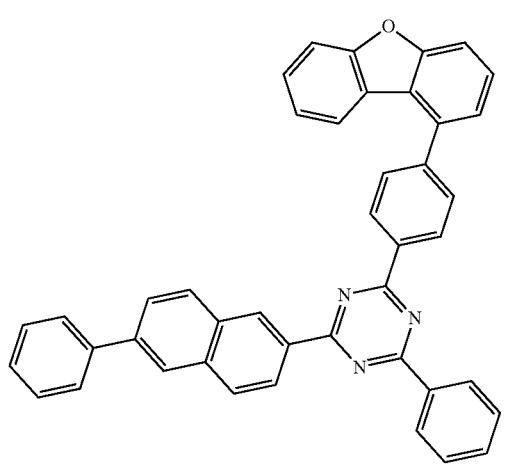
P-3
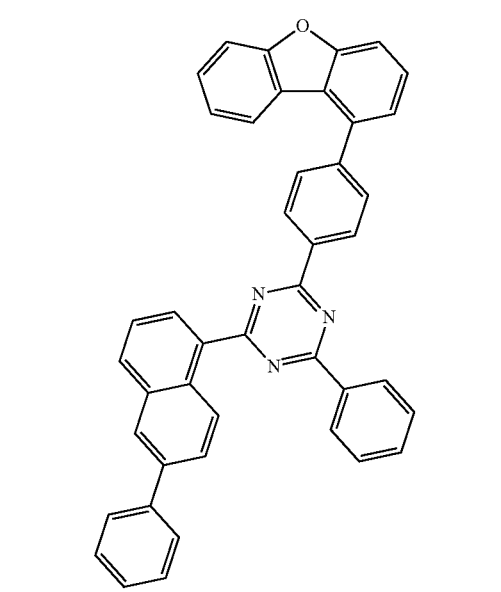
P-4
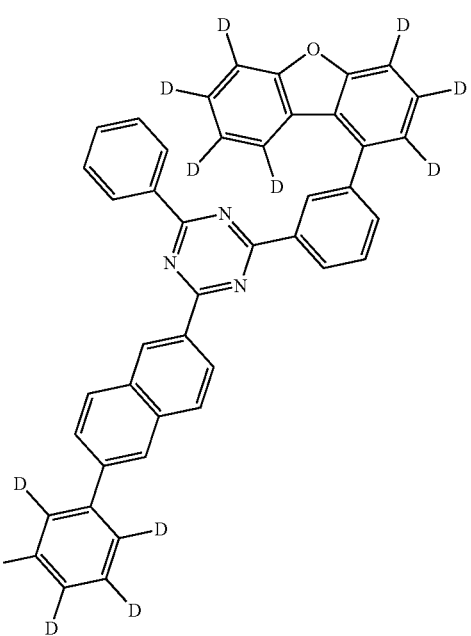
P-6

P-7
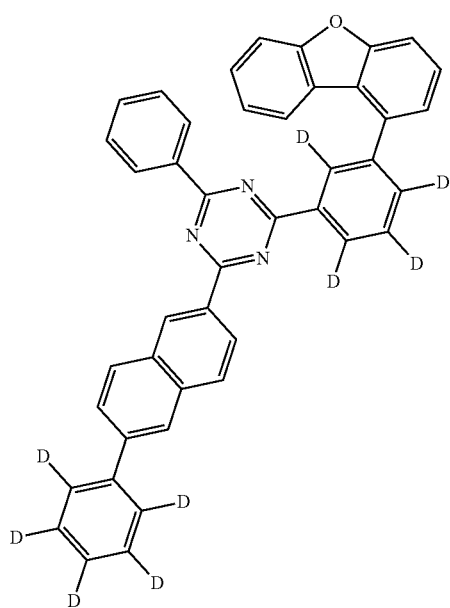
P-8
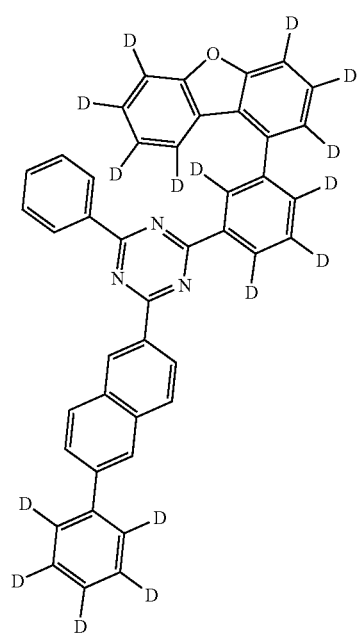
P-9
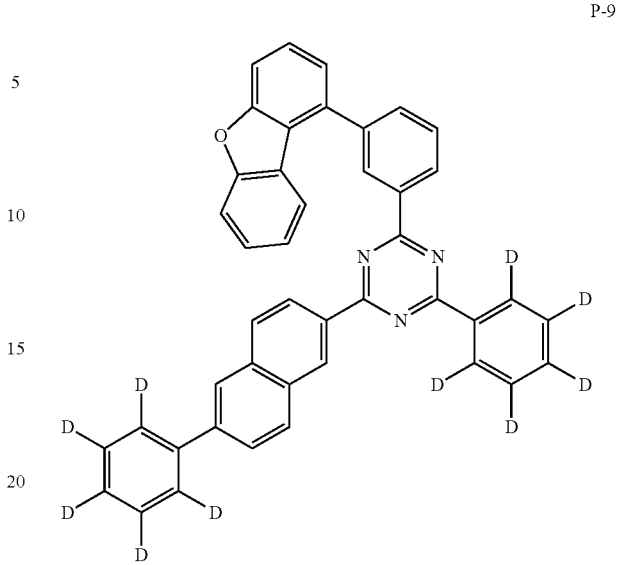
P-10
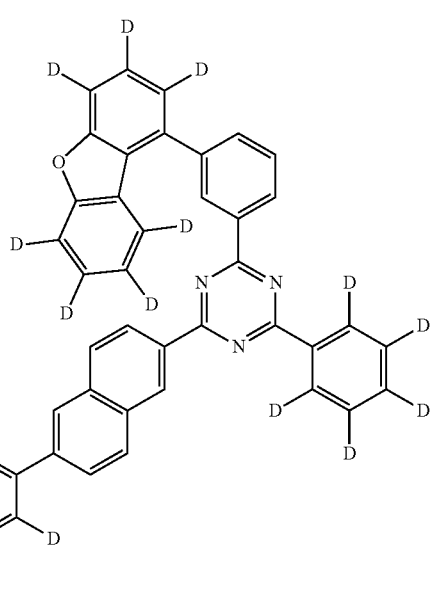

P-11
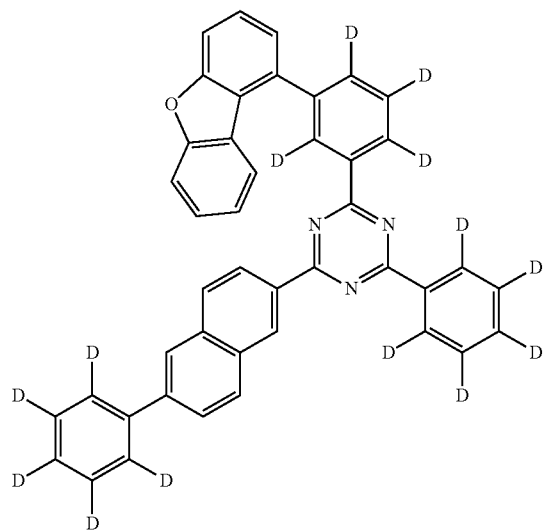
P-12
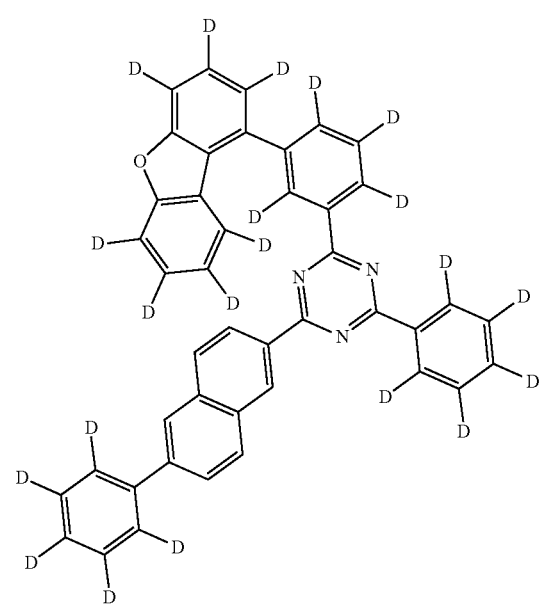
P-13
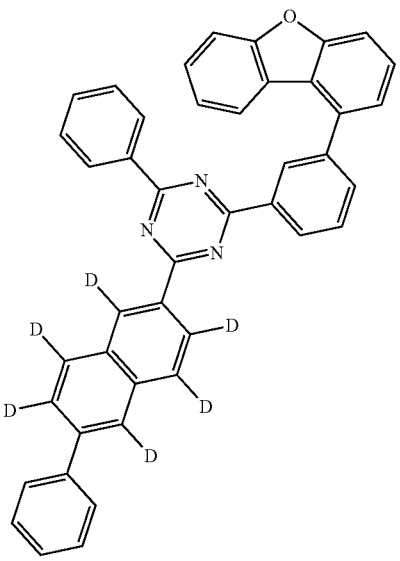
P-14
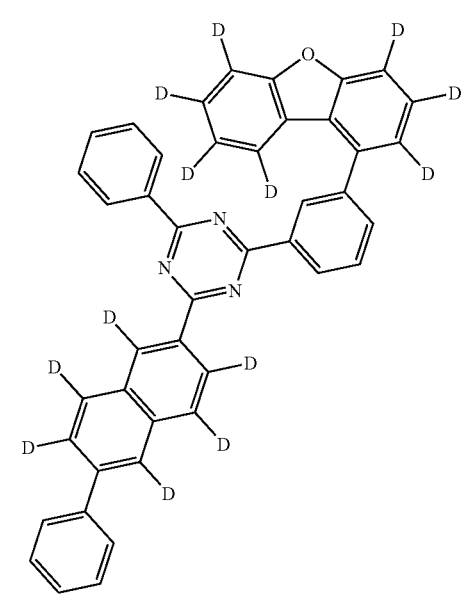

-continued
P-15
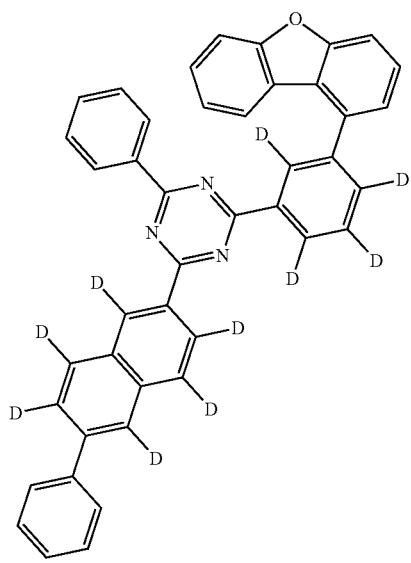
P-16
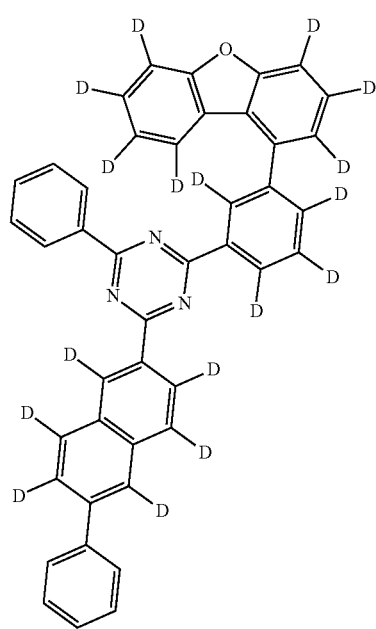
P-17
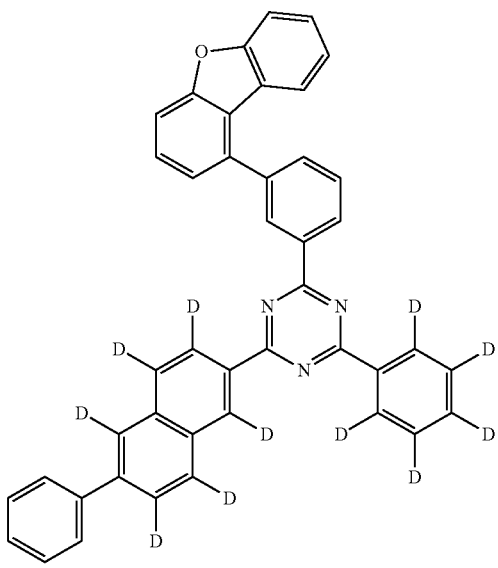
P-18
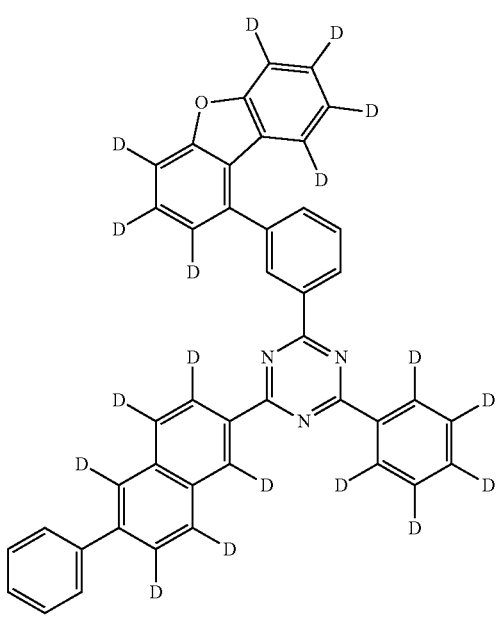

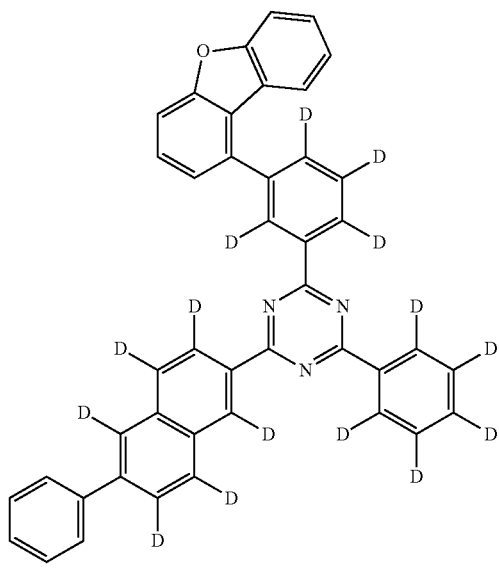
P-19
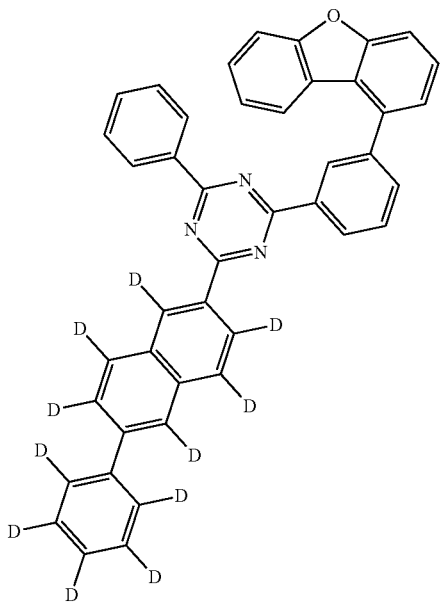
P-21
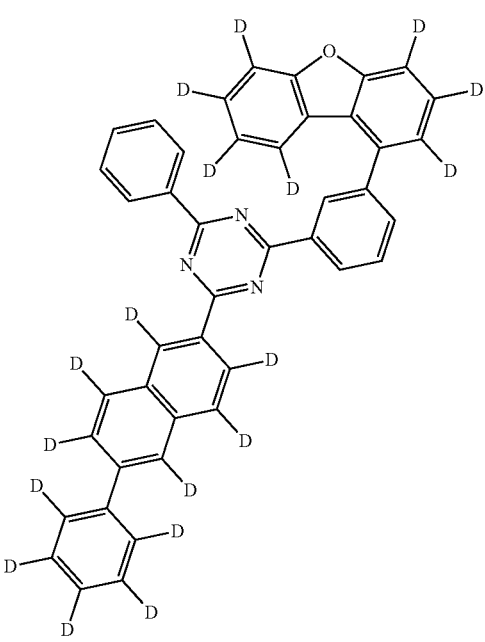
P-22
P-20

P-23
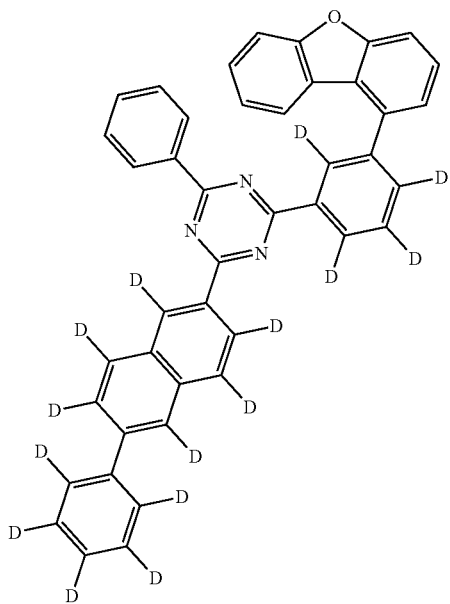
P-25
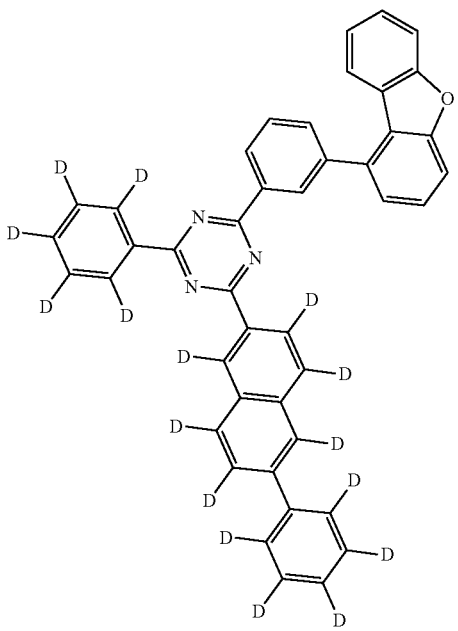
P-24
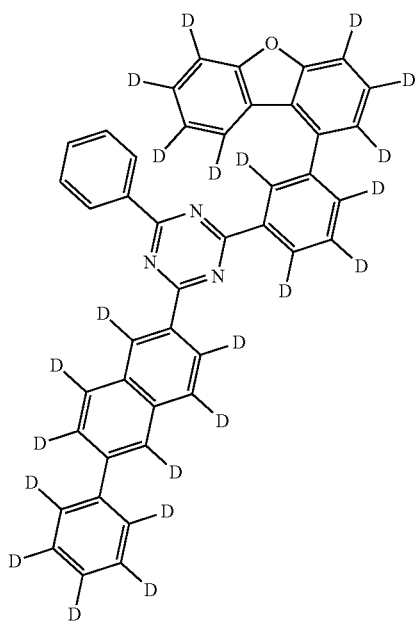
P-26
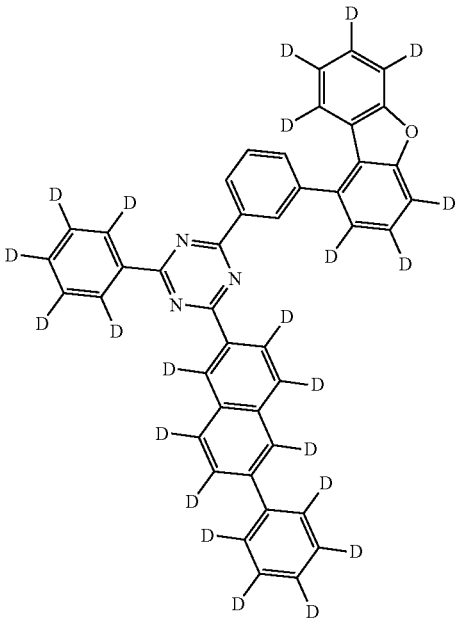

P-27
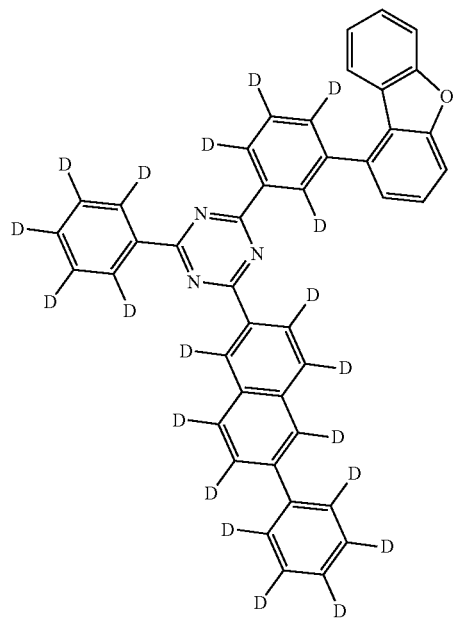
P-28
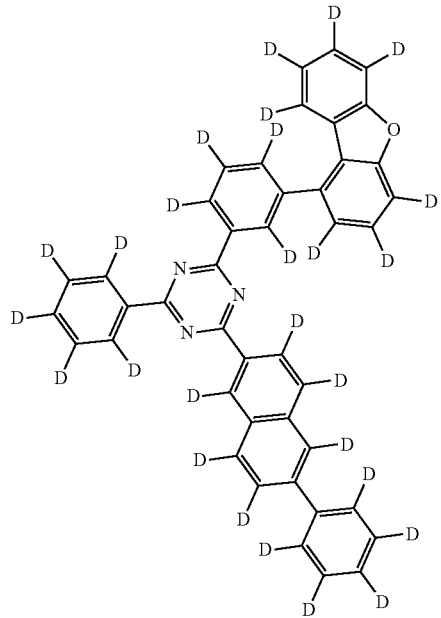
P-29
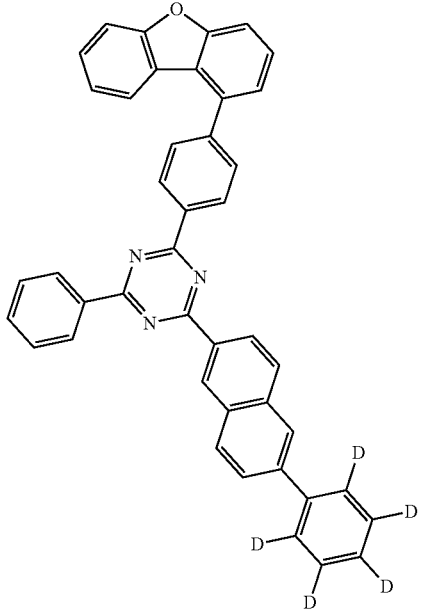
P-30
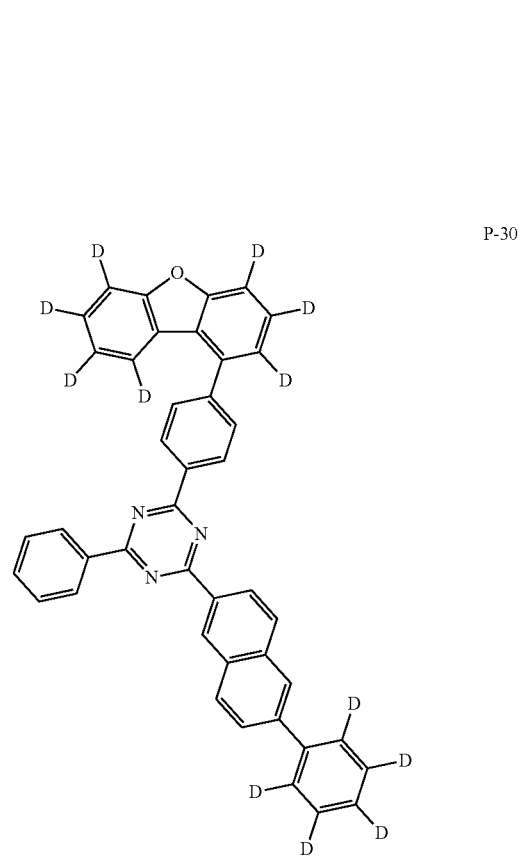

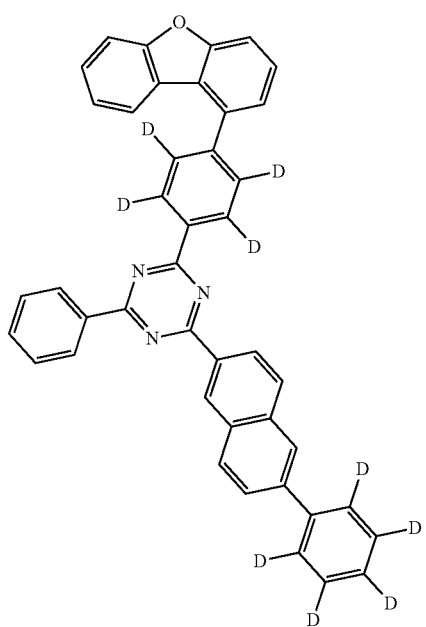
P-31
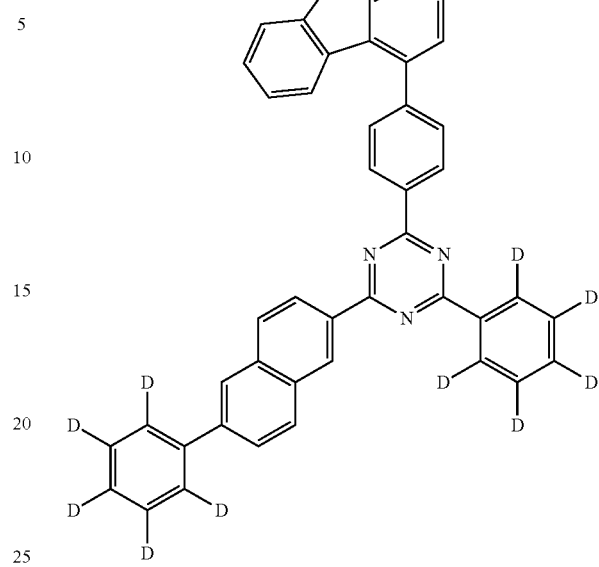
P-33
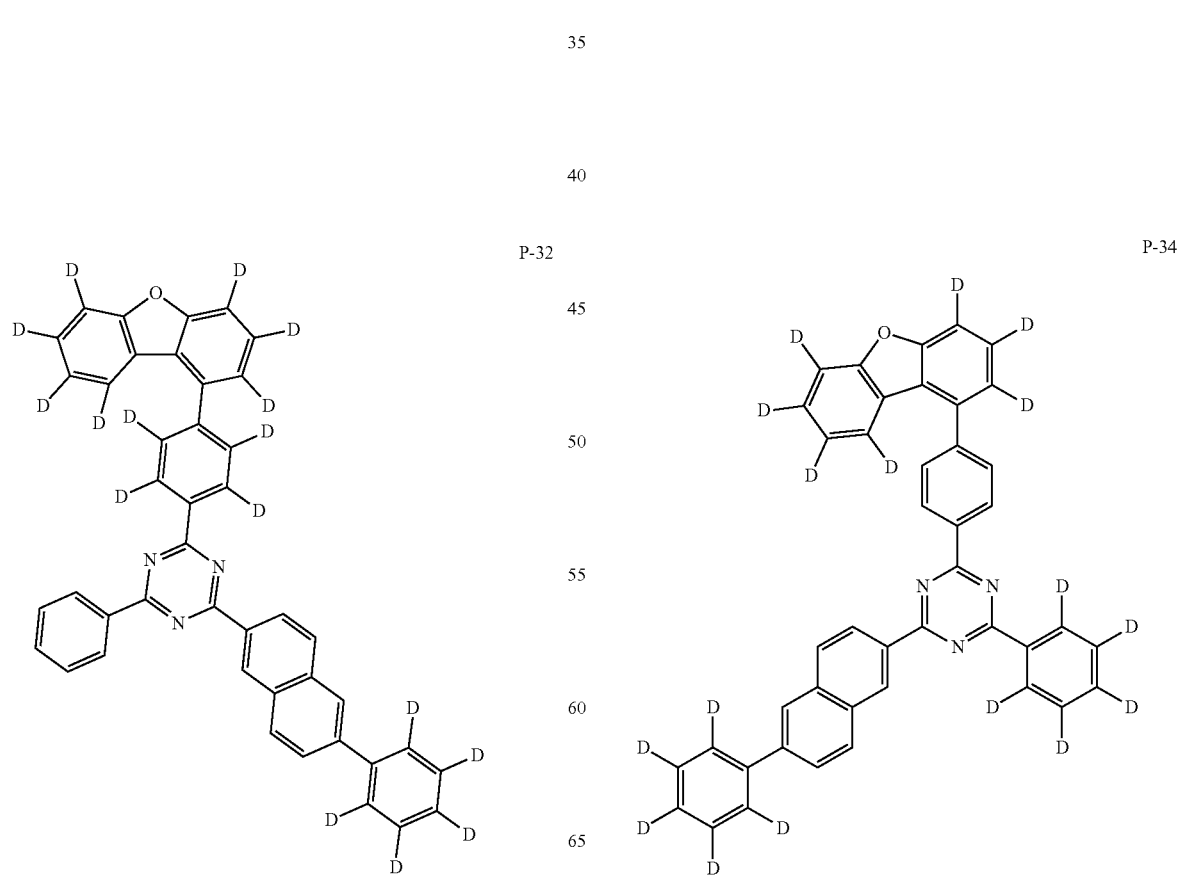
P-32
P-34

P-35
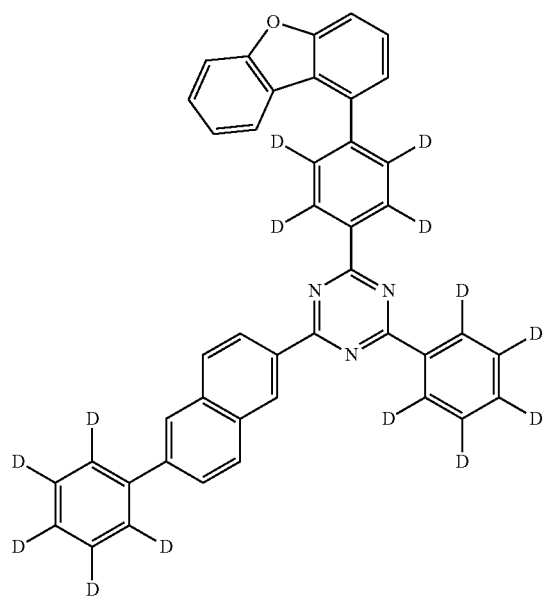
P-36
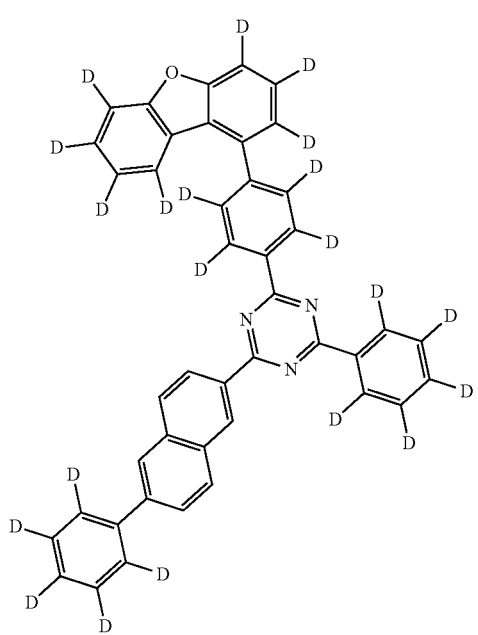
P-37
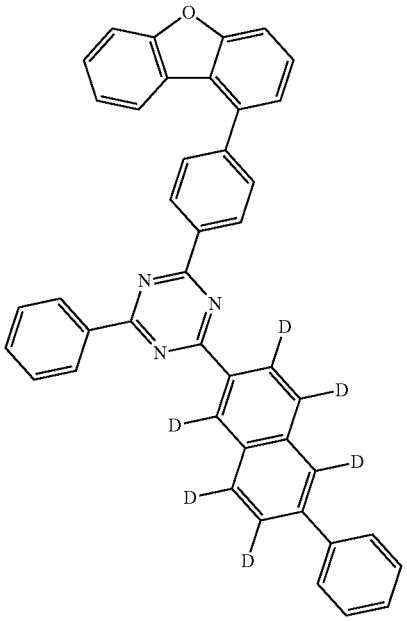
P-38
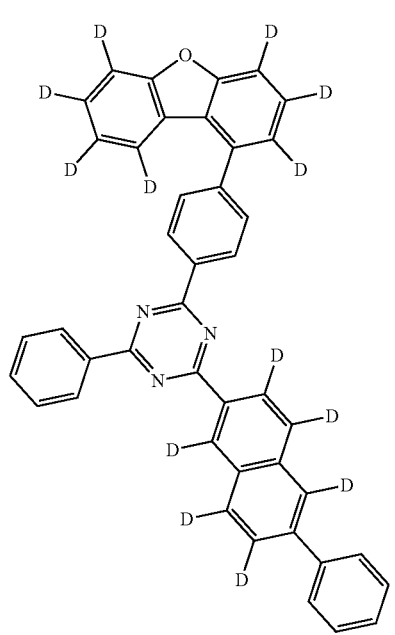

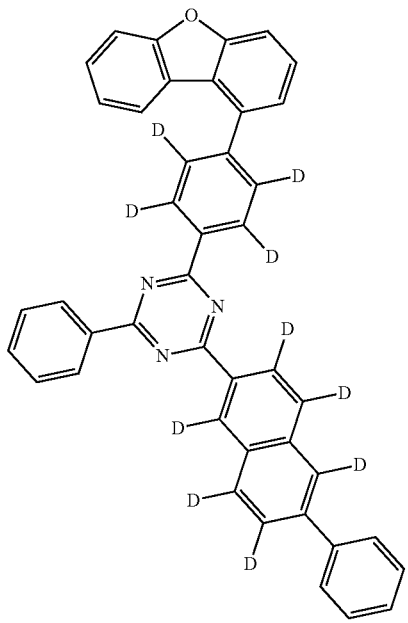
P-39
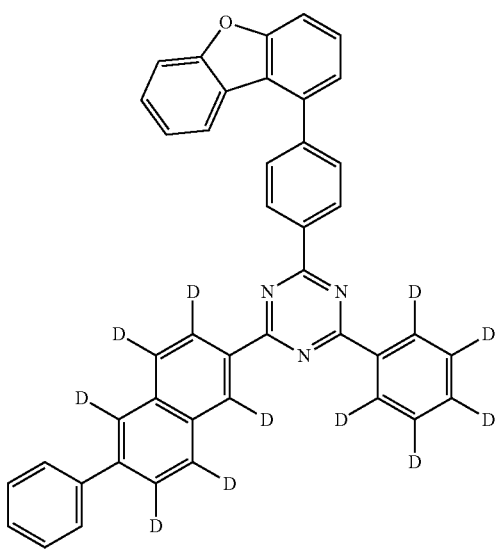
P-41
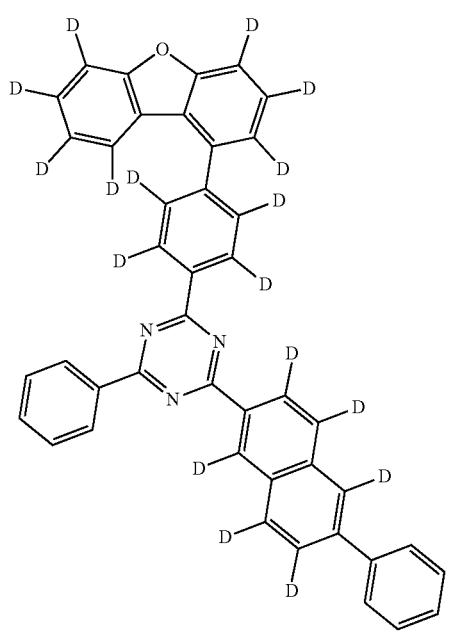
P-40
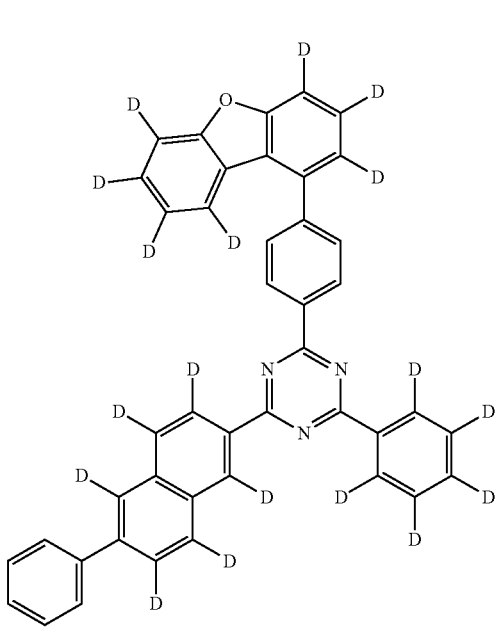
P-42

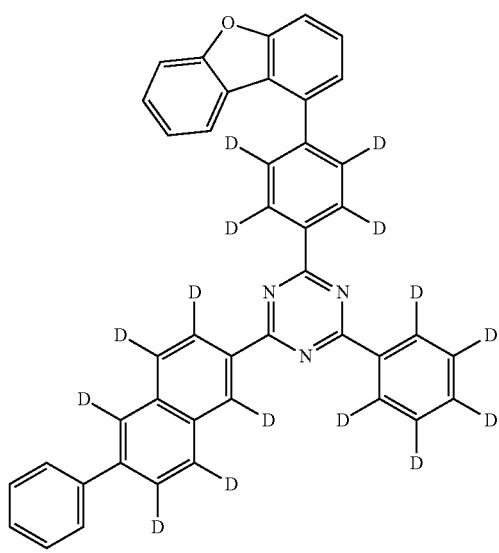
P-43
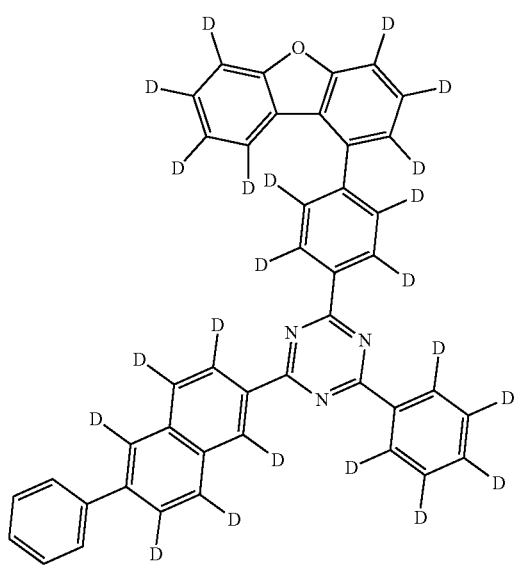
P-44
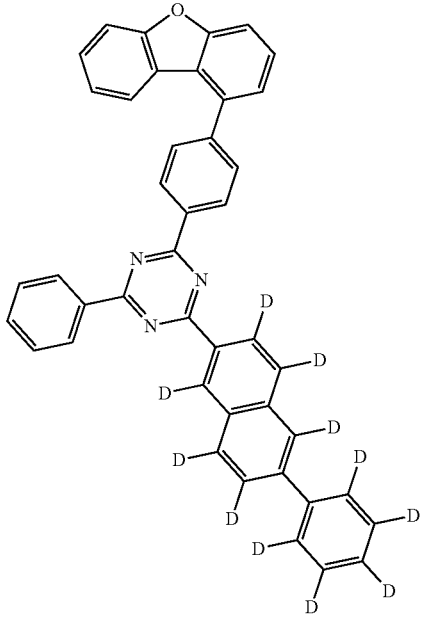
P-45
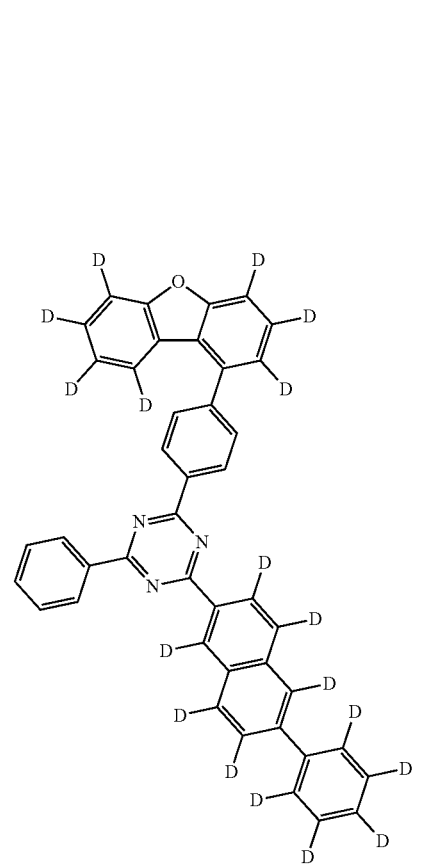
P-46

P-47
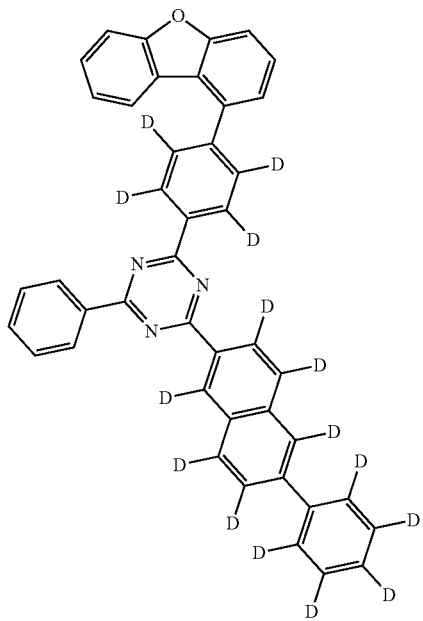
P-48
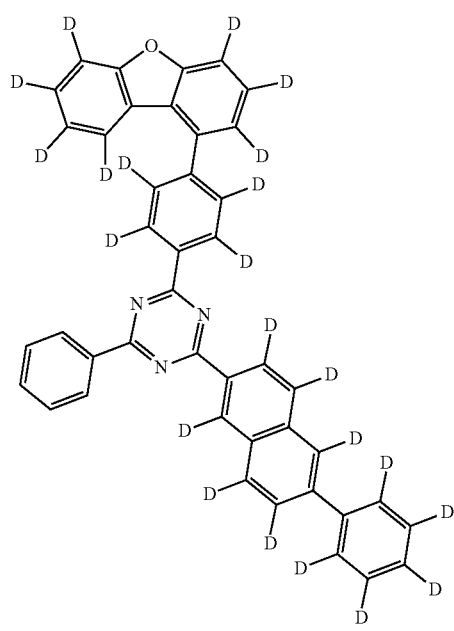
P-49
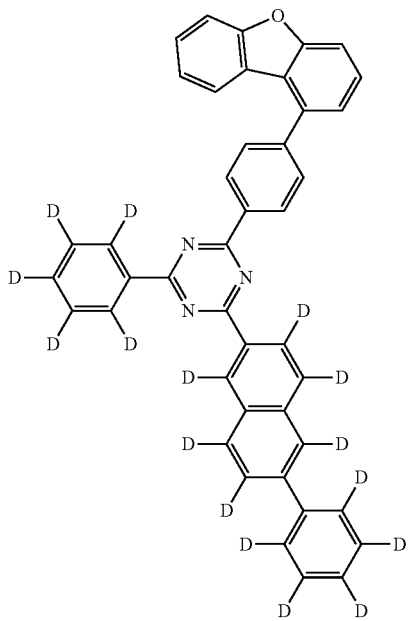
P-50

P-51
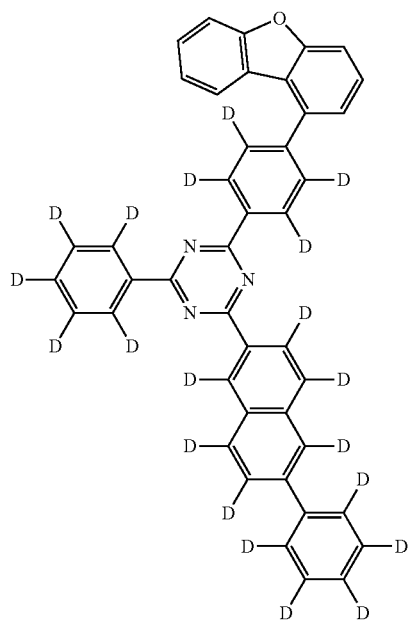
P-52
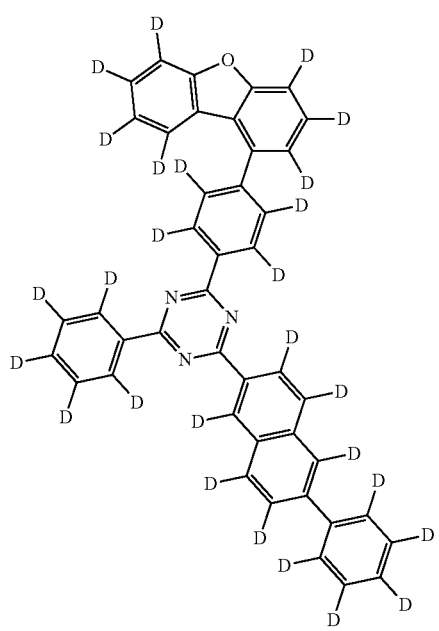
P-53
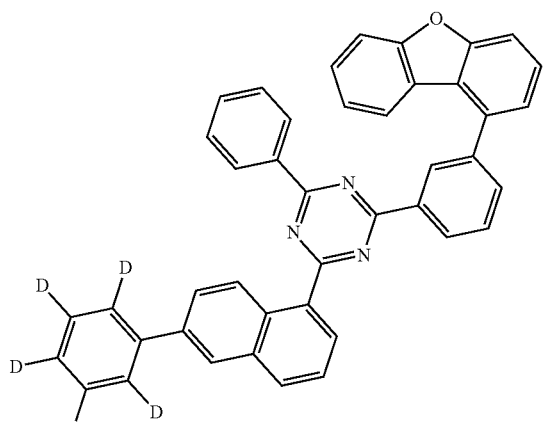
P-54
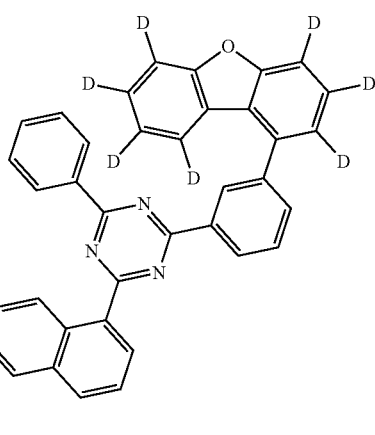
P-55
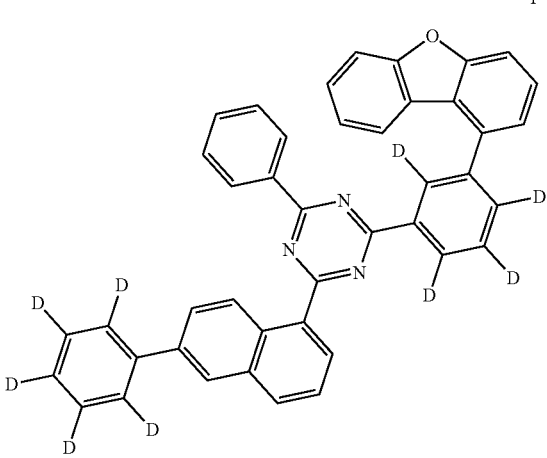

P-56
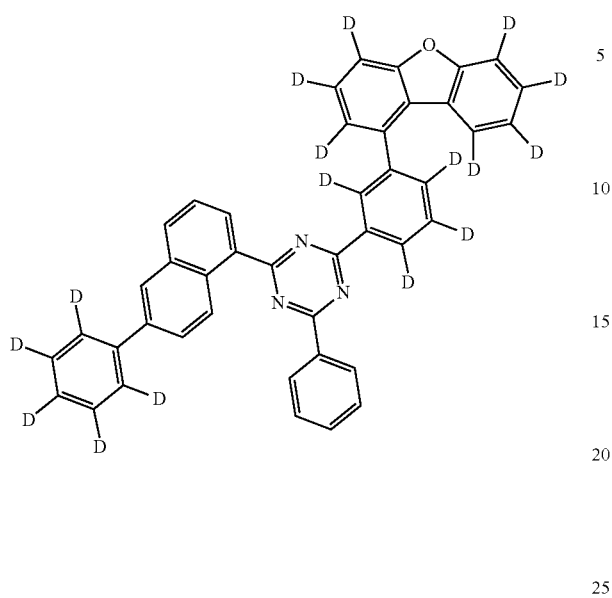
P-58
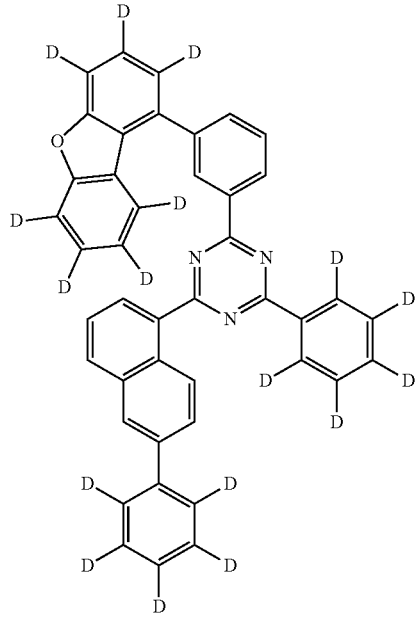
P-57
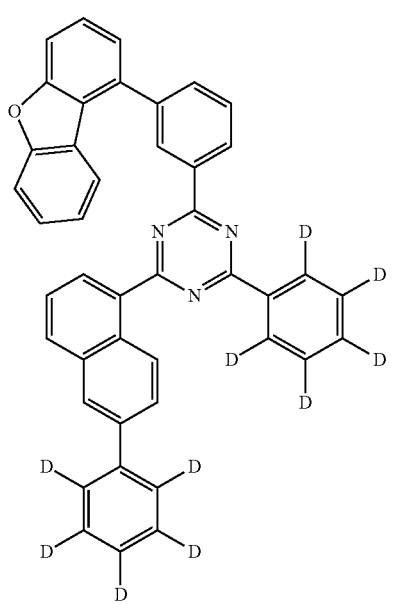
P-59
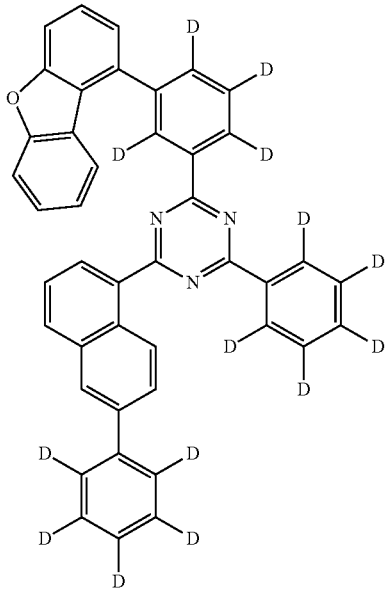

P-60
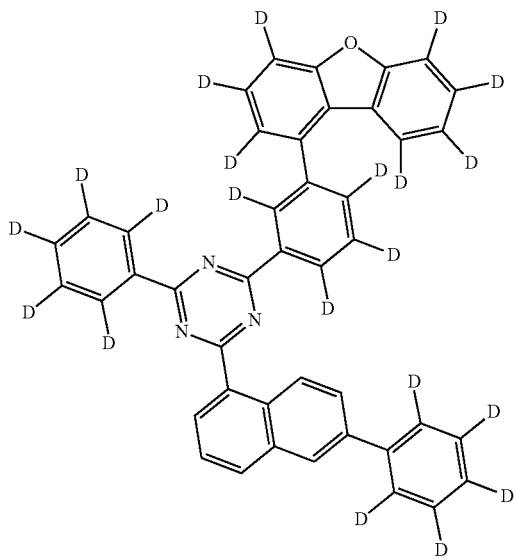
P-61
P-62
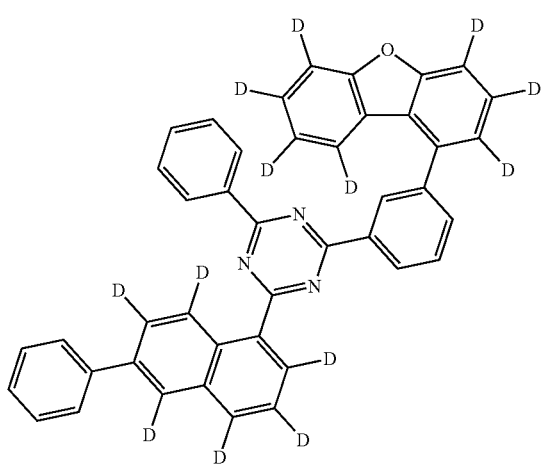
P-63
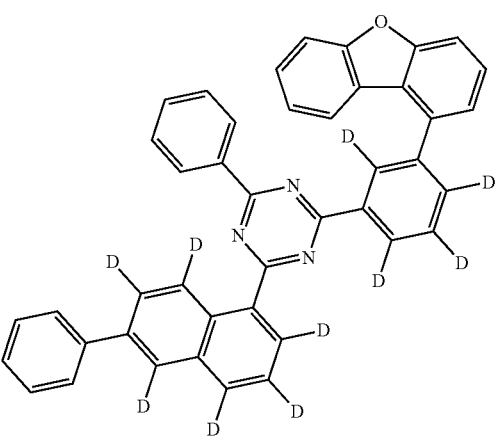
P-64
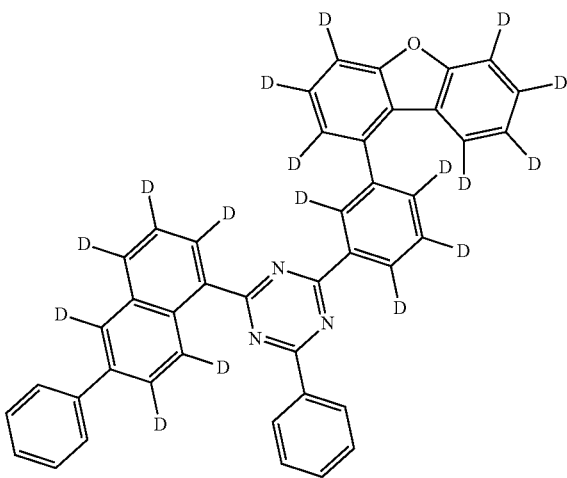
P-65
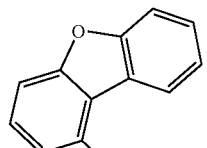

P-66
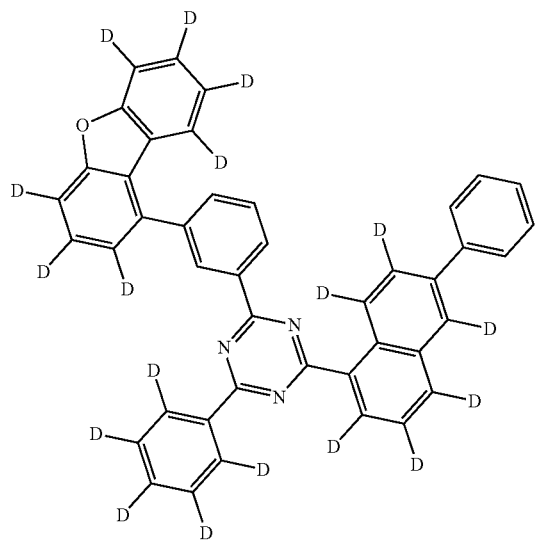
P-67
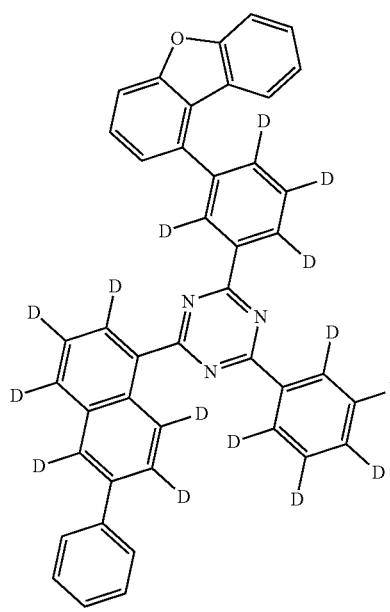
P-68
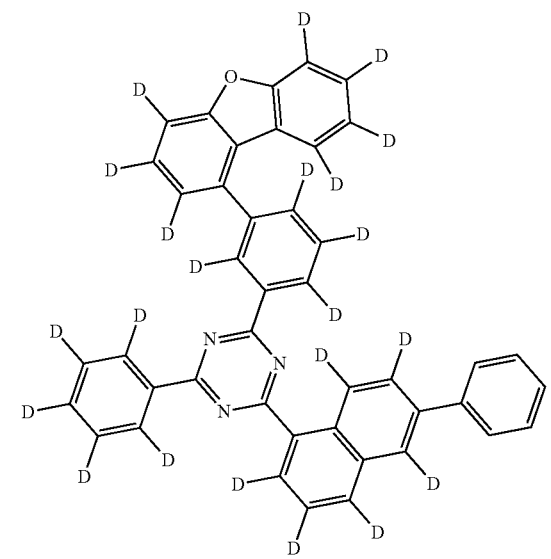
P-69
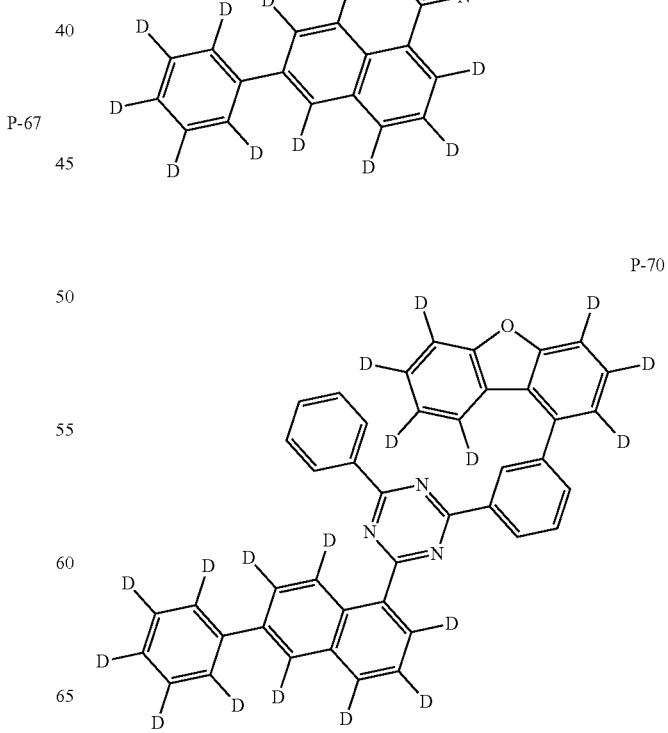
P-70

-continued
P-71
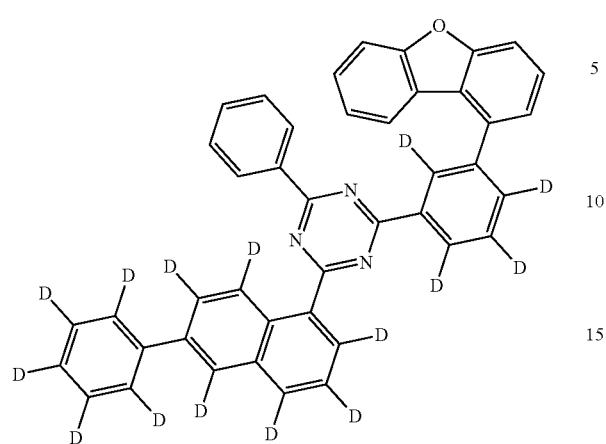
P-72
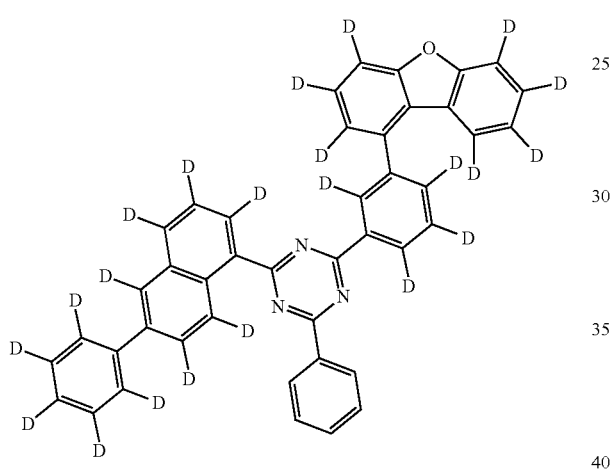
P-73
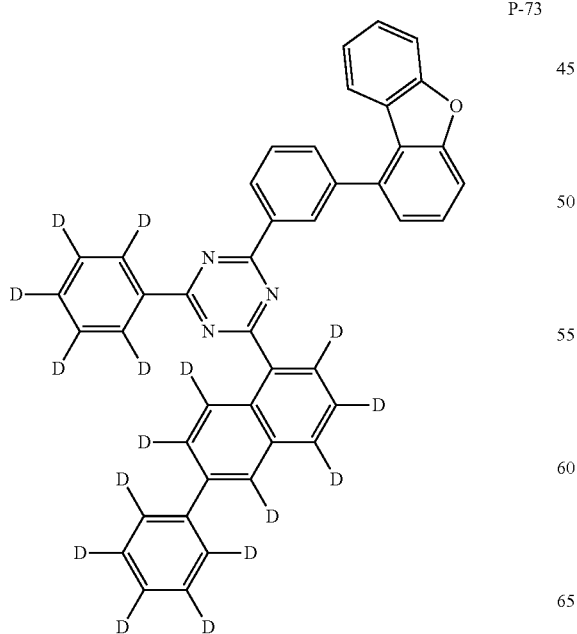
-continued
P-74
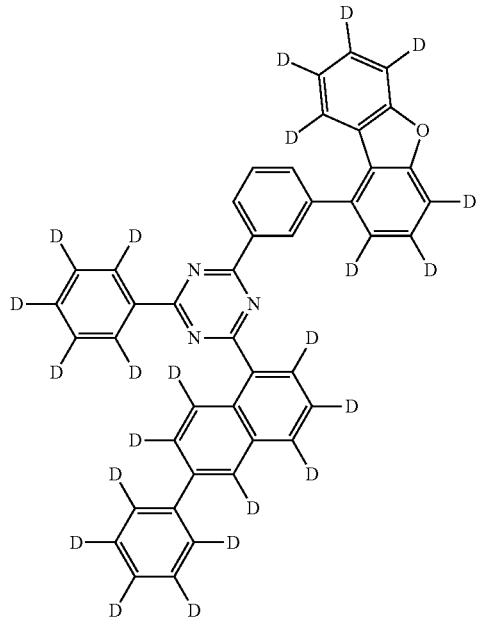
P-75
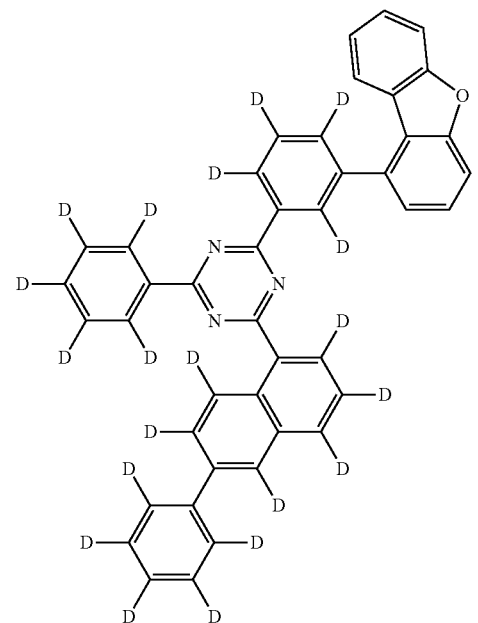

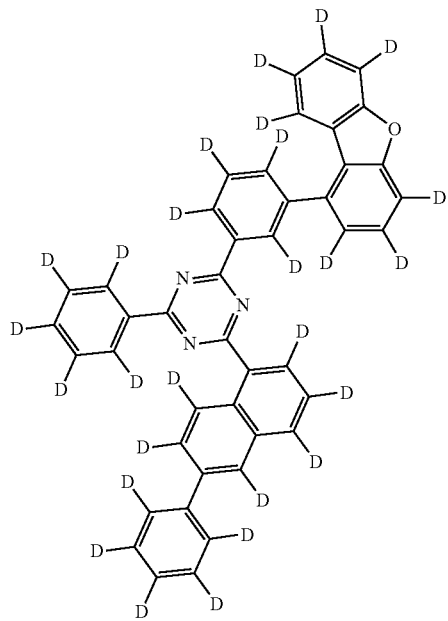

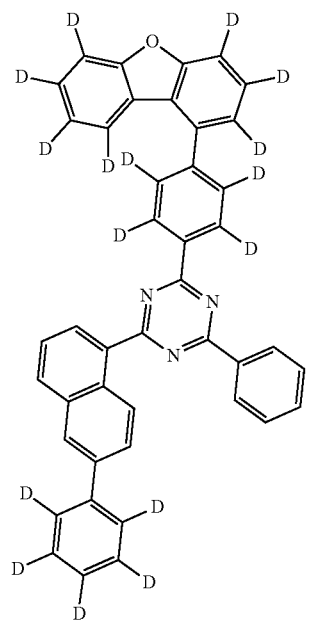
P-80
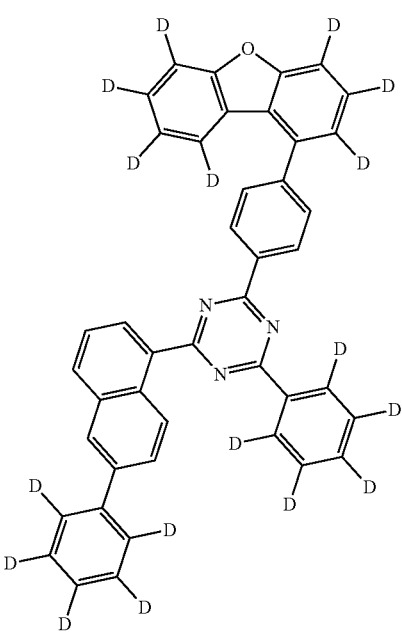
P-82
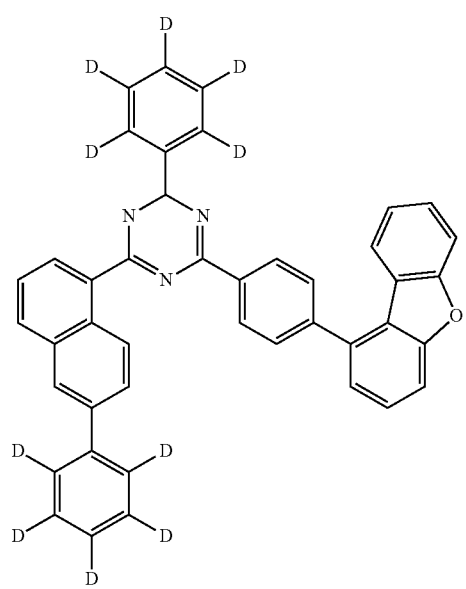
P-81
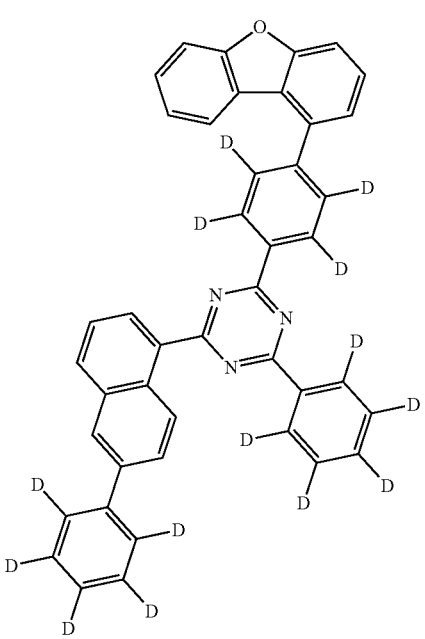
P-83

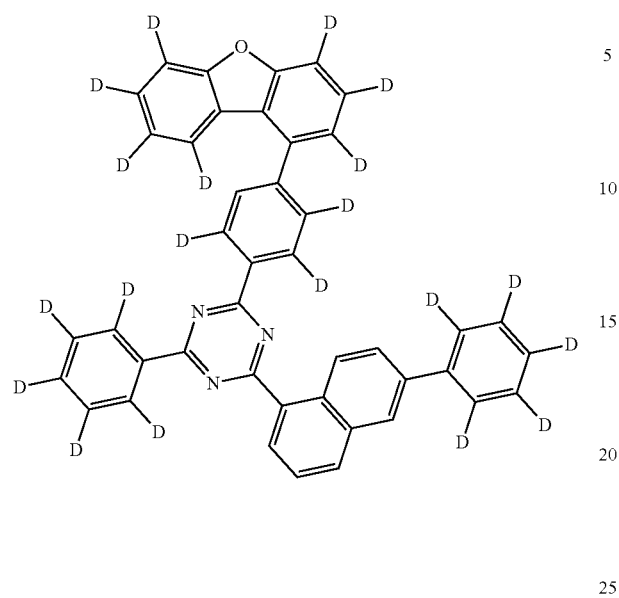
P-84
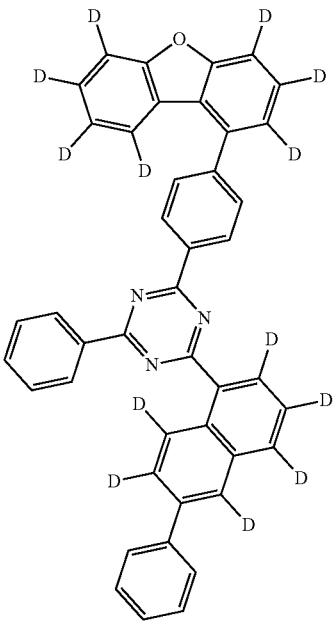
P-86
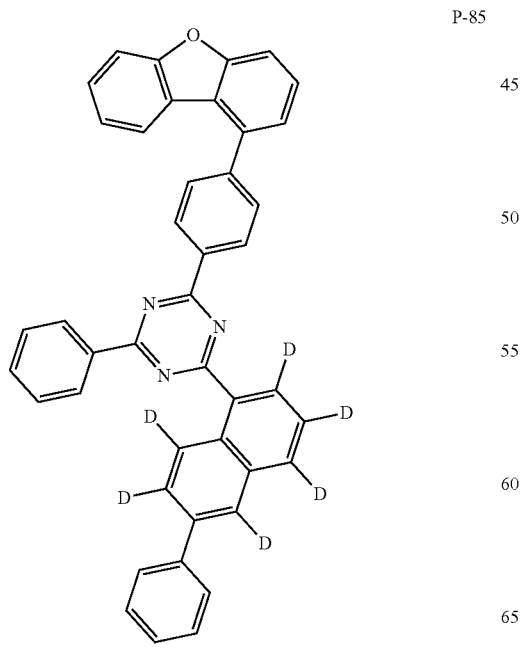
P-85
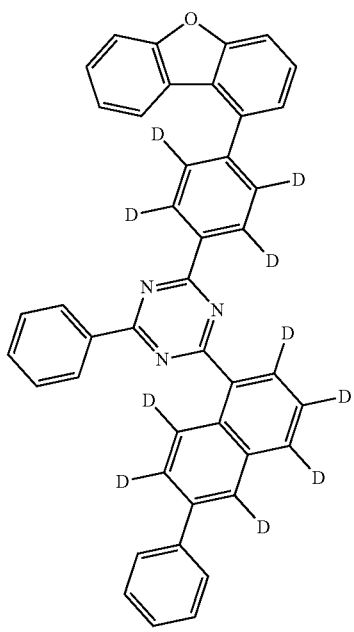
P-87

P-88
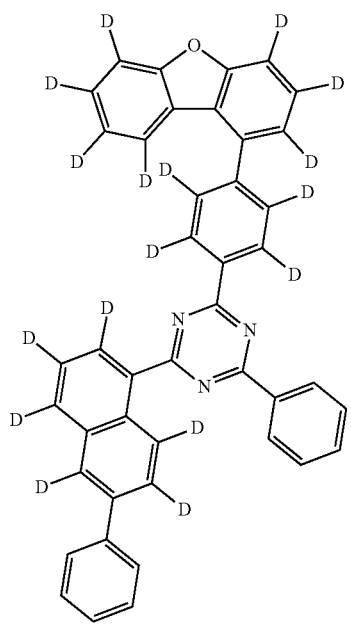
P-89
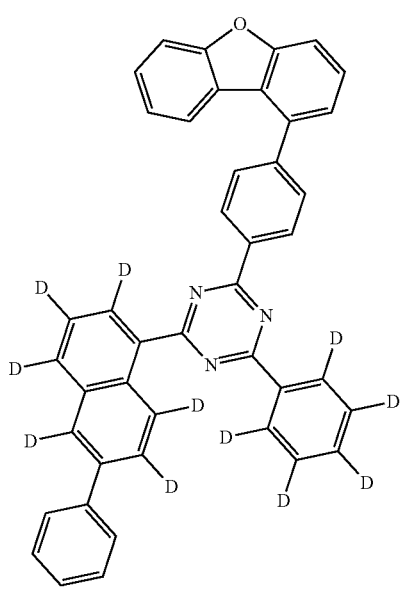
P-90
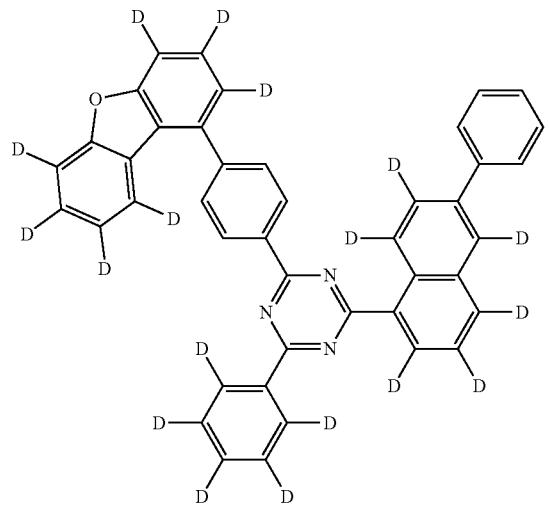
P-91
P-92

P-93
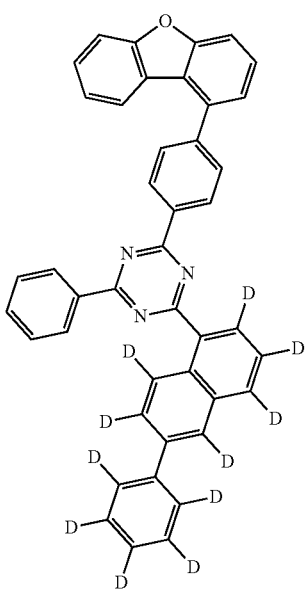
P-94
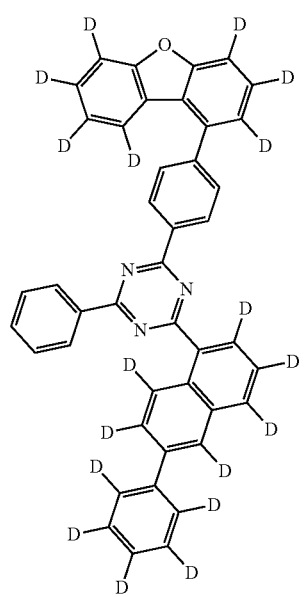
P-95
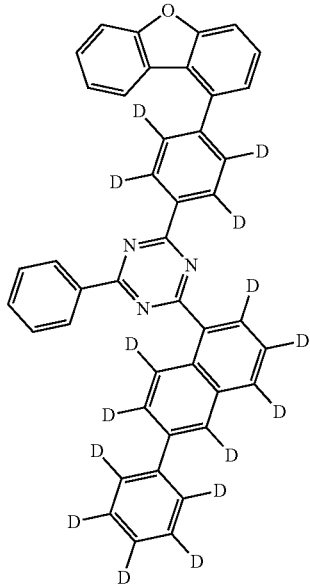
P-96
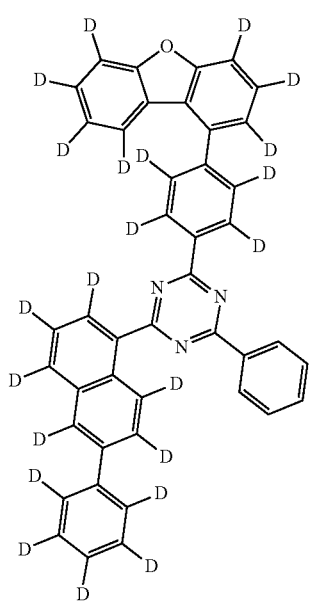

P-97
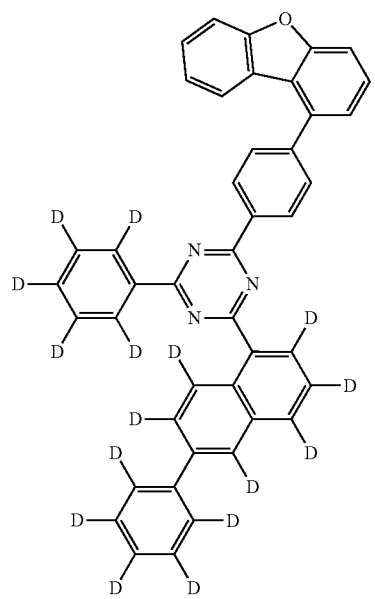
P-98
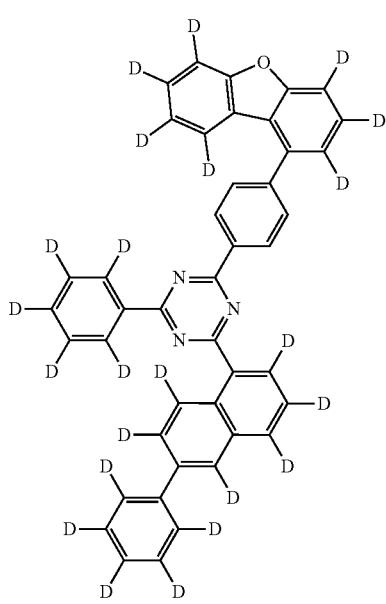
P-99
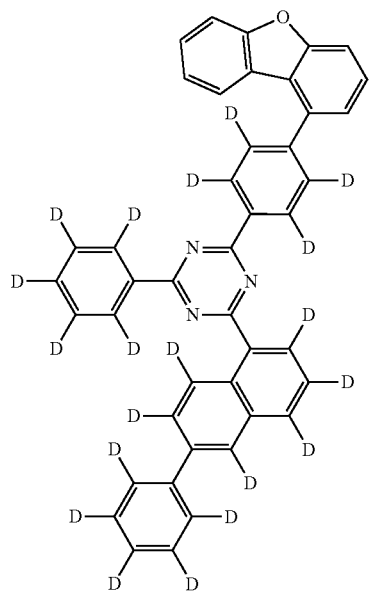
P-100
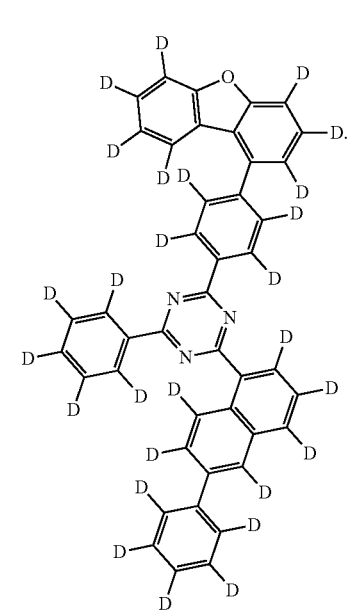
13. The composition for an organic electronic element according to claim 9, wherein the compound represented by Formula 5 is any one of compounds S-1 to S-116:
S-1
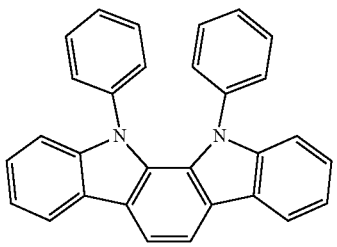

-continued
S-2
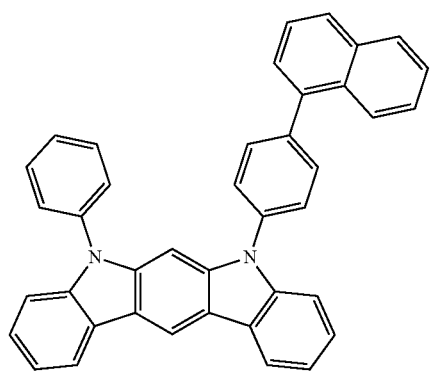
S-3
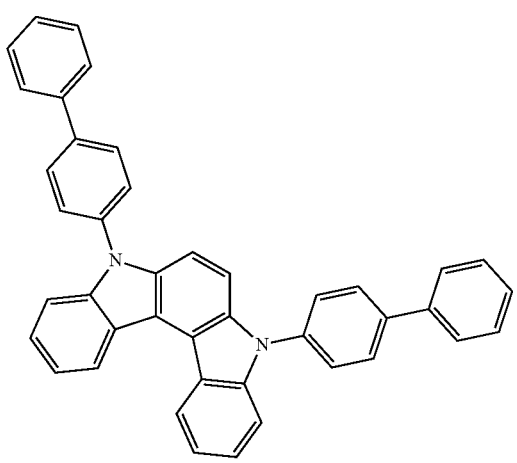
S-4
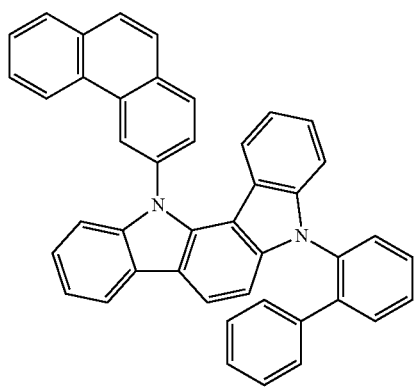
-continued
S-5
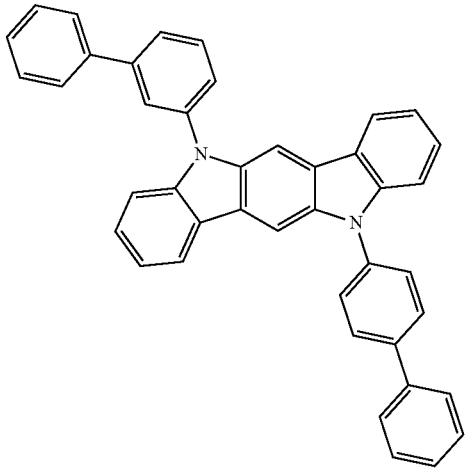
S-6
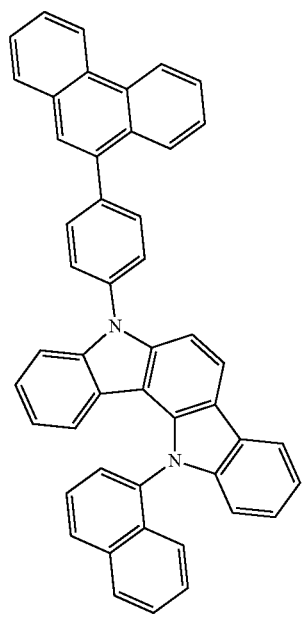
S-7
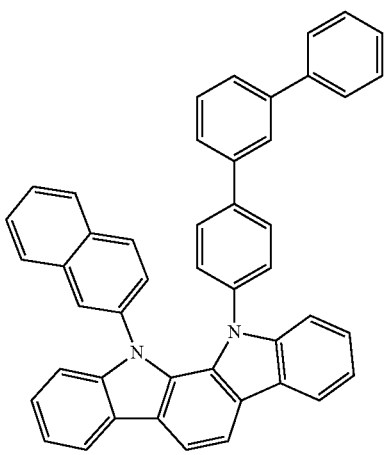

-continued
S-8
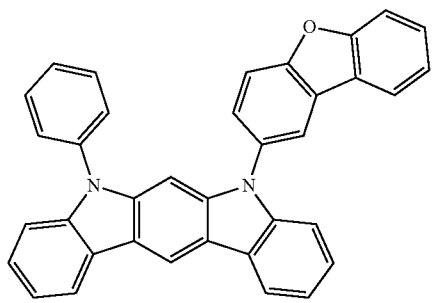
S-9
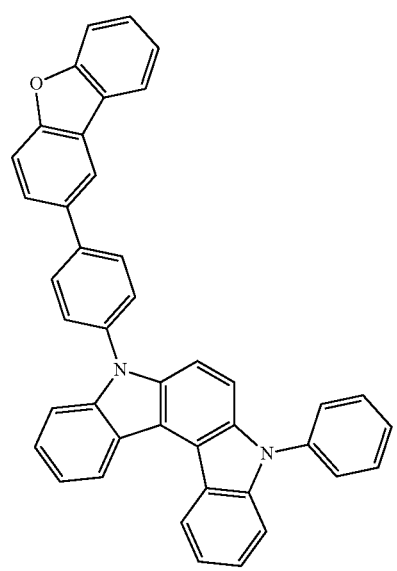
S-10
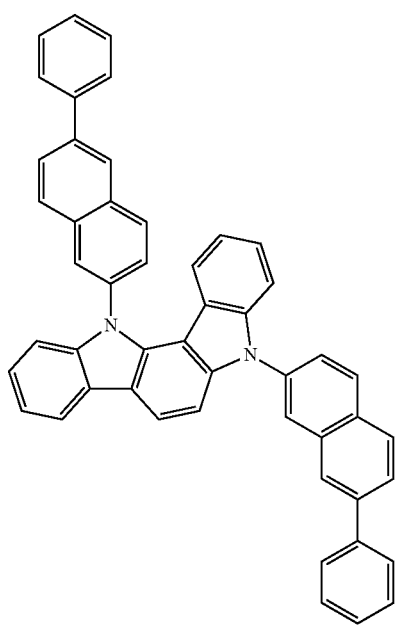
-continued
S-11
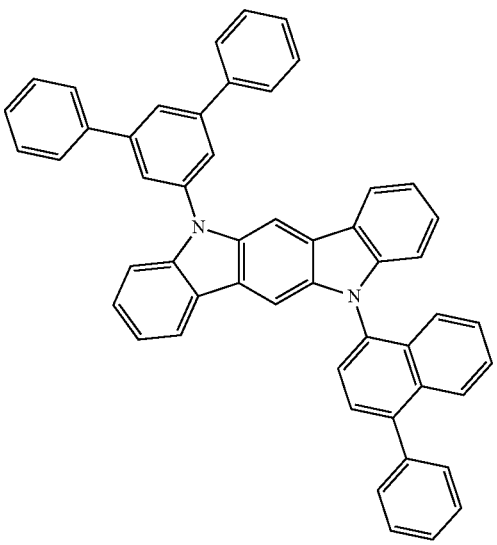
S-12
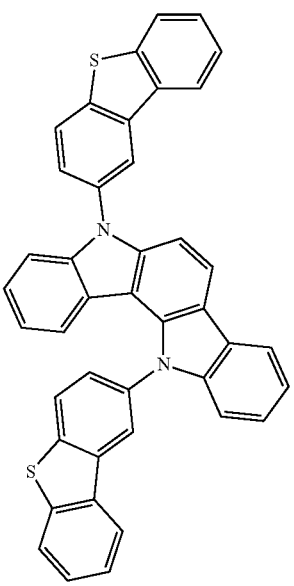
S-13
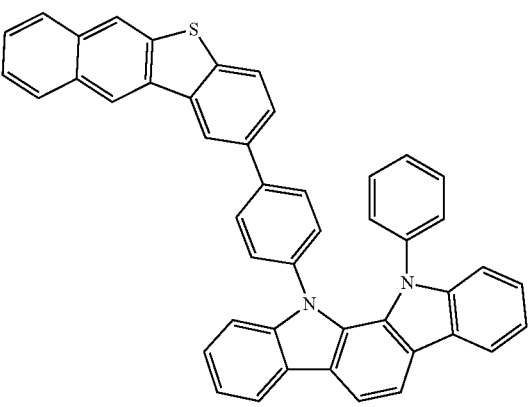

-continued
S-14
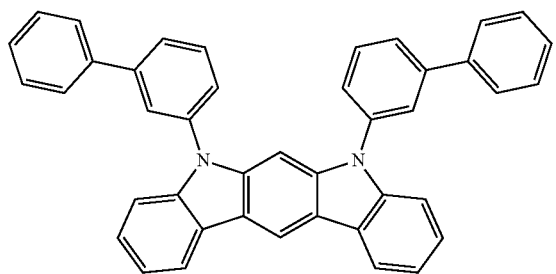
S-15
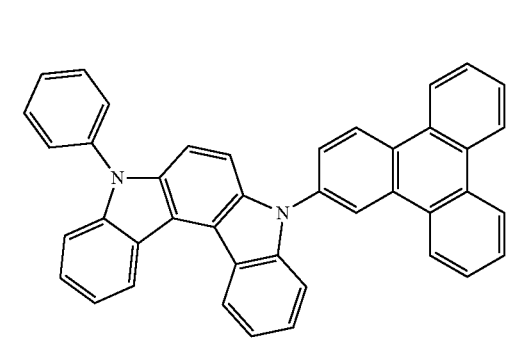
S-16
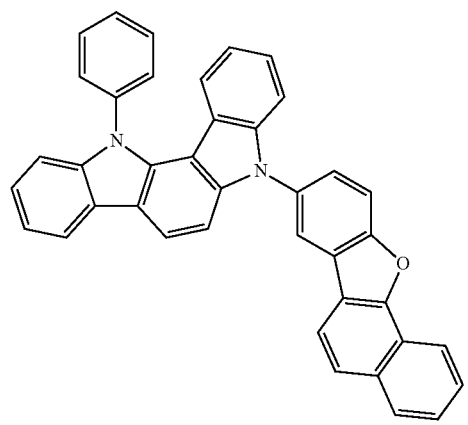
S-17
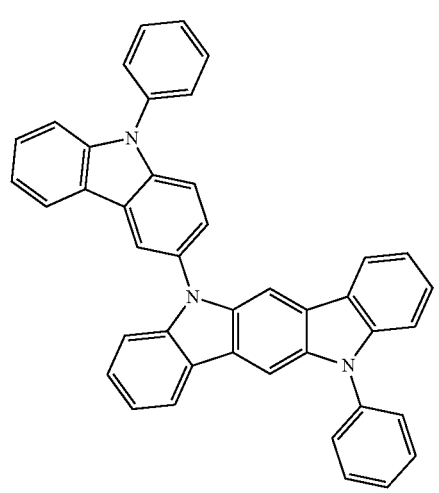
S-18
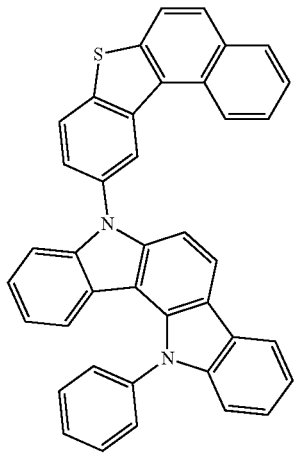
S-19
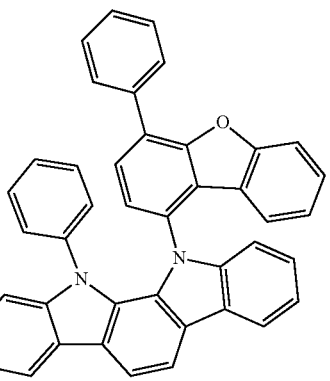
S-20
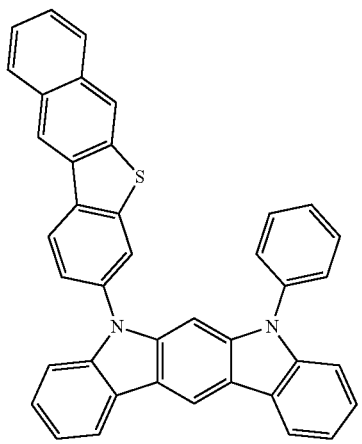

S-21
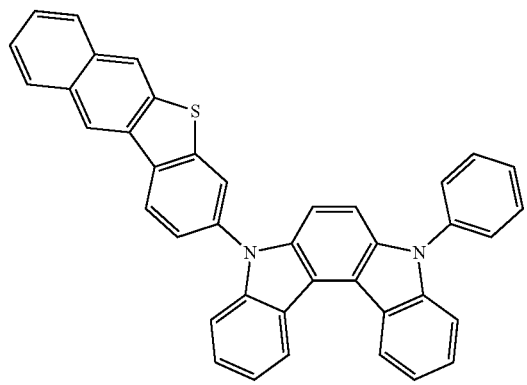
S-22
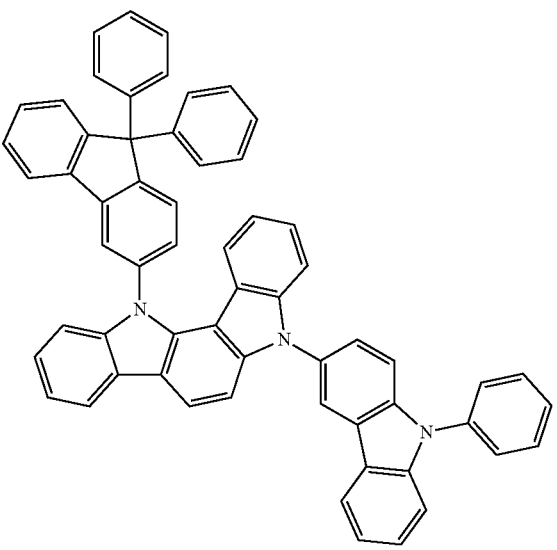
S-23
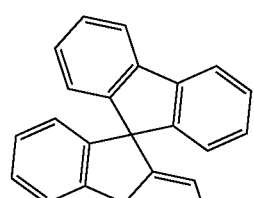
S-24
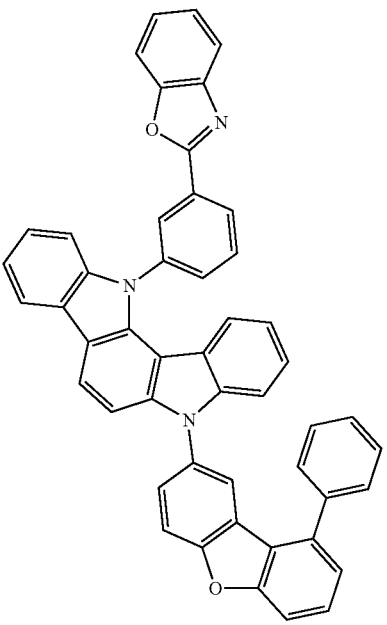
S-25
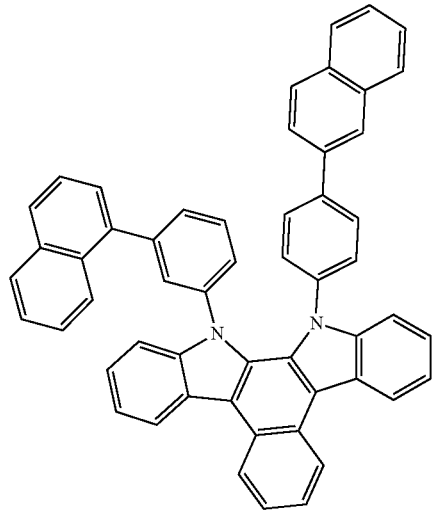
S-26
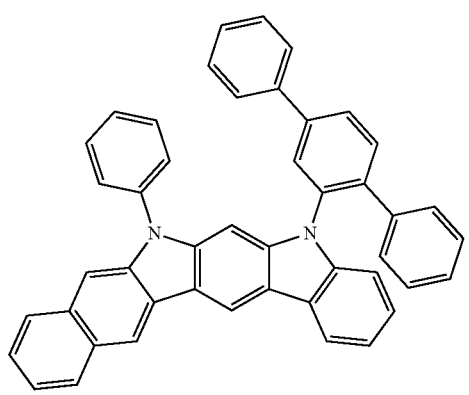

-continued
S-27
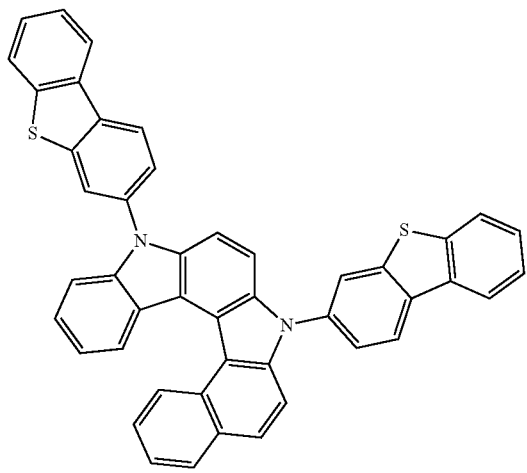
S-28
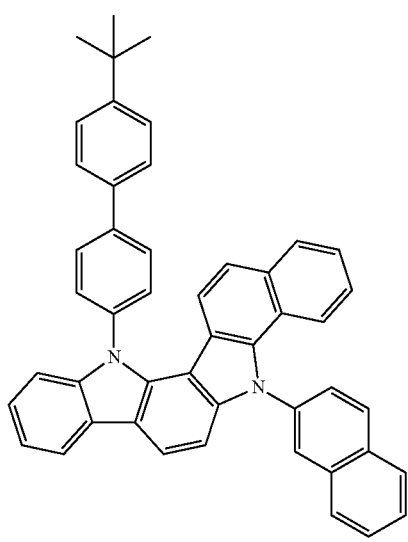
S-29
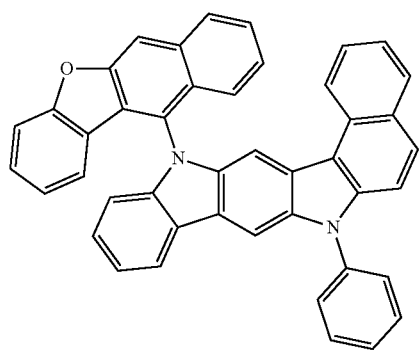
S-30
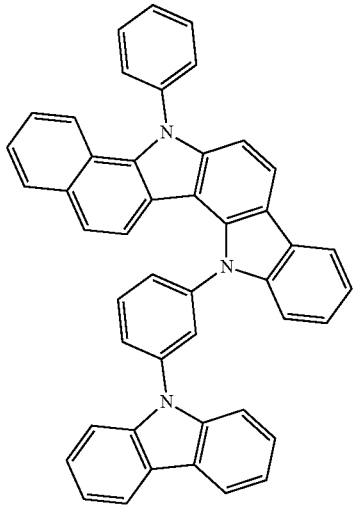
S-31
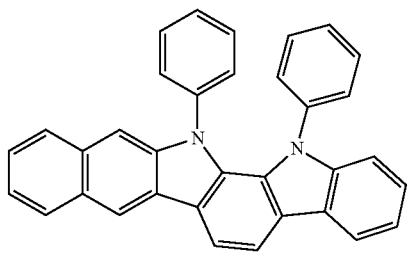
S-32
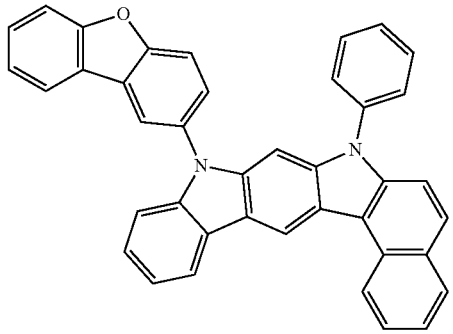
S-33
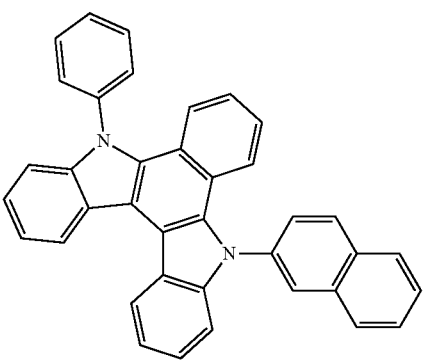

-continued
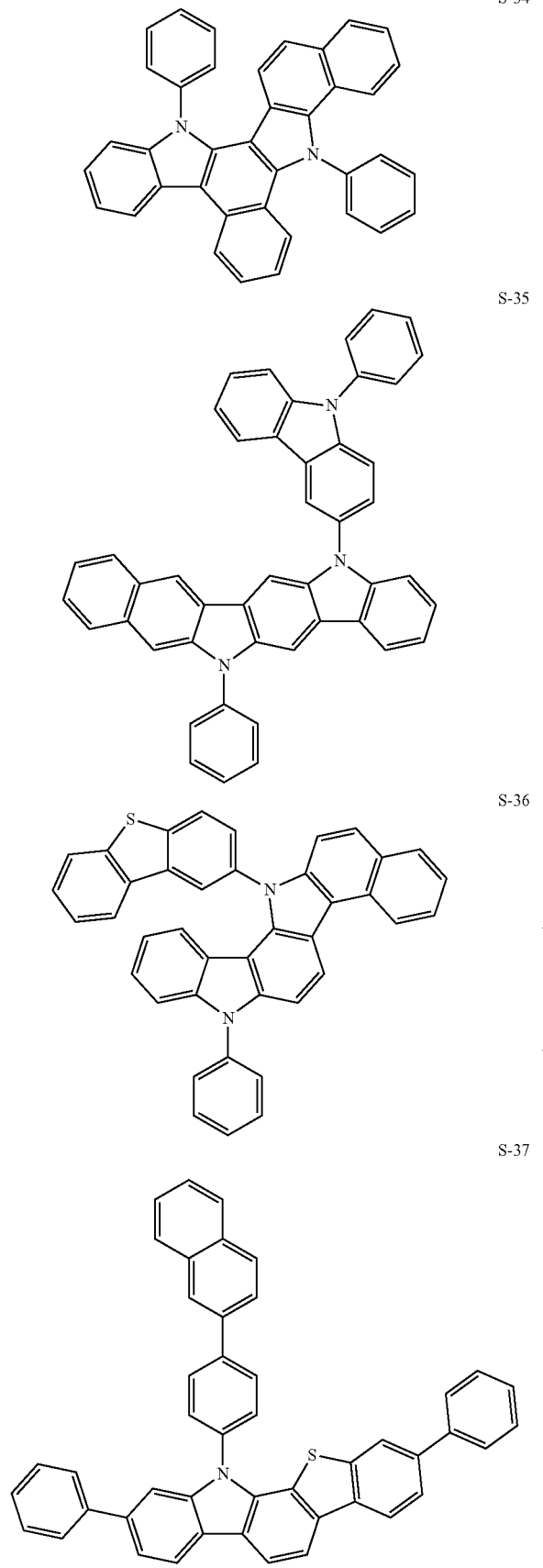
S-34
S-35
S-36
S-37
-continued
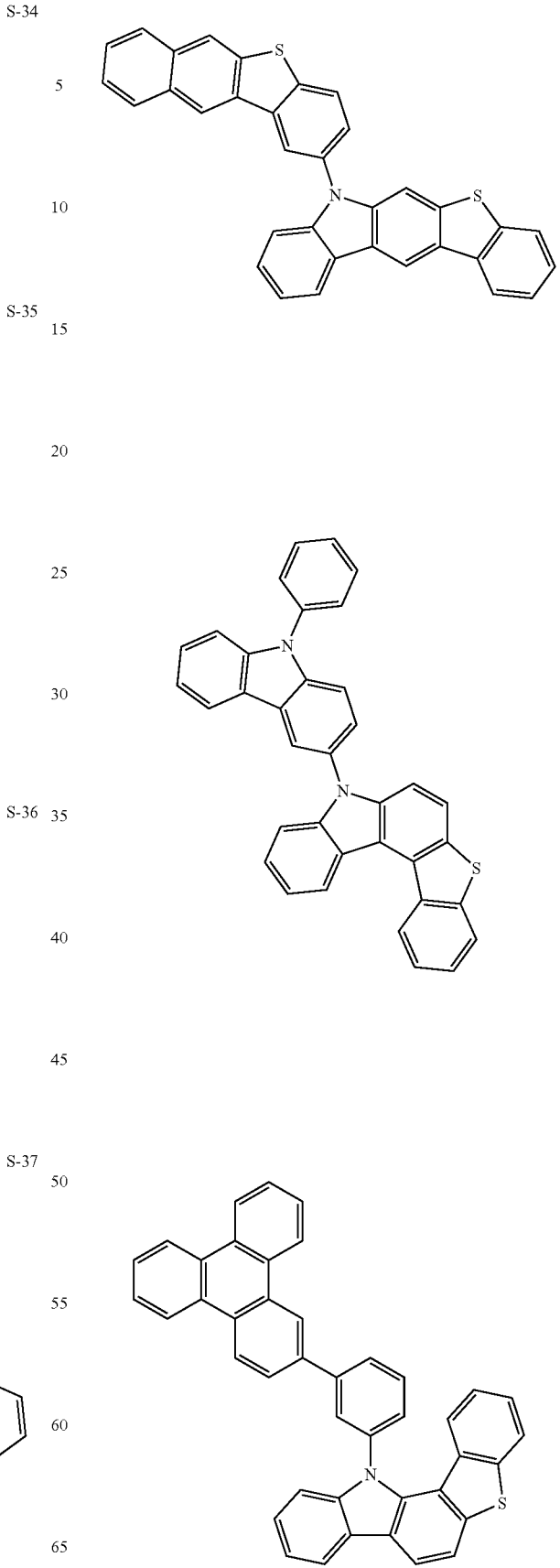
S-38
S-39
S-40

-continued
S-41
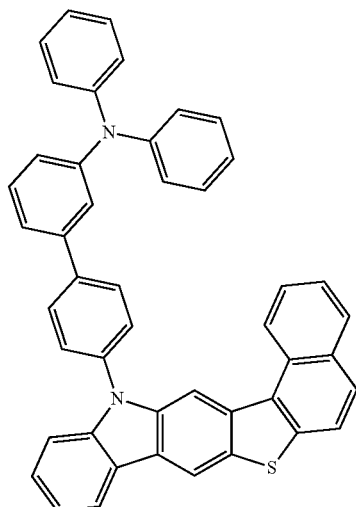
S-42
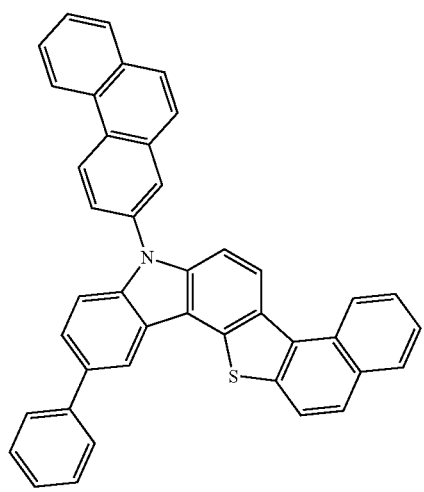
S-43
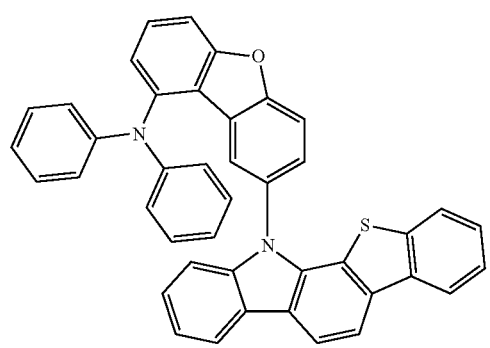
S-44
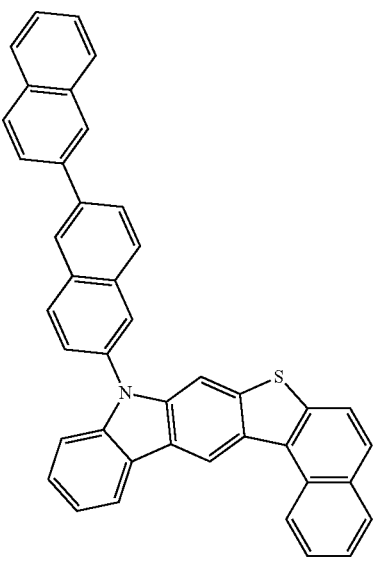
S-45
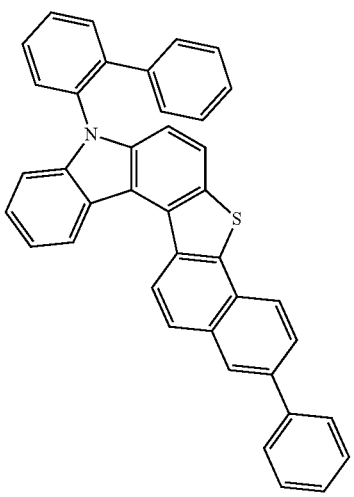
S-46
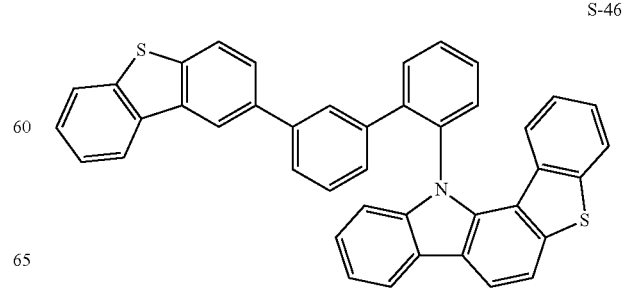

S-47
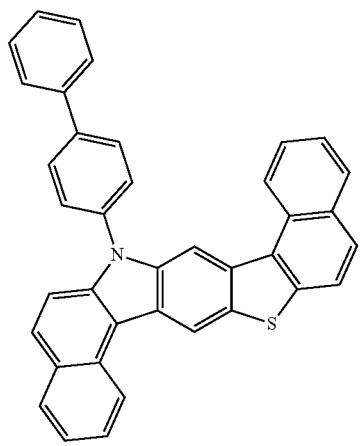
S-50
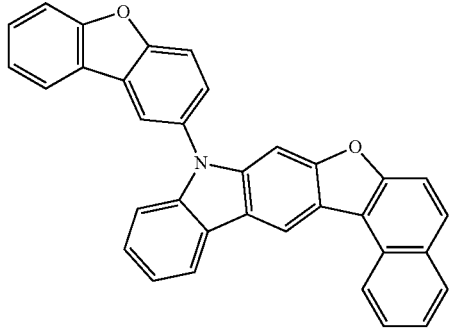
S-51
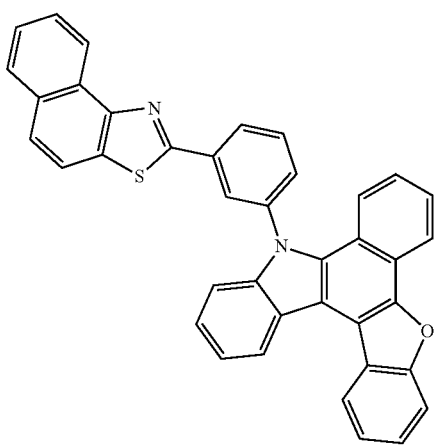
S-48
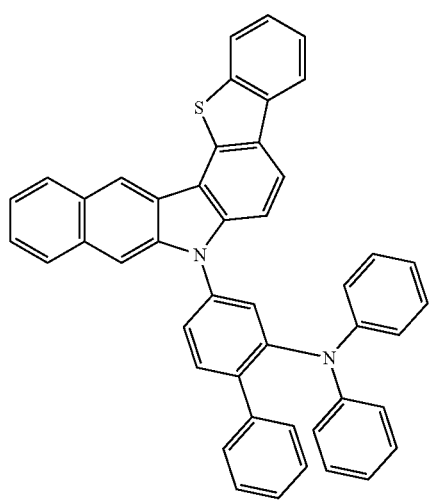
S-52
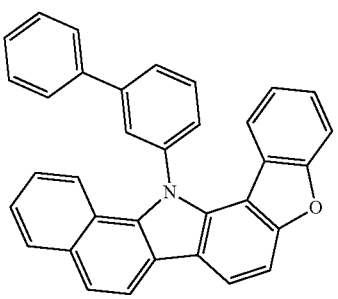
S-49
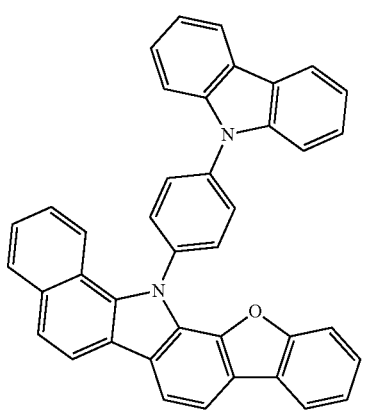
S-53
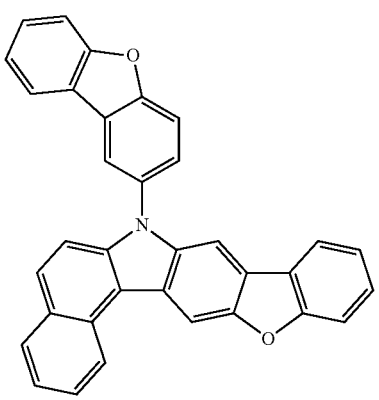

-continued
S-54
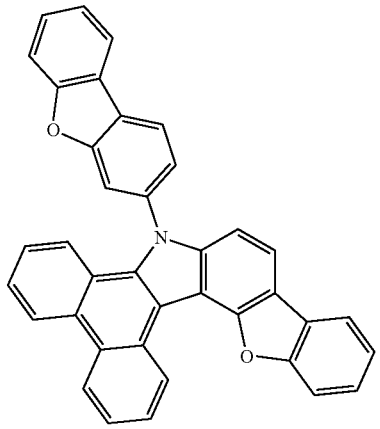
S-55
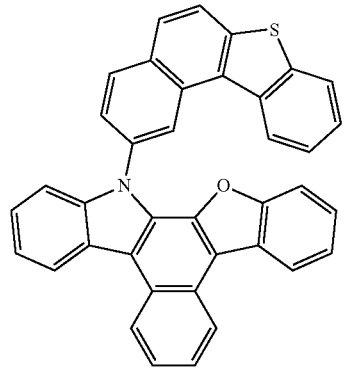
S-56
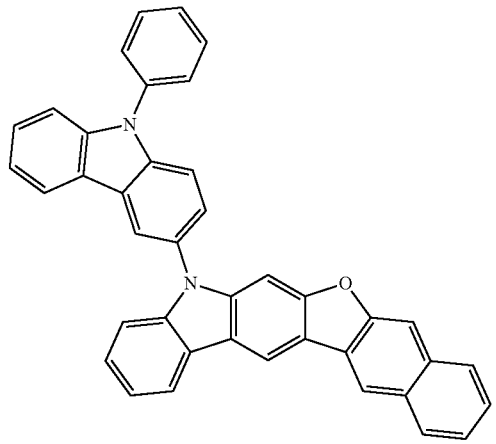
S-57
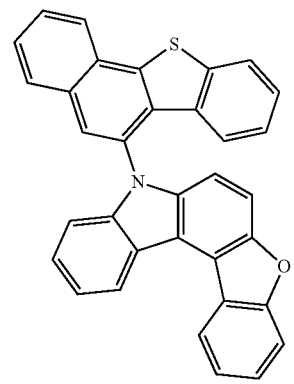
-continued
S-58
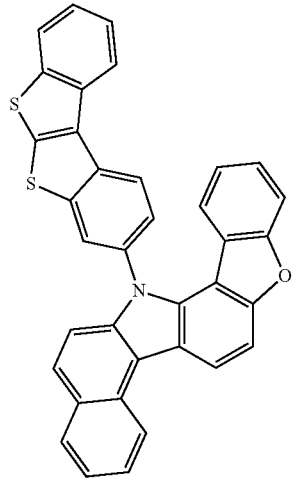
S-59
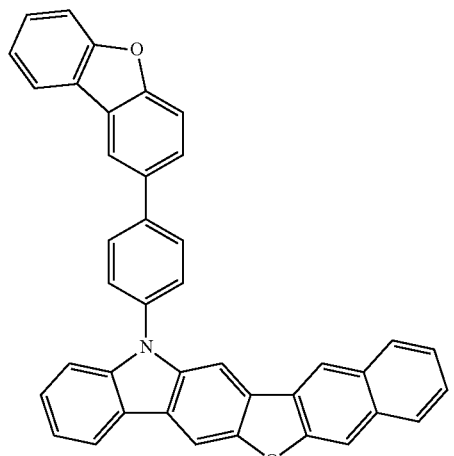
S-60
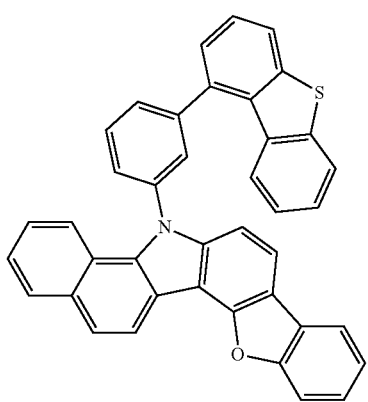

-continued
S-61
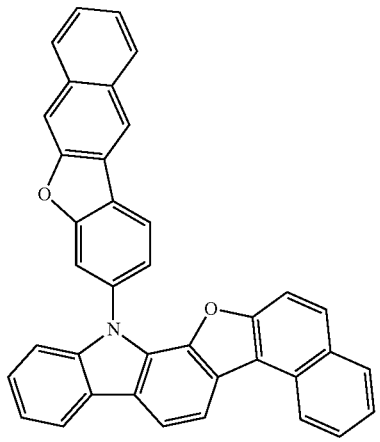
S-62
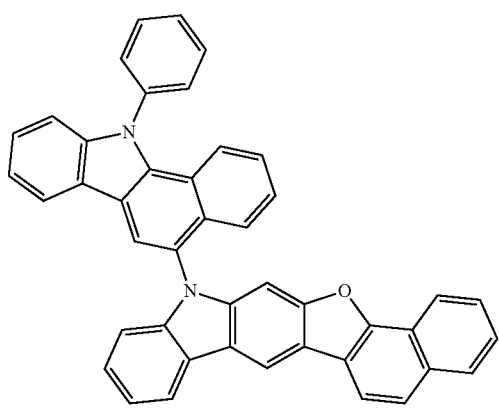
S-63
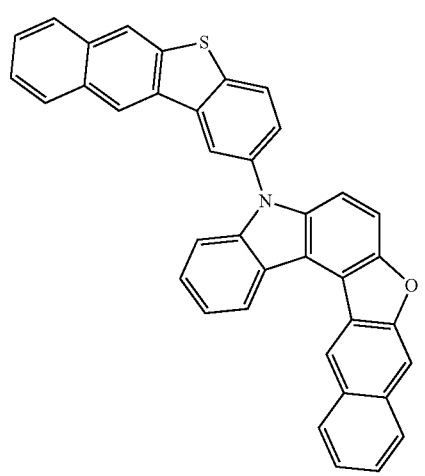
-continued
S-64
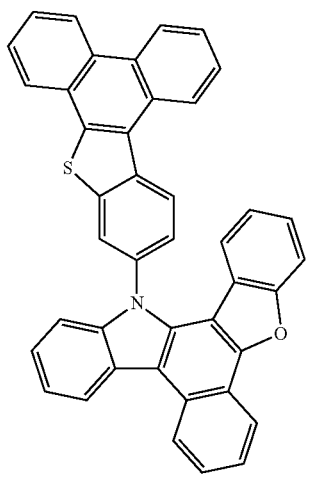
S-65
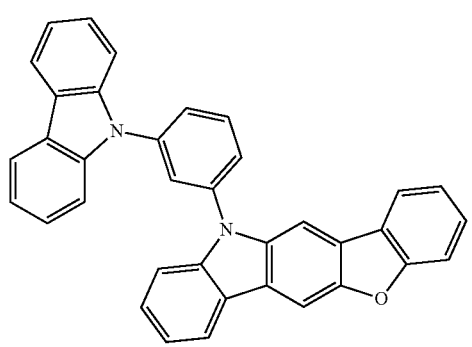
S-66
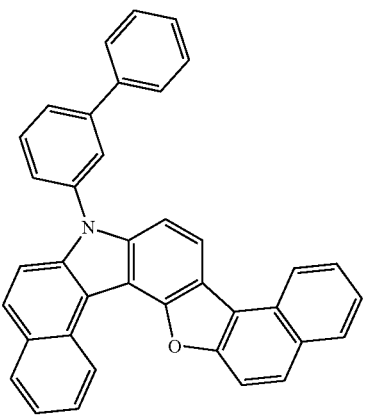
S-67
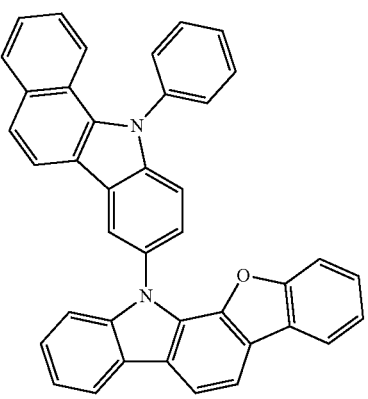

-continued
S-68
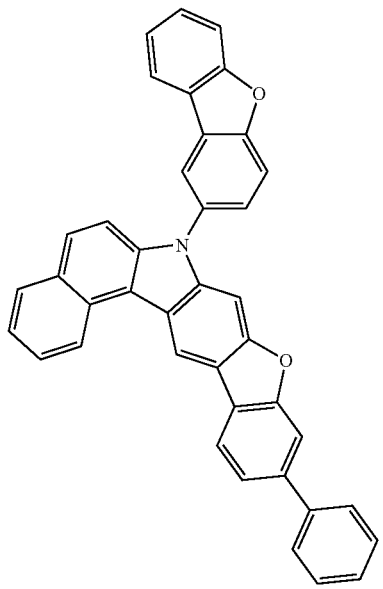
S-69
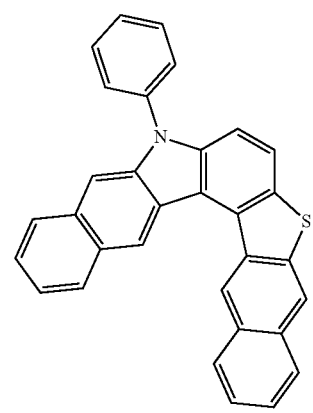
S-70
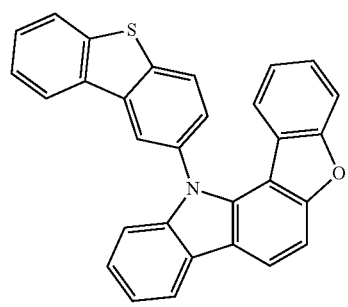
-continued
S-71
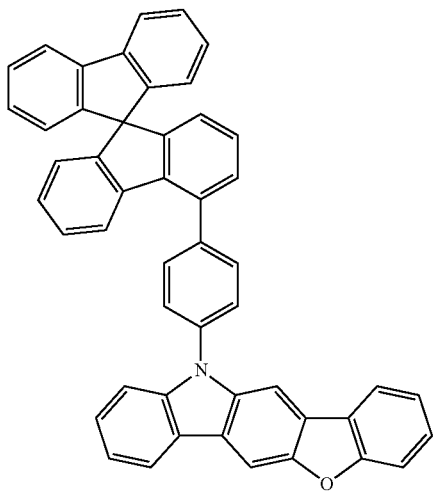
S-72
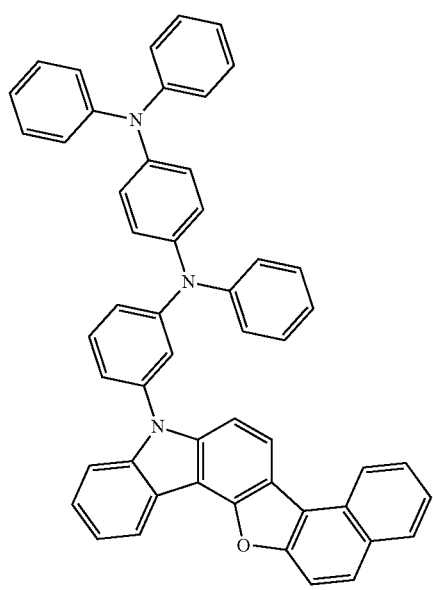
S-73
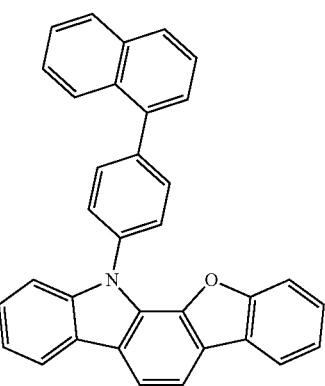

S-74
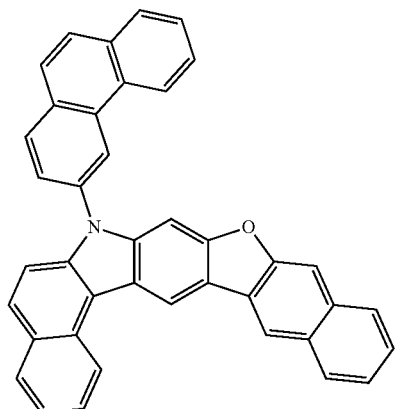
S-75
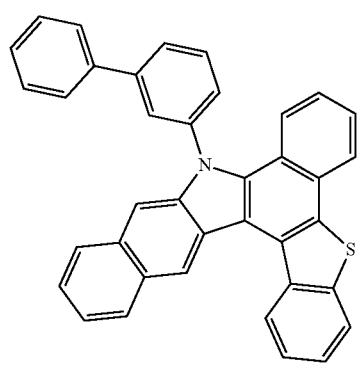
S-76
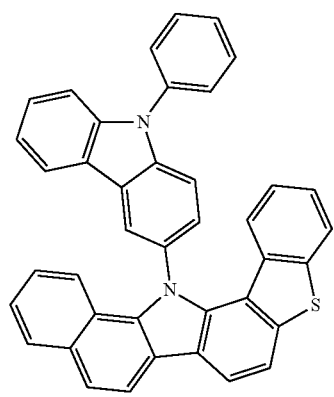
S-77
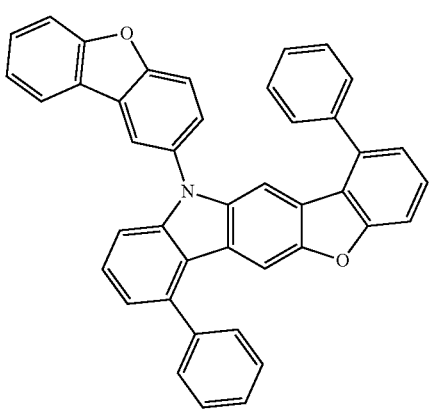
S-78
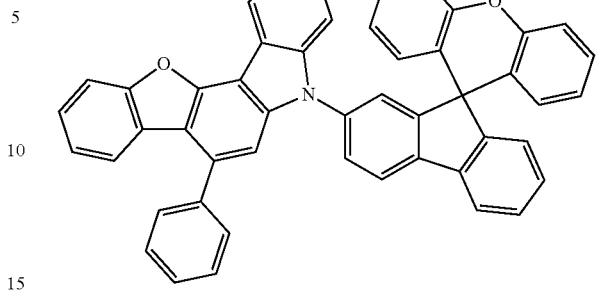
S-79
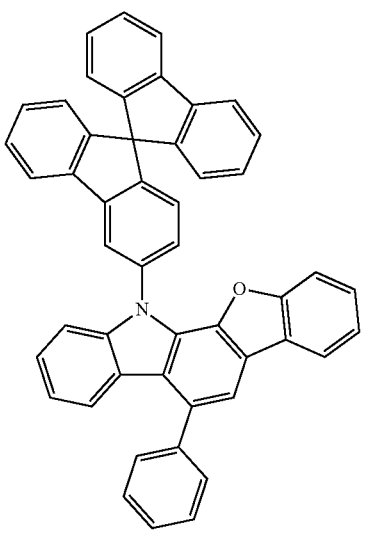
S-80
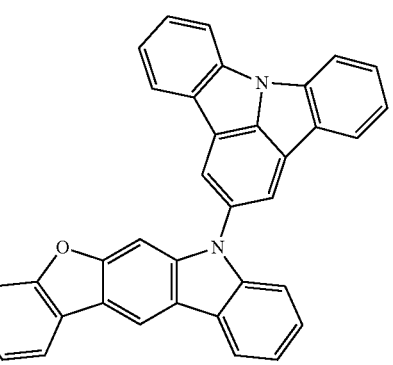
S-81
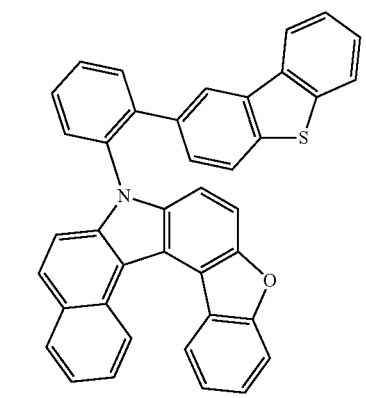

S-82
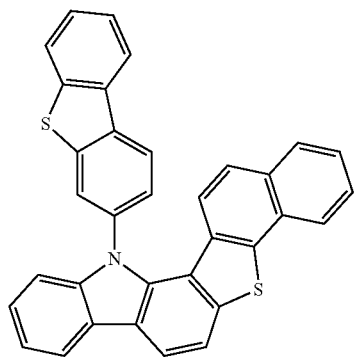
S-85
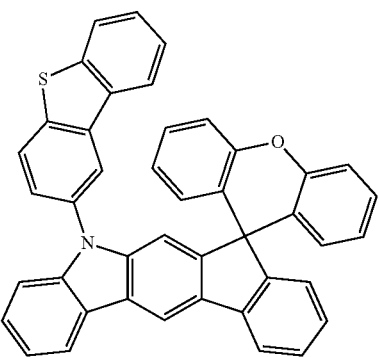
S-83
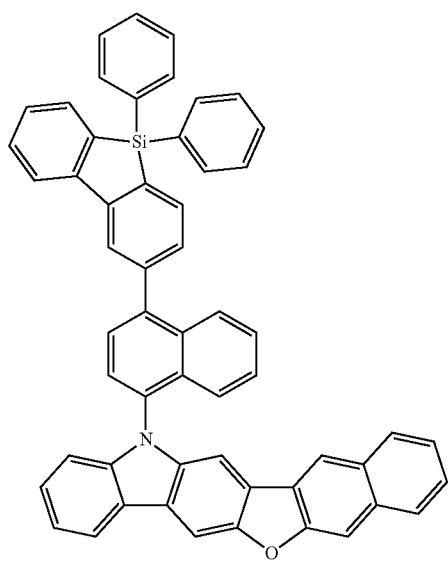
S-86
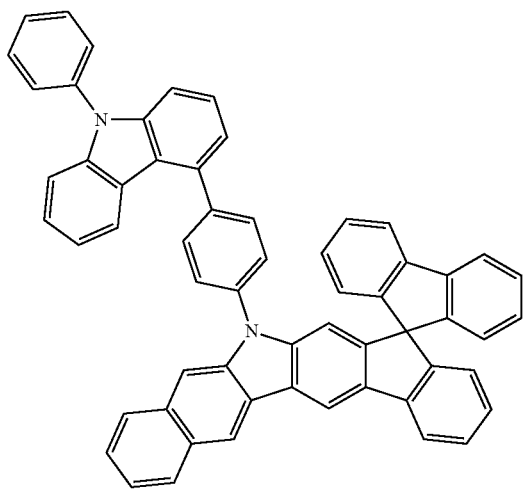
S-84
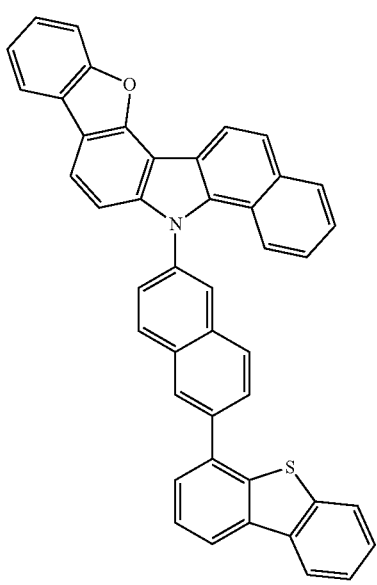
S-87
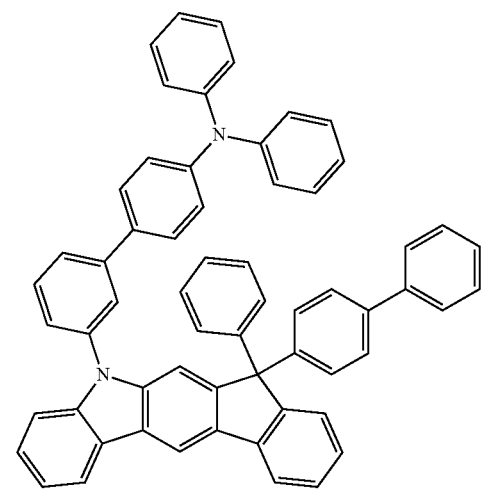

-continued
S-88
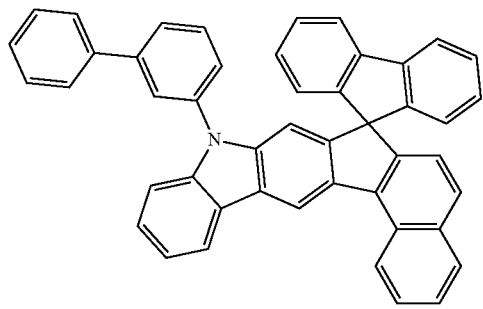
S-89
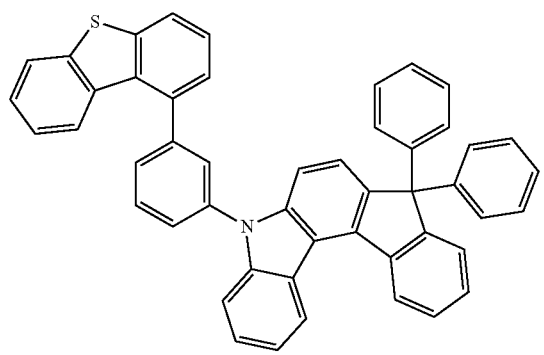
S-90
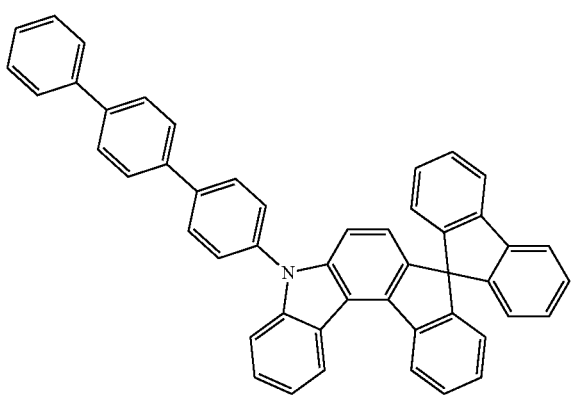
-continued
S-92
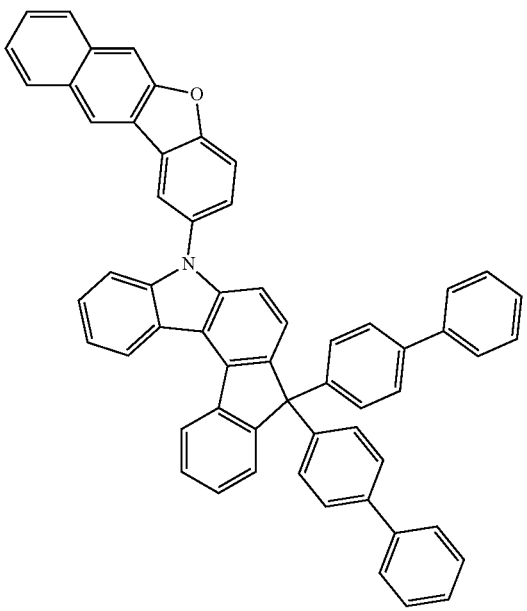
S-93
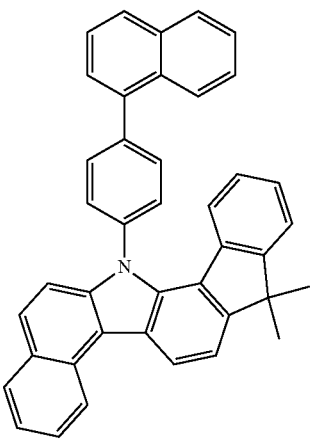
S-94
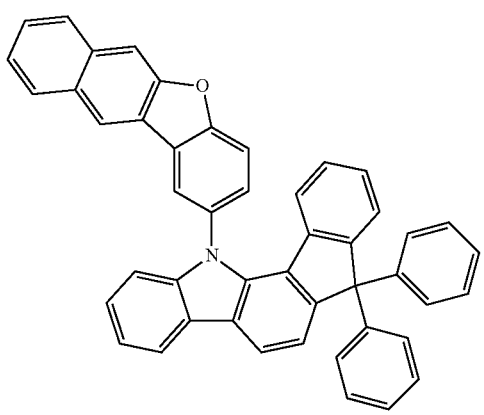

S-95
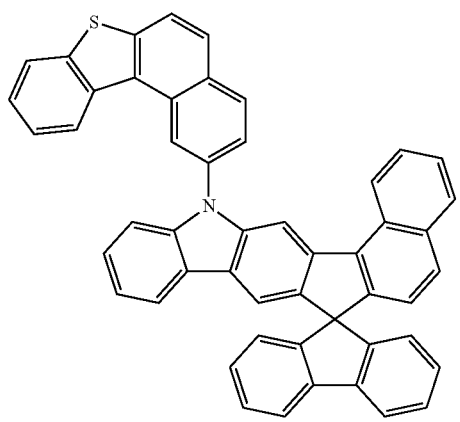
S-96
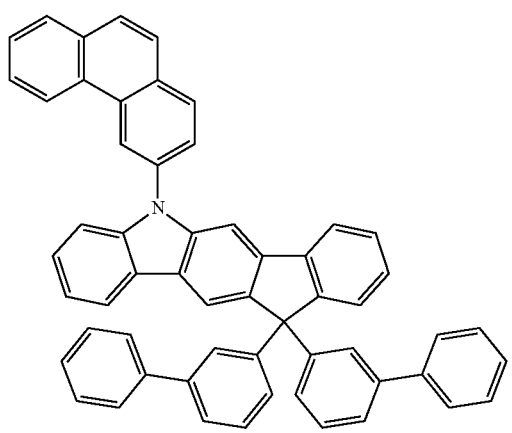
S-97
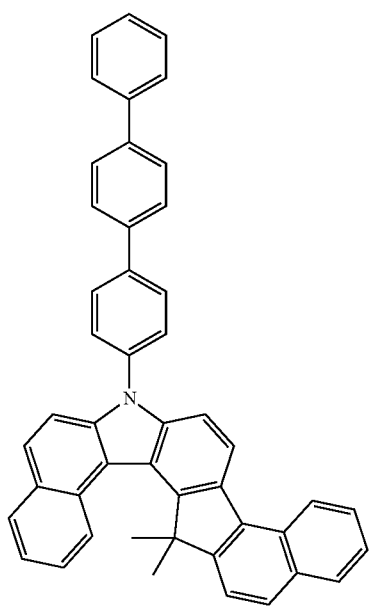
S-98
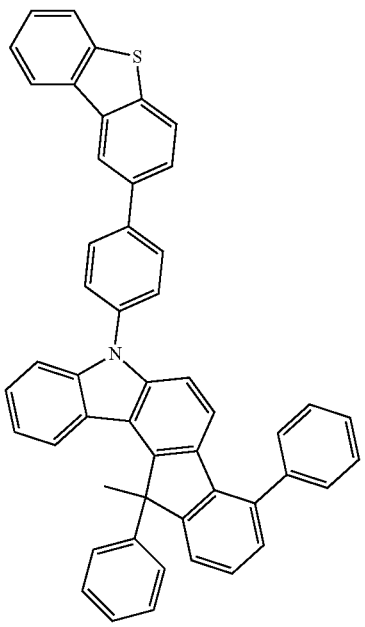
S-99
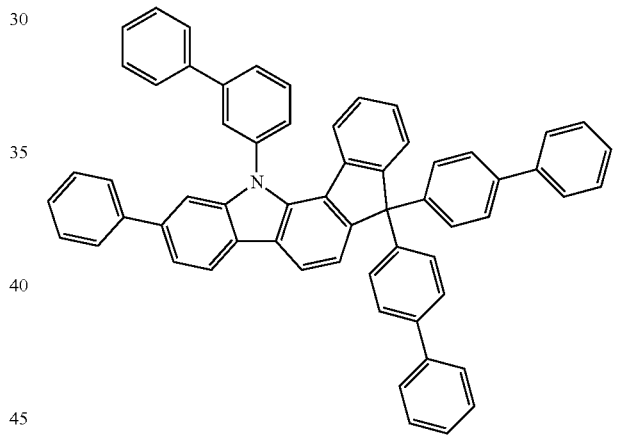
S-100
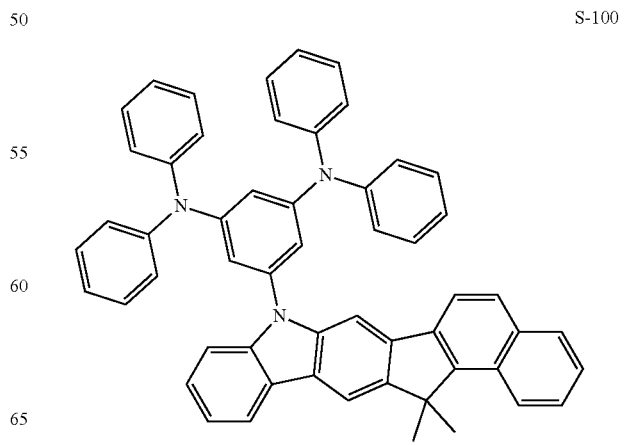

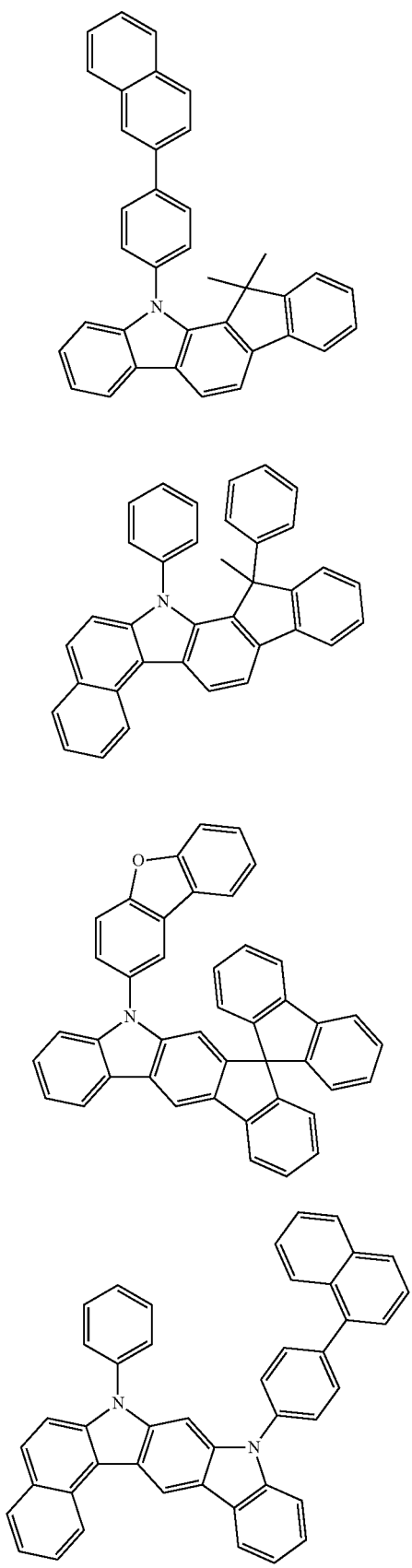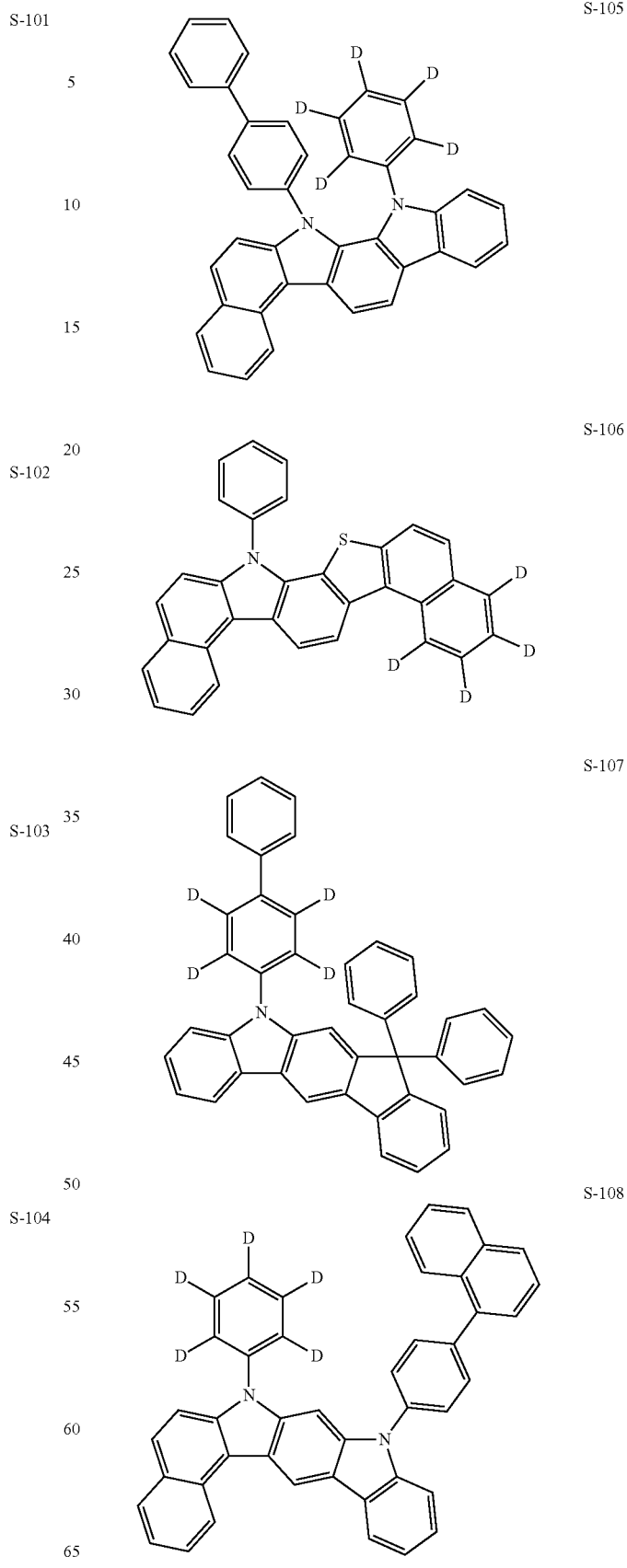

S-109
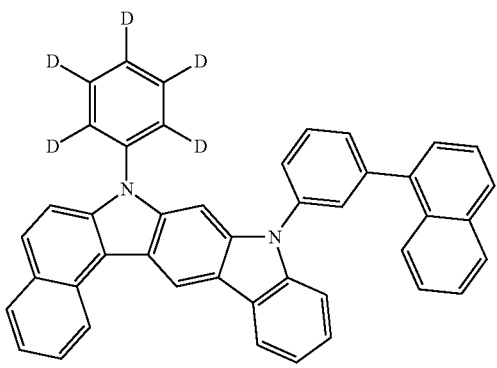
S-110
S-111
S-112
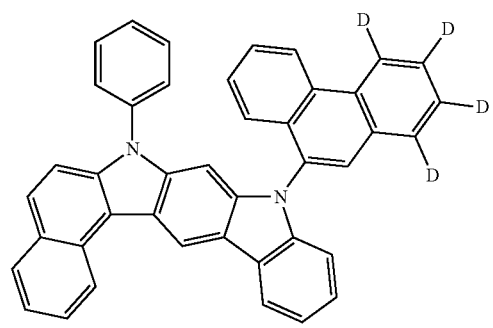
S-113
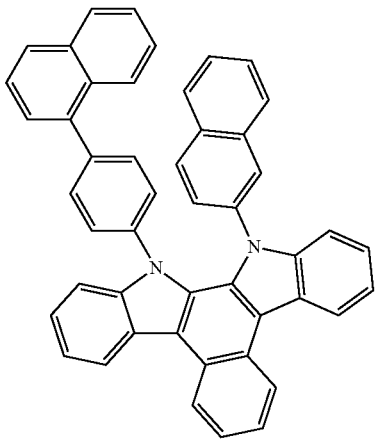
S-114
S-115
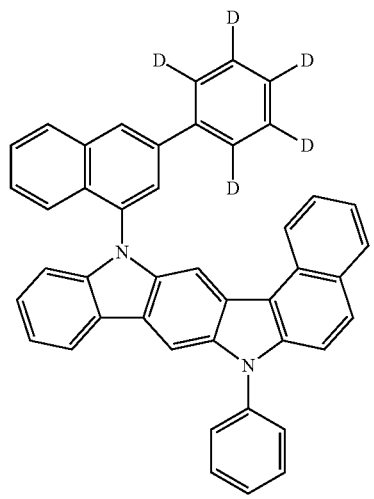
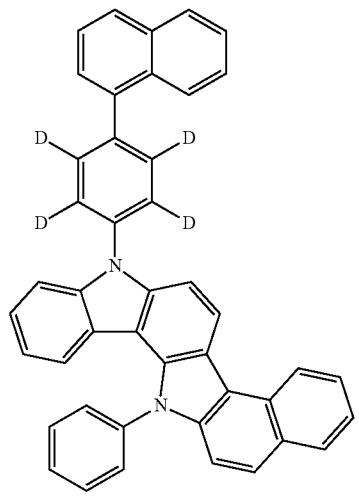

-continued

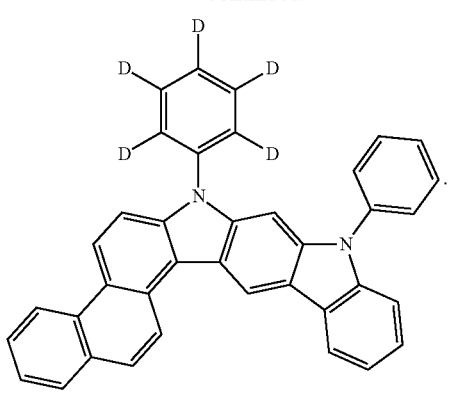

S-116

14. An organic electronic element comprising a first electrode; a second electrode; and an organic material layer formed between the first electrode and the second electrode, wherein the organic material layer comprises the composition for an organic electronic element of claim 9.

15. The organic electronic element according to claim 14, further comprising a light efficiency enhancing layer formed on at least one surface of the first electrode and the second electrode, the surface being opposite to the organic material layer.

16. The organic electronic element according to claim 14, wherein the organic material layer comprises 2 or more stacks comprising a hole transport layer, an emitting layer and an electron transport layer sequentially formed on the first electrode.

17. The organic electronic element according to claim 16, the organic material layer further comprises a charge generation layer formed between the 2 or more stacks.

18. The organic electronic element according to claim 14, wherein the organic material layer comprising the composition is an emitting layer.

19. An electronic device comprising a display device comprising the organic electronic element of claim 14; and a control unit for driving the display device.

20. The electronic device according to claim 19, wherein the organic electronic element is at least one of an OLED, an organic solar cell, an organic photo conductor (OPC), organic transistor (organic TFT) and an element for monochromic or white illumination.

* * * * *